US012709622B2

(12) United States Patent
Mahdavi et al.

(10) Patent No.: US 12,709,622 B2

(45) Date of Patent: Aug. 18, 2026

(54) CONJUGATES FOR SELECTIVE RESPONSIVENESS TO VICINAL DIOLS

(71) Applicant: PROTOMER TECHNOLOGIES, INC., Indianapolis, IN (US)

(72) Inventors: Alborz Mahdavi, Pasadena, CA (US); Ryan Kelly Spencer, Pasadena, CA (US); Jack Joseph Steele, Pasadena, CA (US); JingXin Liang, Pasadena, CA (US); Mirna Ekram Anwar Shaker, Pasadena, CA (US); Diao Chen, Pasadena, CA (US); Sachitanand Mali, Pasadena, CA (US)

(73) Assignee: PROTOMER TECHNOLOGIES, INC., Indianapolis, IN (US)

( * ) Notice: Subject to any disclaimer, the term of this patent is extended or adjusted under 35 U.S.C. 154(b) by 817 days.

(21) Appl. No.: 17/907,711

(22) PCT Filed: Mar. 31, 2021

(86) PCT No.: PCT/US2021/025261

§ 371 (c)(1),
(2) Date: Sep. 29, 2022

(87) PCT Pub. No.: WO2021/202802

PCT Pub. Date: Oct. 7, 2021

(65) Prior Publication Data

US 2023/0134116 A1 May 4, 2023

Related U.S. Application Data

(60) Provisional application No. 63/002,662, filed on Mar. 31, 2020.

(51) Int. Cl.

*C07F 5/02* (2006.01)
*A61K 47/54* (2017.01)
*C07K 14/62* (2006.01)

(52) U.S. Cl.

CPC ............ *C07F 5/025* (2013.01); *A61K 47/542* (2017.08); *A61K 47/545* (2017.08); *C07K 14/62* (2013.01)

(58) Field of Classification Search

CPC ....................................................... C07F 5/025
See application file for complete search history.

(56) References Cited

U.S. PATENT DOCUMENTS

| | | | |
|---|---|---|---|
| 4,888,414 | A | 12/1989 | Knutson |
| 8,846,624 | B2 | 9/2014 | Chaikof et al. |
| 9,867,869 | B2 | 1/2018 | Anderson et al. |
| 10,000,571 | B2 | 6/2018 | Ashkenazi et al. |
| 10,584,156 | B2 | 3/2020 | Weiss |
| 11,052,133 | B2 | 7/2021 | Mahdavi |
| 2004/0001827 | A1 | 1/2004 | Dennis |
| 2007/0219346 | A1 | 9/2007 | Trifiro |
| 2010/0048473 | A1 | 2/2010 | Chaikof et al. |
| 2010/0273979 | A1 | 10/2010 | Abrahmsen et al. |
| 2010/0278845 | A1 | 11/2010 | Heavner |
| 2011/0039769 | A1 | 2/2011 | Tagmose et al. |
| 2012/0014908 | A1 | 1/2012 | Zion et al. |
| 2012/0135919 | A1 | 5/2012 | Lancaster et al. |
| 2013/0028918 | A1 | 1/2013 | Song et al. |
| 2014/0037699 | A1 | 2/2014 | Zion et al. |
| 2015/0025005 | A1 | 1/2015 | Langer et al. |
| 2015/0105317 | A1 | 4/2015 | Lin et al. |
| 2016/0082122 | A1 | 3/2016 | Bachelet et al. |
| 2020/0325160 | A1 | 10/2020 | Kruse et al. |
| 2021/0369815 | A1 | 12/2021 | Mahdavi |

FOREIGN PATENT DOCUMENTS

| | | |
|---|---|---|
| WO | WO 03/048195 A2 | 6/2003 |
| WO | WO 2014/093696 A2 | 6/2014 |
| WO | WO 2017/070617 A1 | 4/2017 |
| WO | WO 2019/092125 A1 | 5/2019 |
| WO | WO 2019/204206 A1 | 10/2019 |
| WO | WO 2020/201041 A2 | 10/2020 |
| WO | WO 2021/022116 A1 | 2/2021 |

OTHER PUBLICATIONS

Dowlut et al., "An Improved Class of Sugar-Binding Boronic Acids, Soluble and Capable of Complexing Glycosides in Neutral Water," *J. Am. Chem. Soc.* 128, 4226-4227 (2006).

Hoeg-Jensen et al., "Insulins with built-in glucose sensors for glucose responsive insulin release," *Journal of Peptide Science*, vol. 11, pp. 339-346 (2005).

Wu, Xin et al., "Selective sensing of saccharides using simple boronic acids and their aggregates," Chem. Soc. Rev., vol. 42, No. 20, pp. 8032-8048 (2013).

Hoeg-Jensen, Thomas, "Preparation and Screening of Diboronate Arrays for Identification of Carbohydrate Binders," QSAR & Combinatorial Science, vol. 23, No. 5, pp. 344-351 (2004).

Pal, Arnab et al., "Design, Synthesis, and Screening of a Library of Peptidyl Bis(Boroxoles) as Oligosaccharide Receptors in Water: Identification of a Receptor for the Tumor Marker TF-Antigen Disaccharide," Angewandte Chemie International Edition, vol. 49, No. 8, pp. 1492-1495 (2010).

Tan, Lei et al., "Glucose- and pH-Responsive Nanogated Ensemble Based on Polymeric Network Capped Mesoporous Silica," Applied Materials & Interfaces, vol. 7, No. 11, pp. 6310-6316 (2015).

(Continued)

*Primary Examiner* — Golam M Shameem

(74) *Attorney, Agent, or Firm* — Parker D. McCrary

(57) ABSTRACT

Embodiments of the present disclosure relate to sensors that can selectively bind to specific vicinal diols in the presence of other diols. These boronated vicinal diol-responsive sensor compounds can sense levels of specific vicinal diols and respond to these molecules in the body. In certain embodiments, the vicinal diol is a cis diol, for example, a hexose such as glucose. In certain embodiments the sensors are conjugated to a drug substance, and the sensors may change the biophysical characteristics, pharmacokinetics, and/or activity of the drug substance in response to the vicinal diol. The drug substance may be or include a polypeptide, such as an insulin, a human endocrine or incretin peptide, or an analogue thereof, and may contain one or more modified amino acids containing a vicinal diol-responsive sensor.

12 Claims, 27 Drawing Sheets

Specification includes a Sequence Listing.

(56) References Cited

OTHER PUBLICATIONS

International Search Report for International Application No. PCT/US2021/025261, dated Jul. 1, 2021.
Written Opinion of the International Search Authority for International Application No. PCT/US2021/025261, mailed Jul. 1, 2021.
Chu, M. K. L. et al., "In vitro and In vivo testing of glucose responsive insulin delivery microdevices in diabetic rats," Lab Chip, vol. 12, pp. 2533-2539 (2012).
Ding, Z. et al., "Synthesis of glucose-sensitive self-assembled films and their application in controlled drug delivery," Polymer, vol. 50, pp. 4205-4211 (2009).
Menting, J. G. et al., "Protective hinge in insulin opens to enable its receptor engagement," PNAS, vol. 111, pp. E3395-E3404 (2014).
Qi, W. et al., "Glucose-sensitive Microcapsules from Glutaraldehyde Cross-Linked Hemoglobin and Glucose Oxidase," Biomacromolecules, vol. 10, pp. 1212-1216 (2009).
European Search Report issued in EP application No. 16790212.1, dated Sep. 5, 2018 (11 pages).
International Search Report of International Application No. PCT/US2021/059802, mail date Mar. 9, 2022 (7 pages).

SEQUENCE LISTING

<160> NUMBER OF SEQ ID NOS: 20

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1 5 10 15

Glu Asn Tyr Cys Asn
20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr
20 25 30

<210> SEQ ID NO 3
<211> LENGTH: 39
<212> TYPE: PRT
<213> ORGANISM: Artificial Sequence
<220> FEATURE:
<223> OTHER INFORMATION: Linking sequence
<220> FEATURE:
<221> NAME/KEY: misc_feature
<222> LOCATION: (1)..(18)
<223> OTHER INFORMATION: Xaa can be any naturally occurring amino acid
<220> FEATURE:
<221> NAME/KEY: misc_feature
<222> LOCATION: (20)..(39)
<223> OTHER INFORMATION: Xaa can be any naturally occurring amino acid

<400> SEQUENCE: 3

Xaa Xaa Xaa Xaa Xaa Xaa Xaa Xaa Xaa Xaa Xaa Xaa Xaa Xaa Xaa Xaa
1 5 10 15

Xaa Xaa Lys Xaa Xaa Xaa Xaa Xaa Xaa Xaa Xaa Xaa Xaa Xaa Xaa Xaa
20 25 30

Xaa Xaa Xaa Xaa Xaa Xaa Xaa
35

<210> SEQ ID NO 4
<211> LENGTH: 32
<212> TYPE: PRT
<213> ORGANISM: Artificial Sequence
<220> FEATURE:
<223> OTHER INFORMATION: Modified insulin 1 - B-Chain

<400> SEQUENCE: 4

Gly Lys Phe Val Asn Gln His Leu Cys Gly Ser His Leu Val Glu Ala
1 5 10 15

Leu Tyr Leu Val Cys Gly Lys Arg Gly Phe Phe Tyr Thr Pro Lys Thr
20 25 30

<210> SEQ ID NO 5
<211> LENGTH: 32
<212> TYPE: PRT
<213> ORGANISM: Artificial Sequence
<220> FEATURE:

<223> OTHER INFORMATION: Modified insulin 5 - B-chain

<400> SEQUENCE: 5

```
Lys Pro Phe Val Asn Gln His Leu Cys Gly Ser His Leu Val Glu Ala
1               5                   10                  15

Leu Tyr Leu Val Cys Gly Glu Arg Gly Phe Phe Tyr Thr Pro Lys Thr
            20                  25                  30
```

<210> SEQ ID NO 6
<211> LENGTH: 38
<212> TYPE: PRT
<213> ORGANISM: Artificial Sequence
<220> FEATURE:
<223> OTHER INFORMATION: Modified insulin 6 - B-chain

<400> SEQUENCE: 6

```
Lys Pro Gly Ser Glu His Glu Ser Ala Phe Val Asn Gln His Leu Cys
1               5                   10                  15

Gly Ser His Leu Val Glu Ala Leu Tyr Leu Val Cys Gly Glu Arg Gly
            20                  25                  30

Phe Phe Tyr Thr Pro Lys
        35
```

<210> SEQ ID NO 7
<211> LENGTH: 30
<212> TYPE: PRT
<213> ORGANISM: Artificial Sequence
<220> FEATURE:
<223> OTHER INFORMATION: Modified Insulin 7 - B-chain

<400> SEQUENCE: 7

```
Phe Val Asn Gln His Leu Cys Gly Ser His Leu Val Glu Ala Leu Tyr
1               5                   10                  15

Leu Val Cys Gly Lys Arg Gly Phe Phe Tyr Thr Pro Lys Thr
            20                  25                  30
```

<210> SEQ ID NO 8
<211> LENGTH: 43
<212> TYPE: PRT
<213> ORGANISM: Artificial Sequence
<220> FEATURE:
<223> OTHER INFORMATION: Modified Insulin 8 - B-chain

<400> SEQUENCE: 8

```
Lys Gly Pro Glu Gly Glu Ser Ala Gly Ser Glu Gly Glu Ser Val Asn
1               5                   10                  15

Gln His Leu Cys Gly Ser His Leu Val Glu Ala Leu Tyr Leu Val Cys
            20                  25                  30

Gly Lys Arg Gly Phe Phe Tyr Thr Pro Arg Thr
        35                  40
```

<210> SEQ ID NO 9
<211> LENGTH: 29
<212> TYPE: PRT
<213> ORGANISM: Artificial Sequence
<220> FEATURE:
<223> OTHER INFORMATION: Modified Insulin 9 - A-chain

<400> SEQUENCE: 9

```
Gly Ile Val Glu Gln Cys Cys Thr Ser Ile Cys Ser Leu Tyr Gln Leu
1               5                   10                  15

Glu Asn Tyr Cys Asn Ala Ser Glu Lys Pro Ser Glu Ala
            20                  25
```

<210> SEQ ID NO 10
<211> LENGTH: 48
<212> TYPE: PRT
<213> ORGANISM: Artificial Sequence
<220> FEATURE:
<223> OTHER INFORMATION: Modified Insulin 9 - B-chain

<400> SEQUENCE: 10

```
Lys Pro Gly Ser Glu Val Gly Glu Ser Ala Ile Lys Pro Gly Ser Glu
1               5                   10                  15

Gly Glu Ser Val Asn Gln His Leu Cys Gly Ser His Leu Val Glu Ala
            20                  25                  30

Leu Tyr Leu Val Cys Gly Glu Arg Gly Phe Phe Tyr Thr Pro Lys Thr
        35                  40                  45
```

<210> SEQ ID NO 11
<211> LENGTH: 49
<212> TYPE: PRT
<213> ORGANISM: Artificial Sequence
<220> FEATURE:
<223> OTHER INFORMATION: Modified Insulin 10 - B-chain

<400> SEQUENCE: 11

```
Lys Pro Gly Ser Ser Ala Glu Glu Gly Glu Ser Ala Lys Pro Gly Ser
1               5                   10                  15

Glu Gly Glu Ser Val Asn Gln His Leu Cys Gly Ser His Leu Val Glu
            20                  25                  30

Ala Leu Tyr Leu Val Cys Gly Lys Arg Gly Phe Phe Tyr Thr Pro Lys
        35                  40                  45

Thr
```

<210> SEQ ID NO 12
<211> LENGTH: 27
<212> TYPE: PRT
<213> ORGANISM: Artificial Sequence
<220> FEATURE:
<223> OTHER INFORMATION: Modified Insulin 11 - A-chain

<400> SEQUENCE: 12

```
Gly Ile Val Glu Gln Cys Cys Thr Ser Ile Cys Ser Leu Tyr Gln Leu
1               5                   10                  15

Glu Asn Tyr Cys Asn Lys Leu Ser Glu Ser Gly
            20                  25
```

<210> SEQ ID NO 13
<211> LENGTH: 51
<212> TYPE: PRT
<213> ORGANISM: Artificial Sequence
<220> FEATURE:
<223> OTHER INFORMATION: Modified Insulin 11 - B-chain

<400> SEQUENCE: 13

```
Lys Gly Arg Glu Asp Glu Ala Tyr Gly Asn Ile Lys Pro Gly Trp Glu
1               5                   10                  15

Gly Glu Ser Lys Pro Phe Val Asn Gln His Leu Cys Gly Ser His Leu
            20                  25                  30

Val Glu Ala Leu Tyr Leu Val Cys Gly Lys Arg Gly Phe Phe Tyr Thr
        35                  40                  45

Pro Lys Thr
    50
```

<210> SEQ ID NO 14
<211> LENGTH: 50
<212> TYPE: PRT
<213> ORGANISM: Artificial Sequence
<220> FEATURE:
<223> OTHER INFORMATION: Modified Insulin 12 - B-chain

<400> SEQUENCE: 14

```
Lys Pro Ser Gly Glu Arg Ser Glu Gly Ala Ile Lys Pro Gly Ser Glu
1               5                   10                  15

Gly Ser Glu Lys Phe Val Asn Gln His Leu Cys Gly Ser His Leu Val
            20                  25                  30

Glu Ala Leu Tyr Leu Val Cys Gly Lys Arg Gly Phe Phe Tyr Thr Pro
        35                  40                  45

Lys Thr
    50
```

<210> SEQ ID NO 15
<211> LENGTH: 39
<212> TYPE: PRT
<213> ORGANISM: Artificial Sequence
<220> FEATURE:
<223> OTHER INFORMATION: Modified Insulin 13 - B-chain

<400> SEQUENCE: 15

```
Lys Pro Gly Ser Glu His Glu Ser Ala Phe Val Asn Gln His Leu Cys
1               5                   10                  15

Gly Ser His Leu Val Glu Ala Leu Tyr Leu Val Cys Gly Lys Glu Gly
            20                  25                  30

Phe Phe Tyr Thr Pro Lys Thr
        35
```

<210> SEQ ID NO 16
<211> LENGTH: 26
<212> TYPE: PRT
<213> ORGANISM: Artificial Sequence
<220> FEATURE:
<223> OTHER INFORMATION: Modified Insulin 14 - A-chain

<400> SEQUENCE: 16

```
Gly Ile Val Glu Gln Cys Cys Thr Ser Ile Cys Ser Leu Tyr Gln Leu
1               5                   10                  15

Glu Asn Tyr Cys Asn Ala Glu Gly Ser Lys
            20                  25
```

<210> SEQ ID NO 17
<211> LENGTH: 39
<212> TYPE: PRT
<213> ORGANISM: Artificial Sequence
<220> FEATURE:
<223> OTHER INFORMATION: Modified Insulin 14 - B-chain

<400> SEQUENCE: 17

```
Lys Pro Gly Ser Glu His Glu Ser Ala Phe Val Asn Gln His Leu Cys
1               5                   10                  15

Gly Ser His Leu Val Glu Ala Leu Tyr Leu Val Cys Gly Glu Arg Gly
            20                  25                  30

Phe Phe Tyr Thr Pro Arg Thr
        35
```

<210> SEQ ID NO 18
<211> LENGTH: 23

-continued

```
<212> TYPE: PRT
<213> ORGANISM: Artificial Sequence
<220> FEATURE:
<223> OTHER INFORMATION: Modified insulin 15 - A-chain

<400> SEQUENCE: 18

Lys Pro Gly Ile Val Glu Gln Cys Cys Thr Ser Ile Cys Ser Leu Tyr
1               5                   10                  15

Gln Leu Glu Asn Tyr Cys Asn
            20


<210> SEQ ID NO 19
<211> LENGTH: 38
<212> TYPE: PRT
<213> ORGANISM: Artificial Sequence
<220> FEATURE:
<223> OTHER INFORMATION: Modified insulin 15 - B-chain

<400> SEQUENCE: 19

Lys Pro Gly Ser Glu His Glu Ser Ala Phe Val Asn Gln His Leu Cys
1               5                   10                  15

Gly Ser His Leu Val Glu Ala Leu Tyr Leu Val Cys Gly Glu Arg Gly
            20                  25                  30

Phe Phe Tyr Thr Pro Lys
        35


<210> SEQ ID NO 20
<211> LENGTH: 21
<212> TYPE: PRT
<213> ORGANISM: Artificial Sequence
<220> FEATURE:
<223> OTHER INFORMATION: Modified insulin 28 - A chain

<400> SEQUENCE: 20

Gly Ile Val Lys Pro Cys Cys Thr Ser Ile Cys Ser Leu Tyr Gln Leu
1               5                   10                  15

Glu Asn Tyr Cys Asn
            20
```

CONJUGATES FOR SELECTIVE RESPONSIVENESS TO VICINAL DIOLS

This application is a national stage filing under 35 U.S.C. § 371 of International Application No. PCT/US2021/025261, filed on Mar. 31, 2021, which claims benefit of U.S. Provisional Application No. 63/002,662, filed Mar. 31, 2020, all of which are incorporated herein by reference.

SEQUENCE LISTING

The present application is being filed along with a Sequence Listing in electronic format. The Sequence Listing is provided as a file titled "X23055A_US_000.xml," created Apr. 3, 2026, and is 24,576 bytes in size. The information in the electronic format of the Sequence Listing is incorporated herein by reference in its entirety.

BACKGROUND

Boronic acids are generally considered Lewis acids that have a tendency to bind to hydroxyls, because, as Lewis acids, boronic acids can form complexes with Lewis bases such as, for example, hydroxide anions. Thus, molecules containing boronates including boronic acids have a general tendency to bind hydroxyl groups. This binding tendency can be used for detection of hydroxyl-containing groups by boronated labeling reagents wherein the boronate groups bind to the hydroxyls and, depending on the solvent and buffer conditions, the boronates can form hydrolysable boronate-ester bonds to the hydroxyl groups of hydroxyl containing molecules. The strength of the boronate ester bond and its reversibility is generally influenced by a variety of factors including the type of boronates, buffer conditions, and the composition of the hydroxyl group-containing molecules to which they bind.

SUMMARY

One or more aspects of embodiments of the present disclosure relate to boronated sensors that can simultaneously have a desirable selectivity or suitable affinity towards a specific vicinal diol, while having reduced affinity towards other diols. In certain embodiments the boronated sensors can be used to modulate pharmacokinetic and pharmacodynamics of a drug substance in the body and in response to particular levels of specific vicinal diols.

One or more embodiments of the present disclosure include the following embodiments 1 to 15:

1. A compound represented by Formula I:

Z—R (Formula I)

wherein, in Formula I,

R is selected from Formulae FF1-FF24; and

Z is selected from one of:

a) $NH_2$ or OH, b) a covalent linkage, either directly or via an optional linker, to a drug substance, c) a covalent linkage, either directly or via the optional linker, to an N-terminal amine or an epsilon amino group of one or more amino acids in a polypeptide drug substance, and d) a group represented by J-$SCH_{2\text{-}ø}$, J-$S(CH_2)_{2\text{-}ø}$, J-NH—ø, J-NH-(the optional linker)—ø, J-$S(CH_2)_k$NH-ø, or J-triazole$(CH_2)_k$NH-ø;

wherein —ø is the covalent bond towards R;

index k is an integer in the range of 3 to 14; and

J is an amino acid or one or more amino acids in a polypeptide drug substance, wherein each of the one or more amino acids in the polypeptide drug substance is represented by Formula I':

(Formula I')

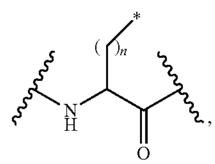

wherein, in Formula I',

 and 

indicate points of attachment to remaining portions of the polypeptide drug substance;

indicates the point of attachment to the remaining portion of Z; and index n is an integer in the range of 1 to 8, wherein for Formulae FF1-FF24:

(FF1)

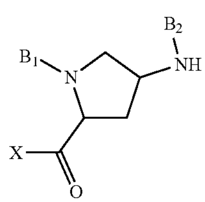

(FF2)

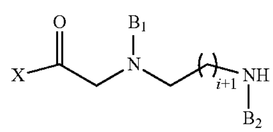

(FF3)

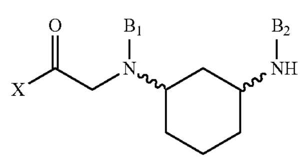

(FF4)

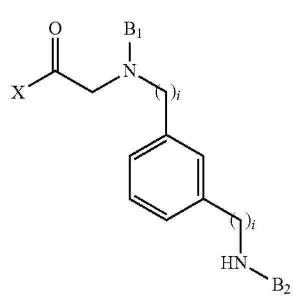

-continued
(FF5)
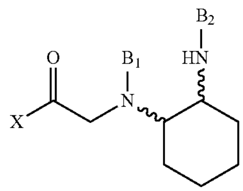
(FF6)
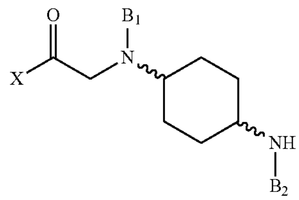
(FF7)
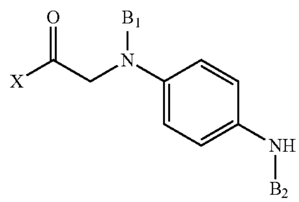
(FF8)
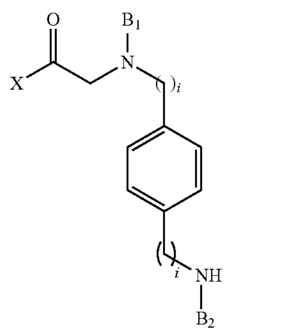
(FF9)
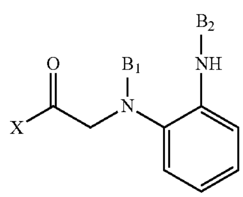
(FF10)
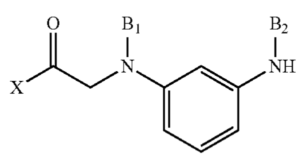
(FF11)
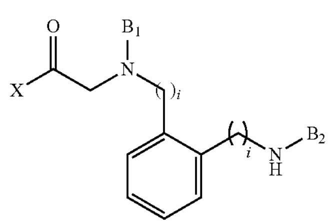
-continued
(FF12)
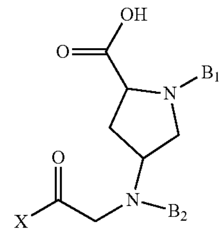
(FF13)
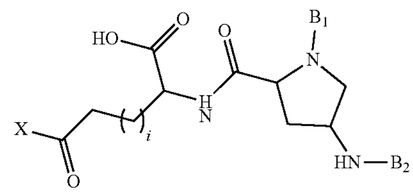
(FF14)
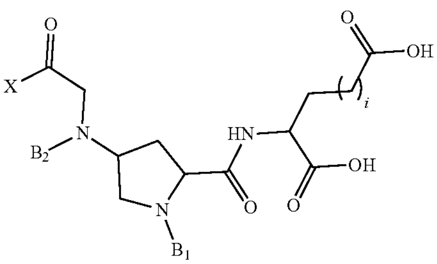
(FF15)
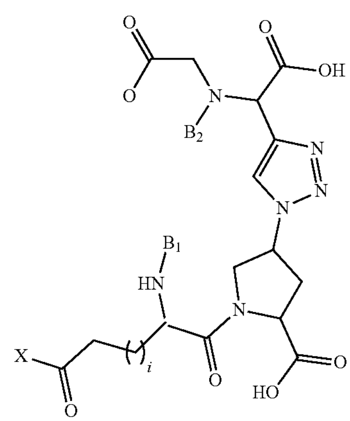
(FF16)
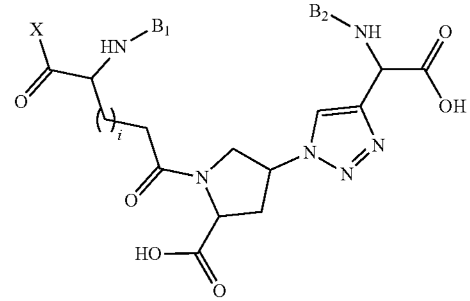

-continued
(FF17)
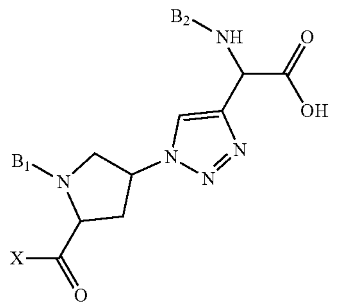
(FF18)
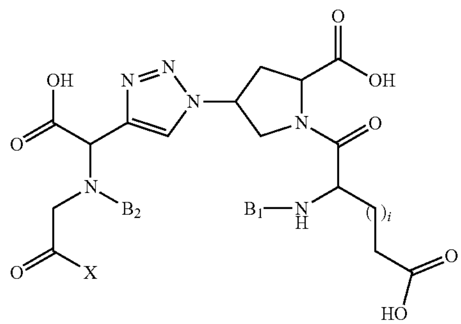
(FF19)
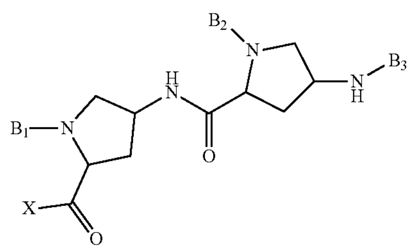
(FF20)
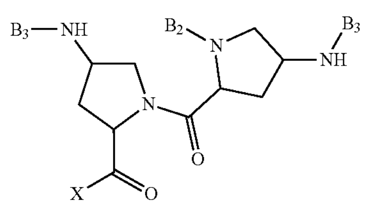
(FF21)
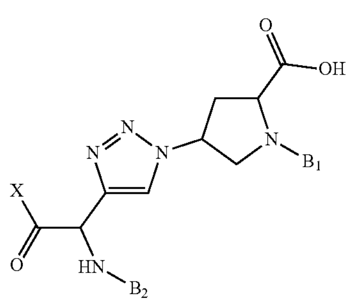
-continued
(FF22)
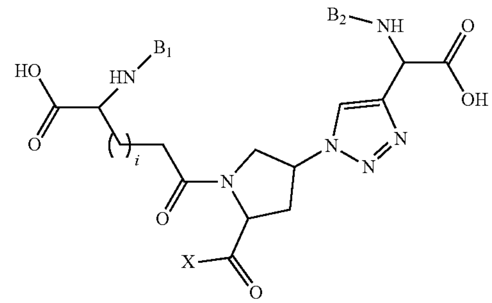
(FF23)
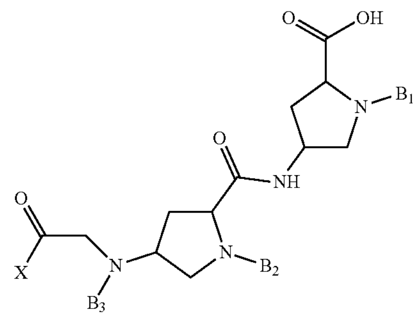
(FF24)
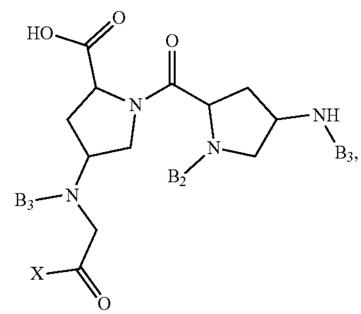
X represents a covalent linkage, either directly or via the optional linker, towards Z in Formula I;
index i is an integer in the range of 1 to 20;
$B_1$ and $B_2$ are identical or different, and are each independently represent a group selected from Formulae F1-F9; and
$B_3$ is a group represented by one selected from Formulae F1-F1 1,
(F1)
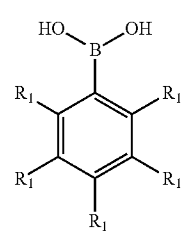

-continued (F2)

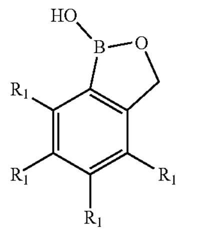

(F3)

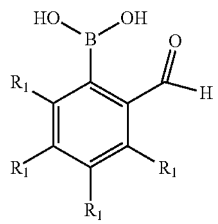

(F4)

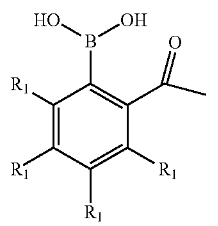

(F5)

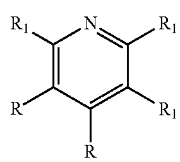

(F6)

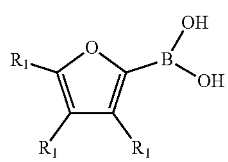

(F7)

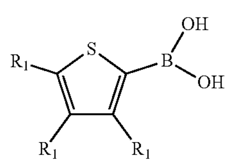

(F8)

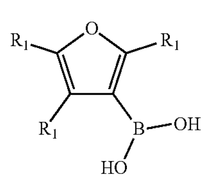

(F9)

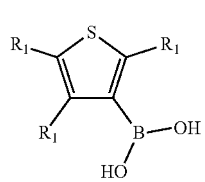

-continued (F10)

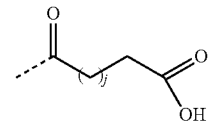

(F11)

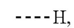

wherein, for each of Formulae F1-F9:

one $R_1$ represents (C═O)—, S(═O)(═O)—, $(CH_2)_m$(C═O)—, or $(CH_2)_m$—, wherein —represents a covalent bond to the remainder of R in Formula I;

none, one, or two $R_1$ each independently represent F, Cl, Br, OH, $CH_2$—$NH_2$, $NH_2$, (C═O)—$NH_2$, $SO_2CH_3$, $CF_3$, $NO_2$, $CH_3$, $OCH_3$, $O(CH_2)_mCH_3$, —$(SO_2)NHCH_3$, —$(SO_2)NH(CH_2)_mCH_3$, or $OCF_3$, index m is an integer in the range of 1 to 14;

one $R_1$ in F5 represents $B(OH)_2$, and all remaining $R_1$ represent H, and in Formula F10, index j is an integer in the range of 1 to 13.

2. A compound represented by Formula II:

Z—R (Formula II)

wherein, in Formula II, either:

(i) R is selected from Formulae FF25-FF31;

$B_1$ and $B_2$ in FF25-FF31 are identical or different, and are each independently selected from Formulae F12-F19; and Z is $NH_2$ and is not conjugated to any drug substance; or (ii) R is selected from Formulae FF25-FF31;

$B_1$ and $B_2$ are each independently selected from Formulae F20-F27; and

Z is selected from one of:

a) OH, b) a covalent linkage, either directly or via an optional linker, to a drug substance, c) a covalent linkage, either directly or via the optional linker, to an N-terminal amine or an epsilon amino group of one or more amino acids in a polypeptide drug substance, and d) a group represented by J-$SCH_{2-ø}$, J-$S(CH_2)_2$—ø, J-NH-ø, J-NH-(the optional linker)—ø, J-$S(CH_2)_k$NH-ø, or J-triazole$(CH_2)_k$NH-ø, wherein —ø is the covalent bond towards R, index k is an integer in the range of 3 to 14; and J is an amino acid or one or more amino acids in a polypeptide drug substance, wherein each of the one or more amino acids in the polypeptide drug substance is represented by Formula II';

or (iii) R is selected from Formulae FF32-FF33, $B_1$ and $B_2$ in FF32 are each independently selected from Formulae F28-F35;

$B_1$ and $B_2$ in FF33 are each independently selected from Formulae F36-F43; and Z is selected from one of:

a) a drug substance, b) a covalent linkage, either directly or via an optional linker, to the N-terminal amine or the epsilon amino group of an amino acid in a polypeptide drug substance, and c) a group represented by J-$SCH_2$—ø, J-$S(CH_2)_2$—ø, J-NH—ø, J-NH— (the optional linker)—ø, J-$S(CH_2)_kNH$-ø, or J-triazole$(CH_2)_kNH$-ø, wherein —ø is the covalent bond towards R, index k is an integer in the range of 3 to 14; and J is an amino acid or one or more amino acids in a polypeptide drug substance, wherein each of the one or more amino acids in the polypeptide drug substance is represented by Formula II';

wherein, for Formula II':

(Formula II')

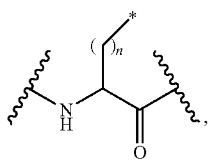

,

and

indicate points of attachment to remaining portions of the polypeptide drug substance;

indicates the point of attachment to the remaining portion of Z; and index n is an integer in the range of 1 to 8;

wherein for Formulae FF25-FF33:

(FF25)

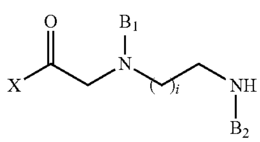

(FF26)

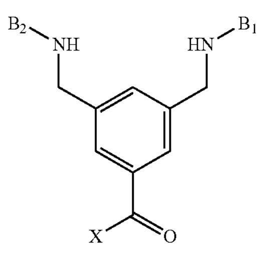

(FF27)

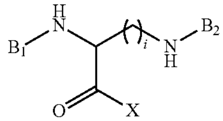

(FF28)

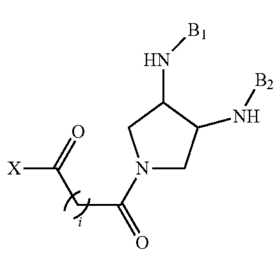

-continued (FF29)

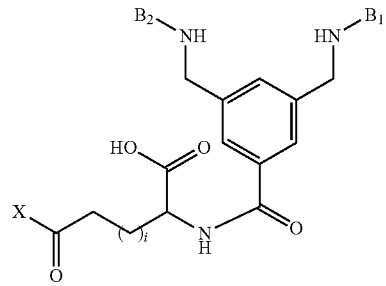

(FF30)

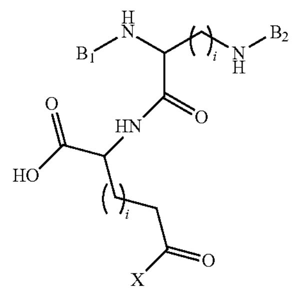

(FF31)

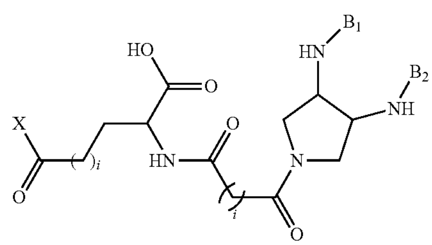

(FF32)

X—$B_1$—$B_2$ (FF32)

X—$B_1$—$B_2$ (FF33)

$B_1$—$B_2$, (FF32)

X—$B_1$—$B_2$ (FF33)

$B_1$—$B_2$,

X represents a covalent linkage, either directly or via the optional linker, towards Z in Formula II; and index i is an integer in the range of 1 to 20;

wherein, for each of Formulae F12-F19:

(F12)

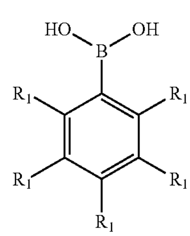

-continued (F13)

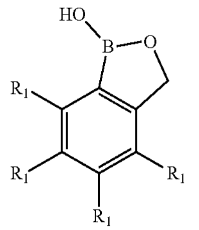

(F14)

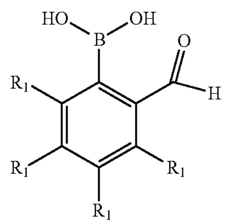

(F15)

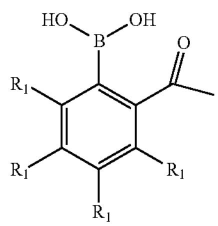

(F16)

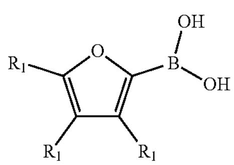

(F17)

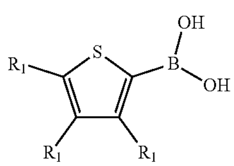

(F18)

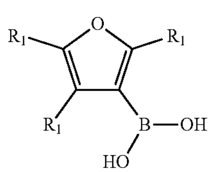

(F19)

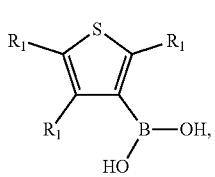

one $R_1$ from either $B_1$ or $B_2$ represents a covalent linkage, either directly or via an optional linker, to a drug substance;

one $R_1$ in each of $B_1$ and $B_2$ is (C═O)—, S(═O)(═O)—, $(CH_2)_m$(C═O)—, or $(CH_2)_m$—, wherein —represents a covalent bond to the remainder of R in Formula II;

none, one, or two $R_1$ in each of $B_1$ and $B_2$ independently represent COOH, F, Cl, Br, OH, $CH_2$—$NH_2$, $NH_2$, (C═O)—$NH_2$, $SO_2CH_3$, $CF_3$, $NO_2$, $CH_3$, $OCH_3$, $O(CH_2)_mCH_3$, —($SO_2$)NH $CH_3$, —($SO_2$) $NH(CH_2)_mCH_3$ or $OCF_3$;

index m is an integer in the range of 1 to 14; and all remaining $R_1$ represent H;

wherein, for each of Formulae F20-F25:

(F20)

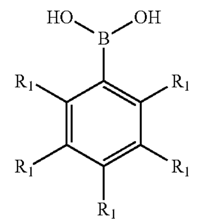

(F21)

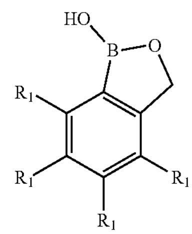

(F22)

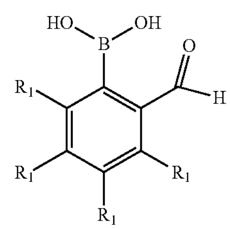

(F23)

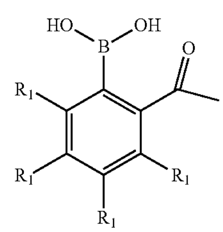

(F24)

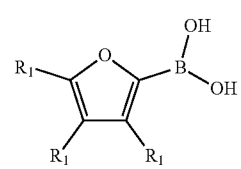

(F25)

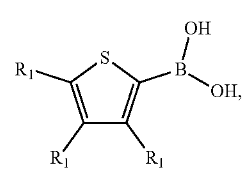

one $R_1$ is (C═O)—, S(═O)(═O)—, $(CH_2)_m$(C═O)—, or $(CH_2)_m$—, wherein —represents a covalent bond to the remainder of R in Formula II;

either:

(a) one or two $R_1$ on the same $B_1$ and/or $B_2$ represent COOH, wherein at least one COOH is not conjugated to a drug substance, and/or (b) one or two $R_1$ each independently represent $NO_2$, $CH_3$, $OCH_3$, $O(CH_2)_mCH_3$, $—(SO_2)NH\ CH_3$, $—(SO_2)NH(CH_2)_mCH_3$, wherein index m is an integer in the range of 1 to 14, and none, one, or two $R_1$ each independently represent $NO_2$, F, Cl, Br, OH, $CH_2—NH_2$, $NH_2$, $(C{=}O)—NH_2$, $SO_2CH_3$, $CH_3$, $CF_3$ or $OCF_3$, and all remaining $R_1$ represent H;

wherein, for each of Formulae F26-F27:

(F26)

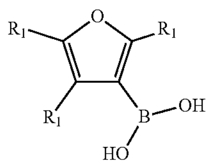

(F27)

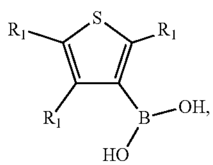

one $R_1$ is $(C{=}O)—$, $S({=}O)({=}O)—$, $(CH_2)_m(C{=}O)—$, or $(CH_2)_m—$, wherein —represents a covalent bond to the remainder of R in Formula II;

none, one, or two $R_1$ each independently represent COOH, F, Cl, Br, OH, $CH_2—NH_2$, $NH_2$, $(C{=}O)—NH_2$, $SO_2CH_3$, $CF_3$, $NO_2$, $CH_3$, $OCH_3$, $O(CH_2)_mCH_3$, $—(SO_2)NH\ CH_3$, $—(SO_2)NH(CH_2)_mCH_3$ or $OCF_3$;

index m is an integer in the range of 1 to 14; and all remaining $R_1$ represent H;

wherein, for each of Formulae F28-F35:

(F28)

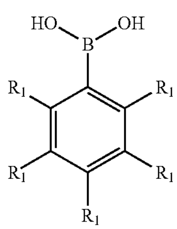

(F29)

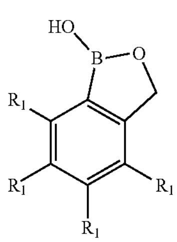

(F30)

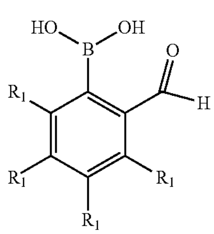

-continued (F31)

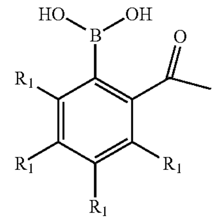

(F32)

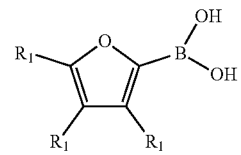

(F33)

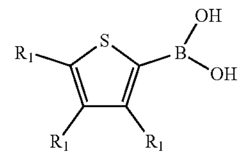

(F34)

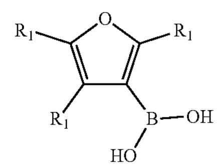

(F35)

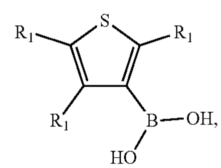

one $R_1$ in $B_1$ represents $(C{=}O)—$, $S({=}O)({=}O)—$, $(CH_2)_m(C{=}O)—$, or $(CH_2)_m—$, wherein —represents a covalent linkage, either directly or via an optional linker, to Z in Formula II;

one $R_1$ for each of $B_1$ and $B_2$ is a covalent linkage between $B_1$ and $B_2$, wherein the covalent linkage is selected from $—(S{=}O)—$, $—(S({=}O)({=}O)—$, $—(CF_2)—$, $—(C{=}O)—$, $—(CH_2)_m\ SCH_2CO(CH_2)_k—$, $—(CH_2)_m\ S(CH_2)_2CO(CH_2)_k—$, and $—(CH_2)_m\ (CO)NH\ (CH_2)_k—$;

either (i) two $R_1$ groups in $B_2$ are COOH and these two $R_1$ groups are not conjugated to a drug substance, or (ii) one or two $R_1$ in either $B_1$ and/or $B_2$ each independently represent $NO_2$, $CH{=}O$, $CH_3$, $OCH_3$, $O(CH_2)_mCH_3$, $—(SO_2)NH\ CH_3$, or $—(SO_2)NH(CH_2)_mCH_3$;

none, one, or two $R_1$ in either $B_1$ and/or $B_2$ each independently represent $CH{=}O$, F, Cl, Br, OH, $CH_2—NH_2$, $NH_2$, $(C{=}O)—NH_2$, $SO_2CH_3$, $CH_3$, $CF_3$, $CHF_2$, or $OCF_3$;

the remaining $R_1$ represent H;

index k is an integer in the range of 1 to 7; and index m is an integer in the range of 1 to 7;

wherein, for each of Formulae F36-F43:

(F36)

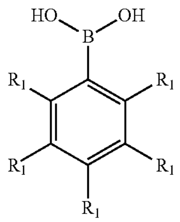

(F37)

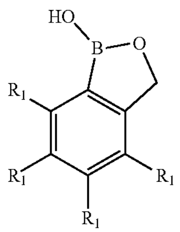

(F38)

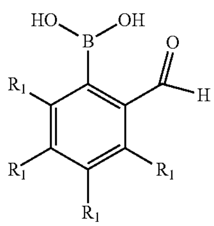

(F39)

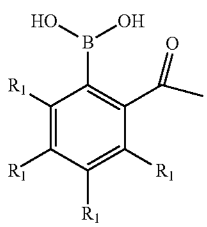

(F40)

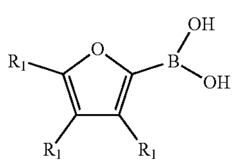

(F41)

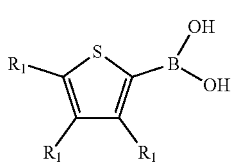

(F42)

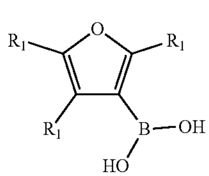

-continued (F43)

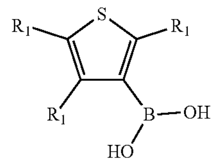

one $R_1$ for each of $B_1$ and $B_2$ is a covalent linkage to a sulfoximine group such that $B_1$ and $B_2$ are connected together by the sulfoximine group, and wherein the amino group of the sulfoximine is covalently linked, either directly through an acid containing linker or via an optional linker, to Z in Formula II;

either (i) two $R_1$ groups in $B_1$ and/or $B_2$ are COOH and these two $R_1$ groups are not conjugated to a drug substance, or (ii) one or two $R_1$ in either $B_1$ and/or $B_2$ each independently represent $NO_2$, CH═O, $CH_3$, $OCH_3$, $O(CH_2)_mCH_3$, —$(SO_2)$NH $CH_3$, or —$(SO_2)$NH $(CH_2)_mCH_3$;

none, one, or two $R_1$ in either $B_1$ and/or $B_2$ each independently represent CH═O, F, Cl, Br, OH, $CH_2$—$NH_2$, $NH_2$, (C═O)—$NH_2$, $SO_2CH_3$, $CH_3$, $CF_3$, $CHF_2$, or $OCF_3$;

the remaining $R_1$ represent H;

index k is an integer in the range of 1 to 7; and index m is an integer in the range of 1 to 7.

3. A compound including a drug substance, wherein the drug substance includes an insulin and the insulin contains one or more modified amino acids represented by Formula III:

Z—R (Formula III)

wherein, in Formula III,

R is selected from Formulae FF1-FF24; and

Z is selected from an optional linker, J-$SCH_2$—ø, J-S$(CH_2)_2$—ø, J-NH-ø, J-NH(CO) linker-ø, J-S$(CH_2)_k$NH-ø, and J-triazole$(CH_2)_k$NH-ø, wherein —ø is the covalent bond towards R, index k is an integer in the range of 3 to 14; and J is described by Formula III':

(Formula III')

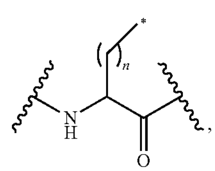

wherein, in Formula III':

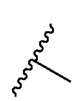 and 

indicates the point of attachment to the remaining portion of Z; and index n is an integer in the range of 1 to 8; wherein for Formulae FF1-FF24:
(FF1)
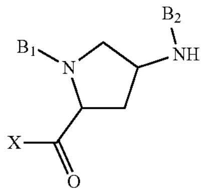
(FF2)
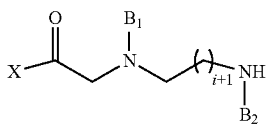
(FF3)
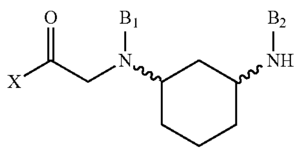
(FF4)
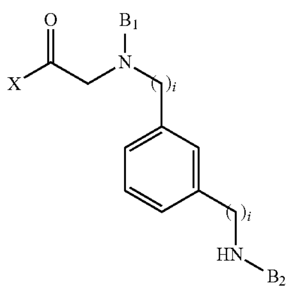
(FF5)
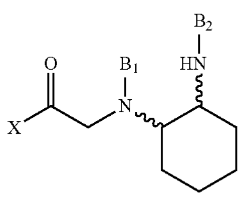
(FF6)
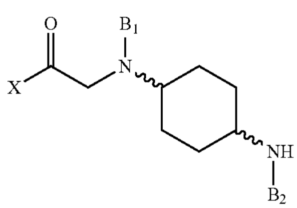
(FF7)
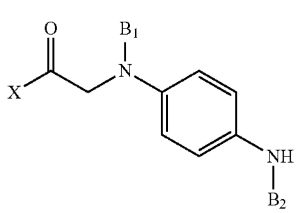
-continued
(FF8)
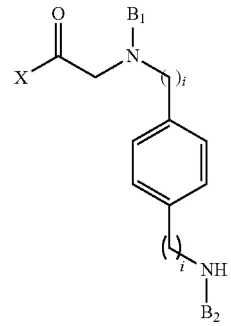
(FF9)
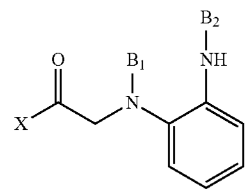
(FF10)
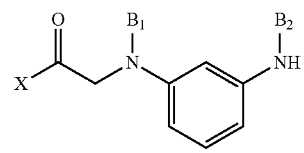
(FF11)
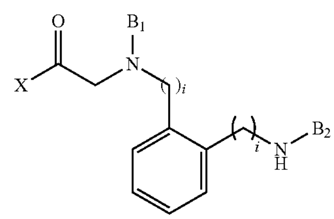
(FF12)
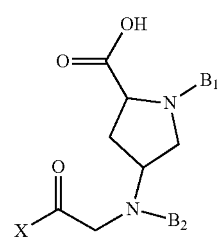
(FF13)
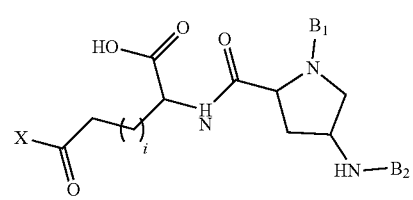
(FF14)
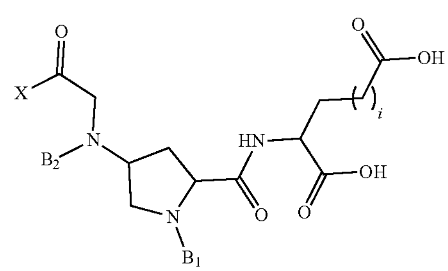

-continued
(FF15)
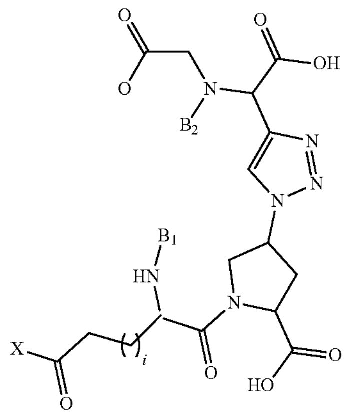
(FF16)
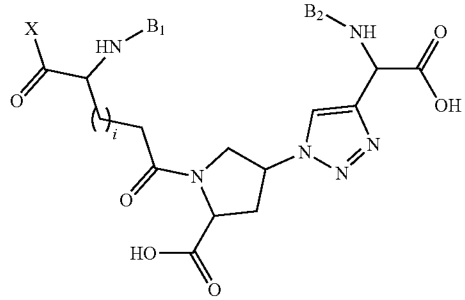
(FF17)
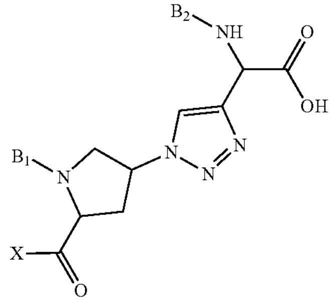
(FF18)
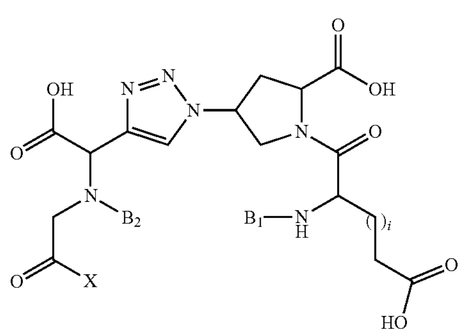
(FF19)
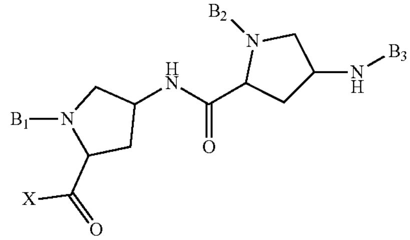
-continued
(FF20)
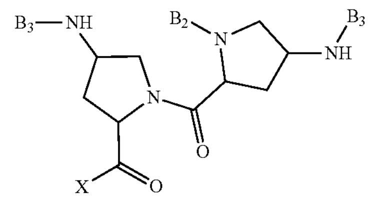
(FF21)
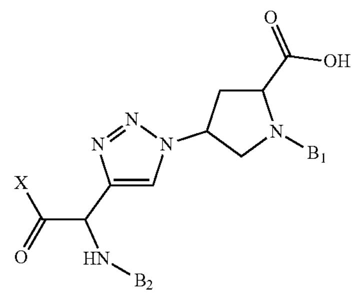
(FF22)
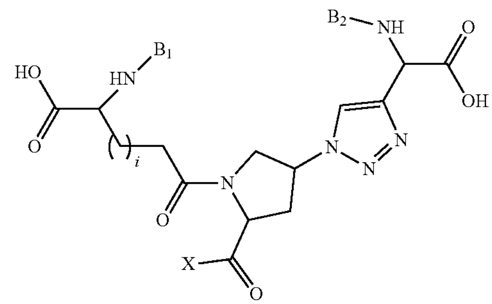
(FF23)
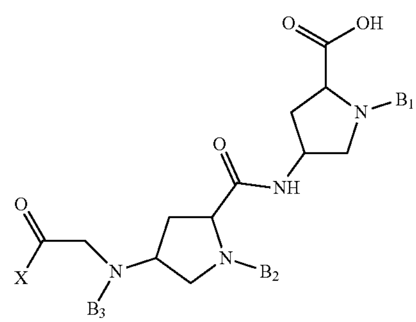
(FF24)
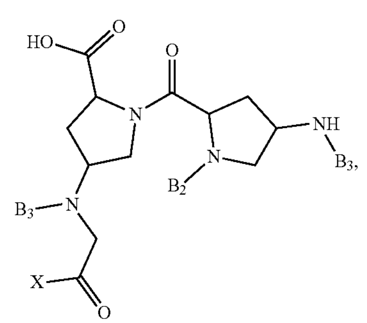
X represents a covalent linkage, either directly or via the optional linker, towards Z in Formula III;
index i is an integer in the range of 1 to 20;
$B_1$ and $B_2$ are identical or different, and each independently represent a group selected from Formulae F1-F9; and $B_3$ represents a group selected from Formulae F1-F11;

(F1)

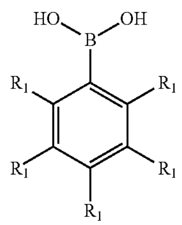

(F2)

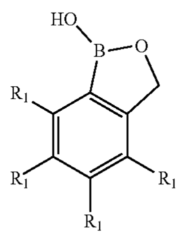

(F3)

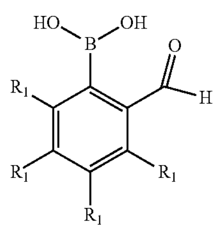

(F4)

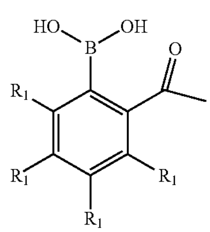

(F5)

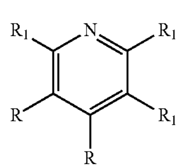

-continued (F6)

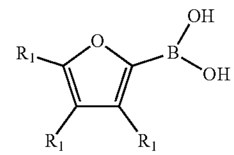

(F7)

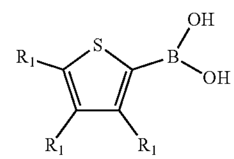

(F8)

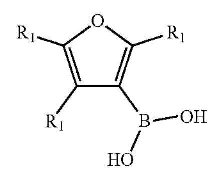

(F9)

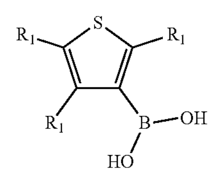

(F10)

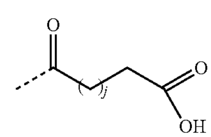

(F11)

----H, wherein, for each of Formulae F1-F9:

one $R_1$ represents (C═O)—, S(═O)(═O)—, $(CH_2)_m$(C═O)—, or $(CH_2)_m$—, wherein —represents a covalent bond to the remainder of R;

none, one, or two $R_1$ each independently represent F, Cl, Br, OH, $CH_2$—$NH_2$, $NH_2$, (C═O)—$NH_2$, $SO_2CH_3$, $CF_3$, $NO_2$, $CH_3$, $OCH_3$, $O(CH_2)_mCH_3$, —$(SO_2)$NH $CH_3$, —$(SO_2)NH(CH_2)_mCH_3$ or $OCF_3$;

index m is an integer in the range of 1 to 14;

one $R_1$ in F5 represents $B(OH)_2$; and all remaining $R_1$ represent H, and in Formula F10, index j is an integer in the range of 1 to 13.

4. The compound of any one of embodiments 1-3, wherein the optional linker is an L- or D-amino acid having at least one functional group directly conjugated to R, or the optional linker is selected from Formulae FL1-FL9:

(FL1)

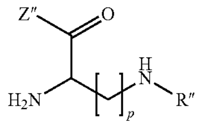

(FL2)

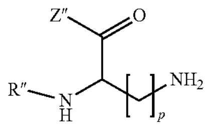

(FL3)

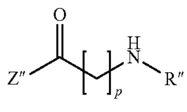

(FL4)

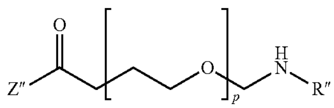

(FL5)

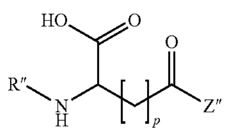

(FL6)

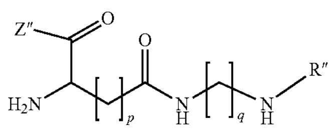

(FL7)

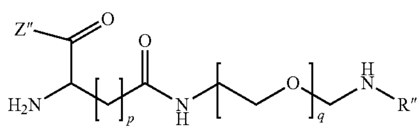

(FL8)

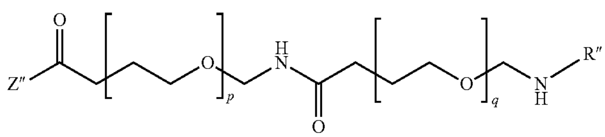

(FL9)

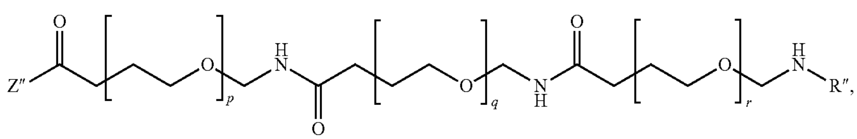

wherein, in Formulae FL1-FL9:

Z" represents a covalent bond towards Z;

R" represents a covalent bond towards R;

p is an integer in the range of 1 to 5;

q is an integer in the range of 1 to 5; and r is an integer in the range of 1 to 5.

5. The compound of any one of embodiments 1-3, wherein the compound is a drug substance that is additionally modified as described by embodiments 1-3 and/or wherein the one or more amines are each independently acetylated or alkylated.

6. The compound of any one of embodiments 1-3, wherein the drug substance is an insulin including human insulin or an analog thereof, and the insulin includes an A-chain and a B-chain.

7. The compound of any of embodiments 1-2, wherein the drug substance includes a polypeptide drug substance or a human peptide hormone.

8. The compound of embodiment 6, wherein the insulin includes one or two peptide sequences each independently added to the A-chain and/or the B-chain of insulin, and each peptide sequence independently includes 1 to 20 continuous residues.

9. The compound of embodiment 6, wherein the insulin includes 2 to 10 amino acids that are each independently modified as described by Formula I, II or III.

10. The compound of embodiment 6, wherein the insulin includes one or more modifications each independently described by Formula I, II or III, wherein each of the one or more modifications is positioned:

(i) on the side chain of an amino acid and/or to the N-terminus of a polypeptide of up to 20 residues appended to the N- and/or C- terminus of the A-chain and/or the B-chain of insulin; and/or (ii) within 4 residues of the B1, B21, B22, B29, A1, A22 or A3 residues in the insulin A- or B-chain; and/or (iii) on the side chain of an amino acid and/or to the N-terminus of a polypeptide appended or integrated into the A-chain and or the B-chain of insulin, wherein the polypeptide includes the sequence $(X_2)_nX_1(X_2)_m$ wherein: $X_1$ is a lysine residue in which the side chain of the lysine residue is modified as described by Formulae I, II, or III; each $X_2$ is independently selected from the group of amino acids K, P, E, G, N, M, A, R, L, W, S, F, V, C, H, D, I, Y, Q, T or $X_1$; index m is an integer in the range of 0 to 20; and index n is an integer in the range of 0 to 18.

11. A conjugate including the compound according to any one of embodiments 1-2, wherein the compound according to any one of embodiments 1-2 is conjugated, either directly or via an covalent linker, to a drug substance, provided that the conjugation is not through Z when Z is $NH_2$ in Formula II.

12. The compound of any one of embodiments 1-3, wherein the compound of any one of embodiments 1-3 is used as an intermediate compound for the manufacture of any compounds in embodiments 1-11.

13. The compound of any one of embodiments 5-6, wherein the compound contains one or more modifications as described by Formulae IV, V or VI, wherein for Formula IV:

(Formula IV)

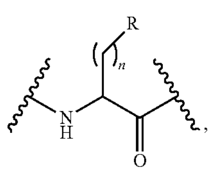

 and 

indicate points of attachment to remaining portions of the drug substance; index n is an integer in the range of 1 to 8; and R is selected from the group consisting of Formulae F111, F222, F333, F444, and F555:

(F111)

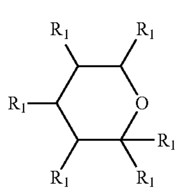

-continued (F222)

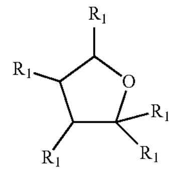

(F333)

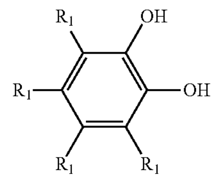

(F444)

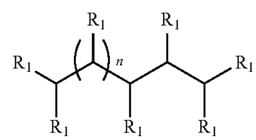

(F555)

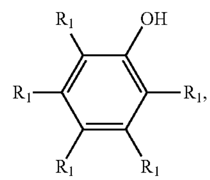

wherein in Formulae F111, F222, F333, F444, and F555:

index n is an integer in the range of 1 to 8;

each carbon atom attached to an $R^1$ independently has (R) or (S) stereochemistry;

each $R_1$ is independently selected from —H, —$OR^3$, —$N(R^3)_2$, —$SR^3$, —OH, —$OCH_3$, —$OR^5$, NHC(O)$CH_3$, —$CH_2R^3$, —C(O)NHOH, —NHC(O)$CH_3$, —$CH_2OH$, —$CH_2OR^5$, —$NH_2$, —$CH_2R^4$, —$OR^8$, —$R^6$, —$R^8$, and —$R^7$, each $R^3$ is independently selected from —H, acetyl, phosphate, —$R^2$, —$SO_2R^2$, —S(O)$R^2$, —P(O)$(OR^2)_2$, —C(O)$R^2$, —$CO_2R^2$, and —C(O)$N(R^2)_2$, each $R^2$ is independently selected from —H, an optionally substituted $C_{1-6}$ aliphatic ring, an optionally substituted phenyl ring, an optionally substituted 5-6 membered monocyclic heteroaryl ring having 1-4 heteroatoms selected from nitrogen, oxygen, and sulfur, a 4-7 membered heterocyclic ring having 1-2 heteroatoms selected from nitrogen, oxygen, and sulfur, and an alkyl or amide covalent linkage to R in Formula IV, each $R^4$ is independently selected from —H, —OH, —$OR^3$, —$N(R^3)_2$, —$OR^5$ and —$SR^3$;

each $R^5$ is independently selected from a mono-saccharide, a di-saccharide, a tri-saccharide, a pentose, and a hexose, each $R^6$ is independently selected from —$NCOCH_2$—, —$(OCH_2CH_2)_n$—, a —O—$C_{1-9}$ alkylene group, and a substituted $C_{1-9}$ alkylene group in which one or more methylene groups are optionally replaced by —O—, —$(CH_2)$—, —$OCH_2$—, — $N(R^2)C(O)$—, —$N(R^2)C(O)N(R^2)$—, —$SO_2$—, —$SO_2N(R^2)$—, —$N(R^2)SO_2$—, —S—, —$N(R^2)$—, —C(O)—, —OC(O)—, —C(O)O—, —C(O)$N(R^2)$—, or —$N(R^2)SO_2N(R^2)$—, wherein index n is an integer in a range 1 to 8, each $R^7$ is independently selected from —$N(R^2)_2$, —F, —Cl, —Br, —I, —SH, —$OR^2$, —$SR^2$, —$NH_2$, —$N_3$, —C≡$CR^2$, —$CH_2C$≡CH, —C≡CH, —$CO_2R^2$, —C(O)$R^2$, —$OSO_2R^2$—$N(R^2)_2$, —$OR^2$, —$SR^2$, —$CH_3$, —$CH_2NH_2$, and a direct linkage to R in Formula IV, $R^8$ is (i) the sidechain of one of L-serine, D-serine, L-threonine, D-threonine, L-allothreonine, or D-allo-threonine and corresponds to R in Formula IV, wherein index n=1 in Formula IV, (ii) an amide linkage to the C-terminus of lysine, cysteine, 2,3-diaminopropionic acid, or (iii) —$CH_2C(CH_2OH)_2CH_2NH_2$, and structures F111, F222, F333, F444, and/or F555 optionally include one or more acetyl, acetylene, acetonide, and/or pinacol protecting groups;

wherein for Formula V:

(Formula V)

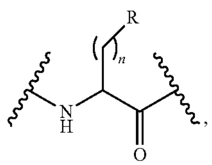

and

indicate points of attachment to remaining portions of the drug substance; index n is an integer in the range of 1 to 8;

R represents X-Y, wherein X is a covalent linkage selected from the group consisting of a triazole, an amide bond, an imine bond or a thioether bond;

Y is selected from the group consisting of structures represented by Formulae F200-F203:

($F_{200}$)

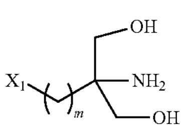

($F_{201}$)

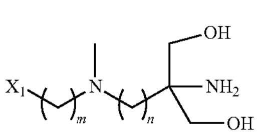

($F_{202}$)

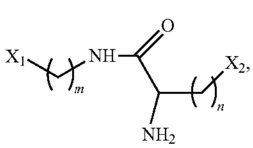

$X_1$ represents the covalent bond towards X;

$X_2$ represents SH, OH or $NH_2$;

index m is an integer in the range of 1 to 8; and index n is an integer in the range of 1 to 8;

wherein for Formula VI:

(Formula VI)

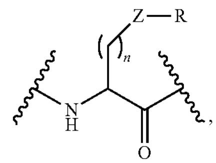

and

indicate points of attachment to remaining portions of the drug substance; index n is an integer in the range of 1 to 8;

Z is selected from the group consisting of: an amino acid, —$(CH_2)_p$—, —$CH_2(OCH_2CH_2)_p$—, —$SCH_2$—, —$S(CH_2)_2$—, —NH—, —NH(CO)—, —(CO)NH—, —$S(CH_2)_k$NH—, -triazole-$(CH_2)_k$—NH—, a triazole, an amide bond, an imine bond, and a thioether bond;

index k is an integer in the range of 3 to 5;

index p is an integer in the range of 1 to 8; and

R is selected from the group consisting of structures represented by Formulae F203-F205:

(F203)

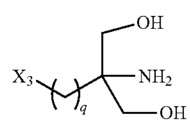

(F204)

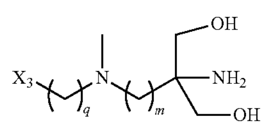

(F205)

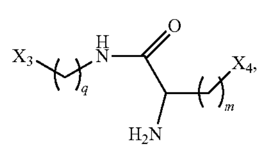

wherein $X_3$ represents the covalent bond towards Z;

$X_4$ represents SH, OH or $NH_2$ index q is an integer in the range of 1 to 8; and index m is an integer in the range of 1 to 8.

14. A method of manufacturing the compound of any one of embodiments 1-13, wherein optionally, $B_1$ and $B_2$ are first conjugated to one of structures represented by FF1-FF33 and the resultant conjugate is then covalently linked to a drug substance, or optionally, structures represented by FF1-FF33 are first conjugated to a drug substance and thereafter $B_1$ and $B_2$ are covalently linked to the corresponding structures in FF1-FF33.

15. A method of administering the compound of any one of embodiments 1-13 to a human subject as a therapeutic or prophylactic agent.

BRIEF DESCRIPTION OF THE DRAWINGS

The features and advantages of embodiments of the present disclosure will be better understood by reference to the following detailed description when considered in conjunction with the accompanying drawings.

DETAILED DESCRIPTION

Figure 1:
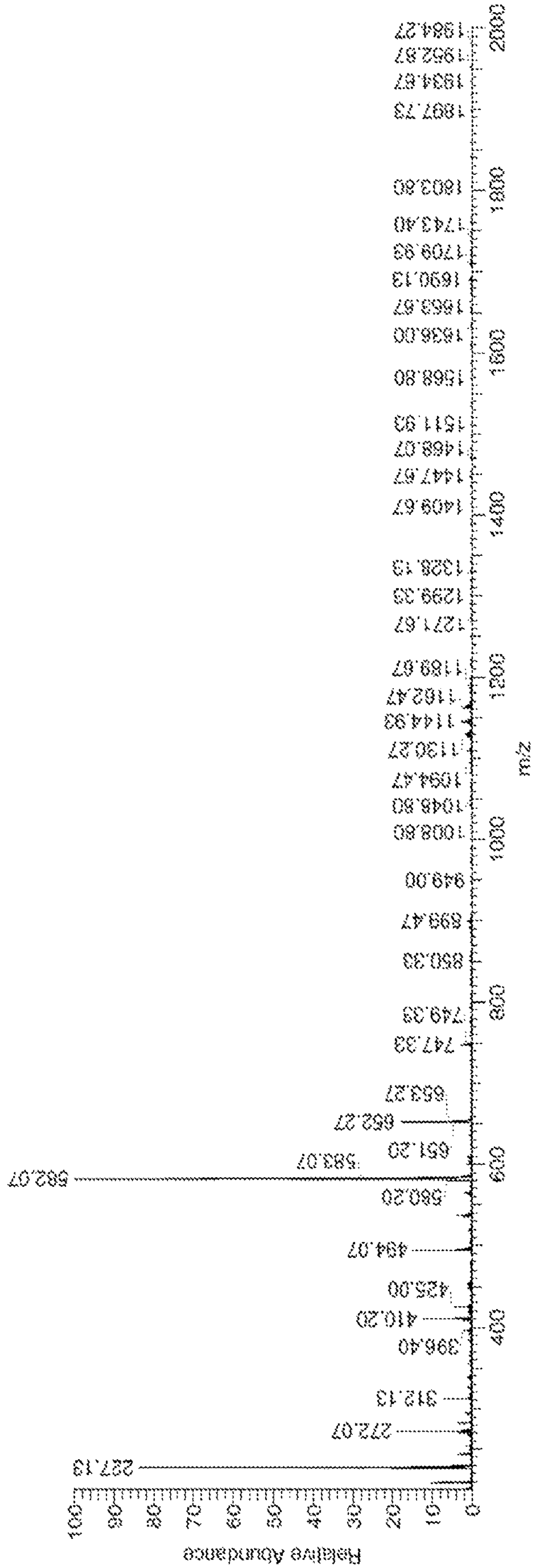
FIGS. 1 to 24 are mass spectrum plots confirming the synthesis of Examples 1-24, respectively.

The ability of sensors (e.g., molecular sensors) to selectively bind and respond to a specific vicinal diol in the body is facilitated by binding to the vicinal diol of interest while reducing binding to other diols or other vicinal diols. While most boronates bind to diol containing molecules, achieving selectivity using boronates (e.g., boronate-based sensors) is not always readily done; this is because of their general tendency to bind most diols, including cis diols, to varying degrees. Improved binding affinity of such sensors towards a specific vicinal diol of interest is often achieved at the expense of selectivity or affinity; development of selectivity towards a specific vicinal diol within a range of physiological levels is facilitated by the identification of specific molecular scaffolds that can distinguish between the hydroxyl orientations of different vicinal diols. The development of scaffolds that position boronates in a specific or particular geometry so as to increase selectivity towards a specific vicinal diol while simultaneously maintaining affinity to the diol of interest is facilitated by understanding or identifying which of the different pendant groups on the boronates along with which specific scaffold geometries impact binding to hydroxyls.

In certain embodiments of the present disclosure, specific scaffold molecules have been identified to orient boronates (e.g., in three dimensional space) so that the hydroxyl groups of the boronates are spatially oriented to engage hexoses containing vicinal diols, and wherein matching the orientation of the hydroxyl on boron groups and the hydroxyls in the vicinal diol molecule provides enhancement of selectivity. To further provide selectivity, the boronates are modified with specific functional groups on the benzene ring of phenylboronates that, together with an appropriate or suitable scaffold, may provide higher selectivity of binding towards a vicinal diol of interest and away from other diols in the body. In certain embodiments, the vicinal diol sensors are conjugated to a drug substance wherein the vicinal diol sensors provide intramolecular and intermolecular interactions with the drug substance and/or with proteins in the body, such as circulating proteins in the blood and/or plasma including albumin and/or globulins. In certain embodiments, the selective binding of the sensors to specific vicinal diols changes the extent of those intramolecular and intermolecular bindings and thereby modulates the pharmacokinetics and overall activity of the drug substance in the body; this effect can be controlled by the level of the vicinal diols present. In certain embodiments the drug substance is a peptide hormone, and in certain embodiments, the peptide hormone is a human peptide hormone such as insulin, glucagon, or another incretin hormone. In certain embodiments the sensors are selective towards the vicinal diols in glucose, and this selectivity is enhanced while maintaining affinity to glucose and simultaneously reducing affinity to other sugars in the blood. In certain embodiments, the scaffolds as well as (e.g., in combination with) the pendant groups on boronates enable controlling the overall activity and/or pharmacokinetics of the conjugated drug substances based on levels of glucose and/or other vicinal diols in the blood.

One or more embodiments of the present disclosure provides sensors containing specific scaffold molecules with conjugated boronates, wherein the scaffolds have been used to orient boronates in three dimensional geometries so that the hydroxyl groups of the boronates are oriented near each other and within a distance that helps engage specific hydroxyl orientations of select hexoses such as glucose. The sensor molecules presented in this disclosure enhance selectivity through three mechanisms: (1) the scaffold facilitates matching the orientation of the hydroxyl on boron groups in the phenylboronates and the hydroxyls in the vicinal diol molecule which enhances selectivity; (2) further selectivity gain is obtained by identifying specific functional groups attached to, or near, the benzene ring of the phenylboronic acids which impact the electronic structure of the phenylboronate and thereby favoring reversible binding to the vicinal diols at physiological pH; and (3) functional groups attached to the phenylboronates or the sensor scaffold help to provide steric hindrance to reduce binding to unwanted hexoses while maintaining binding to the sugar of interest such as glucose. These effects as combined together in the present disclosure provide desired or suitable selectivity of binding towards a vicinal diol-containing molecule of interest and away from other diols in the body. In certain embodiments, the vicinal diol sensors are conjugated to a drug substance wherein the vicinal diol sensors provide intramolecular and/or intermolecular interactions with proteins in the body. Such proteins may include circulating proteins in the blood and/or human plasma such as albumin, glycosylated proteins and/or immunoglobulins. In certain embodiments the selective binding of the sensors to specific vicinal diols in a molecule of interest changes the extent of intramolecular and intermolecular bindings and thereby modulates the pharmacokinetics and overall activity of the drug substance in the body. In certain embodiments the drug substance is a peptide hormone and in certain embodiments thereof the peptide hormone is an incretin hormone such as insulin and the vicinal diol containing molecule is glucose, but the present disclosure is not limited thereto.

Definitions

The following description shows and describes selected example embodiments of the subject matter of the present disclosure. As those skilled in the art would recognize, the subject matter of the present disclosure may be embodied in many different forms, and should not be construed as being limited to the embodiments set forth herein.

In the detailed description that follows, numerous specific details are set forth in order to provide a more thorough understanding of some of the embodiments of the present disclosure. However, those skilled in the art will understand that embodiments of the present disclosure may be practiced in various suitable forms, and is not necessarily limited to these specific details. All disclosed features may be replaced by comparable features serving the same, equivalent, or similar purpose, unless expressly stated otherwise. Thus, unless expressly stated otherwise, each feature disclosed is only one example of a series of equivalent or similar features. Similarly, unless indicated to the contrary, features of one embodiment may be incorporated into other embodiments without departing from the spirit and scope of the present disclosure.

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

For example, unless otherwise defined, all chemical terms and functional group names used throughout the specification are identified in accordance with the Periodic Table of the Elements, CAS version, Handbook of Chemistry and Physics, $75^{th}$ Ed., inside cover. Specific functional groups are given their meaning as described by general principles of organic chemistry, as well as specific functional moieties and reactivity, as described in Organic Chemistry, Thomas Sorrell, University Science Books, Sausalito, 1999; Larock, Comprehensive Organic Transformations, VCH Publishers, Inc., New York, 1989; Carruthers, Some Modem Methods of Organic Synthesis, $3^{rd}$ Edition, Cambridge University Press, Cambridge, 1987; and Smith and March, March's Advanced Organic Chemistry, $5^{th}$ Edition, John Wiley & Sons, Inc., New York, 2001.

The terminology used herein is for the purpose of describing particular embodiments only and is not intended to be limiting of the present disclosure. As used herein, singular forms such as "a," "an," and "the" are intended to include the plural forms as well and vice versa, unless the context clearly indicates otherwise. It will be further understood that the terms "comprises," "comprising," "includes," "including," and variations thereof, when used in this specification, specify the presence of the stated additives, ingredients, features, integers, acts, operations, elements, groups, components, and/or moieties, but do not preclude the presence or addition of one or more other additives, ingredients, features, integers, acts, operations, elements, groups, components, or moieties. As used herein, the term "and/or" includes any and all combinations of one or more of the associated listed items. Expressions such as "at least one of," when preceding a list of elements, modify the entire list of elements and do not modify the individual elements of the list.

It will be understood that, although the terms "first," "second," "third," etc., may be used herein to describe various elements, components, regions, layers and/or sections, these elements, components, regions, layers and/or sections should not be limited by these terms. These ordinal terms are used to distinguish one element, component, region, layer or section from another element, component, region, layer or section. Thus, a first element, component, region, layer or section described below could be termed a second element, component, region, layer or section, without departing from the spirit and scope of the present disclosure.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

The term "CAS #" as used herein and interchangeably used with the terms "CASRN" or "CAS Number" refers to a unique numerical identifier assigned by Chemical Abstracts Service (CAS) to every chemical substance described in the open scientific literature.

In certain embodiments the terms "covalently connected," "covalently conjugated," or "through a covalent conjugation" may be interchangeably used to indicate that two or more atoms, groups, or chemical moieties are bonded or connected via a chemical linkage. In certain embodiments, the chemical linkage (which in certain embodiments may be referred to as a covalent linkage) may be (e.g., consist of) one or more shared electron pairs (e.g., in a single bond, a double bond, or a triple bond) that is directly between two atoms, groups, or chemical moieties, as indicated by the term "directly bonded". In certain embodiments, the chemical (covalent) linkage may further include one or more atoms or functional groups, and may be referred to using the corresponding name of that functional group in the art. For example, a 30 covalent linkage including a —S—S— group may be referred to as a disulfide linkage; a covalent linkage including a —(C═O)— group may be referred to as a carbonyl linkage; a covalent linkage including a $-(CF_2)-$ group may be referred to as a difluoromethylene linkage, etc. The type of linkage or functional group within the covalent bond is not limited unless expressly stated, for example when it is described as including or being selected from certain groups. The types or kinds of suitable covalent linkages will be understood from the description and/or context.

In certain embodiments, side chains of amino acids may be covalently connected (e.g., linked or cross-linked) through any number of chemical bonds (e.g., bonding moieties) as generally described in Bioconjugate Techniques (Third edition), edited by Greg T. Hermanson, Academic Press, Boston, 2013. For example, the side chains may be covalently connected through an amide, ester, ether, thioether, isourea, imine, triazole, or any suitable covalent conjugation chemistry available in the art for covalently connecting one peptide, protein, or synthetic polymer to a second peptide, protein, or synthetic polymer. The term polymer includes polypeptide. The term "covalent conjugation chemistry" may refer to one or more functional groups included in the bonding moiety, and/or the chemical reactions used to form the bonding moiety.

The term "vicinal diol" refers to a group of molecules in which two hydroxyl groups occupy vicinal positions, that is, they are attached to adjacent atoms. Such molecules may include, but are not limited to, sugars such as hexoses, glucose, mannose and fructose.

In certain embodiments, a peptide, protein, or synthetic polymer may be linked to a modified insulin using click chemistry reactions as is understood and defined in the art. Non-limiting examples of suitable click chemistry reactions may include cycloaddition reactions such as 3+2 cycloadditions, strain-promoted alkyne-nitrone cycloaddition, reactions of strained alkenes, alkene and tetrazine inverse-demand Diels-Alder, Copper(I)-Catalyzed Azide-Alkyne Cycloaddition (CuAAC), strain-promoted azide-alkyne cycloaddition, Staudinger ligation, nucleophilic ring-opening reaction, and additions to carbon-carbon multiple bonds. Some of these reactions are described for example in H. C. Kolb, M. G. Finn and K. B. Sharpless (2001); Click Chemistry: Diverse Chemical Function from a Few Good Reactions, Angewandte Chemie International Edition 40 (11): 2004-2021; Kolb and Sharpless, *Drug Discovery Today* 8:1128-1137, 2003; Huisgen, R. Angew. Chem. Int. Ed. Engl. 1963, 2, 565; and Agard, N. J.; Baskin, J. M.; Prescher, J. A.; Lo, A.; Bertozzi, C. R. ACS Chem. Biol. 2006, 1, 644. Those having ordinary skill in the art are capable of selecting suitable buffers, pH and reaction conditions for such click reactions. For example, the use of chelators such as EDTA is to be avoided for CuAAC reaction. In certain embodiments covalent conjugation may be the result of a "bioorthogonal reaction" as is known in the art. Such reactions are, for example, described by Sletten, Ellen M.; Bertozzi, Carolyn R. (2009). Bioorthogonal Chemistry: Fishing for Selectivity in a Sea of Functionality, Angewandte Chemie International Edition 48 (38): 6974-98.; and Prescher, Jennifer A; Bertozzi, Carolyn R (2005). Chemistry in living systems, Nature Chemical Biology 1 (1): 13-21. In certain embodiments, units may be linked using native chemical ligation as described for example by Dawson, P. E.; Muir, T. W.; Clark-Lewis, I.; Kent, S. B. (1994) Synthesis of proteins by native chemical ligation, Science 266 (5186): 776-778.

The term "substituted" indicates that at least one hydrogen atom of the named group is replaced with a non-hydrogen atom, functional group, peptide, linker, etc. The replacement structures (which may be referred to herein as "substituents") are not particularly limited unless expressly stated, and may include any suitable functional group, amino acid, polypeptide, etc. available in the art. In certain embodiments, a substituent may itself be further substituted.

The term "insulin" encompasses both wild-type and altered forms of insulin that are capable of binding to and activating the insulin receptor, or capable of causing a measurable reduction in blood glucose when administered in vivo. In certain embodiments, insulin includes insulin from any species whether in purified, synthetic, or recombinant form, and for example may include human insulin, porcine insulin, bovine insulin, sheep insulin and rabbit insulin.

In certain embodiments the insulin may be or include a proinsulin as is known in the art (e.g., a precursor to insulin) which can be further processed into mature insulin.

When the insulin is an altered form of insulin, the insulin may be altered using any suitable technique in the art. For example, the insulin may be chemically altered (such as by addition of a chemical moiety such as a PEG group or a fatty acyl chain) and/or may be mutated (e.g., may include additions, deletions or substitutions of amino acids). When the insulin includes one or more mutations, the mutations may be indicated using standard terminology in the art, but it is understood that an insulin analogue may contain one or more mutations that are known in the art, some of these mutations may change (enhance) various aspects of the molecule including biophysical characteristics or stability and resistance to degradation. In certain embodiments, for example, the term "desB30" refers to an insulin lacking the B30 amino acid residue.

In certain embodiments, the term "percentage homology" refers to the percentage of sequence identity between two sequences after optimal alignment; identical sequences have a percentage homology of 100%. Optimal alignment may be performed using any suitable homology alignment algorithm described by the search for similarity method of Pearson and Lipman, *Proc. Natl. Acad. Sci. USA* 85:2444 (1988), or by general methods described for search for similarities by Neddleman and Wunsch, J. Mol. Biol. 48:443 (1970), including implementation of these algorithms or visual comparison. An "insulin A-chain" is the chain of insulin that has the highest percentage homology to the A-chain of wild-type human insulin. An "insulin B-chain" is the chain of insulin that has the highest percentage homology to the B-chain of wild-type human insulin. In certain embodiments, the A-chain and B-chain of the insulin may be connected together through one or more peptides, for example, the c-peptide as is known in the art, or a shortened version thereof.

In certain embodiments the term "albumin" refers to human serum albumin or a protein with at least 60% percentage homology to human serum albumin protein. It is to be understood that in certain embodiments the albumin may be further chemically modified for the purposes of conjugation. Such modifications may include one or more covalently connected linkers.

In certain embodiments "therapeutic composition" as used herein refers to a substance or mixture of substances that are intended to have a therapeutic effect, such as pharmaceutical compositions, genetic materials, biologics, and other substances. Pharmaceutical compositions may be configured to function in inside the body with therapeutic qualities, concentration to reduce the frequency of replenishment, and the like. In certain embodiments "therapeutically effective amount" and "prophylactically effective amount" refer to an amount that provides a therapeutic benefit in the treatment, prevention, or management of a disease or an overt symptom of the disease. The therapeutically effective amount may treat a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. The set or specific amount that is therapeutically effective can be readily determined by an ordinary medical practitioner, and may vary depending on factors known in the art, such as, e.g. the type of disease, the patient's history and age, the stage of disease, and the administration of other therapeutic agents.

Vicinal Diol Sensors

The sensor scaffolds and specific boronate functional groups presented in this disclosure provide a framework for molecules (sensors) that can differentiate between a vicinal diol-containing molecule and other diol-containing molecules, for example, by preferentially binding to one vicinal diol-containing molecule over the other diol-containing molecules. For example, sensor scaffolds with appropriate or suitable boronates can be synthesized using methods presented herein to provide sensor molecules that can bind to a specific hexose while also rejecting or ignoring other sugars having similar structures that lack a vicinal diol. For example, sensors can be developed that bind to glucose but actively reject or ignore (e.g., do not bind to) lactate and/or fructose. Without being bound by the correctness of any theory of explanation, it is believed the sensor molecules presented in this disclosure may have enhanced selectivity through any combination of three mechanisms: (1) the scaffold may position the boron hydroxyl groups in the phenylboronates and the hydroxyls in the vicinal diol molecule into complementary orientations; (2) specific functional groups attached to or near the benzene ring of the phenylboronic acids may alter the electronic structure of the phenylboronate to favor reversible binding to the vicinal diols at physiological pH; and (3) functional groups attached to the phenyl boronates and/or the sensor scaffold may increase steric hindrance and reduce binding to unwanted (e.g., non-targeted) hexoses (diols) while maintaining binding to the molecule of interest (which may also be referred to as a sugar of interest) such as glucose. These effects, individually, or as combined together, in embodiments of the present disclosure, provide selective binding towards a vicinal diol of interest and away from other diols in the body. In certain embodiments, the vicinal diol sensors are conjugated to a drug substance, and the vicinal diol sensors may provide and/or enhance intramolecular and/or intermolecular interactions between the drug substance and one or more proteins in the body.

The impacts of the above mechanisms on sensor selectivity can be illustrated in part, from the data provided in Table 1. Selectivity may be achieved or enhanced firstly through appropriate or suitable use of scaffold molecules (e.g., fragments). For example, the compounds of Examples 9, 10, 11, 12, and 13 all utilize similar phenylboronates, but exhibit vastly different affinities for glucose. As shown in Table 1, Example 9 provides the lowest Kd value for glucose (e.g., highest affinity) within the group, while Example 11 provides the highest Kd (e.g., lowest affinity) for fructose. This non-intuitive selectivity response is mainly driven by the scaffold molecule, because all of these examples utilize similar nitro-substituted phenylboronates. A comparison of Examples 9 and 10 shows that the additional $CH_2$—$CH_2$ group in the scaffold (e.g., as in Example 10) can substantially disrupt glucose binding while having little impact on fructose binding. Conversely, the addition of the $CH_2$—$CH_2$ group in the scaffold increases affinity for lactate (e.g., reduces the Kd value for lactate). Hence, whereas glucose affinity is reduced by the extra distance between the boronates, the lactate affinity is increased. This example illustrates that the scaffolds presented in this disclosure can have a large impact on the ability of the vicinal diol sensors to selectively bind a specific hexose (e.g., at a higher affinity with respect to a series of competing hexoses).

As an example, another comparison can be made between two sensors utilizing the same boronates but with different scaffold molecules (e.g., fragments). Comparison of the diol affinities of Example 2 and Example 14 from Table 1 shows that the scaffold of Example 14 provides a higher selectivity value for glucose over lactate, whereas the scaffold of Example 2 provides a higher selectivity value for fructose over lactate. This unexpected result was discovered by experimental identification of the scaffold of Examples 2 and 14 and subsequent analysis of their binding specificities.

The second factor that impacts selectivity of binding is the position and the nature (e.g., composition) of the functional groups on the benzene ring of the phenylboronates. Both the conjugation point of the phenylboronate on the vicinal diol sensor (e.g., the point of conjugation on the benzene ring with respect to the boron attachment (substituent) on the benzene ring), as well as the positions and identities (e.g., compositions) of other functional groups on the benzene ring (e.g., ortho-, meta- or para- with respect to the boron group on the phenylboronate ring) impacts selectivity. Electron withdrawing groups on the phenylboronates generally provide for lower pKa values (e.g., because they help with ionization), and in general, the ring strain in the 5-membered oxaborole ring boronates (e.g., Formulae F2, F13, or F29) distorts geometry and also leads to lower pKa values. While fluorine and/or $CF_3$ groups can be utilized as the electron withdrawing groups, the introduction of nitro groups to the benzene ring can have dramatic effects on lowering the pKa. These effects are easiest to observe when the scaffold molecule is kept constant while changing the boronates. For example, the compounds of Examples 4-8 utilize the same scaffold molecule but have phenylboronates containing different functional groups, and show different binding selectivity towards glucose, fructose, and lactate. This example illustrates, for example, that the presence of $NO_2$ groups on the phenylboronate ring can enhance affinity towards glucose, and that heterobifunctional sensors containing two different boronates or phenylboronates show different sugar selectivities than vicinal diol sensors containing two similar (or identical) boronates. Moreover, aspects of the present disclosure include nitro-substituted boronates combined with boroxole boronates on the same scaffold, as shown, for example, by comparison of affinities of Examples 5 and 7 in Table 1. The homobifunctional boronate groups of Example 5 provide a worse affinity for glucose compared to the heterobifunctional boronates of Example 7. The use of ring strained boroxole provide an approximate 7-fold increase in affinity to glucose, fructose, and lactate, even though the rest of the structure of the compound is similar between Examples 5 and 7.

Similarly, for example, comparison of the compounds of Examples 9 and 15 shows that the introduction of nitro groups in the boronates enhances glucose affinity in specific scaffolds, and that this affinity enhancement is not just due to the electron withdrawing nature of the functional groups of the boronates (as fluorine are also electron withdrawing). Hence, in contrast to the long-standing assumption that stronger electron withdrawing groups on the phenylboronate ring always enhance sugar binding at physiological pH by modulating the pKa of the boronate, this is not always the case (e.g., other aspects of the functional group may come into play). Examples 9 and 15 show that for some scaffolds of this disclosure, the nitro group better enhances affinity than the equivalent fluoro group on the phenylboronate ring. The importance of the functional groups on the phenylboronates is further highlighted by comparison of example compounds having similar scaffold structures. For example, the importance of the functional groups on the sensor selectivity can be seen by comparison of Example 14 versus Example 18, Example 11 versus Example 20, Example 12 versus Examples 21 and 23, and comparisons within Examples 1-3 or within Examples 4-8 and the corresponding affinities of these molecules listed in Table 1. These examples illustrate the effects of functional group placement on the phenylboronate ring for a given scaffold molecule can enhance sensor binding and selectivity towards a sugar of interest, for example towards glucose and away from other hydroxyl containing molecules including fructose or lactate. Therefore, in some embodiments the scaffolds molecules identified and the specific boronates conjugated to these scaffolds as described in this disclosure include vicinal diol sensors having preferential binding selectivities towards a vicinal diol of interest (for example glucose) and away from other vicinal diols (for example fructose) or hydroxyl containing molecules (for example lactate).

The third structural factor impacting selectivity is steric hindrance or charge effects that favor binding to one sugar molecule over another. For example, the impact of amine (amide) groups versus acid groups on the scaffolds can be seen by comparing Examples 1-3 in Table 1. The substituent acid or amide group on the scaffold may contribute to differences in binding affinity of these sensors to glucose versus lactate or fructose. Comparison of Examples with scaffolds including an acid group or amide group, with Examples 1-3 and 4-8 in Table 1 shows the overall impact of the acid versus amid group on the scaffold, wherein such effects are further extended to substituents on the boronates which do not directly impact the electronic structure of the boronate but can sterically hinder the engagement of the sensor with one pair of vicinal diols versus another, and thereby influence selectivity. Taken together, the combined effects of the scaffold molecule, the functional groups on the phenylboronate ring, and the functional groups either directly near the phenylboronate ring or on the scaffold as included in certain embodiment of this disclosure show some of the approaches by which the sensors disclosed achieve binding for specific vicinal diols. These Examples and the associated binding affinities in Table 1 demonstrate at least some of the effects that are identified in selectivity enhancements.

In certain embodiments the vicinal diol sensors are conjugated to an incretin peptide to control pharmacokinetics in the body in response to a specific vicinal diol such as glucose. In certain embodiments the incretin peptide is a polypeptide and it may be, for example, insulin. Insulin is an important regulator of blood glucose levels. In a healthy individual, insulin is present and when released by the pancreas it acts to reduce blood sugar levels. Diabetes mellitus (DM), commonly referred to as diabetes, is a group of metabolic diseases in which there are high blood sugar levels over a prolonged period.

In certain embodiments the vicinal diol sensor may contain a single boronic acid molecule (or groups) or multiple boronic acid molecules (or groups), and the sensor scaffold and/or the boronates are attached directly to, or include, a naphthalene, anthracene, biphenyl, anthraquinone, phenanthrene, chrysene, pyrene, coronene, corannulene, tetracene, pentacene, or triphenylene scaffold. These scaffolds may include but are not limited to additional substituents such as nitro, fluoro, alcohol, thiol, trifluoromethyl, and/or methoxy functional groups. Two or more scaffolds may be conjugated together, either directly or through one or more amino acids. The scaffolds may be further conjugated to a drug or drug substance and impart the ability to distinguish desirable diol containing molecules or proteins. Certain embodiments may include multiple copies of these scaffolds which may provide further selectivity and functionality.

In certain uses modified insulins described herein may be delivered to the body by injection, or by other routes and can reversibly bind to soluble glucose in a non-depot form. In certain uses modified insulins described herein may be delivered to the body by injection or by other routes, and can reversibly bind to soluble glucose in a depot and/or soluble form. In certain embodiments modified insulins described herein can additionally be released over an extended period of time from a local depot in the body. In certain embodiments themodified insulins bind to proteins in blood and/or in plasma such as serum albumin and the release of the modified insulins is dependent on levels of glucose in the blood such that at elevated blood glucose levels a higher amount of the modified insulins releases from serum albumin. Such release rate may be dependent on blood sugar levels or levels of other small molecules in the blood including diol containing molecules. In certain embodiments the release, bioavailability, and/or solubility of modified insulins described herein can be controlled as a function of blood and/or serum glucose concentrations and/or concentrations of other small molecules in the body. Certain embodiments include intermediate compounds of any of the compounds described herein; wherein the intermediate compounds may optionally contain one or more protecting groups (example: Boc, Fmoc, etc.), and in certain embodiments the one or more protecting groups are independently on any of the subsets of the compounds or intermediates in this disclosure.

Modified insulin describes insulin that is chemically altered as compared to wild type insulin, such as, but not limited to, by addition of a chemical moiety such as a PEG group or a fatty acyl chain. Altered insulins may be mutated including additions, deletions or substitutions of amino acids. Different protomers of insulin may result from these changes and be incorporated into certain embodiments. Generally active forms of insulins have less than 11 such modifications (e.g., 1-4, 1-3, 1-9, 1-8, 1-7, 1-6, 2-6, 2-5, 2-4, 1-5, 1-2, 2-9, 2-8, 2-7, 2-3, 3-9, 3-8, 3-7, 3-6, 3-5, 3-4, 4-9, 4-8, 4-7, 4-6, 4-5, 5-9, 5-8, 5-7, 5-6, 6-9, 6-8, 6-7, 7-9, 7-8, 8-9, 9, 8, 7, 6, 5, 4, 3, 2 or 1). The wild-type sequence of human insulin (A-chain and B-chain), has an A-chain with the amino acid sequence GIVEQCCTSICSLYQLENYCN (SEQ ID NO:1), and a B-chain having the amino acid sequence FVNQHLCGSHLVEALYLVCGERGFFYTPKT (SEQ ID NO:2).

Human insulin differs from rabbit, porcine, bovine, and sheep insulin in amino acids A8, A9, A10, and B30 which are in order the following: Thr, Ser, Ile, Thr for human; Thr, Ser, Ile, Ser for rabbit; Thr, Ser, Ile, Ala for porcine; Ala, Gly, Val, Ala for sheep; and Ala, Ser, Val, Ala for bovine. A modification to insulin may in certain embodiments include an insulin which is mutated at $B_1$, $B_2$, B28 or the B29, or B28 and B29 positions of the B-chain. A modification to insulin may in certain embodiments include an insulin which is mutated at A1, A2, A21 or other positions of the A-chain. For example, insulin lispro is a fast acting modified insulin in which the lysine and proline residues on the C-terminal end of the B-chain have been reversed. Insulin aspart is a fast-acting modified insulin in which proline has been substituted with aspartic acid at position B28. It is contemplated in certain embodiments of the present disclosure that mutations at B28 and B29 may come with additional mutations. Insulin glulisine is a fast-acting modified insulin in which aspartic acid has been replaced by a lysine residue at position B3, as well as the replacement of lysine with a glutamic acid residue at position B29.

In certain embodiments the isoelectric point of insulins herein may be shifted relative to wild-type human insulin by addition or substitution of amino acids or otherwise achieved, and in certain embodiments the isoelectric point of the modified insulins may be modulated by glucose. For example, insulin glargine is a basal insulin in which two arginine residues have been added to the C-terminus of the B-peptide and A21 has been replaced by glycine. The insulin may not have one or more of the residues B1, B2, B3, B26, B27, B28, B29, B30. In certain embodiments, the insulin molecule contains additional amino acid residues on the N- or C-terminus of the A-chain or B-chain. In certain embodiments, one or more amino acid residues are located at positions A0, A21, B0 and/or B31 or are missing. In certain embodiments, an insulin molecule of the present disclosure is mutated such that one or more amino acids are replaced with acidic forms. By way of example, an asparagine may be replaced with aspartic acid or glutamic acid, similarly glutamine may be replaced with aspartic acid or glutamic acid. In certain embodiments A21 may be an aspartic acid, B3 may be an aspartic acid, or both positions may contain an aspartic acid (e.g., simultaneously). One skilled in the art will recognize that it is possible to make any previously reported, or widely accepted mutations or modifications to insulin that retains biological activity, and that the modified insulin can be used in embodiments of the present disclosure. In certain embodiments, an insulin may be linked at any position to a fatty acid, or acylated with a fatty acid at any amino group, including those on side chain of lysines or alpha-amino group on the N-terminus of insulin and the fatty acid may include C8, C9, C10, C11, C12, C14, C15, C16, C17, C18. In certain embodiments a combination of fatty acids or fatty diacids and PEG linker conjugations to the modified insulins are used to increase the serum half-life of the modified insulins or to endow the modified insulins with extended release characteristics, such extended release may be anywhere from 12 hours to 7 days. In certain embodiments, the fatty acid chain is 8-20 carbons long. By way of example, such modifications can resemble those in insulin detemir in which a myristic acid is covalently conjugated to lysine at B29 and B30 is deleted or absent. In certain embodiments, position B28 of the insulin molecule is lysine and the epsilon(c)-amino group of this lysine is conjugated to a fatty acid or a modified fatty acid or diacid. In certain embodiments the lysine at or near the C-terminus of the B-chain of insulin is replaced by an amino acid described by Formulae I-III. In certain embodiments activity, bioavailability, solubility, isoelectric point, charge and/or hydrophobicity of the modified insulins can be controlled through chemical modifications or as result of interaction of a small molecule such as a sugar with the modified insulins described herein which is either covalently linked or mixed with insulin.

In certain embodiments, a modified insulin molecule of the present disclosure includes the mutations and/or chemical modifications including, but not limited to one of the following insulin molecules: N$^{\varepsilon B29}$-octanoyl-Arg$^{B0}$Gly$^{A21}$Asp$^{B3}$Arg$^{B31}$Arg$^{B32}$-HI, N$^{\varepsilon B29}$-octanoyl-Arg$^{B31}$Arg$^{B32}$-HI, N$^{\varepsilon B29}$-octanoyl-Arg$^{A0}$Arg$^{B31}$Arg$^{B32}$-HI, N$^{\varepsilon B28}$-myristoyl-Gly$^{A21}$Lys$^{B28}$Pro$^{B29}$Arg$^{B31}$Arg$^{B32}$-HI, N$^{\varepsilon B28}$-myristoyl-Gly$^{A21}$Gln$^{B3}$Lys$^{B28}$Pro$^{B30}$Arg$^{B31}$Arg$^{B32}$-HI, N$^{\varepsilon B28}$-myristoyl-Arg$^{A0}$Gly$^{A21}$Lys$^{B28}$Pro$^{B29}$Arg$^{B31}$Arg$^{B32}$-HI, N$^{\varepsilon B28}$-myristoyl-Arg$^{A0}$Gly$^{A21}$Gln$^{B3}$Lys$^{B28}$Pro$^{B29}$Arg$^{B31}$Arg$^{B32}$-HI, N$^{\varepsilon B28}$-myristoyl-Arg$^{A0}$Gly$^{A21}$Asp$^{B3}$Lys$^{B28}$Pro$^{B29}$Arg$^{B31}$Arg$^{B32}$-HI, N$^{\varepsilon B28}$-myristoyl-Lys$^{B28}$Pro$^{B29}$Arg$^{B31}$Arg$^{B32}$-HI, N$^{\varepsilon B28}$-myristoyl-Arg$^{A0}$Lys$^{B28}$Pro$^{B29}$Arg$^{B31}$Arg$^{B32}$-HI, N$^{\varepsilon B28}$-octanoyl-Gly$^{A21}$Lys$^{B28}$Pro$^{B29}$Arg$^{B31}$Arg$^{B32}$-HI, N$^{\varepsilon B28}$-octanoyl-Gly$^{21}$GnB$^{3}$Ly$^{B28}$PrB$^{29}$Arg$^{B31}$rg$^{B32}$-HI, N$^{\varepsilon B28}$-octanoyl-Arg$^{A0}$Gly$^{A2}$ILys$^{B28}$Pro$^{B29}$Arg$^{B31}$Arg$^{B32}$-HI, N$^{\varepsilon B29}$-palmitoyl-HI, N$^{\varepsilon B29}$-myrisotyl-HI, N$^{\varepsilon B28}$-palmitoyl-Lys$^{B28}$Pro$^{B29}$-HI, N$^{\varepsilon B28}$-myristoyl-Lys$^{B28}$Pro$^{B29}$-HI, N$^{\varepsilon B29}$-palmitoyl-des(B 30)-HI, N$^{\varepsilon B30}$-myristoyl-Thr$^{B2}$Lys$^{B30}$-HI, N$^{\varepsilon B30}$-palmitoyl-Thr$^{B29}$Lys$^{B30}$-HI, N$^{\varepsilon B29}$-(N-palmitoyl-γ-glutamyl)-des(B30)-HI, N$^{\varepsilon B29}$-(N-lithocolyl-γ-glutamyl)-des(B30)-HI, N$^{\varepsilon B29}$-(ω-carboxyheptadecanoyl)-des(B30)-HI, N$^{\varepsilon B29}$-(ω-carboxyheptadecanoyl)-HI, N$^{\varepsilon B29}$-octanoyl-HI, N$^{\varepsilon B29}$-myristoyl-Gly$^{A21}$Arg$^{B31}$Arg$^{B31}$-HI, N$^{\varepsilon B29}$-myristoyl-Gly$^{A21}$Gln$^{B3}$Arg$^{B31}$Arg$^{B32}$-HI, N$^{\varepsilon B29}$-myristoyl-Arg$^{A0}$Gly$^{A21}$Arg$^{B31}$Arg$^{B32}$-HI, N$^{\varepsilon B29}$-Arg$^{A0}$Gly$^{A21}$Gln$^{B3}$Ar$^{B31}$Arg$^{B32}$-HI, N$^{\varepsilon B29}$-myristoyl-Arg$^{A0}$Gly$^{A21}$Asp$^{B3}$Arg$^{B31}$Arg$^{B32}$-HI, N$^{\varepsilon B29}$-myristoyl-Arg$^{B31}$Arg$^{B32}$-HI, N$^{\varepsilon B29}$-myristoyl-Arg$^{A0}$Arg$^{B31}$Arg$^{B32}$-HI, N$^{\varepsilon B29}$-octanoyl-Gly$^{A21}$Arg$^{B31}$Ag$^{B32}$-HI, N$^{\varepsilon B29}$-octanoyl-Gly$^{A21}$Gln$^{B3}$Arg$^{B31}$Arg$^{B32}$-HI, N$^{\varepsilon B29}$-octanoyl-Arg$^{A0}$Gly$^{A21}$Arg$^{B31}$Arg$^{B32}$-HI, N$^{\varepsilon B29}$-octanoyl-Arg$^{A0}$Gly$^{A21}$Gln$^{B3}$Arg$^{B31}$Arg$^{B32}$-HI, N$^{\varepsilon B28}$-octanoyl-Arg$^{A0}$Gly$^{A21}$Gln$^{B3}$Lys$^{B28}$Pro$^{B29}$Arg$^{B31}$Arg$^{B32}$-HI, N$^{\varepsilon B28}$-octanoyl-Arg$^{A0}$Gly$^{A21}$Asp$^{B3}$Lys$^{B28}$Pro$^{B29}$Ag$^{B31}$Ag$^{B32}$-HI, N$^{\varepsilon B28}$-octanoyl-Lys$^{B28}$PrB$^{29}$Arg$^{B31}$Arg$^{B32}$-HI, N$^{\varepsilon B2}$s-octanoyl-Arg$^{A0}$Lys$^{B28}$Pro$^{B29}$Arg$^{B31}$Arg$^{B32}$-HI. N$^{\varepsilon B29}$-pentanoyl-Gly$^{A21}$Ag$^{B31}$Ag$^{B32}$-HI, N$^{\alpha B1}$-hexanoyl-Gly$^{A21}$Arg$^{B31}$Arg$^{B32}$-HI, N$^{\alpha A1}$-heptanoyl-Gly$^{A21}$Arg$^{B31}$Arg$^{B32}$-HI, N$^{\varepsilon B29}$-octanoyl-N$^{\alpha B1}$-octanoyl-Gly$^{A21}$Arg$^{B31}$Arg$^{B32}$-HI, N$^{\varepsilon B29}$-propionyl-N$^{\alpha A1}$-propionyl-Gly$^{A21}$Arg$^{B31}$Arg$^{B32}$-HI, N$^{\alpha A1}$-acetyl-N$^{\alpha B1}$-acetyl-Gly$^{A21}$Arg$^{B31}$Arg$^{B32}$-HI, N$^{\varepsilon B29}$-formyl-N$^{\alpha A1}$-formyl-N$^{\alpha B1}$-formyl-Gly$^{A21}$Arg$^{B31}$Arg$^{B32}$-HI, N$^{\varepsilon B29}$-formyl-des(B26)-HI, N$^{\alpha B}{}_{1}$-acetyl-Asp$^{B28}$-HI, N$^{\varepsilon B29}$-propionyl-N$^{\alpha A1}$-propionyl-N$^{\alpha B1}$-propionyl-Asp$^{B1}$Asp$^{B3}$Asp$^{B21}$-HI, N$^{\varepsilon B29}$-pentanoyl-Gly$^{A21}$-HI, N$^{\alpha B1}$-hexanoyl-Gly$^{A21}$-HI, N$^{\alpha A1}$-heptanoyl-Gly$^{A21}$-HI, N$^{\varepsilon B29}$-octanoyl-N$^{\alpha B}{}_{1}$-octanoyl-Gly$^{A21}$-HI, N$^{\varepsilon B29}$-propionyl-N$^{\alpha A1}$propionyl-Gly$^{A21}$-HI, N$^{\alpha A1}$-acetyl-N$^{\alpha B}{}_{1}$-acetyl-Gly$^{A21}$-HI, N$^{\varepsilon B29}$-formyl-N$^{\alpha B1}$formyl-Gly$^{A21}$-HI, N$^{\varepsilon B29}$-butyryl-des(B30)-HI, N$^{\alpha B31}$-butyryl-des(B30)-HI, N$^{\alpha A1}$-butyryl-des(B30)-HI, N$^{\varepsilon B29}$-butyryl-N$^{\alpha B31}$-butyryl-des(B30)— HI, N$^{\varepsilon B29}$-butyryl-N$^{\alpha A1}$-butyryl-des(B30)-HI, N$^{\alpha A1}$-butyryl-N$^{\alpha B31}$-butyryl-des(B30)-HI, N$^{\varepsilon B29}$-butyryl-N$^{\alpha A1}$-butyryl-N$^{\alpha B31}$-butyryl-des(B30)-HI, Lys$^{B28}$Pro$^{B29}$-HI (insulin lispro), Asp$^{B28}$-HI (insulin aspart), Lys$^{B3}$Glu$^{B29}$-HI (insulin glulisine), Arg$^{B31}$Arg$^{B32}$-HI (insulin glargine), N$^{EB29}$-myristoyl-des(B30)-HI (insulin detemir), Ala$^{B26}$-HI, Asp$^{B1}$-HI, Arg$^{A0}$-HI, Asp$^{B1}$Glu$^{B13}$-HI, Gly$^{A21}$-HI, Gly$^{A21}$Arg$^{B31}$Ag$^{B32}$-HI, Arg$^{B31}$ Arg$^{B32}$-HI, Arg$^{A0}$Gly$^{A21}$Arg$^{B31}$Ag$^{B32}$-HI, des(B30)-HI, des(B27)-HI, des(B28-B30)-HI, des(B1)-HI, des(B1-B3)-HIN$^{\varepsilon B29}$-tridecanoyl-des(B30)-HI, N$^{\varepsilon B29}$-tetradecanoyl-des(B30)-HI, N$^{\varepsilon B29}$-decanoyl-des(B30)-HI, N$^{\varepsilon B29}$ -dodecanoyl-des(B30)-HI, N$^{\varepsilon B29}$-tridecanoyl-Gly$^{A21}$-des(B30)-HI, N$^{\varepsilon B29}$-tetradecanoyl-Gly$^{A21}$-des(B30)-HI, N$^{\varepsilon B29}$-decanoyl-Gly$^{A21}$-des(B30)-HI, N$^{\varepsilon B29}$-dodecanoyl-Gly$^{A21}$-des(B30)-HI, N$^{\varepsilon B29}$-tridecanoyl-Gly$^{A21}$Gln$^{B3}$-des(B30)-HI, N$^{\varepsilon B29}$-tetradecanoyl-Gly$^{A21}$Gln$^{B3}$-des(B30)-HI, N$^{\varepsilon B29}$-decanoyl-Gly$^{A21}$-Gly$^{B3}$-des(B30)-HI, N$^{\varepsilon B29}$-dodecanoyl-Gly$^{A21}$-Gln$^{B3}$-des(B30)-HI, N$^{\varepsilon B29}$-tridecanoyl-Ala$^{A21}$-des(B30)-HI, N$^{\varepsilon B29}$-tetradecanoyl-Ala$^{A21}$-des(B30)-HI, N$^{\varepsilon B29}$-decanoyl-Ala$^{A21}$-des(B30)-HI, N$^{\varepsilon B29}$-dodecanoyl-Ala$^{A21}$-des(B30)-HI, N$^{\varepsilon B29}$-tridecanoyl-Ala$^{A21}$-Gln$^{B3}$-des(B30)-HI, N$^{\varepsilon B29}$-tetradecanoyl-Ala$^{A21}$Gln$^{B3}$-des(B30)-HI, N$^{\varepsilon B29}$-decanoyl-Ala$^{A21}$Gln$^{B3}$-des(B30)-HI, N$^{\varepsilon B29}$-dodecanoyl-Ala$^{A21}$Gln$^{B3}$-des(B30)-HI, N$^{\varepsilon B29}$-tridecanoyl-Gln$^{B3}$-des(B30)-HI, N$^{\varepsilon B29}$-tetradecanoyl-Gln$^{B3}$-des(B30)-HI, N$^{\varepsilon B29}$-decanoyl-Gln$^{B3}$-des(B30)-HI, N$^{\varepsilon B29}$-dodecanoyl-Gln$^{B3}$-des(B30)-HI, N$^{\varepsilon B29}$-Z1-Gly$^{A21}$-HI, N$^{\varepsilon B29}$-Z2-Gly$^{A21}$-HI, N$^{\varepsilon B29}$-Z4-Gly$^{A21}$-HI, N$^{\varepsilon B29}$-Z3-Gly$^{A21}$-HI, N$^{\varepsilon B29}$-Z1-Ala$^{A21}$-HI, N$^{\varepsilon B29}$-Z2-Ala$^{A21}$-HI, N$^{\varepsilon B29}$-Z4-Ala$^{A21}$-HI, N$^{\varepsilon B29}$-Z3-Ala$^{A21}$-HI, N$^{\varepsilon B29}$-Z1-Gly$^{A21}$Gln$^{B3}$-HI, N$^{\varepsilon B29}$-Z2-Gly$^{A21}$Gln$^{B3}$-HI, N$^{\varepsilon B29}$-Z4-Gly$^{A21}$Gln$^{B3}$-HI, N$^{\varepsilon B29}$-Z3-Gly$^{A21}$Gln$^{B3}$-HI, N$^{\varepsilon B29}$-Z1-Ala$^{A21}$Gln$^{B3}$-HI, N$^{\varepsilon B29}$-Z2-Ala$^{A21}$Gln$^{B3}$-HI, N$^{\varepsilon B29}$-Z4-Ala$^{A2'}$1Gln$^{B3}$-HI, N$^{\varepsilon B29}$-Z3-Ala$^{A2}$Gln$^{B3}$-HI, N$^{\varepsilon B29}$-Z1-Gln$^{B3}$-HI, N$^{\varepsilon B29}$-Z2-Gln$^{B3}$-HI, N$^{\varepsilon B29}$-Z4-Gln$^{B3}$-HI, N$^{\varepsilon B29}$-Z3-Gln$^{B3}$-HI, N$^{\varepsilon B29}$-Z1-Glu$^{B30}$-HI, N$^{\varepsilon B29}$-Z2-Glu$^{B30}$-HI, N$^{\varepsilon B29}$-4-Glu$^{B30}$-HI, N$^{\varepsilon B29}$-Z3-Glu$^{B30}$-HI, N$^{\varepsilon B29}$-Z1-Gly$^{A2}$Glu$^{B30}$-HI, N$^{\varepsilon B29}$-Z2-Gly$^{A21}$Glu$^{B30}$-HI, N$^{\varepsilon B29}$-Z4-Gly$^{A21}$Glu$^{B30}$-HI, N$^{\varepsilon B29}$-Z3Gly$^{A21}$Glu$^{B30}$-HI, N$^{\varepsilon B29}$-Z1-Gly$^{A21}$Glu$^{B3}$Glu$^{B30}$-HI, N$^{\varepsilon B29}$-Z2-Gly$^{A21}$Glu$^{B3}$Glu$^{B30}$-HI, N$^{\varepsilon B29}$-Z4-

Gly$^{A21}$Glu$^{B3}$Glu$^{B30}$-HI, N$^{\varepsilon B29}$-Z3-Gly$^{A21}$Glu$^{B3}$Glu$^{B30}$-HI, N$^{\varepsilon B29}$-Z1-Ala$^{A21}$Glu$^{B30}$-HI, N$^{\varepsilon B29}$-Z2-Ala$^{A2}$Glu$^{B30}$-HI, N$^{\varepsilon B29}$-Z4-Ala$^{A21}$Gln$^{B30}$-HI, N$^{\varepsilon B29}$-Z3-Ala$^{A21}$Glu$^{B30}$-HI, N$^{\varepsilon B29}$-Z1-Ala$^{A21}$Glu$^{B3}$Glu$^{B30}$-HI, N$^{\varepsilon B29}$-Z2-Ala$^{A21}$Glu$^{B3}$Glu$^{B30}$-HI, N$^{\varepsilon B2}$9-Z4-Ala$^{A21}$Glu$^{B3}$Glu$^{B30}$-HI, N$^{\varepsilon B29}$-Z3-Ala$^{A21}$Glu$^{B3}$Glu$^{B30}$-HI, N$^{\varepsilon B29}$-Z1-Gln$^{B3}$Glu$^{B30}$-HI, N$^{\varepsilon B29}$-Z2-Glu$^{B3}$Glu$^{B30}$-HI, N$^{\varepsilon B29}$-Z4-Glu$^{B3}$Glu$^{B30}$-HI, N$^{\varepsilon B29}$-Z3-Glu$^{B3}$Glu$^{B30}$-HI and where Z1 is tridecanoyl, Z2 is tetradecanoyl, Z3 is dodecanoyl, Z4 is decanoyl, and HI is human insulin.

In certain embodiments, an insulin molecule has the following mutations and/or chemical modifications: N$^{\varepsilon B28}$-XXXXX-Lys$^{B28}$Pro$^{B29}$-HI, N$^{\alpha B1}$-XXXXX-Lys$^{B28}$Pro$^{B29}$-HI, N$^{\alpha A1}$-XXXXX-Lys$^{B28}$Pro$^{B29}$-HI, N$^{\varepsilon B28}$-XXXXX-N$^{\alpha B1}$-XXXXX-Lys$^{B28}$Pro$^{B29}$-HI, N$^{\varepsilon B28}$-XXXXX-N$^{\alpha A1}$-XXXXX-Lys$^{B28}$Pro$^{B29}$-HI, N$^{\alpha A1}$-XXXXX-N$^{\alpha B1}$-XXXXX-LyS$^{B28}$PrO$^{B29}$-HI, N$^{\varepsilon B28}$-XXXXXX-N$^{\alpha A1}$-XXXXX-N$^{\alpha B1}$-HI, N$^{\varepsilon B29}$-XXXXX-HI, N$^{\alpha B1}$ -XXXXX-HI, N$^{\alpha A1}$-XXXXX-HI, N$^{\varepsilon B29}$-XXXXX-N$^{\alpha B1}$-XXXXX-HI, N$^{\varepsilon B29}$-XXXXX-N$^{\alpha A1}$-XXXXX-HI, N$^{\alpha A1}$-XXXXX-N$^{\alpha B1}$-XXXXX-HI, N$^{\varepsilon B29}$-XXXXX-N$^{\alpha A1}$-XXXXX-N$^{\alpha B1}$-XXXXX-HI, N$^{\varepsilon B29}$-YYYYY-HI, N$^{\alpha B1}$-YYYYY-HI, N$^{\alpha A1}$-YYYYY-HI, N$^{\varepsilon B29}$-YYYYY-N$^{\alpha B1}$-YYYYY-HI, N$^{\varepsilon B29}$-YYYYY-N$^{\alpha A1}$-YYYYY-HI, N$^{\alpha A1}$-YYYYY-N$^{\alpha B1}$-YYYYY-HI, N$^{\varepsilon B29}$-YYYYY-N$^{\alpha A1}$-YYYYY-N$^{\alpha B1}$-YYYYY-HI, N$^{\varepsilon B28}$-YYYYY-Lys$^{B28}$Pro$^{B29}$-HI, N$^{\varepsilon B21}$-YYYYY-Lys$^{B28}$Pro$^{B29}$-HI, N$^{\alpha A1}$-YYYYY-Lys$^{B28}$Pro$^{B29}$-HI, N$^{\varepsilon B28}$-YYYYY-N$^{\alpha B1}$-YYYYY-Lys$^{B28}$Pro$^{B29}$-HI, N$^{\varepsilon B28}$-YYYYY-N$^{\varepsilon BA1}$-YYYYY-LyS$^{B28}$Pro$^{B29}$-HI, N$^{\alpha A1}$-YYYYY-N$^{\alpha B1}$-YYYYY-Lys$^{B28}$Pro$^{B29}$-HI, N$^{\varepsilon B28}$-YYYYY-N$^{\alpha A1}$-YYYYY-N$^{\alpha B1}$-YYYYY-LyS$^{B28}$Pro$^{B29}$-HI, and where YYYYY is one of acetyl or formyl and where XXXXX is one of: propionyl, butyryl, pentanoyl, hexanoyl, heptanoyl, octanoyl, nonanoyl or decanoyl and HI is human insulin.

As discussed herein, the insulin molecule may be conjugated through a reactive moiety that is naturally present within the insulin structure and/or added prior to conjugation, including, for example, carboxyl or reactive ester, amine, hydroxyl, aldehyde, sulfhydryl, maleimidyl, alkynyl, azido, etc. moieties. Insulin naturally includes reactive alpha-terminal amine and epsilon-amine lysine groups to which NHS-ester, isocyanates, and/or isothiocyanates can be covalently conjugated. In certain embodiments, a modified insulin may be employed in which a suitable amino acid (e.g., a lysine and/or a non-natural amino acid) has been added or substituted into the amino acid sequence in order to provide an alternative (e.g., additional) point of conjugation in addition to the modified amino acids of the embodiments described herein. In addition, it will be appreciated that the conjugation process may be controlled by selectively blocking or protecting certain reactive moieties prior to conjugation. It is to be understood that insulin in certain embodiments may include any combination of these modifications and the present disclosure also encompasses modified forms of non-human insulins (e.g., porcine insulin, bovine insulin, rabbit insulin, sheep insulin, etc.) that include any one of the aforementioned modifications. It is understood that certain embodiments may include these and certain other previously described modified insulins such as those described in U.S. Pat. Nos. 5,474,978; 5,461,031; 4,421,685; 7,387,996; 6,869,930; 6,174,856; 6,011,007; 5,866,538; 5,750,4976; 906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; and 5,504,188; and US Patent Application No. 2015/0353619, including non-natural amino acids described or referenced herein and including such modifications to the non-human insulins described herein. It is also to be understood that in certain embodiments the insulin may be covalently conjugated to polyethylene glycol polymers of no more than Mn 218,000, or covalently conjugated to albumin.

In certain embodiments the modified insulin is further conjugated to a non-boronated polypeptide by using an enzyme. In certain embodiments the N- or C-terminal residues of the peptide fragment can serve as recognition sequences for a peptide ligase to allow for conjugation of the peptide to insulin, and certain other embodiments the insulin can be expressed using one or more additional amino acids so that one of the ends of the A- or B-chain of insulin is recognized by an enzyme that then appends a non-boronated polypeptide of interest to insulin. In certain embodiments the polypeptide is added to the C-terminus of insulin A- and/or B-chain using a protein ligase. In certain embodiments the polypeptide is added to the N-terminus of insulin A- and/or B-chain using a protein ligase. In certain embodiments the polypeptide is conjugated to the modified insulin using a protein ligase selected from the group consisting of sortases, butelases, Trypsiligases, Subtilisins, Peptiligases or enzymes having at least 75% homology to these ligases. In certain embodiments this is achieved through expressed protein ligation as described in: Muir T W, Sondhi D, Cole P A. Expressed protein ligation: a general method for protein engineering. *Proc Nat Acad Sci USA*. 1998; 95(12):6705-6710. In certain other embodiments the polypeptide is linked to the modified insulin using Staudinger ligation, utilizing the Staudinger reaction and as described for example in Nilsson, B. L.; Kiessling, L. L.; Raines, R. T. (2000). "Staudinger ligation: A peptide from a thioester and azide". *Org. Lett.* 2 (13): 1939-1941. In certain other embodiments a polypeptide is conjugated to the modified insulin using Ser/Thr ligation as, for example, described in: Zhang Y, Xu C, Kam H Y, Lee C L, Li X. 2013, "Protein chemical synthesis by serine/threonine ligation." *Proc. Natd. Acad. Sci. USA*. 17:6657-6662. In certain embodiments the B-chain itself has less than 32 amino acids or 34 amino acids and in certain embodiments the insulin has 4 disulfide bonds instead of 3.

Covalent conjugation of the modified insulins to a peptide or protein or synthetic polymer or the modified insulins themselves, as well as molecular characteristics, can be tested by LC-MS or SDS-polyacrylamide gel shift assays to verify conjugation and correct stoichiometry. Different linker chemistries and end functionalization can be tested. Some of these linkers may contain orthogonal chemistries to proteins, and in certain embodiments the linkers covalently connect the vicinal diol sensors with a drug substance and any optional molecules that further interact with the vicinal diol sensors can be achieved in what is known as click chemistry or a variety of similar biorthogonal chemical reactions, for example, by way of a copper-catalyzed 3+2 cycloaddition reaction (click reaction) using appropriate or suitable copper-coordinating ligands, as for example described by: Rostovtsev, V. V., Green, L. G., Fokin, V. V. & Sharpless, K. B. A stepwise huisgen cycloaddition process: copper(I)-catalyzed regioselective "ligation" of azides and terminal alkynes. Angew. Chem. Int. Ed. 41, 2596-2599 (2002). In addition, copper free conjugation of terminal azides to alkyne or alkynyl probes can be used as described by: Liang, Y., Mackey, J. L., Lopez, S. A., Liu, F. & Houk, K. N. Control and design of mutual orthogonality in bioorthogonal cycloadditions. J. Am. Chem. Soc. 134, 17904-17907 (2012) and Beatty, K. E. et al. Live-cell imaging of cellular proteins by a strain-promoted azide-alkyne cycloaddition. Chembiochem 11, 2092-2095 (2010).

In certain embodiments further modification to the compounds of this disclosure may include attachment of a chemical entity containing one or more hydroxyls that interact the vicinal diol sensors. In certain embodiments the groups that interact with the vicinal diol sensors include groups such as a carbohydrate, one or more cis-diol containing molecules, one or more phosphate groups, one or more catechol groups, one or more farnesyl groups, isofarnesyl groups, fatty acid or diacid groups, and/or other diol-containing molecules.

In certain embodiments, the drug substance is insulin and additional groups that interact with the vicinal diol sensors are added to modulate the response profile of the sensors to glucose levels in the body. In certain embodiments thereof, the side chains of amino acids in the modified insulins contain one or more chemical structures, or the protein and/or polypeptides to which the modified insulin is conjugated, and in certain embodiments the one or more chemical structures are described by Formulae F111, F222, F333:

F111

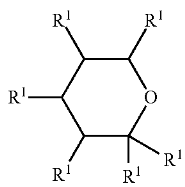

F222

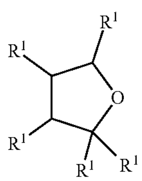

F333

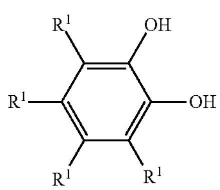

wherein:

each $R^1$ can independently have (R) or (S) stereochemistry and is independently selected from H, $OR^3$, $N(R^3)_2$, $SR^3$, OH, $OCH_3$, $OR^5$, $R^6$—$R^7$, $NHC(O)CH_3$, $CH_2R^3$, $NHC(O)CH_3$, $CH_2OH$, $CH_2OR^5$, $NH_2$, $R^2$, or $CH_2R^4$;

each $R^2$ is independently selected from H or an optionally substituted group selected from $C_{1-6}$ aliphatic, phenyl, a 5-6 membered monocyclic heteroaryl ring having 1-4 heteroatoms selected from nitrogen, oxygen, or sulfur, or a 4-7 membered heterocyclic ring having 1-2 heteroatoms selected from nitrogen, oxygen, or sulfur;

each $R^3$ is independently selected from H, acetyl, phosphate, $R^2$, $SO_2R^2$, $S(O)R^2$, $P(O)(OR^2)_2$, $C(O)R^2$, $CO_2R^2$, or $C(O)N(R^2)_2$;

each $R^4$ is independently selected from H, OH, $OR^3$, $N(R^3)_2$, $OR^5$ or $SR^3$;

each $R^5$ is independently selected from either a mono- di- or tri-saccharide, a pentose or a hexose;

each $R^6$ is independently selected from a linker, $NCOCH_2$, $OCH_2CH_2$, $OC_{1-9}$ alkylene, a substituted $C_{1-9}$ alkylene in which one or more methylene is optionally replaced by —O—, —$CH_2$—, —$OCH_2$—, —$N(R^2)C(O)$—, —$N(R^2)C(O)N(R^2)$—, —$SO_2$—, —$SO_2N(R^2)$—, —$N(R^2)SO_2$—, —S—, —$N(R^2)$—, —C(O)—, —OC(O)—, —C(O)O—, —$C(O)N(R^2)$—, or —$N(R^2)SO_2N(R^2)$—;

each $R^7$ is independently selected from $N(R^2)_2$, F, Cl, Br, I, SH, $OR^2$, $SR^2$, $NH_2$, $N_3$, C═$CR^2$, $CH_2C$═CH, C═CH, $CO_2R^2$, $C(O)R^2$, or $OSO_2R^2$. $N(R^2)_2$, $OR^2$, $SR^2$ or $CH_2NH_2$; and in certain embodiments, structures F111, F222 and F333 may be covalently conjugated through a variety of linkers to the modified insulin or to the drug or protein to which the modified insulin is covalently conjugated.

In certain embodiments the glycosidic bond resulting from —$OR^5$ being connected to an anomeric carbon can be in the a: DOWN or p: UP configuration. In certain embodiments, the modified insulin is mixed or covalently conjugated to a drug substance which has been modified from its original form to contain one or more covalent conjugates containing, in part or selected from, the group consisting of: aminoethylglucose, aminoethylbimannose, aminoethyltrimannose, D-glucose, D-galactose, D-Allose, D-Mannose, D-Gulose, D-Idose, D-Talose, N-Azidomannosamine (ManNAz) or N-Azidogalactoseamine (GalNAz), or N-azidoglucoseamine (GIcNAz), 2'-fluororibose, 2'-deoxyribose, glucose, sucrose, maltose, mannose, derivatives of these (e.g., glucosamine, mannosamine, methylglucose, methylmannose, ethylglucose, ethylmannose, etc.), sorbitol, inositol, galactitol, dulcitol, xylitol, arabitol and/or higher order combinations of these (such as linear and/or branched bimannose, linear and/or branched trimannose), molecules containing cis-diols, catechols, tris, DOPA molecules such as L-DOPA or L-3,4-dihydroxyphenylalanine. In certain embodiments the modified insulin is conjugated to a catechol.

In certain embodiments, structures represented by F111, F222 and F333 may be covalently conjugated through a variety of linkers to the modified insulin or drug substance such as through an amide bond, one or more alkyl groups, a triazole linkage, an optional covalent linker, or a combination thereof.

In certain embodiments the modified insulins containing one or more vicinal diol sensors is mixed or covalently conjugated to a substance which contains one or more covalent conjugates containing, in part or selected from, the group consisting of: aminoethylglucose, aminoethylbimannose, aminoethyltrimannose, D-glucose, D-galactose, D-Allose, D-Mannose, D-Gulose, D-Idose, D-Talose, N-Azidomannosamine (ManNAz), or N-Azidogalactoseamine (GalNAz) or N-azidoglucoseamine (GlcNAz), 2'-fluororibose, 2'-deoxyribose, glucose, sucrose, maltose, mannose, derivatives of these (e.g., glucosamine, mannosamine, methylglucose, methylmannose, ethylglucose, ethylmannose, etc.), sorbitol, inositol, galactitol, dulcitol, xylitol, arabitol and/or higher order combinations of these (such as linear and/or branched bimannose, linear and/or branched trimannose), molecules containing cis-diols, catechols, tris, DOPA molecules such as L-DOPA or L-3,4-dihydroxyphenylalanine. In certain embodiments the modified insulin contains amino acids including:

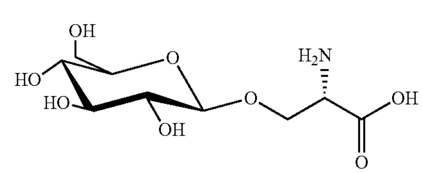

-continued

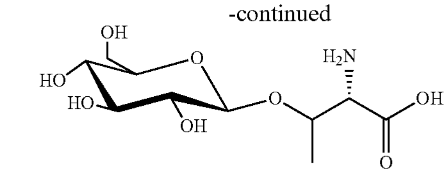

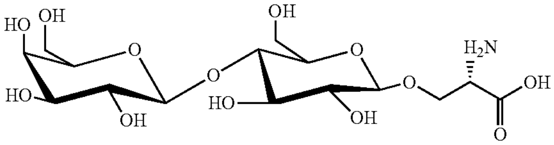

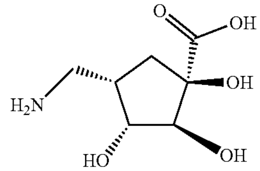

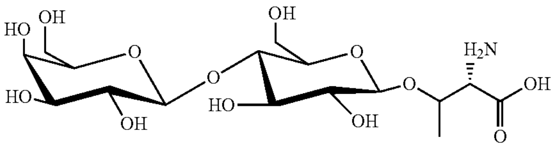

In certain embodiments the modified insulin containing one or more vicinal diol sensors is conjugated to a modified glucose such as an azidoglucose. For example, M-Azido-M-deoxy-D-glucose where M is one of 1,2,3,4,5,6. In certain embodiments, an azide containing sugar can, for example, be linked through click chemistry with a terminal alkyne (such terminal alkyne may, for example, be present as a side chain of an amino acid in such as L-homopropargylglycine or other amino acids described herein with alkyne side chains). The azide group on the sugar can be linked to an alkyne group by, for example, a copper catalyzed click reaction resulting in a triazole linkage, or linked to a cyclooctyne which in certain embodiments is itself linked to a side chain of an amino acid. In certain embodiments the modified insulin can by itself, or through a covalent modification such as covalent conjugation to a fatty acyl or fatty-diacid, interact with albumin in blood, and in certain embodiments the affinity of this interaction can be modulated based on glucose. In certain embodiments the insulin is mixed as part of a pharmaceutically accepted carrier including a polymer of sugars, a polymer containing diols, and/or a polysaccharide.

In certain embodiments, one or more artificial amino acids may be included in the modified insulin or the linkers connected to the structure of the vicinal diol sensors. There are 20 different natural (canonical) amino acids that are the building-blocks of all natural proteins. Non-canonical amino acids or artificial amino acids have side chains that are distinct from canonical amino acids and are not generally present in proteins. The incorporation of artificial amino acids into recombinant proteins, and/or synthesized peptides, enables introduction of chemical groups that can be selectivity functionalized and modified. This is particularly useful for development of modified insulins because it enables selective chemical modifications of insulin at specified positions in the protein sequence. In certain embodiments, artificial amino acids can be used in the modified insulin to modulate pKa, local hydrophobicity of protein domains as well as aggregation and folding properties, or to introduce new chemistries and/or chemical and/or physical properties including thermostability, aggregation behavior, solution stability, reduced aggregation, conformation changes and/or movements of A and B chains of insulin with respect to each other. In certain embodiments, one or more of the following artificial amino acids described by formulae FX15-28 may be used in the modified insulin:

FX15

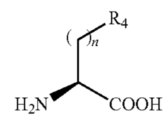

FX16

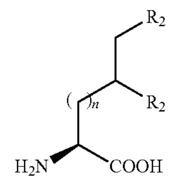

FX17

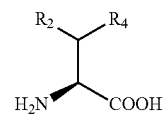

FX18

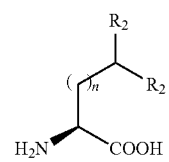

FX19

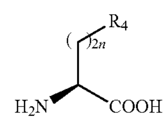

FX20

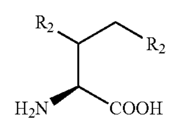

FX21

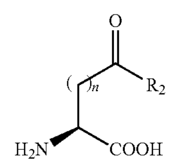

FX22

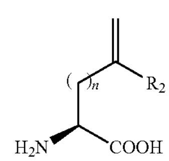

FX23

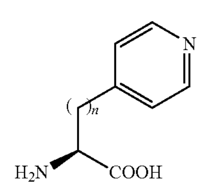

-continued

FX24

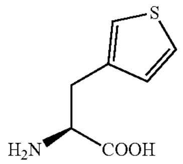

FX25

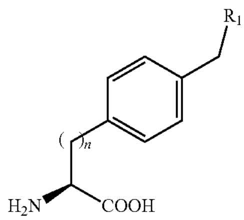

FX26

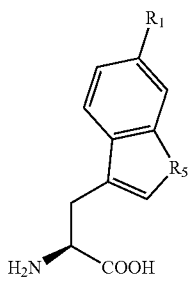

FX27

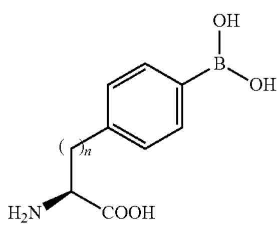

FX28

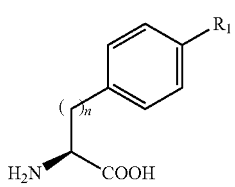

wherein, each $R_1$ is independently selected from H, $NH_2$, $NO_2$, Cl, $CF_3$, I, $COCH_3$, CN, C═CH, $N_3$, or Br;

each $R_2$ is independently selected from $NH_2$, $CF_3$, H, or $CH_3$;

a. each $R_3$ is independently selected from C═CH, H, $N_3$, or a vinyl group b. each $R_4$ is independently selected from $NH_2$, $R_2$ or $R_3$ c. each $R_5$ is independently selected from S or NH d. the index n is an integer in the range of 1 to 4, wherein j is an integer in the range of 1 to 14, and k is an integer in the range of 1 to 14.

Moreover, in certain embodiments, one or more of the previously published proteogenic or nonproteogenic artificial amino acids can be used either as part of the structure connecting the vicinal diol sensor to the drug substance and/or as part of the drug substance, wherein if the drug substance is insulin or other peptides, the artificial amino acid may be present in the insulin or the peptides. For example, in certain embodiments one or more of the following artificial amino acids can be used based on methods described in and referenced through, and the list of amino acid provided in: Liu, C. C.; Schultz, P. G. (2010). "Adding new chemistries to the genetic code". Annual Review of Biochemistry 79: 413-44. In certain embodiments artificial amino acids can be incorporated by peptide synthesis and these include the amino acids referenced herein as well as previously reported non-proteinogenic amino acids. For example, but not limited to, a portfolio of such non-proteinogenic amino acids including β-amino acids is available commercially from Sigma Aldrich and include amino acids such as 2,3 diaminopropinoic acid, 2,4 diaminopropinoic acid, ornithine, any beta or alpha amino acid. As an example, proteinogenic artificial amino acids described in F26-F41 can be incorporated through recombinant protein expression using methods and approaches described in United States Patent and Patent Application Nos. including: US2008/0044854, U.S. Pat. Nos. 8,518,666, 8,980,581, US2008/0044854, US2014/0045261, US2004/0053390, U.S. Pat. Nos. 7,229,634, 8,236,344, US2005/0196427, US2010/0247433, U.S. Pat. Nos. 7,198,915, 7,723,070, US2002/0042097, US2004/0058415, US2008/0026422, US2008/0160609, US2010/0184193, US2012/0077228, US2014/025599, U.S. Pat. Nos. 7,198,915, 7,632,492, and 7,723,070, as well as other proteinogenic artificial amino acids may be introduced recombinantly using methods and approaches described in: U.S. Pat. Nos. 7,736,872, 7,816,320, 7,829,310, 7,829,659, 7,883,866, 8,097,702, and 8,946,148.

In certain embodiments cyclic amino acid such as 3-hydroxyproline, 4-hydroxyproline, aziridine-2-carboxylic acid, azetidine-2-carboxylic acid, piperidine-2-carboxylic acid, 3-carboxy-morpholine, 3-carboxy-thiamorpholine, 4-oxaproline, pyroglutamic acid, 1,3-oxazolidine-4-carboxylic acid, 1,3-thiazolidine-4-carboxylic acid, 3-thiaproline, 4-thiaproline, 3-selenoproline, 4-selenoproline, 4- ketoproline, 3,4-dehydroproline, 4-aminoproline, 4-fluoroproline, 4,4-difluoroproline, 4-chloroproline, 4,4-dichloroproline, 4-bromoproline, 4,4-dibromoproline, 4-methylproline, 4-ethylproline, 4-cyclohexylproline, 3-phenylproline, 4-phenylproline, 3,4-phenylproline, 4-azidoproline, 4-carboxyproline, a-methylproline, a-ethylproline, a-propylproline, a-allylproline, a-benzylproline, a-(4-fluorobenzyl)proline, a-(2 -chlorobenzyl)proline, a-(3-chlorobenzyl)proline, a-(2-bromobenzyl)proline, a-(4-bromobenzyl)proline, a-(4-methylbenzyl)proline, a-(diphenylmethyl)proline, a-(naphthylmethyl)-proline, D-proline, or L-homoproline, (2S, 4S)-4-fluoro-L-proline, (2S, 4R)— 4-fluoro-L-proline, (2S)-3,4-dehydro-L-proline, (2S, 4S)-4-hydroxy-L-proline, (2S, 4R)-4-hydroxy-L-proline, (2S,4S)-4-azido-L-proline, (2S)-4,4-difluoro-L-proline, (2S)-azetidine-2-carboxylic acid, (2S)-piperidine-2-carboxylic acid, or (4R)-1,3-thiazolidine-4-carboxylic acid, can be used in the modified insulin.

It is to be understood that in certain embodiments, a set or specific orientation of amino acids is achieved by synthesis of the modified insulin using for example methods of Albericio, F. (2000). Solid-Phase Synthesis: A Practical Guide (1 ed.). Boca Raton: CRC Press. P. 848.

In certain embodiments the modified insulin can bind to a diol, a catechol, a hexose sugar, glucose, xylose, fucose, galactosamine, glucosamine, mannosamine, galactose, mannose, fructose, galacturonic acid, glucuronic acid, iduronic acid, mannuronic acid, acetyl galactosamine, acetyl glucosamine, acetyl mannosamine, acetyl muramic acid, 2-keto-3-deoxy-glycero-galacto-nononic acid, acetyl neuraminic acid, glycolyl neuraminic acid, a neurotransmitter, dopamine, and/or a disaccharide, and/or a polymer of saccharides and/or diols.

In certain embodiments, set or specific modified insulins that bind to proteins of interest (or molecules of interest) or have biophysical characteristics of interest including binding and responsiveness to small molecules of interest can be obtained by screening libraries of modified insulins which are either recombinantly expressed and chemically modified and/or chemically synthesized using standard FMOC or BOC protected amino acid synthesis on a solid support.

In certain embodiments the modified insulin is further conjugated to a chemical structure described by the following structures:

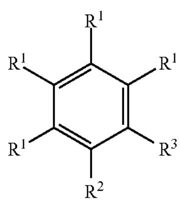

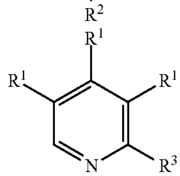

wherein:

- each $R^1$ is independently selected from H, F, Cl, $CH_3$, $B(OH)_2$, C═N, $NO_2$, $R^4$ or two adjacent $R^1$ groups are $CH_2$—O— and B(OH)—wherein —is the linkage between the two adjacent RI groups;
- each $R^2$ is independently selected from H, C═N, $(SO_2)NH(R^4)$, or $R^4$;
- each $R^3$ is independently selected from C° N, $CONH(R^4)$, $NH(R^4)$, $(SO_2)NH(R^4)$, or $R^4$.
- each $R^4$ is independently selected from H, $N_3$, C═CH, —$CH_2N(R^5)$ or a linker; and
- each $R^5$ is independently selected from H or a linker which covalently connects the structure to an amino acid side chain such as to a lysine side chain, for example through an amide bond to the epsilon amine of lysine.

In certain embodiments the modified insulin or the drug substance to which the vicinal diols sensor is conjugated may be further covalently conjugated using amide bonds to structures described by formulas F500-F520 below:

F500

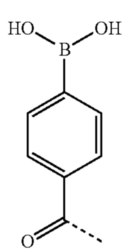

-continued

F501

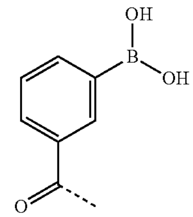

F502

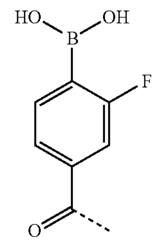

F503

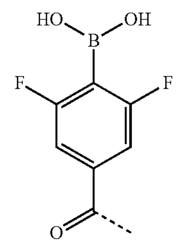

F504

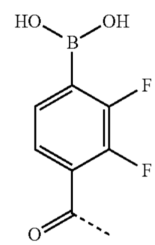

F505

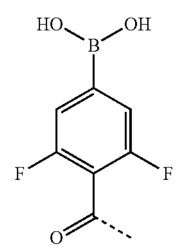

F506

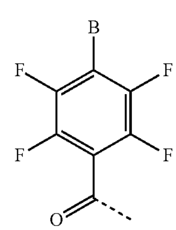

-continued
F507
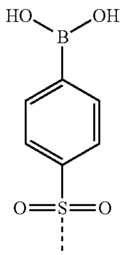
F508
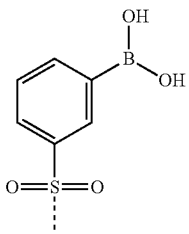
F509
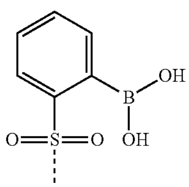
F510
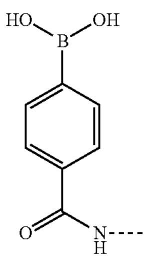
F511
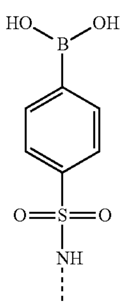
F512
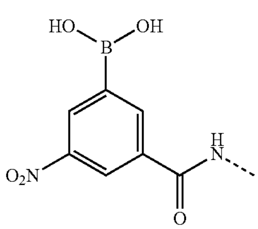
-continued
F513
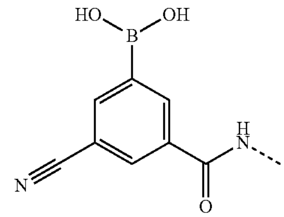
F514
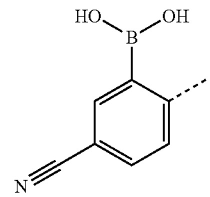
F515
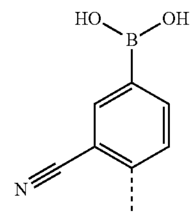
F516
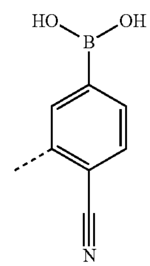
F517
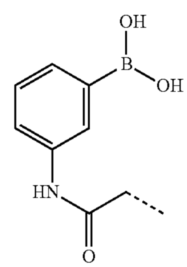
F518
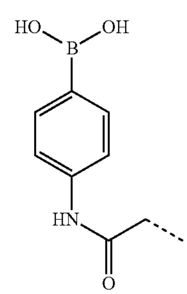

-continued

F519

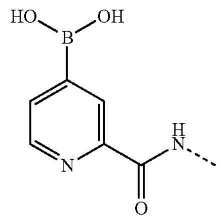

F520

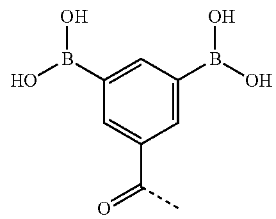

In certain embodiments such modifications may include the use of an N-methyliminodiacetic acid (MIDA) group to make a MIDA conjugated boronate or a MIDA boronate and that such modifications can be used during preparation of the boronates towards the final structures of use. In certain embodiments boronic acid pinacol esters are used towards the final structures and wherein the pinacol group can be readily removed by one skilled in the art. The MIDA-protected boronate esters are easily handled, stable under air, compatible with chromatography, and unreactive under standard anhydrous cross-coupling conditions and easily deprotected at room temperature under mild aqueous basic conditions such as 1M NaOH, or even $NaHCO_3$, or as described by Lee, S. J. et al. J. Am. Chem. Soc. 2008, 130, 466.

The biological mechanism by which wild type insulin binds to the insulin receptor as previously reported such in Nature 493, 241-245 (2013); Menting, J. G. et al. Protective hinge in insulin opens to enable its receptor engagement. Proc. Natl. Acad. Sci. U.S.A. 111, E3395-3404 (2014). In certain embodiments, binding of glucose to the vicinal diols on the modified insulin can be used to modulate the bioavailability of insulin, its solubility and/or its ability to engage the insulin receptor. The activity of such an insulin can be measured by, for example, but not limited to, using in vitro insulin receptor binding with TyrA14-$^{125}$I human insulin as a tracer and utilizing antibody binding beads together with an insulin receptor monoclonal antibody. In one or more embodiments, animal models can be used for in vivo assessment of insulin activity, including during glucose challenge using methods that are readily apparent to one skilled in the art. In certain embodiments the modified insulins are further modified or engineered to bind to a glucose transporter such that changes in concentrations of soluble glucose can modulate the affinity with which the modified insulins bind to the glucose transporter. In certain embodiments the modified insulins can bind in the body to an orally administered small molecule, and in certain embodiments such binding can be used to modulate the activity of modified insulins. In certain embodiments the modified insulin can be attached to another protein and/or drug that directly or indirectly impacts blood glucose levels and/or metabolism in the body. In addition to insulin, in certain embodiments the vicinal diol sensors are conjugated to a peptide and/or incretin hormone selected from the group consisting of glucagon, GLP-1, a GLP-1 analog, GLP-1 receptor agonist, IGF1, Amylin, and Relaxin. In certain embodiments insulin and/or these incretins contain at least one structure described by Formulae I, II or III. In certain embodiments an insulin contains at least two structures, each independently described by Formulae I, II, or III. In certain embodiments, at least one peptide sequence including 2 to 20 amino acids may be independently added to or removed (deleted) from the A-chain and/or the B- chain of the insulin.

In certain embodiments, the modified insulin is partially or fully expressed as a recombinant protein and side chains corresponding Formulas I-VI are introduced to side chains of existing amino acids, such as lysine, through chemical modification. The processes for expression of insulin in *E. coli* are known and can be easily performed by one skilled in the art for using the procedures outlined in Jonasson, Eur. J. Biochem. 236:656-661 (1996); Cowley, FEBS Lett. 402: 124-130 (1997); Cho, Biotechnol. Bioprocess Eng. 6: 144-149 (2001); Tikhonov, Protein Exp. Pur. 21: 176-182 (2001); Malik, Protein Exp. Pur 55: 100-1 1 1 (2007); Min, J. Biotech. 151:350-356 (2011)). In the most common process, the protein is expressed as a single-chain proinsulin construct with a fission protein or affinity tag. The modified insulin can be expressed as part of proinsulin, then modified chemically to conjugate through amide linkages to boronates of interest. This approach provides good yield and reduces experimental complexity by decreasing the number of processing steps and allows refolding in a native-like fashion; see for example, Jonasson, Eur. J. Biochem. 236:656-661 (1996); Cho, Biotechnol Bioprocess Eng. 6: 144-149 (2001); Tikhonov, Protein Exp. Pur. 21: 176-182 (2001); Min, J. Biotech. 151:350-356 (201 1)). When expressed in *E. coli*, proinsulin is usually found in inclusion bodies and can be easily purified by one skilled in the art.

In certain embodiments the modified insulin containing one or more of the vicinal diol sensors may be formulated for injection. For example, it may be formulated for injection into a subject, such as a human, the composition may be a pharmaceutical composition, such as a sterile, injectable pharmaceutical composition. The composition may be formulated for subcutaneous injection. In certain embodiments, the composition is formulated for transdermal, intradermal, transmucosal, nasal, inhalable, or intramuscular administration. The composition may be formulated in an oral dosage form or a pulmonary dosage form. Pharmaceutical compositions suitable for injection may include sterile aqueous solutions containing for example, sugars, polyalcohols such as mannitol and sorbitol, phenol, meta cresol, sodium chloride and dispersions may be prepared in glycerol, liquid polyethylene glycols, and mixtures thereof and in oils and the carrier can for example be a solvent or dispersion medium containing, for example, water, saccharides, ethanol, polyol (for example, glycerol, propylene glycol, and liquid polyethylene glycol, and the like), and/or suitable mixtures thereof. One skilled in the art recognizes that set or specific formulations can be developed to best suit the application and method of use of the modified insulins of the present disclosure. General considerations in the formulation and manufacture of pharmaceutical compositions, routes of administrating and including suitable pharmaceutically acceptable carriers may be found, for example, in Remington's Pharmaceutical Sciences, 19th ed., Mack Publishing Co., Easton, Pa., 1995. In certain embodiments the pharmaceutical composition may include zinc, i.e., $Zn^{2+}$ and/or polysaccharides. Certain zinc formulations for example described in U.S. Pat. No. 9,034,818. For example, the pharmaceutical composition may include zinc at a molar ratio to the modified insulin of about M:N where M is 1-11 and N is 6-1. In certain embodiments, such modified insulins may be stored in a pump, and that pump being either external or internal to the body releases the modified insulins. In certain cases, a pump may be used to release a constant amount of modified insulins wherein the insulin is glucose responsive based on the vicinal diol sensor on the insulin, and can automatically adjust activity based on the levels of glucose in the blood or release rate from injection site. In certain cases, the compositions may be formulated in dosage unit form for ease of administration and uniformity of dosage. In certain cases, the pharmaceutical composition may further include a second insulin type which provides fast-acting or basal-insulin in addition to the effect afforded by the modified insulin.

In another aspect the present disclosure includes kits wherein the kit includes modified insulins which contain vicinal diol sensors as well as a pharmaceutically acceptable carrier and for injections may include a syringe or pen. In various embodiments, a kit may include a syringe or pen which is pre-filled with a pharmaceutical composition that includes the modified insulin together with a liquid carrier. In certain embodiments, a kit may include a separate container such as a vial including a pharmaceutical composition that includes the modified insulin together with a dry carrier and an empty syringe or pen. In certain embodiments, such a kit may include a separate container which has a liquid carrier that can be used to reconstitute a given composition that can then be taken up into the syringe or pen. In certain embodiments, a kit may include instructions. In certain embodiments the kit may include blood glucose measuring devices which either locally or remotely calculate an appropriate or suitable dose of the modified insulin that is to be injected at a given point in time, or at regular intervals. Such a dosing regimen is unique to the patient and may, for example, be provided as instruction to program a pump either by a person or by a computer. The kit may include an electronic device which transfers blood glucose measurements to a second computer, either locally or elsewhere (for example, in the cloud) which then calculate the correct amount of modified insulin that needs to be used by the patient at a certain time.

In some aspects, embodiments of the present disclosure relate to a method for treating a disease or condition in a subject, including administering to the subject a composition including a modified insulin described herein wherein the insulin contains vicinal diol sensors responsive to glucose. In certain cases, the disease or condition may be hyperglycemia, type 2 diabetes, impaired glucose tolerance, type 1 diabetes, obesity, metabolic syndrome X, or dyslipidemia, diabetes during pregnancy, pre-diabetes, Alzheimer's disease, MODY 1, MODY 2 or MODY 3 diabetes, mood disorders, and/or psychiatric disorders. It will be appreciated that this combination approach may also be used with insulin resistant patients who are receiving an insulin sensitizer or a secondary drug for diabetes (such as, for example, a biguanide such as metformin, a glitazone) or/and an insulin secretagogue (such as, for example, a sulfonylurea, GLP-1, exendin-4 etc.) and/or amylin.

A modified insulin of the present disclosure may be administered to a patient who is receiving at least one additional therapy or taking at least one additional drug or therapeutic protein. At least one additional therapy is intended to treat the same disease or disorder as the administered modified insulin. In certain embodiments, at least one additional therapy is intended to treat a side-effect of the modified insulin. The timeframe of the two therapies may differ or be the same, they may be administered on the same or different schedules as long as there is a period when the patient is receiving a benefit from both therapies. The two or more therapies may be administered within the same or different formulations as long as there is a period when the patient is receiving a benefit from both therapies. Any of these approaches may be used to administer more than one anti-diabetic drug to a subject.

In one or more embodiments a therapeutically effective amount of the modified insulin, which is a suitable or sufficient amount to treat (meaning for example to ameliorate the symptoms of, delay progression of, prevent or delay recurrence of, delay onset of) the disease or condition at a reasonable benefit to risk ratio will be used. This may involve balancing of the efficacy and additional safety with toxicity. By additional safety, for example, it is meant that the modified insulin can be responsive to changes in blood glucose levels or level of other molecules to which the peptide is responsive, even when the patient is not actively monitoring the levels of that molecule, such as blood glucose levels at a given timeframe, for example during sleep. In general, therapeutic efficacy and toxicity may be determined by standard pharmacological procedures in cell cultures or in vivo with experimental animals, and for example measuring $ED_{50}$ and $LD_{50}$ for therapeutic index of the drug. In various embodiments, the average daily dose of insulin with the modified insulin is in the range of 5 to 400 U, (for example 30-150 U where 1 Unit of insulin is about 0.04 mg). In certain embodiments, an amount of modified insulin is administered on a daily basis or a bi-daily basis or every three days or every 4 days. In certain embodiments the basis is determined by an algorithm which can be computed by a computer. In certain embodiments, an amount of modified insulin with 5 to 10 times of these doses are administered on a weekly basis or at regular intervals. In certain embodiments, an amount of modified insulin with 10 to 20 times of these doses are administered on a bi-weekly basis or at regular intervals. In certain embodiments, an amount of modified insulin with 20 to 40 times of these doses are administered on a monthly basis.

The following examples and experimental data are provided for illustrative purposes only, and do not limit the scope of the embodiments of the present disclosure.

EXAMPLES

Preparation of small molecules diol-sensors and modified insulins

Example 1

(3-((2R,4R)-4-(5-borono-2-(methylsulfonyl)benzamido)-2-carbamoylpyrrolidine-1-carbonyl)-4-(methylsulfonyl)phenyl)boronic acid

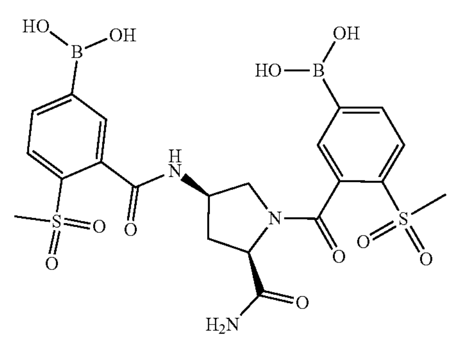

Synthesis of Example 1

Rink-amide resin (1.2 mmol/eq, 150 mg) was swelled in DMF (5 mL) for 20 minutes. The solution was removed under a stream of nitrogen and a solution of 20% piperidine in DMF (5 mL) was added to the resin and mixed for 5 minutes. The resin was washed with DMF (3×5 mL). A solution of (2R,4R)-1-(((9H-fluoren-9-yl)methoxy)carbonyl)-4-((((9H-fluoren-9-yl)methoxy)carbonyl)amino)pyrrolidine-2-carboxylic acid (280 mg, 0.5 mmol) with 1-[Bis(dimethylamino)methylene]-1H-1,2,3-triazolo[4,5-b]pyridinium 3-oxide hexafluorophosphate (HATU, 190 mg, 0.5 mmol), and DIPEA (200 μL) in DMF (5 mL) was added to the resin and mixed at 50° C. for 20 minutes. The resin was washed with DMF (3×5 mL) and a solution of 20% piperidine in DMF (5 mL) was added to the resin and mixed for 5 minutes. The resin was washed with DMF (3×5 mL) and a solution of 5-borono-2-(methylsulfonyl)benzoic acid (244 mg, 1 mmol) with HATU (380 mg, 1 mmol) and DIPEA (200 μL) in DMF (5 mL) was added to the resin and mixed at 50° C. for 30 minutes. The resin was washed with DMF (3×5 mL) and then with DCM (2×5 mL). A solution of trifluoroacetic acid with triisopropyl silane and water (95:2.5:2.5, 5 mL) was added to the resin and mixed for 90 minutes. The solution was collected and dried under vacuum, dissolved in DMSO (100 μL) and fractionated by reverse-phase (RP) flash chromatography on a C18 column with a gradient of 20% ACN in water with 0.1% TFA to 60% ACN in water with 0.1% TFA over 10 minutes. Pure fractions were isolated, combined, frozen, and lyophilized to yield Example 1 as a white powder (20 mg). Expected mass [M+H]: 582.11; Observed [M+H]:582.07

FIG. 1 is a mass spectrum plot confirming the synthesis of Example 1.

Example 2

((2S,4S)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carbonyl)glycine

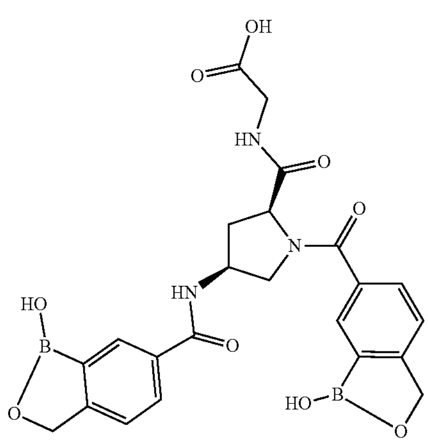 [SMILES: O=C(O)CNC(=O)[C@@H]1C[C@H](NC(=O)c2ccc3c(c2)B(O)OC3)CN1C(=O)c1ccc2c(c1)B(O)OC2]

Synthesis of Example 2

Chlorotrityl resin (1.5 mmol/eq, 300 mg) was swelled in dry DCM (5 mL) for 30 minutes. The solvent was removed under a stream of nitrogen and a solution of Fmoc-glycine (0.5M) in DCM with DIPEA (1M) was added immediately and gently mixed for 1 hr. The mixture was washed with DCM, and unreacted sites were capped with a solution of 20% MeOH in a solution of DCM and DIEA (1M) and mixed for 1 hr. The resin was washed with DCM (2×5 mL) and then DMF (2×5 mL). The solution was removed under a stream of nitrogen, and a solution of 20% piperidine in DMF (5 mL) was added to the resin and mixed for 5 minutes. The resin was washed with DMF (3×5 mL). A solution of (2R,4R)-1-(((9H-fluoren-9-yl)methoxy)carbonyl)-4-((((9H-fluoren-9-yl)methoxy)carbonyl)amino)pyrrolidine-2-carboxylic acid (280 mg, 0.5 mmol) with 1-[Bis(dimethylamino)methylene]-1H-1,2,3-triazolo[4,5-b]pyridinium 3-oxide hexafluorophosphate (HATU, 190 mg, 0.5 mmol), and DIPEA (200 μl) in DMF (5 mL) was added to the resin and mixed at 50° C. for 20 minutes. The resin was washed with DMF (3×5 mL), and a solution of 20% piperidine in DMF (5 mL) was added to the resin and mixed for 5 minutes. The resin was washed with DMF (3×5 mL), and a solution of 1-hydroxy-1,3-dihydrobenzo[c][1,2]oxaborole-6-carboxylic acid (177 mg, 1 mmol) with HATU (380 mg, 1 mmol) and DIPEA (200 μL) in DMF (5 mL) was added to the resin and mixed at 50° C. for 30 minutes. The resin was washed with DMF (3×5 mL) and then DCM (3×5 mL). A solution of trifluoroacetic acid with triisopropyl silane and water (95:2.5:2.5, 5 mL) was added to the resin and mixed for 90 minutes. The solution was collected and dried under vacuum, dissolved in DMSO (100 μL) and fractionated by reverse-phase (RP) flash chromatography on a C18 column with a gradient of 20% ACN in water with 0.1% TFA to 60% ACN in water with 0.1% TFA over 10 minutes. Pure fractions were isolated, combined, frozen, and lyophilized to yield Example 2 as a white powder (27 mg). Expected mass [M+H]: 508.16; Observed [M+H]: 508.13

Figure 2:
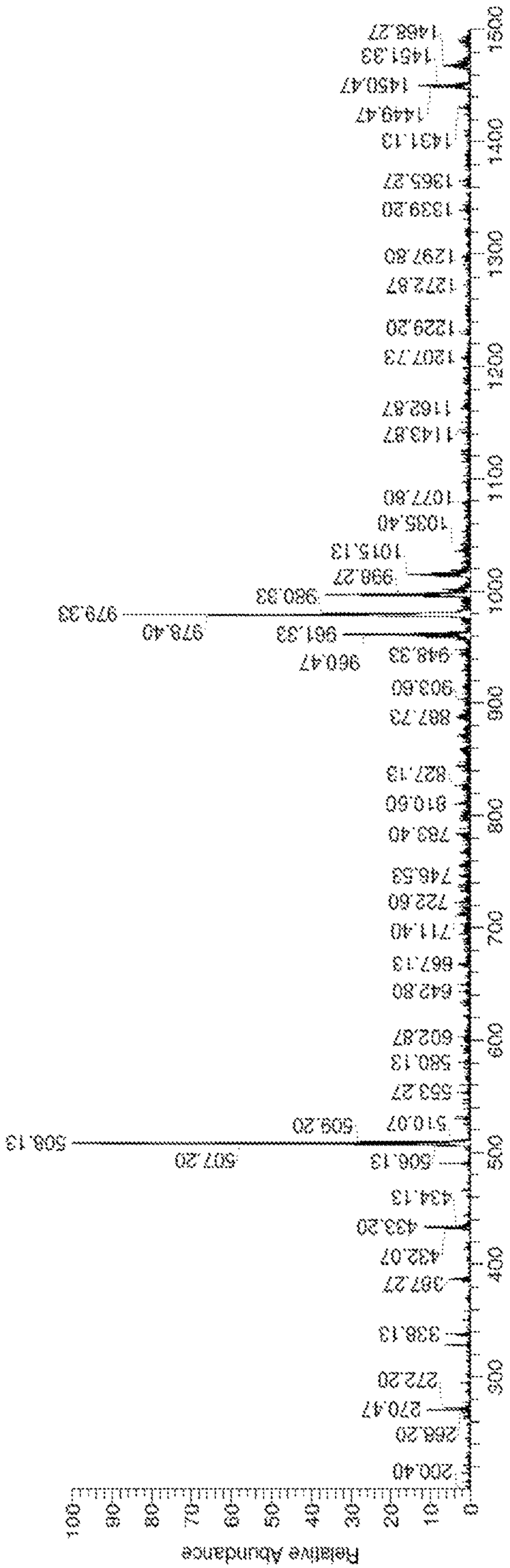

FIG. 2 is a mass spectrum plot confirming the synthesis of Example 2.

Example 3

((2S,4S)-1-(5-borono-2-nitrobenzoyl)-4-(1-hydroxy-1,3-dihydrobenzo[c][1,2]oxaborole-6-carboxamido)pyrrolidine-2-carbonyl)glycine

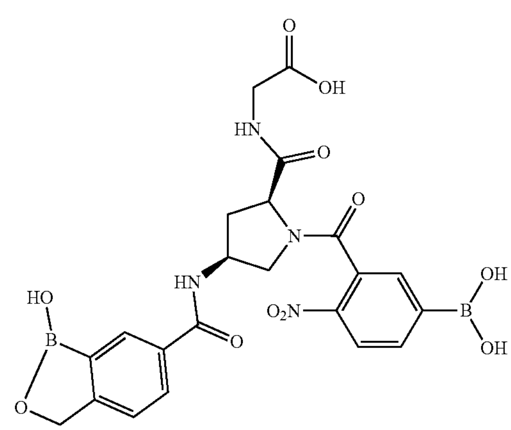 [SMILES: O=C(O)CNC(=O)[C@@H]1C[C@H](NC(=O)c2ccc3c(c2)B(O)OC3)CN1C(=O)c1cc(B(O)O)ccc1[N+](=O)[O-]]

Synthesis of Example 3

Figure 3:
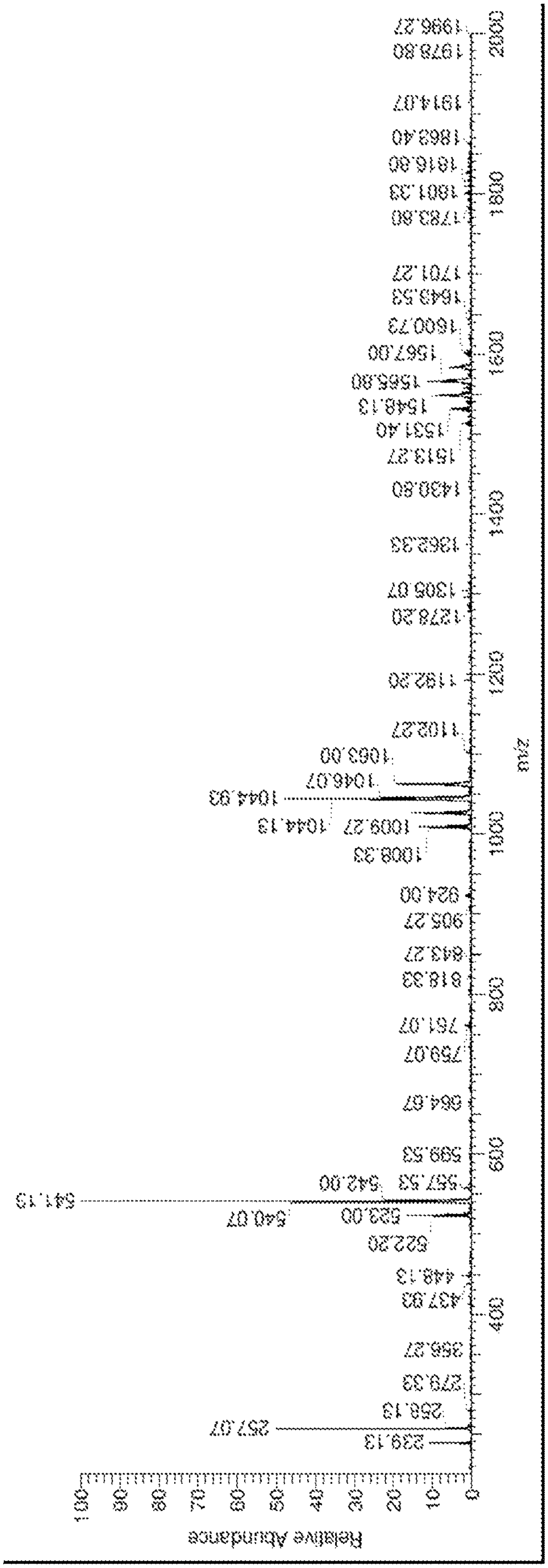

Chlorotrityl resin (1.5 mmol/eq, 300 mg) was swelled in dry DCM (5 mL) for 30 mins. The solvent was removed under a stream of nitrogen and a solution of Fmoc-glycine (0.5M) in DCM with DIPEA (1M) was added immediately and gently mixed for 1 hr. The mixture was washed with DCM, and unreacted sites were capped with a solution of 20% MeOH in a solution of DCM and DIEA (1M) and mixed for 1 hr. The resin was washed with DCM (2×5 mL) and then DMF (2×5 mL). The solution was removed under a stream of nitrogen, and a solution of 20% piperidine in DMF (5 mL) was added to the resin and mixed for 5 minutes. The resin was washed with DMF (3×5 mL). A solution of (2R,4R)-1-(((9H-fluoren-9-yl)methoxy)carbonyl)-4-((1-(4,4-dimethyl-2,6-dioxocyclohexylidene)ethyl)amino)pyrrolidine-2-carboxylic acid (258 mg, 0.5 mmol) with 1-[Bis(dimethylamino)methylene]-1H-1,2,3-triazolo[4,5-b]pyridinium 3-oxide hexafluorophosphate (HATU, 190 mg, 0.5 mmol), and DIPEA (200 p L) in DMF (5 mL) was added to the resin and mixed at 50° C. for 20 minutes. The resin was washed with DMF (3×5 mL) and a solution of 20% piperidine in DMF (5 mL) was added to the resin and mixed for 5 minutes. The resin was washed with DMF (3×5 mL) and a solution of 5-borono-2-nitrobenzoic acid (105 mg, 0.5 mmol) with HATU (190 mg, 0.5 mmol) and DIPEA (200 μL) in DMF (5 mL) was added to the resin and mixed at 50° C. for 30 minutes. The resin was washed with DMF (3×5 mL) and a solution of 4% hydrazine in DMF was added to the resin (3×5 mL) and mixed for 5 minutes. The resin was washed with DMF (3×5 mL) and a solution of 1-hydroxy-1,3-dihydrobenzo[c][1,2]oxaborole-6-caiboxylic acid (89 mg, 0.5 mmol) with HATU (190 mg, 0.5 mmol) and DIPEA (200 μL) in DMF (5 mL) was added to the resin and mixed at 50° C. for 30 minutes. The resin was washed with DMF (3×5 mL) and then DCM (3×5 mL). A solution of trifluoroacetic acid with triisopropyl silane and water (95:2.5:2.5, 5 mL) was added to the resin and mixed for 90 minutes. The solution was collected and dried under vacuum, dissolved in DMSO (100p L) and fractionated by reverse-phase (RP) flash chromatography on a C18 column with a gradient of 20% ACN in water with 0.1% TFA to 60% ACN in water with 0.1% TFA over 10 minutes. Pure fractions were isolated, combined, frozen, and lyophilized to yield Example 3 as a white powder (15 mg). Expected mass [M+H]: 541.15; Observed [M+H]: 541.13 FIG. 3 is a mass spectrum plot confirming the synthesis of Example 3.

Example 4

(S)-(3-((1-amino-3-(1-hydroxy-1,3-dihydrobenzo[c][1,2]oxaborole-6-carboxamido)-1-oxopropan-2-yl)carbamoyl)-5-nitrophenyl)boronic acid

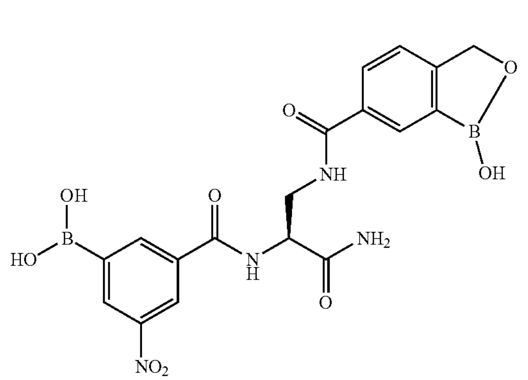 [SMILES: NC(=O)[C@H](CNC(=O)c1ccc2c(c1)B(O)OC2)NC(=O)c1cc(B(O)O)cc([N+](=O)[O-])c1]

Synthesis of Example 4

Rink-amide resin (1.2 mmol/eq, 150 mg) was swelled in DMF (5 mL) for 20 minutes. The solution was removed under a stream of nitrogen and a solution of 20% piperidine in DMF (5 mL) was added to the resin and mixed for 5 minutes. The resin was washed with DMF (3×5 mL). A solution of Fmoc-NR-(4,4-dimethyl-2,6-dioxocyclohex-1-ylidene)-3-methylbutyl-L-2,3-diaminopropionic acid (266 mg, 0.5 mmol) with 1-[Bis(dimethylamino)methylene]-1H-1,2,3-triazolo[4,5-b]pyridinium 3-oxide hexafluorophosphate (HATU, 190 mg, 0.5 mmol), and DIPEA (200 p L) in DMF (5 mL) was added to the resin and mixed at 50° C. for 20 minutes. The resin was washed with DMF (3×5 mL) and a solution of 20% piperidine in DMF (5 mL) was added to the resin and mixed for 5 minutes. The resin was washed with DMF (3×5 mL) and a solution of 20% piperidine in DMF (5 mL) was added to the resin and mixed for 5 minutes. The resin was washed with DMF (3×5 mL) and a solution of 3-borono-5-nitrobenzoic acid (105 mg, 0.5 mmol) with HATU (190 mg, 0.5 mmol) and DIPEA (200 μL) in DMF (5 mL) was added to the resin and mixed at 50° C. for 30 minutes. The resin was washed with DMF (3×5 mL) and a solution of 4% hydrazine in DMF was added to the resin (3×5 mL) and mixed for 5 minutes. The resin was washed with DMF (3×5 mL) and a solution of 1-hydroxy-1,3-dihydrobenzo[c][1,2]oxaborole-6-carboxylic acid (89 mg, 0.5 mmol) with HATU (190 mg, 0.5 mmol) and DIPEA (200 μL) in DMF (5 mL) was added to the resin and mixed at 50° C. for 30 minutes. The resin was washed with DMF (3×5 mL) and then DCM (3×5 mL). A solution of trifluoroacetic acid with triisopropyl silane and water (95:2.5:2.5, 5 mL) was added to the resin and mixed for 90 minutes. The solution was collected and dried under vacuum, dissolved in DMSO (100 μL) and fractionated by reverse-phase (RP) flash chromatography on a C18 column with a gradient of 20% ACN in water with 0.1% TFA to 60% ACN in water with 0.1% TFA over 10 minutes. Pure fractions were isolated, combined, frozen, and lyophilized to yield Example 4 as a white powder (11 mg). Expected mass [M+H]: 457.13; Observed [M+H]: 457.00 [M+H−$H_2O$]: 440.13

Figure 4:
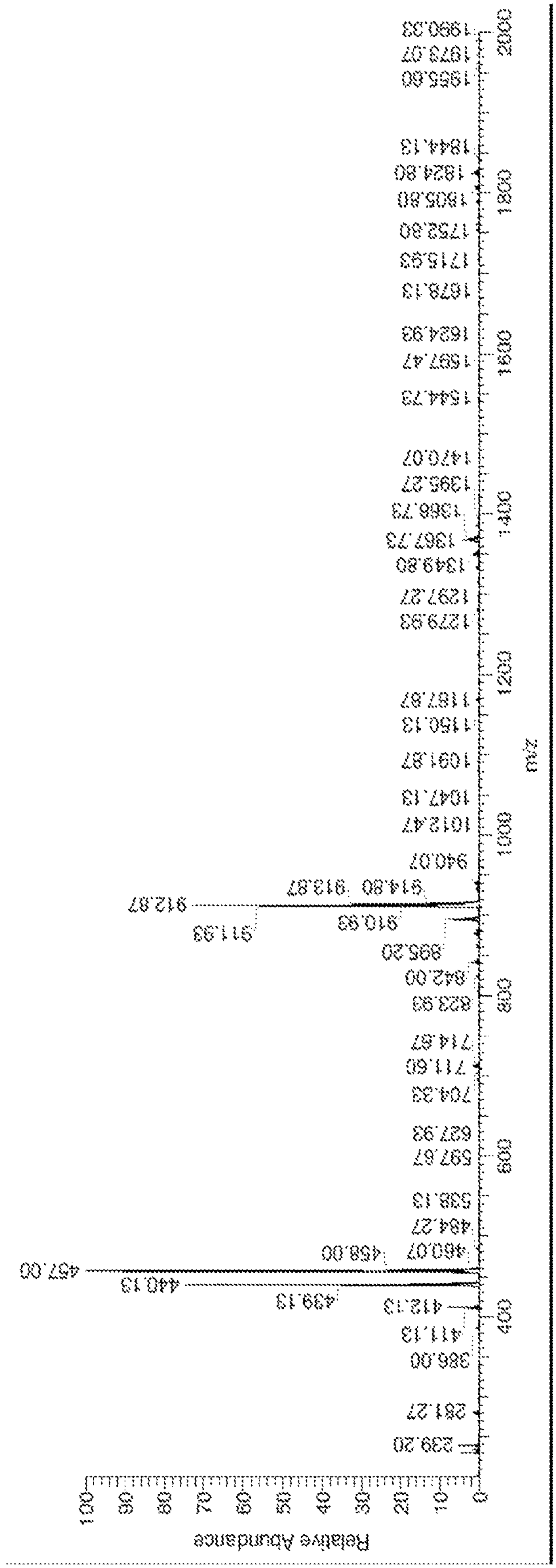

FIG. 4 is a mass spectrum plot confirming the synthesis of Example 4.

Example 5

(S)-(3-((1-amino-3-(5-borono-2-nitrobenzamido)-1-oxopropan-2-yl)carbamoyl)-4-nitrophenyl)boronic acid

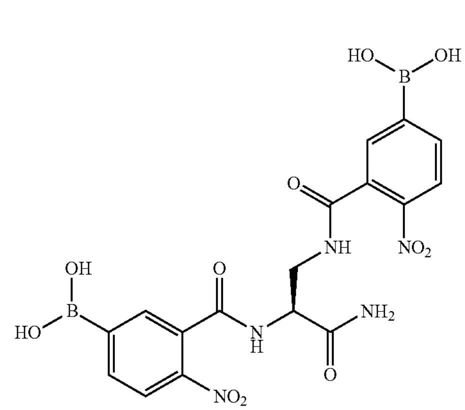 [SMILES: NC(=O)[C@H](CNC(=O)c1cc(B(O)O)ccc1[N+](=O)[O-])NC(=O)c1cc(B(O)O)ccc1[N+](=O)[O-]]

Figure 5:
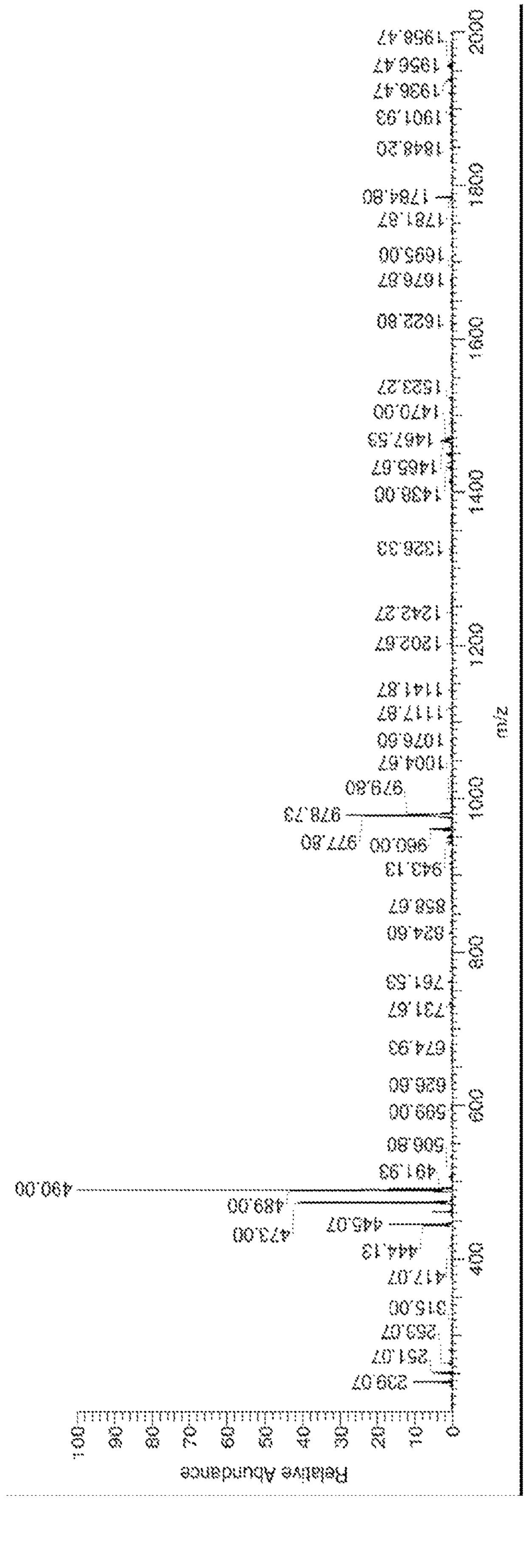

Example 5 was synthesized similar to Example 4 and contains F27 and F1. Expected mass [M+H]: 490.11; Observed [M+H]: 490.00 FIG. 5 is a mass spectrum plot confirming the synthesis of Example 5.

Example 6

(S)-(3-((1-amino-3-(1-hydroxy-4-(trifluoromethyl)-1,3-dihydrobenzo[c][1,2]oxaborole-6-carboxamido)-1-oxopropan-2-yl)carbamoyl)-5-nitrophenyl)boronic acid

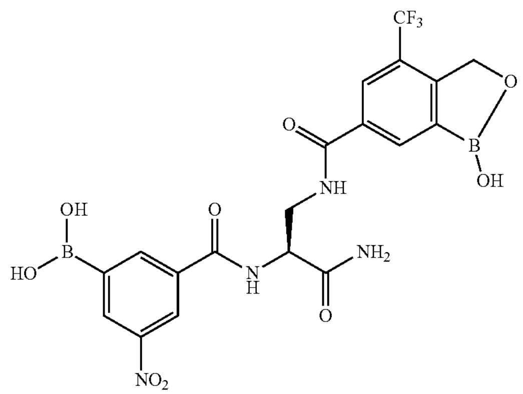 [SMILES: NC(=O)[C@H](CNC(=O)c1cc2c(c(C(F)(F)F)c1)COB2O)NC(=O)c1cc(B(O)O)cc([N+](=O)[O-])c1]

Example 6 was synthesized similar to Example 4 and contains F27, F1, and F2. Expected mass [M+H]: 525.11; Observed [M+H]: 525.00 [M+H−$H_2O$]: 508.07

Figure 6:
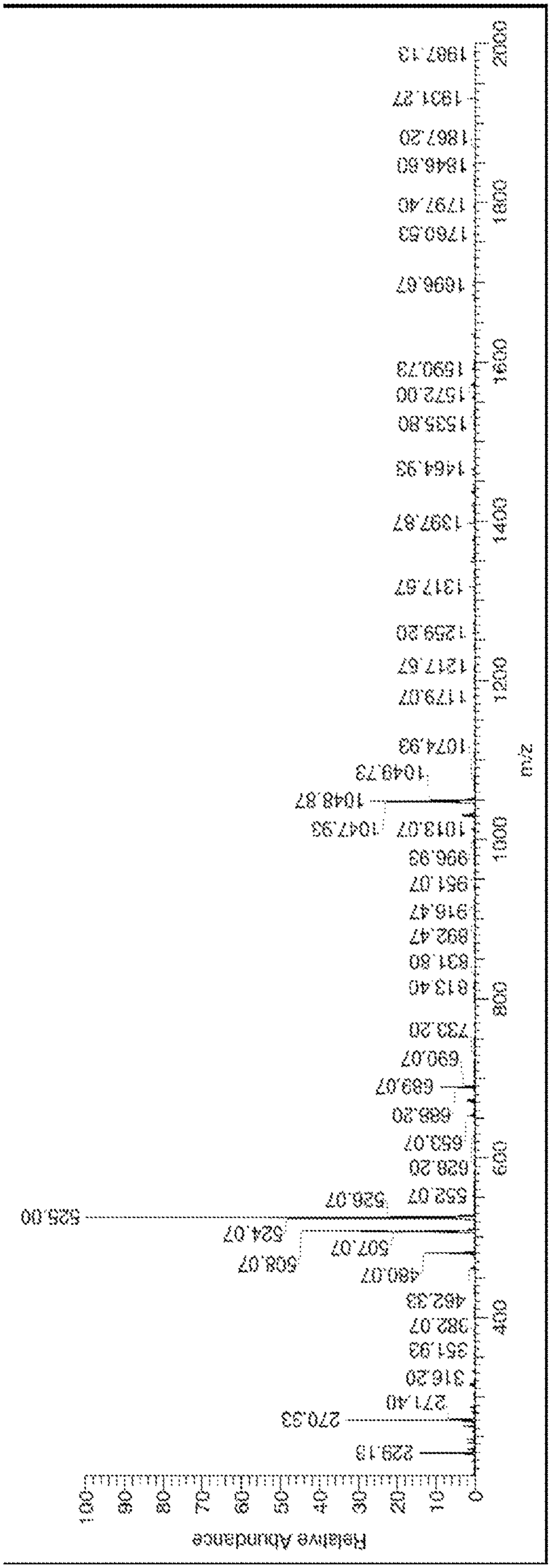

FIG. 6 is a mass spectrum plot confirming the synthesis of Example 6.

10 Example 7

(S)-(3-((1-amino-3-(J-hydroxy-1,3-dihydrobenzo[c][1,2]oxaborole-6-carboxamido)-1-oxopropan-2-yl)carbamoyl)-4-nitrophenyl)boronic acid

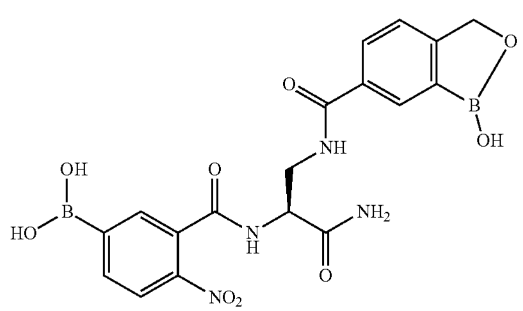 [SMILES: NC(=O)[C@H](CNC(=O)c1ccc2c(c1)B(O)OC2)NC(=O)c1cc(B(O)O)ccc1[N+](=O)[O-]]

Example 7 was synthesized similar to Example 4 and contains F27, F1, and F2. Expected mass [M+H]: 457.13; Observed [M+H]: 457.07 [M+H−$H_2O$]: 439.07

Figure 7:
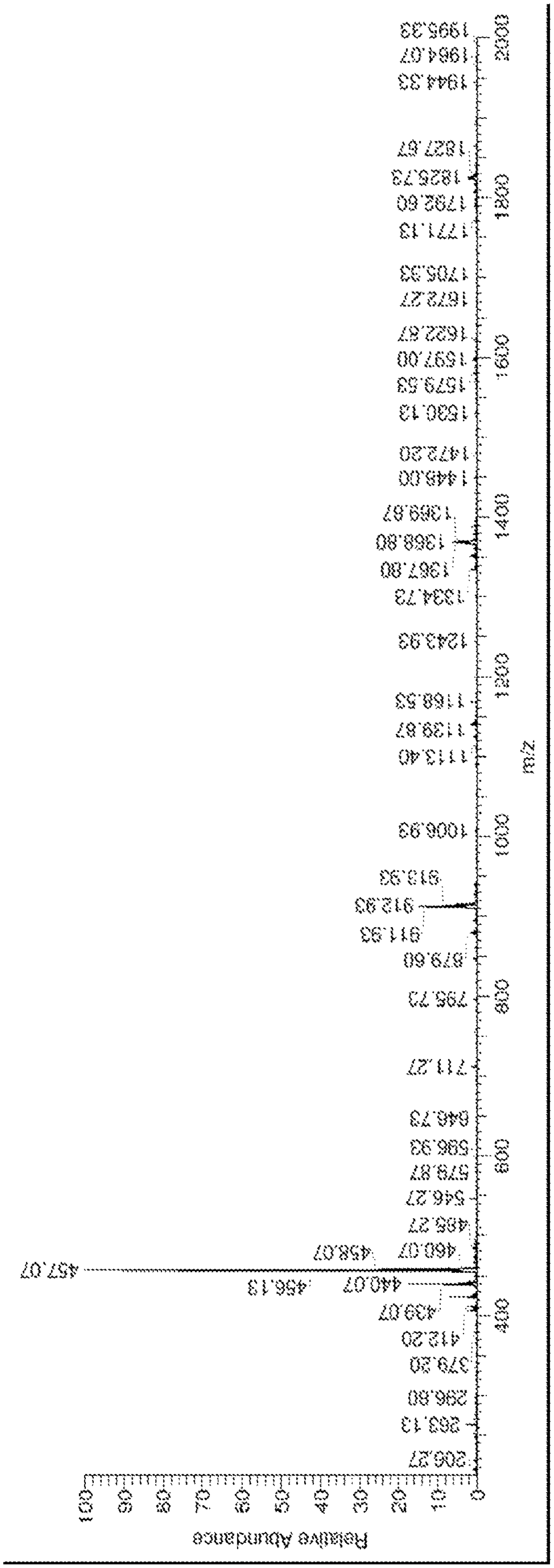

FIG. 7 is a mass spectrum plot confirming the synthesis of Example 7.

Example 8

(S)-(2-((1-amino-3-(3-boronothiophene-2-carboxamido)-1-oxopropan-2-yl)carbamoyl)thiophen-3-yl)boronic acid

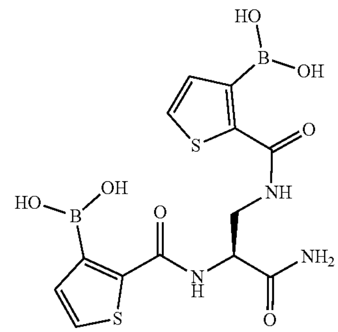 [SMILES: NC(=O)[C@H](CNC(=O)c1sccc1B(O)O)NC(=O)c1sccc1B(O)O]

Example 8 was synthesized similar to Example 4 and contains F27, F1, and F2. Expected mass [M+H]: 411.05; [M+H−2×$H_2O$]: 376.00

Figure 8:
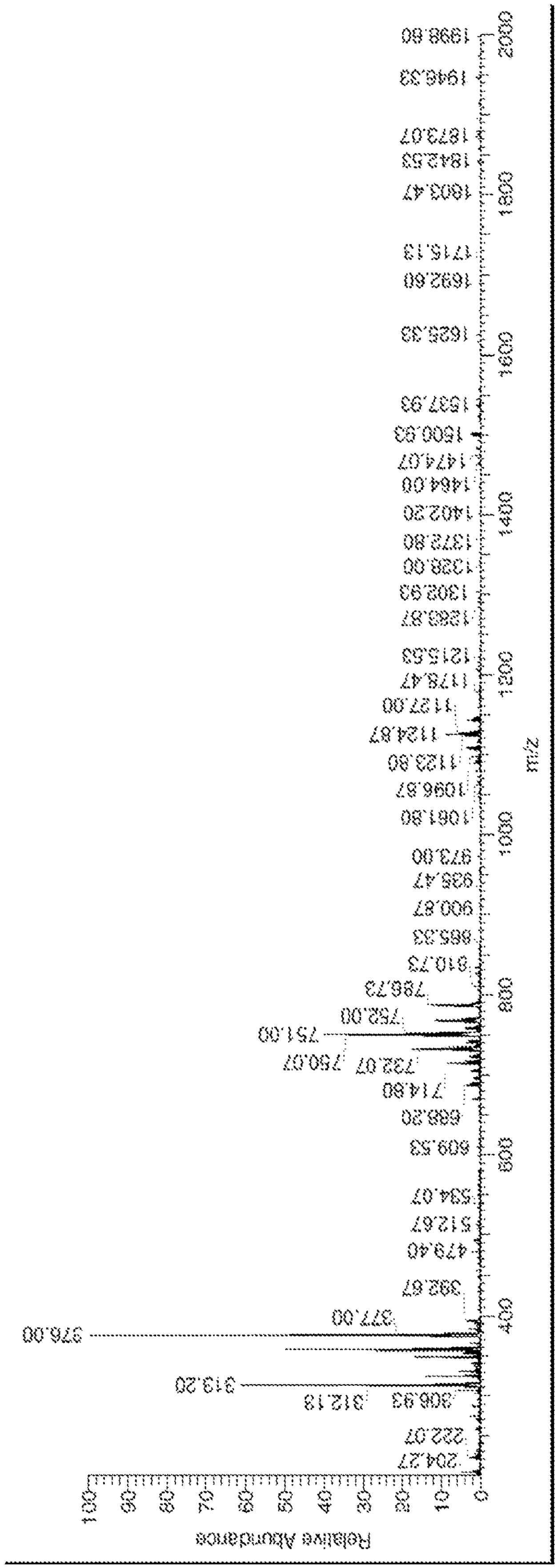

FIG. 8 is a mass spectrum plot confirming the synthesis of Example 8.

Example 9

N-(3-(3-borono-5-nitrobenzamido)propyl)-N-(3-borono-5-nitrobenzoyl)glycine

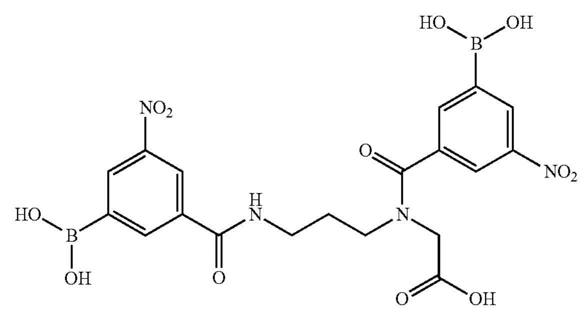 [SMILES: O=C(O)CN(CCCNC(=O)c1cc(B(O)O)cc([N+](=O)[O-])c1)C(=O)c1cc(B(O)O)cc([N+](=O)[O-])c1]

Synthesis of Example 9

Chlorotrityl resin (1.5 mmol/eq, 300 mg) was swelled in dry DCM (5 mL) for 30 mins. The solvent was removed under a stream of nitrogen and a solution of bromoacetic acid (1M) in DCM with DIPEA (1M) was added immediately and gently mixed for 1 hr. The mixture was washed with DCM and unreacted sites were capped with a solution of 20% MeOH in a solution of DCM and DIEA (1M) and mixed for 1 hr. The resin was washed with DCM (2×5 mL) and then DMF (2×5 mL). A solution of 1,3-diaminopropane (1M) in DMF (5 mL) was added to the resin and heated at 50° C. for 10 minutes. The resin was washed with DMF (3×5 mL), and a solution of 3-borono-5-nitrobenzoic acid (0.2 M, 5 mL) in DMF with 1 M N,N'-diisopropylcarbodiimide (DIC, 1M, 1 mL), Oxyma (0.5 M, 2 mL) in DMF and heated at 50° C. for 30 min. The resin was washed with DMF (3×5 mL) and then DCM (3×5 mL). A solution of trifluoroacetic acid with triisopropyl silane and water (95:2.5:2.5, 5 mL)

was added to the resin and mixed for 90 minutes. The solution was collected and dried under vacuum, dissolved in DMSO (100 μL) and fractionated by reverse-phase (RP) flash chromatography on a C18 column with a gradient of 20% ACN in water with 0.1% TFA to 60% ACN in water with 0.1% TFA over 10 minutes. Pure fractions were isolated, combined, frozen, and lyophilized to yield example 9 as a white powder (15 mg). Expected mass [M+H]: 519.13; Observed [M+H]:519.20 [M+H−$H_2O$]:501.33

Figure 9:
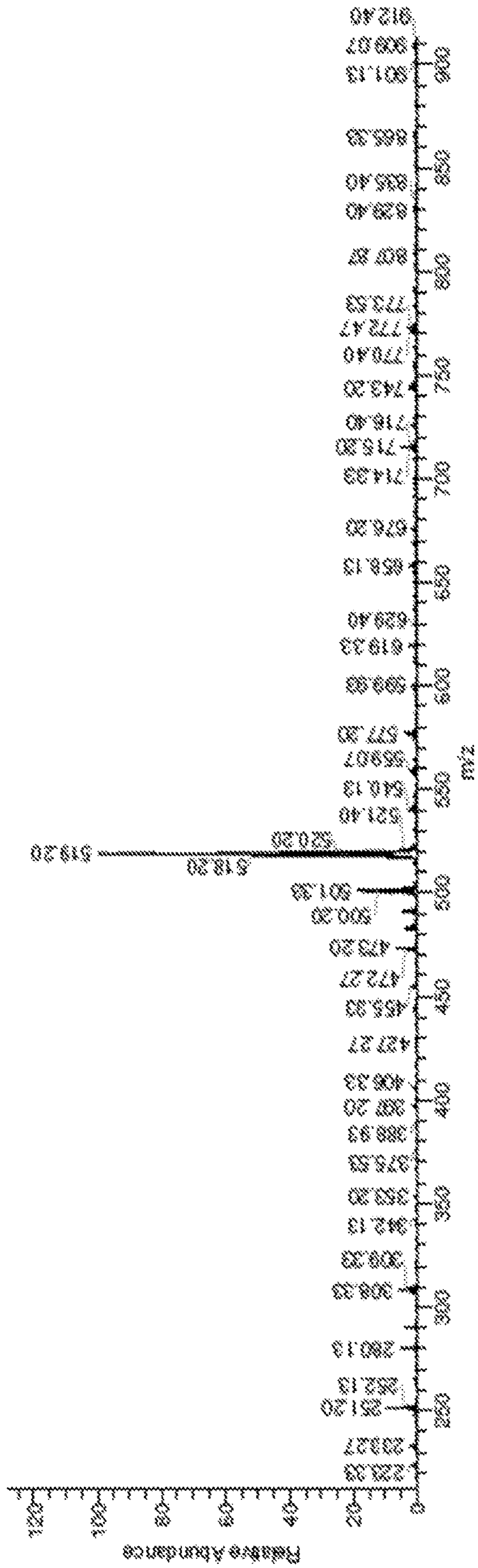

FIG. 9 is a mass spectrum plot confirming the synthesis of Example 9.

Example 10

N-(4-(3-borono-5-nitrobenzamido)butyl)-N-(3-borono-5-nitrobenzoyl)glycine

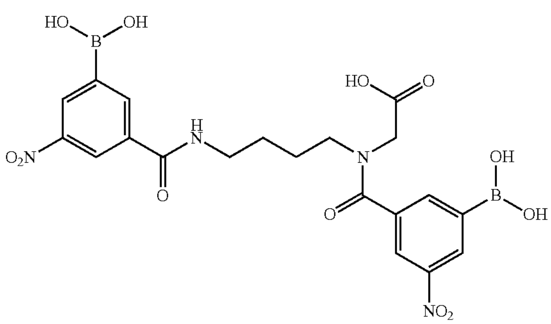 [SMILES: O=C(O)CN(CCCCNC(=O)c1cc(B(O)O)cc([N+](=O)[O-])c1)C(=O)c1cc(B(O)O)cc([N+](=O)[O-])c1]

Example 10 was synthesized similar to Example 9 and is derived from FF2 and F1. Expected mass [M+H]: 533.14; Observed [M+H]: 533.27; [M+H−$H_2O$]: 515.2

Figure 10:
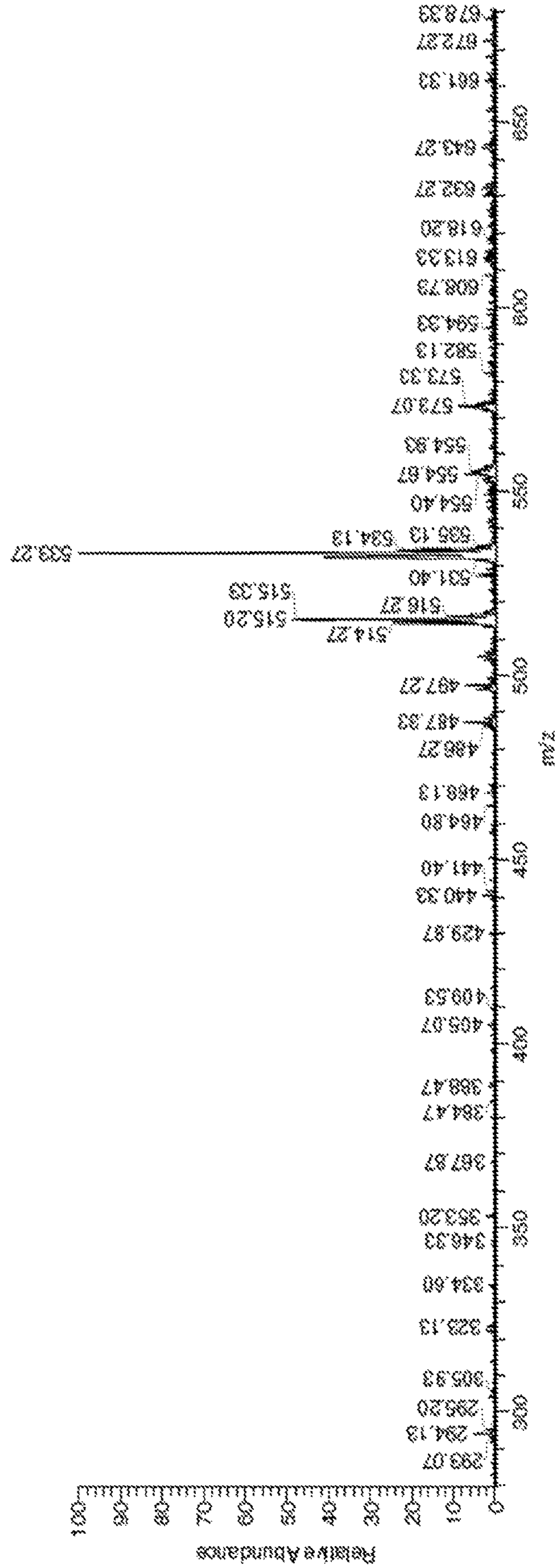

FIG. 10 is a mass spectrum plot confirming the synthesis of Example 10.

Example 11

N-(5-(3-borono-5-nitrobenzamido)pentyl)-N-(3-borono-5-nitrobenzoyl)glycine

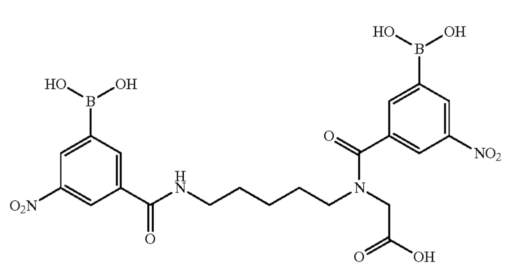 [SMILES: O=C(O)CN(CCCCCNC(=O)c1cc(B(O)O)cc([N+](=O)[O-])c1)C(=O)c1cc(B(O)O)cc([N+](=O)[O-])c1]

Example 11 was synthesized similar to Example 9 and is derived from FF2 and F1. Expected mass [M+H]: 547.16; Observed [M+H]: 547.18; [M+H−$H_2O$]:529.17

Figure 11:
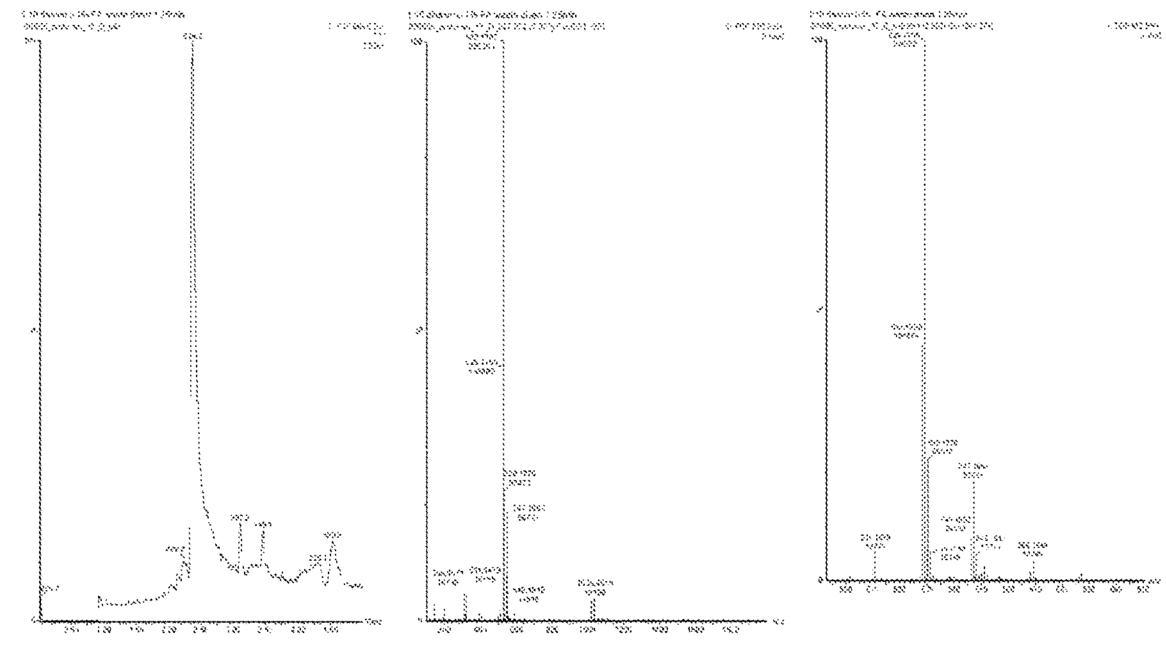

FIG. 11 is a mass spectrum plot confirming the synthesis of Example 11.

Example 12

N-(4-((3-borono-5-nitrobenzamido)methyl)benzyl)-N-(3-borono-5-nitrobenzoyl)glycine

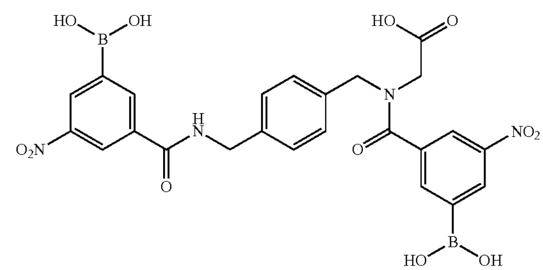 [SMILES: O=C(O)CN(Cc1ccc(CNC(=O)c2cc(B(O)O)cc([N+](=O)[O-])c2)cc1)C(=O)c1cc(B(O)O)cc([N+](=O)[O-])c1]

Example 12 was synthesized similar to Example 9 and is derived from FF8 and F1. Expected mass [M+H]: 581.14; Observed [M+H−$H_2O$]: 563.16

Figure 12:
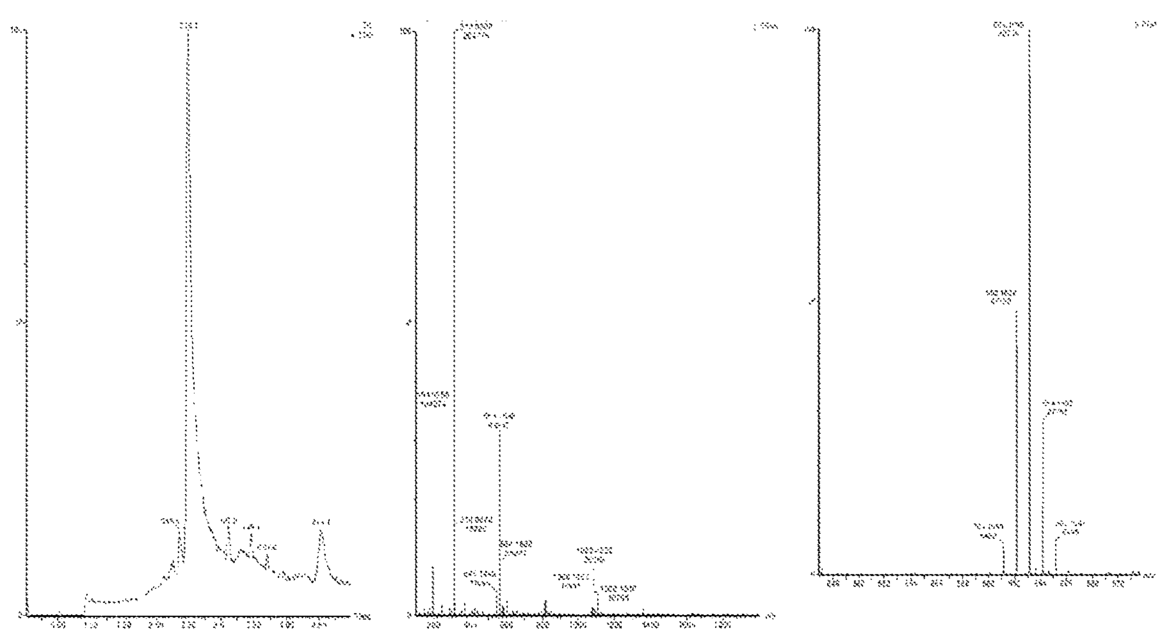

FIG. 12 is a mass spectrum plot confirming the synthesis of Example 12.

Example 13

N-(3-((3-borono-5-nitrobenzamido)methyl)benzyl)-N-(3-borono-5-nitrobenzoyl)glycine

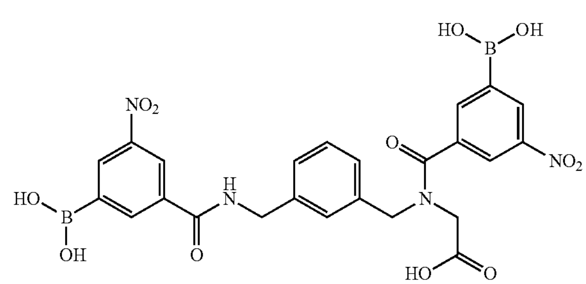 [SMILES: O=C(O)CN(Cc1cccc(CNC(=O)c2cc(B(O)O)cc([N+](=O)[O-])c2)c1)C(=O)c1cc(B(O)O)cc([N+](=O)[O-])c1]

Example 13 was synthesized similar to Example 9 and is derived from FF4 and F1. Expected mass [M+H]: 581.14; Observed [M+H]: 581.18 [M+H−$H_2O$]:563.16

Figure 13:
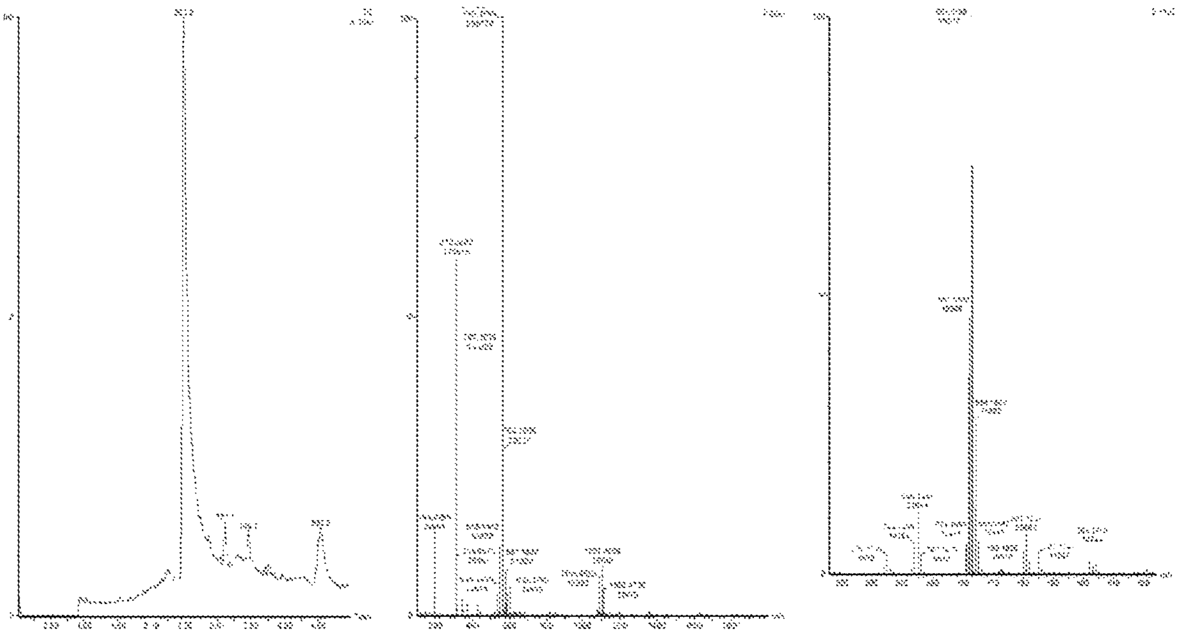

FIG. 13 is a mass spectrum plot confirming the synthesis of Example 13.

Example 14

N-(2-amino-2-oxoethyl)-1-hydroxy-N-((1R,2R)-2-(1-hydroxy-1,3-dihydrobenzo[c][1,2]oxaborole-6-carboxamido)cyclohexyl)-1,3-dihydrobenzo[c][1,2]oxaborole-6-carboxamide

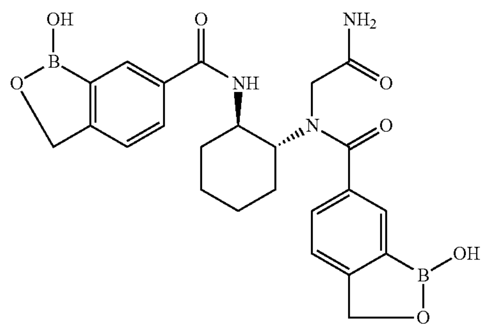 [SMILES: NC(=O)CN(C(=O)c1ccc2c(c1)B(O)OC2)[C@@H]1CCCC[C@H]1NC(=O)c1ccc2c(c1)B(O)OC2]

Synthesis of Example 14

Rink-amide resin (1.2 mmol/eq, 150 mg) was swelled in DMF (5 mL) for 20 minutes. The solution was removed under a stream of nitrogen and a solution of 20% piperidine in DMF (5 mL) was added to the resin and mixed for 5 minutes. The resin was washed with DMF (3×5 mL). Bromoacetic acid in DMF (1 M, 5 mL) with 1 M N,N'-diisopropylcarbodiimide (DIC, 1M, 1 mL) in DMF was added to the resin and heated at 50° C. for 10 min. The reaction mixture was washed with DMF (2×5 mL). A solution of (1R,2S)-cyclohexane-1,2-diamine (2 M, 5 mL) in DMF was added to the reaction mixture and heated at 50° C. for 10 min. The resin 20 was washed with DMF (3×5 mL), and a solution of 1-hydroxy-1,3-dihydrobenzo[c][1,2]oxaborole-6-carboxylic acid (0.2 M, 5 mL) in DMF with 1 M N,N'-diisopropylcarbodiimide (DIC, 1M, 1 mL), Oxyma (0.5 M, 2 mL) in DMF was added and heated at 50° C. for 30 min. The resin was washed with DMF (3×5 mL) and then DCM (3×5 mL). A solution of trifluoroacetic acid with triisopropyl silane and water (95:2.5:2.5, 5 mL) was added to the resin and mixed for 90 minutes. The solution was collected and dried under vacuum, dissolved in DMSO (100 μL) and fractionated by reverse-phase (RP) flash chromatography on a C18 column with a gradient of 20% ACN in water with 0.1% TFA to 60% ACN in water with 0.1% TFA over 10 minutes. Pure fractions were isolated, combined, frozen, and lyophilized to yield Example 14 as a white powder (5 mg). Expected mass [M+H]: 492.19; Observed [M+H]: 492.14 [M+H−$H_2O$]: 475.27; [M+Na]:513.07

Figure 14:
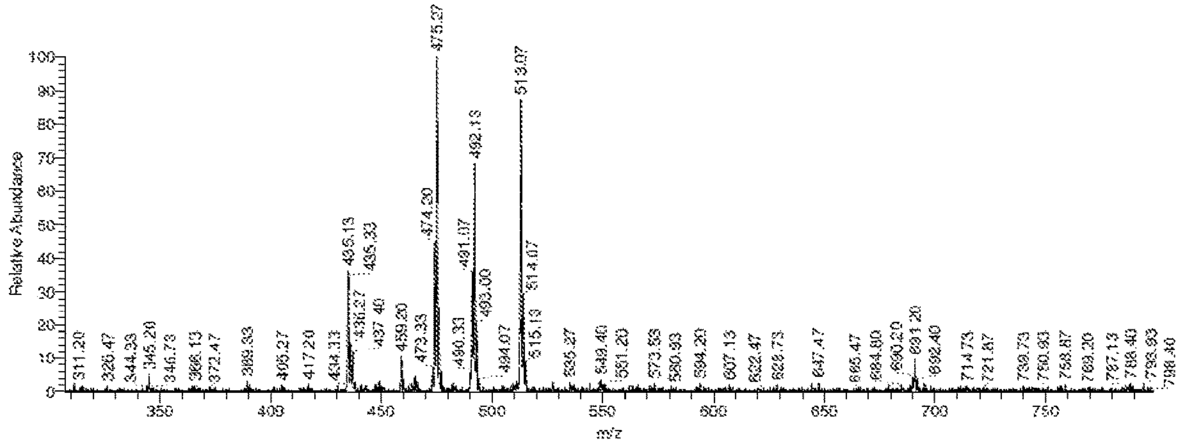

FIG. 14 is a mass spectrum plot confirming the synthesis of Example 14.

Example 15

N-(3-(3-borono-4-fluorobenzamido)propyl)-N-(3-borono-4-fluorobenzoyl)glycine

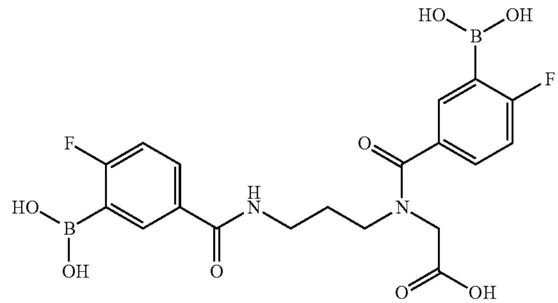 [SMILES: O=C(O)CN(CCCNC(=O)c1ccc(F)c(B(O)O)c1)C(=O)c1ccc(F)c(B(O)O)c1]

Example 15 was synthesized similar to Example 9 and is derived from FF2 and F1. Expected mass [M+H]: 465.14; Observed [M+H]: 465.2; [M+H−$H_2O$]:447.1

Figure 15:
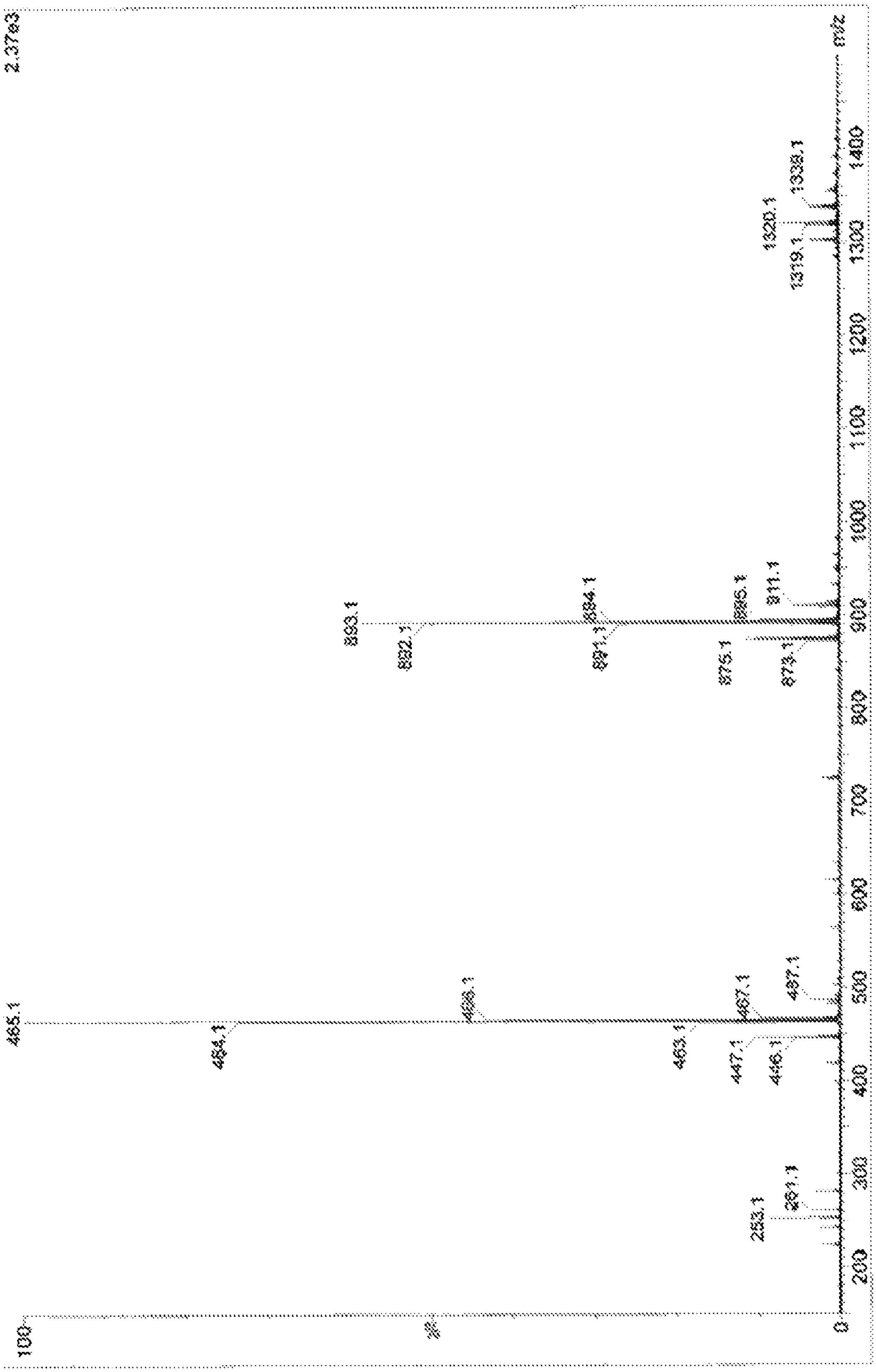

FIG. 15 is a mass spectrum plot confirming the synthesis of Example 15.

Example 16

N-(5-(3-borono-4-fluorobenzamido)pentyl)-N-(3-borono-4-fluorobenzoyl)glycine

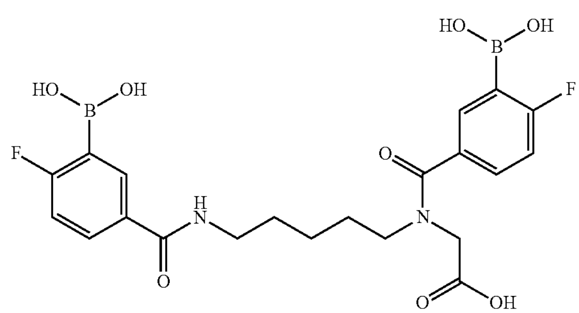 [SMILES: O=C(O)CN(CCCCCNC(=O)c1ccc(F)c(B(O)O)c1)C(=O)c1ccc(F)c(B(O)O)c1]

Example 16 was synthesized similar to Example 9 and is derived from FF2 and F1. Expected mass [M+H]: 493.17; Observed [M+H]: 493.1

Figure 16:
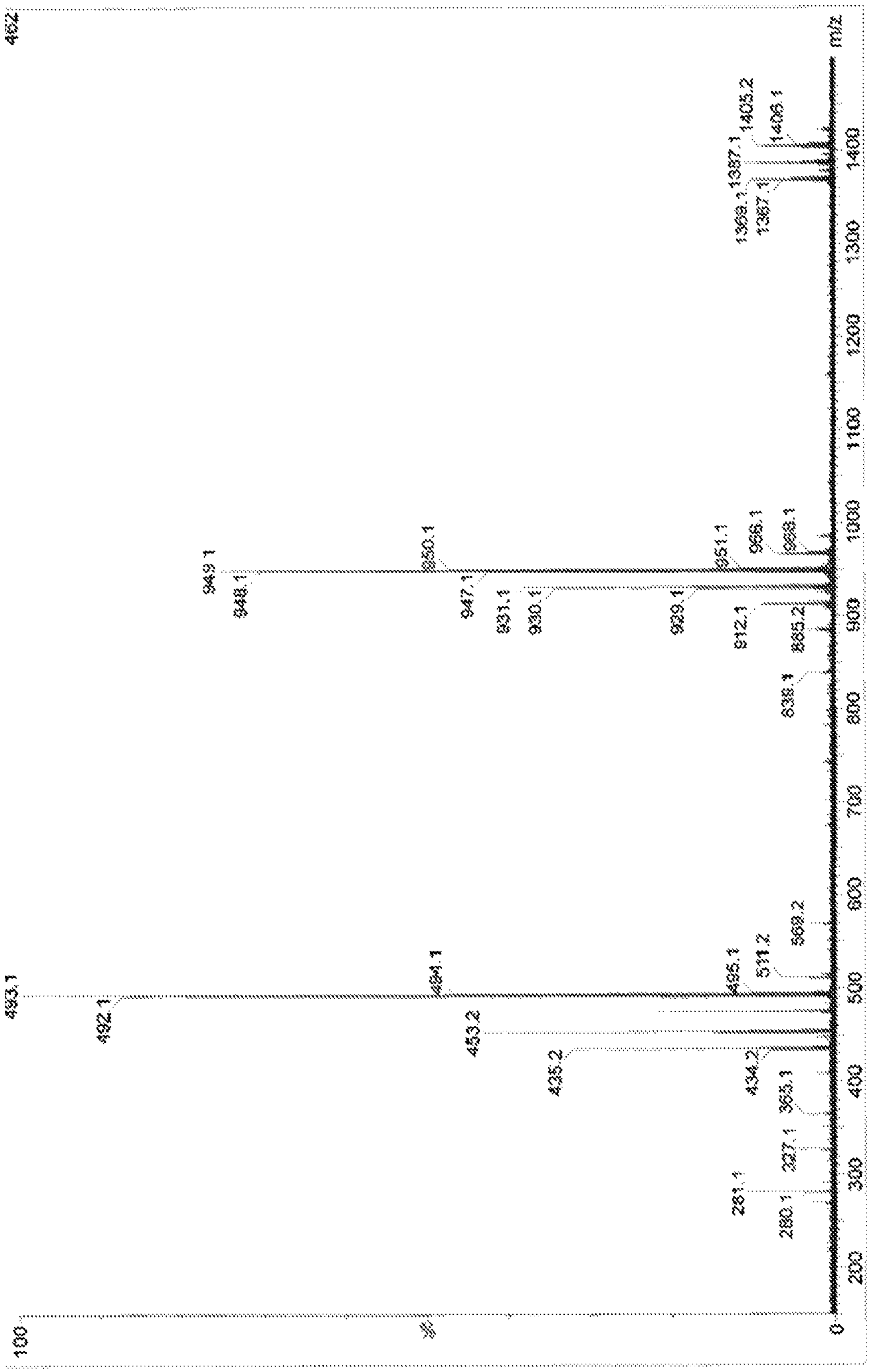

FIG. 16 is a mass spectrum plot confirming the synthesis of Example 16.

Example 17

N-(3-((3-borono-4-fluorobenzamido)methyl)benzyl)-N-(3-borono-4-fluorobenzoyl)glycine

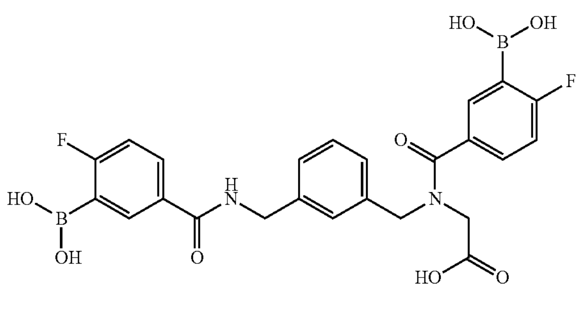 [SMILES: O=C(O)CN(Cc1cccc(CNC(=O)c2ccc(F)c(B(O)O)c2)c1)C(=O)c1ccc(F)c(B(O)O)c1]

Example 17 was synthesized similar to Example 9 and is derived from FF4 and F1. Expected mass [M+H]: 527.15; Observed [M+H]: 527.1; [M+H−H2O]:509.1

Figure 17:
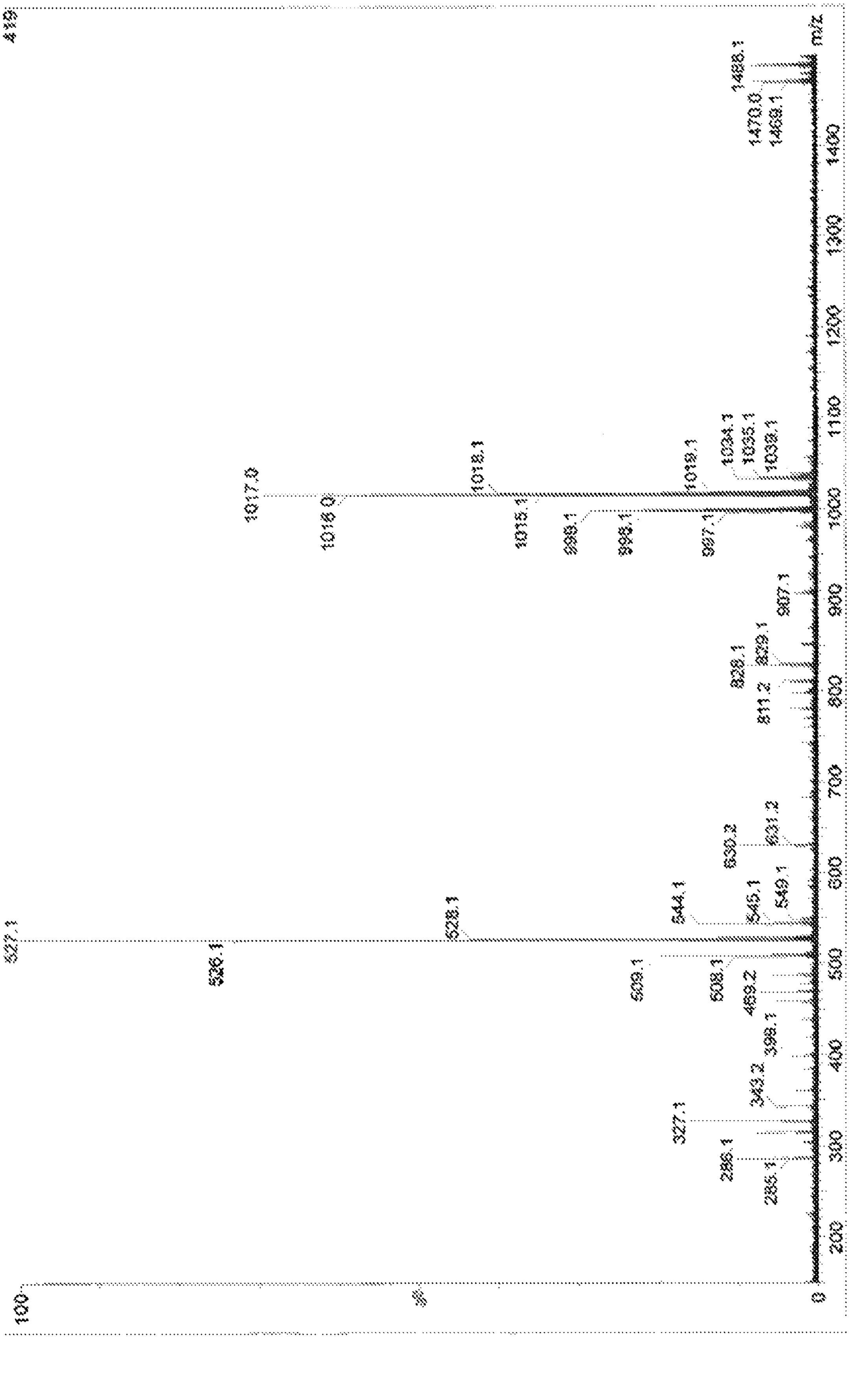

FIG. 17 is a mass spectrum plot confirming the synthesis of Example 17.

Example 18

N-((1S,2R)-2-(3-borono-4-fluorobenzamido)cyclohexyl)-N-(3-borono-4-fluorobenzoyl)glycine

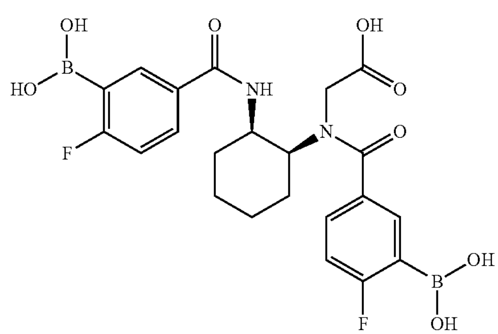 [SMILES: O=C(O)CN(C(=O)c1ccc(F)c(B(O)O)c1)[C@H]1CCCC[C@H]1NC(=O)c1ccc(F)c(B(O)O)c1]

Example 18 was synthesized similar to Example 9 and is derived from FF5 and F1. Expected mass [M+H]: 505.17; Observed [M+H]: 505.1

Figure 18:
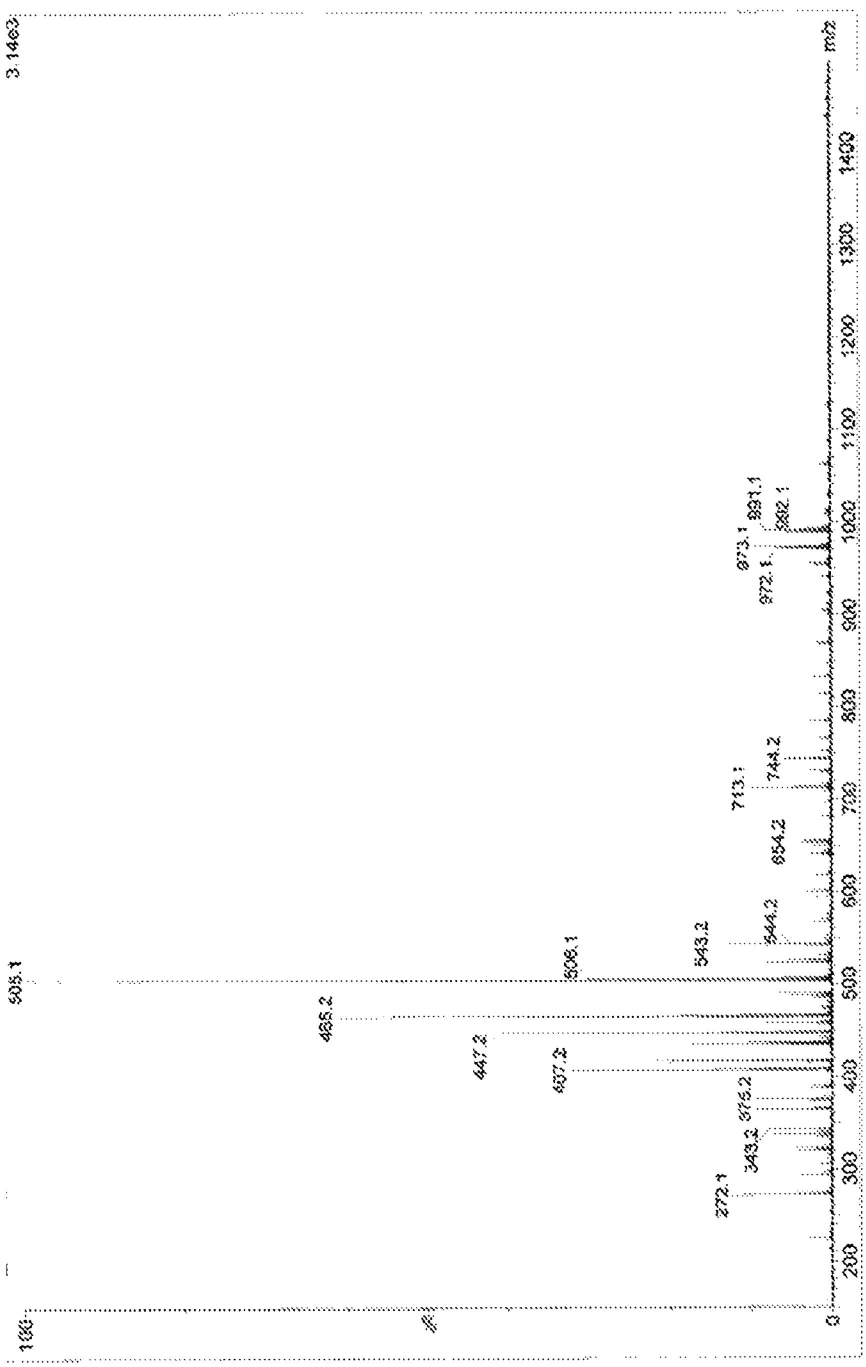

FIG. 18 is a mass spectrum plot confirming the synthesis of Example 18.

Example 19

N-(3-(4-borono-3-fluorobenzamido)propyl)-N-(4-borono-3- fluorobenzoyl)glycine

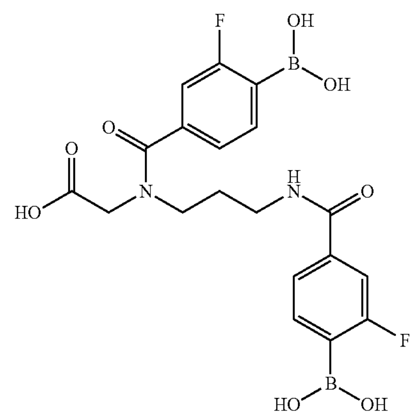 [SMILES: O=C(O)CN(CCCNC(=O)c1ccc(B(O)O)c(F)c1)C(=O)c1ccc(B(O)O)c(F)c1]

Example 19 was synthesized similar to Example 9 and contains FF2 and F1. Expected mass [M+H]: 465.14; Observed [M+H]: 465.1; [M+H−$H_2O$]:447.1

Figure 19:
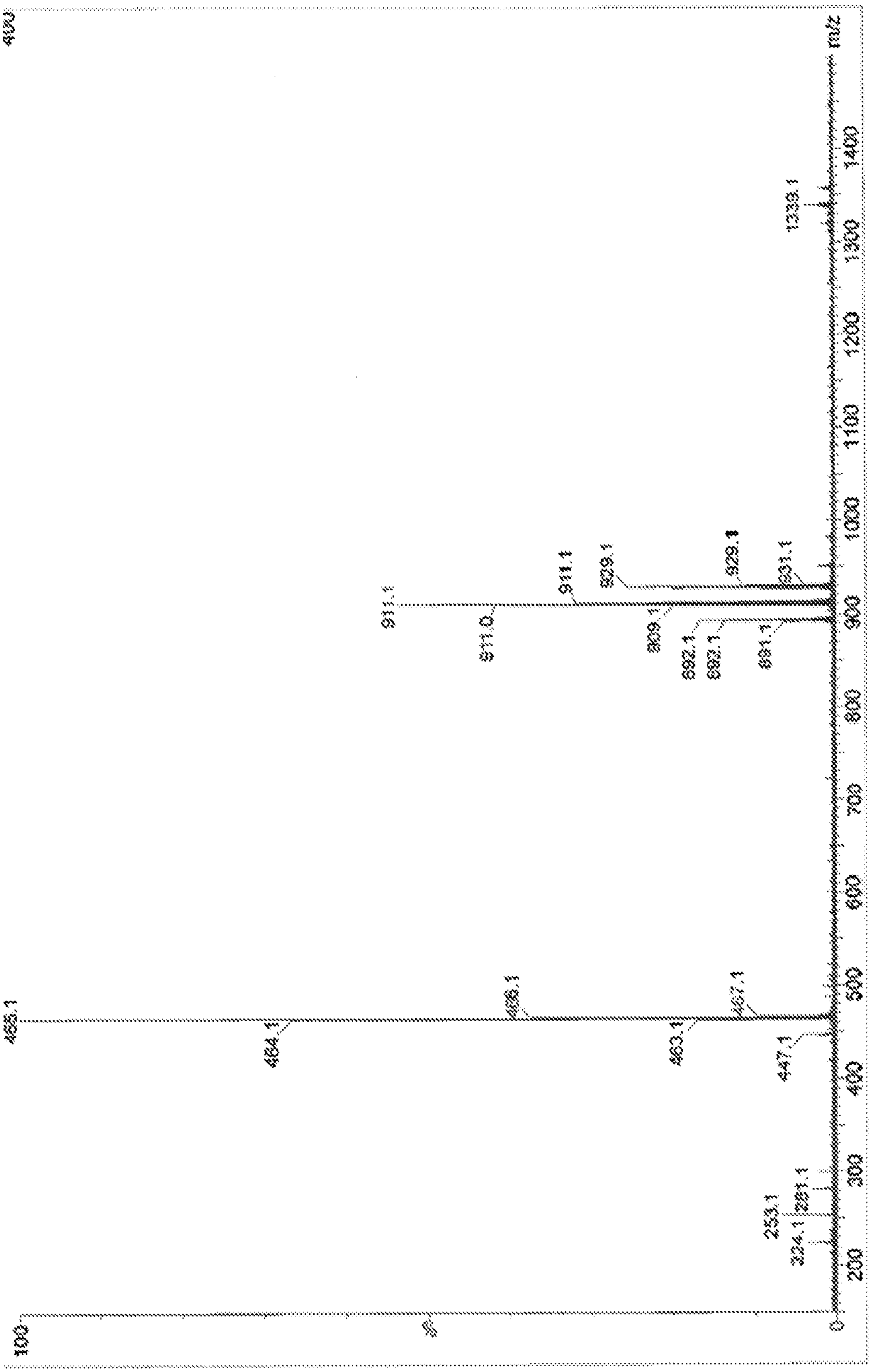

FIG. 19 is a mass spectrum plot confirming the synthesis of Example 19.

Example 20

N-(S-(4-borono-3-fluorobenzamido)pentyl)-N-(4-borono-3-fluorobenzoyl)glycine

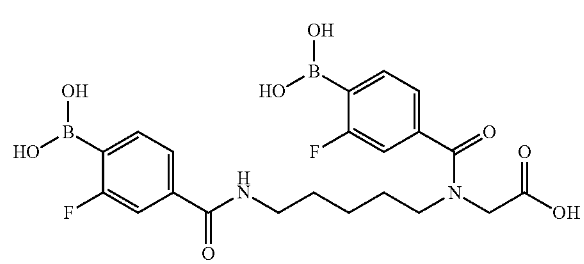 [SMILES: O=C(O)CN(CCCCCNC(=O)c1ccc(B(O)O)c(F)c1)C(=O)c1ccc(B(O)O)c(F)c1]

Example 20 was synthesized similar to Example 9 and contains FF2 and F1. Expected mass [M+H]: 493.17; Observed [M+H]: 493.1; [M+H−$H_2O$]:475.1

Figure 20:
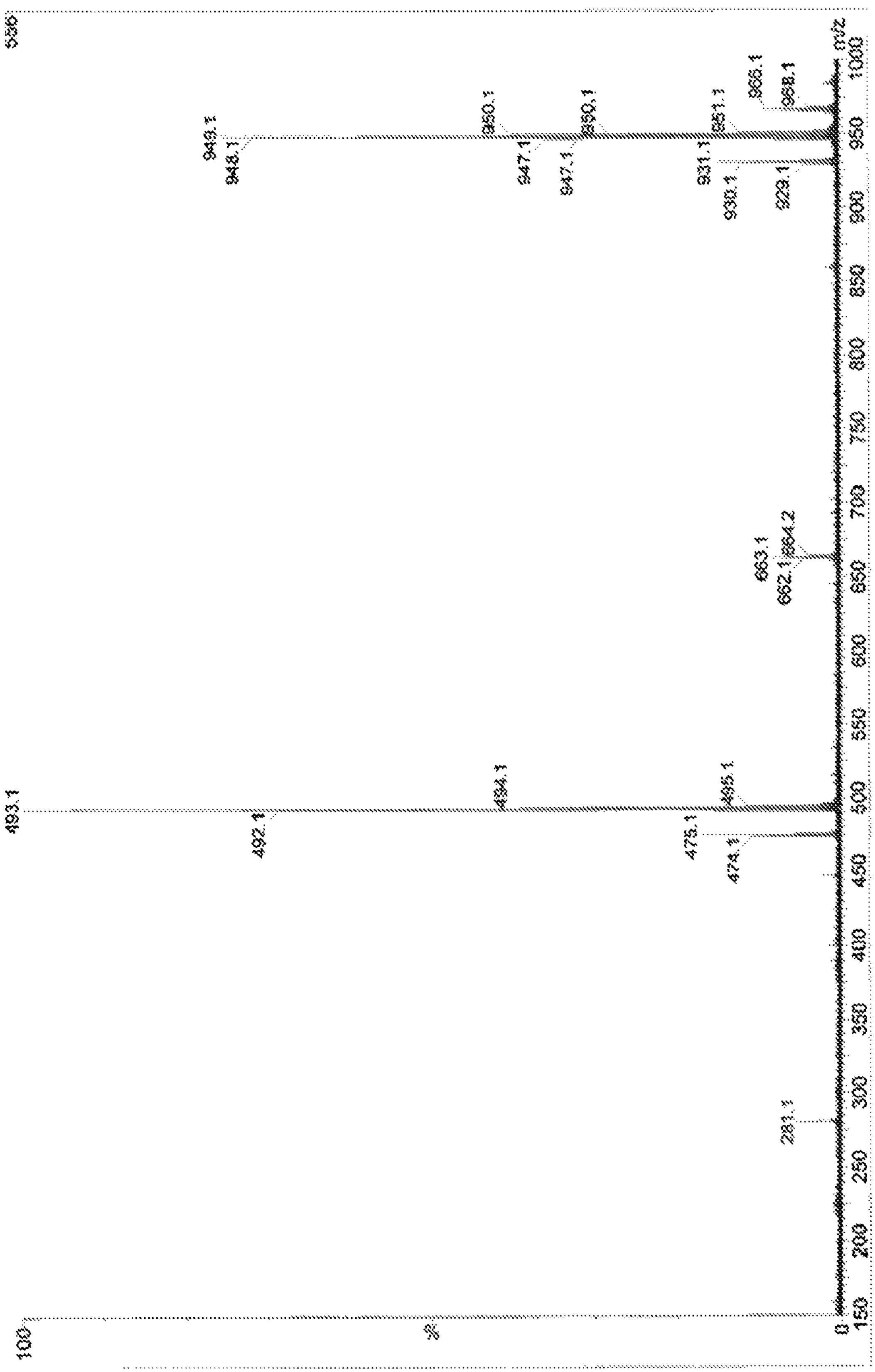

FIG. 20 is a mass spectrum plot confirming the synthesis of Example 20.

Example 21

N-(4-((4-borono-3-fluorobenzamido)methyl)benzyl)-N-(4-borono-3-fluorobenzoyl)glycine

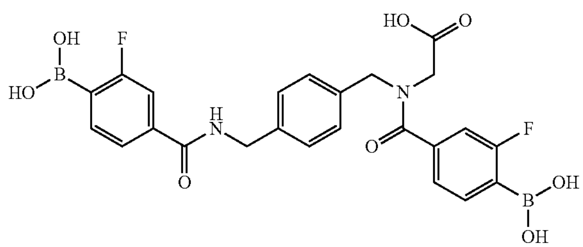 [SMILES: O=C(O)CN(Cc1ccc(CNC(=O)c2ccc(B(O)O)c(F)c2)cc1)C(=O)c1ccc(B(O)O)c(F)c1]

Example 21 was synthesized similar to Example 9 and contains FF8 and F1. Expected mass [M+H]: 527.15; Observed [M+H]: 527.0

Figure 21:
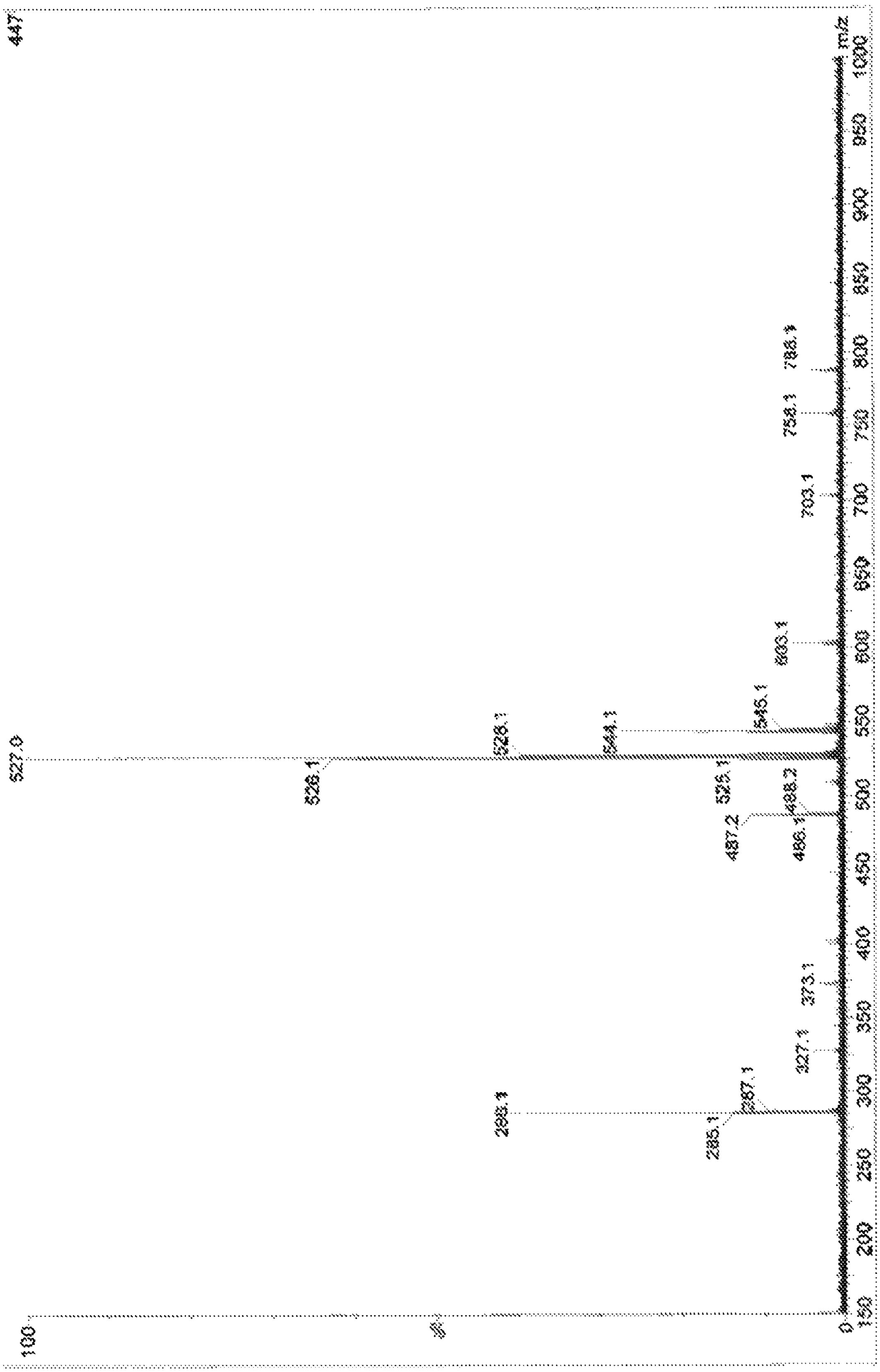

FIG. 21 is a mass spectrum plot confirming the synthesis of Example 21.

Example 22

N-(3-((4-borono-3-fluorobenzamido)methyl)benzyl)-N-(4-borono-3-fluorobenzoyl)glycine

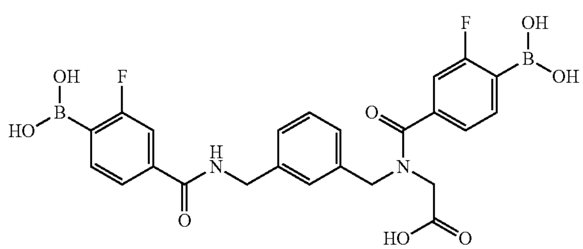 [SMILES: O=C(O)CN(Cc1cccc(CNC(=O)c2ccc(B(O)O)c(F)c2)c1)C(=O)c1ccc(B(O)O)c(F)c1]

Example 22 was synthesized similar to Example 9 and contains FF4 and F1. Expected mass [M+H]: 527.15; Observed [M+H]: 527.05

Figure 22:
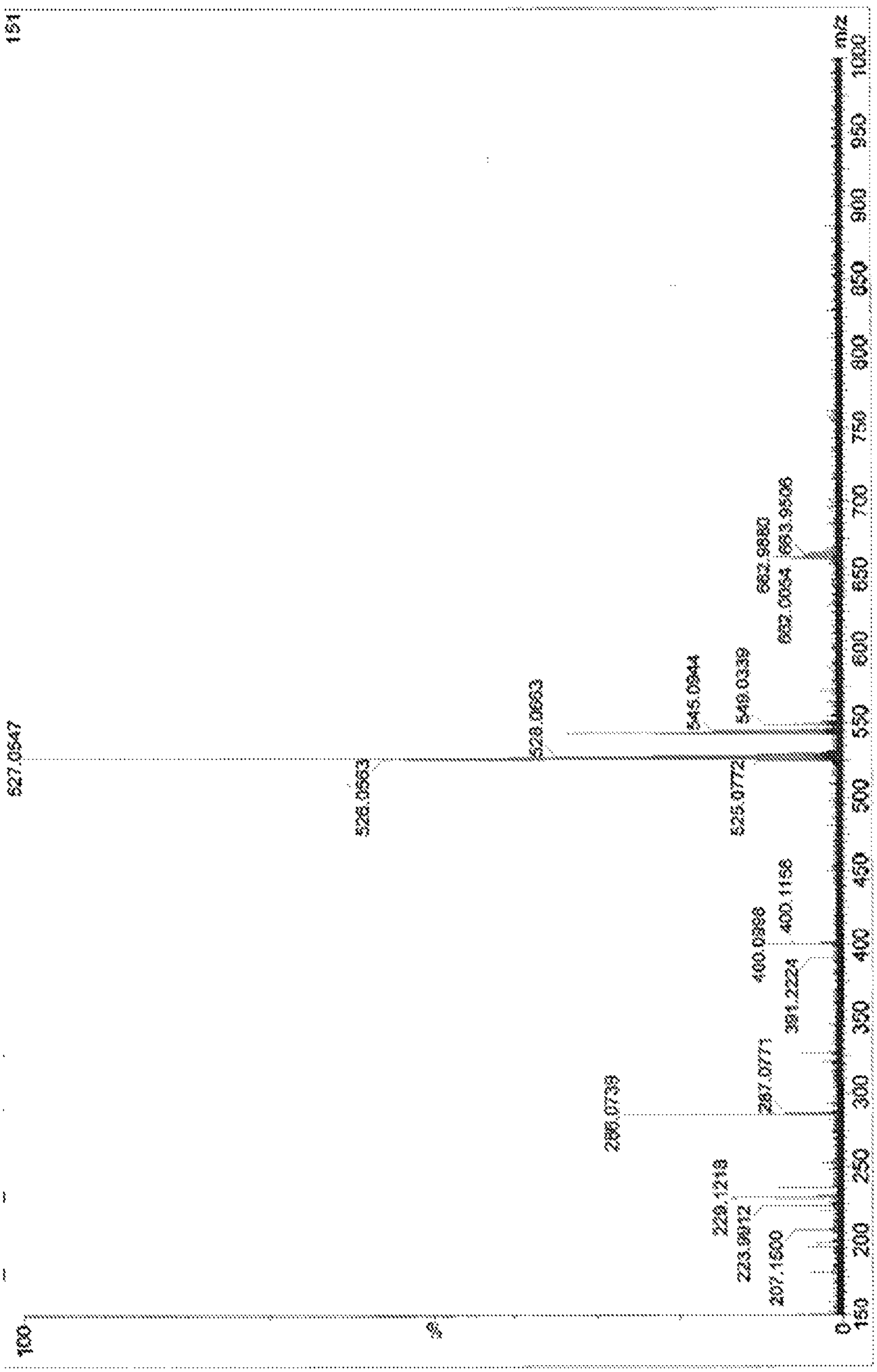

FIG. 22 is a mass spectrum plot confirming the synthesis of Example 22.

Example 23

(3-((4-((N-(2-amino-2-oxoethyl)-3-borono-5-bromobenzamido)methyl)benzyl)carbamoyl)-5-bromophenyl)boronic acid

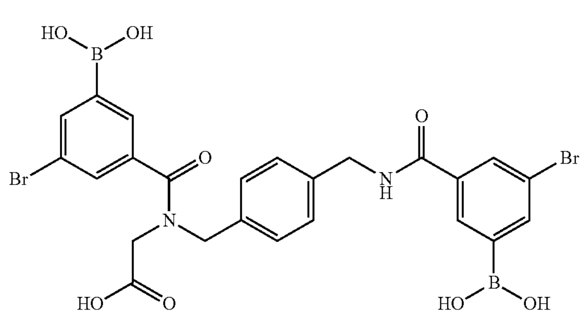 [SMILES: O=C(O)CN(Cc1ccc(CNC(=O)c2cc(Br)cc(B(O)O)c2)cc1)C(=O)c1cc(Br)cc(B(O)O)c1]

Example 23 was synthesized similar to Example 9 and contains FF8 and F1. Expected mass [M+H]:648.87; Observed [M+H]: 648.9

Figure 23:
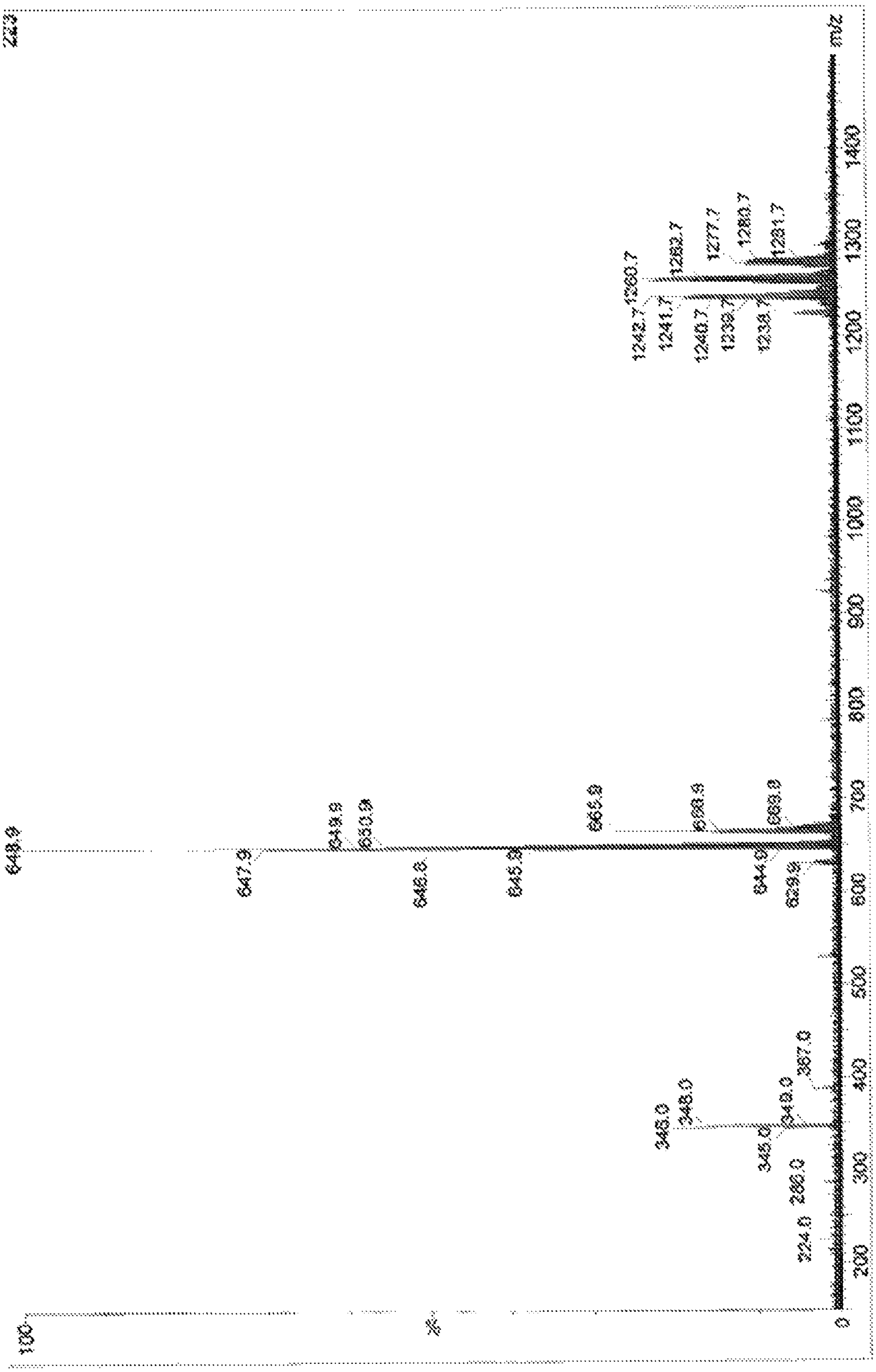

FIG. 23 is a mass spectrum plot confirming the synthesis of Example 23.

Example 24

N-(3-((3-borono-5-bromobenzamido)methyl)benzyl)-N-(3-borono-5-bromobenzoyl)glycine

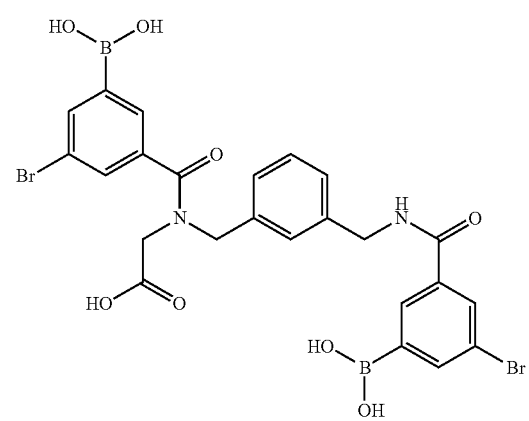 [SMILES: O=C(O)CN(Cc1cccc(CNC(=O)c2cc(Br)cc(B(O)O)c2)c1)C(=O)c1cc(Br)cc(B(O)O)c1]

Example 24 was synthesized similar to Example 9 and contains FF4 and F1. Expected mass [M+H]:648.87; Observed [M+H]: 648.9

Figure 24:
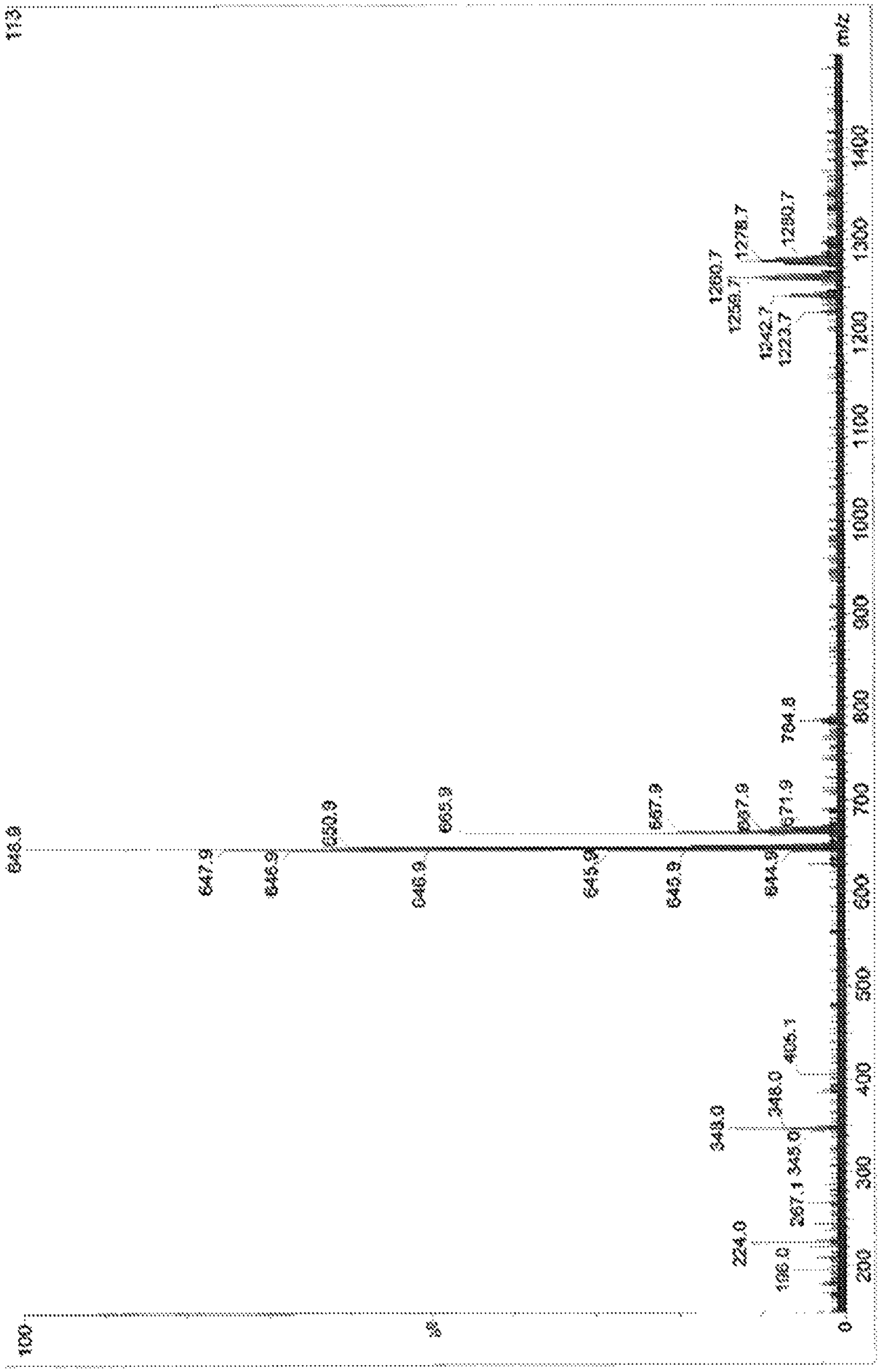

FIG. 24 is a mass spectrum plot confirming the synthesis of Example 24.

Examples of Compounds Including a Drug Substance which is Insulin

Modified Insulin 1

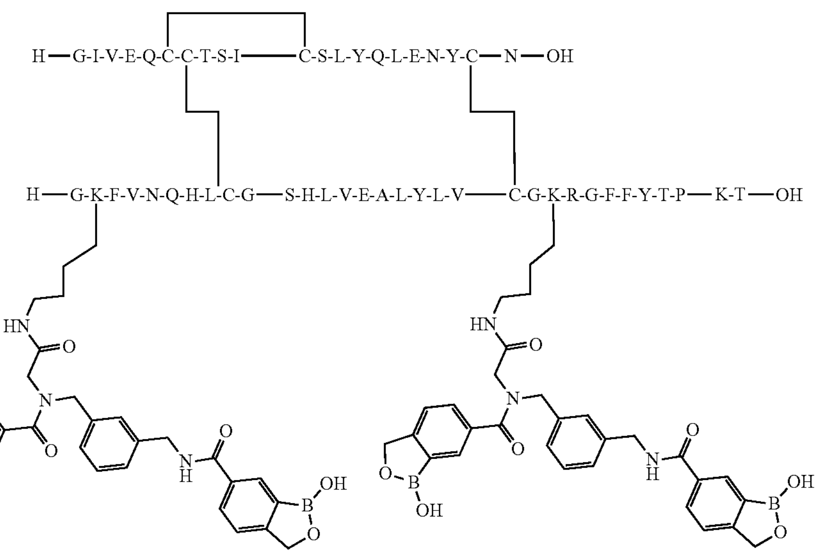

Synthesis of Modified insulin 1

Synthesis of modified insulin containing two modified amino acids from Formulae I-VI Described below is an example method of generating insulins with modified amino acids. The following methods are merely examples of how to synthesize insulin with modified amino acids. It should be understood that other methods may be suitably used to generate similar insulins with similar desirable properties. Furthermore, although a described method may be associated with the synthesis of a modified insulin in a particular example, those having ordinary skill in the art are capable of utilizing the described methods to synthesize other insulin analogues and/or their associated sequences. In addition, those having ordinary skill in the art are similarly capable of utilizing the described methods to select and combine suitable A-chains, B-chains, and/or complete insulins with the various sensor molecules described herein. The following insulin chain sequences are described or referenced below:

(SEQ ID NO: 1)
GIVEQCCTSICSLYQLENYCN (SEQ ID NO: 2)
FVNQHLCGSHLVEALYLVCGERGFFYTPKT (SEQ ID NO: 3)
GKFVNQHLCGSHLVEALYLVCGKRGFFYTPKT (SEQ ID NO: 5)
KPFVNQHLCGSHLVEALYLVCGERGFFYTPKT (SEQ ID NO: 6)
KPGSEHESAFVNQHLCGSHLVEALYLVCGERGFFYTPK (SEQ ID NO: 7)
FVNQHLCGSHLVEALYLVCGKRGFFYTPKT

-continued (SEQ ID NO: 8)
KGPEGESAGSEGESVNQHLCGSHLVEALYLVCGKRGFFYTPRT (SEQ ID NO: 9)
GIVEQCCTSICSLYQLENYCNASEKPSEA (SEQ ID NO: 10)
KPGSEVGESAIKPGSEGESVNQHLCGSHLVEALYLVCGERGFFYTPKT (SEQ ID NO: 11)
KPGSSAEEGESAKPGSEGESVNQHLCGSHLVEALYLVCGKRGFFYTPKT (SEQ ID NO: 12)
GIVEQCCTSICSLYQLENYCNKLSESG (SEQ ID NO: 13)
KGREDEAYGNIKPGWEGESKPFVNQHLCGSHLVEALYLVCGKRGFFYT
PKT (SEQ ID NO: 14)
KPSGERSEGAIKPGSEGSEKFVNQHLCGSHLVEALYLVCGKRGFFYTP
KT (SEQ ID NO: 15)
KPGSEHESAFVNQHLCGSHLVEALYLVCGKEGFFYTPKT (SEQ ID NO: 16)
GIVEQCCTSICSLYQLENYCNAEGSK (SEQ ID NO: 17)
KPGSEHESAFVNQHLCGSHLVEALYLVCGERGFFYTPRT (SEQ ID NO: 18)
KPGIVEQCCTSICSLYQLENYCN (SEQ ID NO: 19)
KPGSEHESAFVNQHLCGSHLVEALYLVCGERGFFYTPK (SEQ ID NO: 20)
GIVKPCCTSICSLYQLENYCN Synthesis of a complete insulin may be performed by the combination (e.g., separate synthesis and then linking) of two chains: chain A and chain B. In the example synthesis of modified insulin 1, chain B is modified with a sensor prior to linking of the A and B chains. The following protocol describes the general synthesis of the first chain of insulin, chain A.

Synthesis of chain A

Sequence: GIVEQC(Acm)C(Acm)TSIC(Acm)SLYQLENYCN

Syntheses of the A-chain and modified A-chain (e.g., A-chains to be conjugated to sensors) were accomplished using conventional solid-phase peptide synthesis (SPPS).

Tentagel S RAM low loading (LL) resin (0.26 mmol/eq) was swelled in a mixture of DMF:DCM (50:50, v:v) for 5 minutes. The Fmoc protecting group on the resin was removed with 20% piperidine in DMF (4 mL) and at 90° C. for 2 min. The deprotected resin was washed with DMF (4×5 mL). A solution of 0.5 M N,N'- diisopropylcarbodiimide (DIC, 1 mL), 0.5 M Oxyma (0.5 mL), and 0.2 M Fmoc-Asp(α-tBu)-OH (0.2 M) in DMF were coupled to the resin at 90° C. Each amino acid coupling step involved: i) deprotection with 20% piperidine in DMF at 90° C.; ii) washing with DMF; iii) activation and coupling of Fmoc protected amino acids with 0.5 M N,N'- diisopropylcarbodiimide (DIC, 1 mL), 0.5 M Oxyma, and 0.2 M Fmoc-amino acid in DMF at 90° C.; iv) washing with DMF.

Global Deprotection and Isolation of the A-Chain.

Crude peptide was globally deprotected in TFA:TIPS:H2O (95:2.5:2.5) and gently agitated for 2h. Crude solution was filtered and peptide was precipitated in cold ether, centrifuged, and washed with additional cold ether. The supernatant was decanted and the crude peptide was dried under a gentle stream of nitrogen gas. Crude peptide was dissolved in 20% ACN in water and fractionated by RP-HPLC on a C18 column.

The following protocol describes the general synthesis of the second chain of insulin, chain B.

B-Chain Synthesis

Syntheses of the B-chain and modified (e.g., sensor-conjugated) B-chains using solid-phase peptide synthesis (SPPS).

MPA resin (0.22 mmol/eq) was swelled in a mixture of DMF:DCM (50:50, v:v). A solution of potassium iodide (125 mM) with DIPEA (1 M) in DMF was added to the reaction vessel along 15 with Fmoc-Thr(tBu)-OH (0.2 M). The reaction vessel was heated to 90° C. Each amino acid coupling step involved: i) deprotection. with 20% piperidine in DMF at 90° C.; ii) washing with DMF; iii) activation and coupling of Fmoc protected amino acids with 0.5 M N,N'-diisopropylcarbodiimide (DIC), 0.5 M Oxyma, and 0.2 M Fmoc-amino acid (2.5 mL) in DMF at 90° C.; iv) washing with DMF. Fmoc-Arg(Pbf)-OH was coupled twice using the methods described above. The last residue in the sequence was coupled as Boc-Gly-OH using the methods above, resulting in a crude peptide with the sequence Boc-GK(Dde) FVNQHLC(Acm)GSHLVEALYLVCGK(Dde) RGFFYTPKT attached to the resin.

Deprotection of Lys-N-E-1-(4,4-dimethyl-2,6-dioxocyclohex-1-ylidene)ethyl (Dde) on Lys residues within the B-chain and addition of ((1S,2R)-2-aminocyclohexyl)glycine The Dde protecting group on the lysine residue was removed with 4% hydrazine in DMF (3×5 mL, 3 min mixing), and then washed with DMF (5×5 mL). The side-chain of the lysine residue was coupled to (3-(aminomethyl) benzyl)glycine via sub-monomer synthesis. Bromoacetic acid in DMF (1 M, 5 mL) with 1 M N,N'diisopropylcarbodiimide (DIC, 1M, 1 mL) in DMF was added to the crude B-chain peptide and heated at 50° C. for 10 min. The reaction mixture was washed with DMF (2×5 mL). A solution of 1,3-phenylenedimethanamine (2 M, 5 mL) in DMF was added to the reaction mixture and heated at 50° C. for 10 min to provide Boc-GK((3-(aminomethyl)benzyl) glycine)FVNQHLC(Acm)GSHLVEALYLVCGK((3-(aminomethyl)benzyl)glycine)RGFFYTPKT Addition of 1-hydroxy-1,3-dihydrobenzo[c][1,2] oxaborole-6-carboxylic acid to (3-(aminomethyl) benzyl)glycine on the crude modified B-chain The free amines of the (3-(aminomethyl)benzyl)glycine were coupled to 1-hydroxy-1,3-dihydrobenzo[c][1,2]oxaborole-6-carboxylic acid (0.2 M, 5 mL) in DMF with 1 M N,N'-diisopropylcarbodiimide (DIC, 1M, 1 mL), Oxyma (0.5 M, 2 mL) in DMF and heated at 50° C. for 30 min. The resin was washed with DMF (3×5 mL), resulting in the functionalized sequence.

Global Deprotection, Resin Cleavage, and Addition of DTDP to Crude B-Chain.

Crude functionalized B-chain sequence from the previous step was globally deprotected with 2,2,-dithiopyridine (DTDP, 100 mg) in TFA:TIPS:H2O (95:2.5:2.5, 5 mL) and gently agitated at room temperature for 2 hours. Crude peptide was precipitated in cold ether (50 mL), centrifuged, decanted, washed with additional cold ether (50 mL), and centrifuged again. The supernatant was decanted and the crude peptide was dried under a gentle stream of nitrogen gas. Crude peptide was dissolved in 20% CAN in water and fractionated by RP-HPLC on a C18 column with a gradient of 20% ACN in water with 0.1% TFA to 50% ACN in water with 0.1% TFA over 30 min. Fractions were collected, frozen, and lyophilized.

Combination of A and B Chains of Insulin and Modified Insulins.

The two synthetic chains (e.g., the A-chain and B-chain), were combined in a 1:1 molar ratio in 0.2 M $NH_4HCO_3$ with 6M urea and at pH 8. The mixture was gently agitated for 1 hour, diluted with water, and fractionated by RP-HPLC on a C18 column with a gradient of 20% ACN in water with 0.1% TFA to 50% ACN in water with 0.1% TFA over 45 min.

Deprotection of Cys-Acm Protecting Groups, Oxidation of Free Thiols and Final Folding of Modified Insulins.

The combined intermediate from the previous step was dissolved in glacial acetic acid and water and vortexed vigorously. A solution of iodine in glacial acetic acid (20 equiv) was added to the reaction mixture and gently agitated for 10 minutes. A solution of ascorbic acid (5 mM) was added directly to the reaction mixture. The mixture was diluted in 20% ACN in water and fractionated by RP-HPLC on a Higgins C18 column with a gradient of 20% ACN in water with 0.1% TFA to 50% ACN in water with 0.1% TFA over 45 min. Fractions were isolated, combined, frozen, and lyophilized to give Example 25 as a white powder (1.1 mg). Expected mass 6940. Observed mass $[M+5-4H_20]^{+5}$:1383.6; $[M+4-4H_2O]^{+4}$: 1729.05

Figure 25:
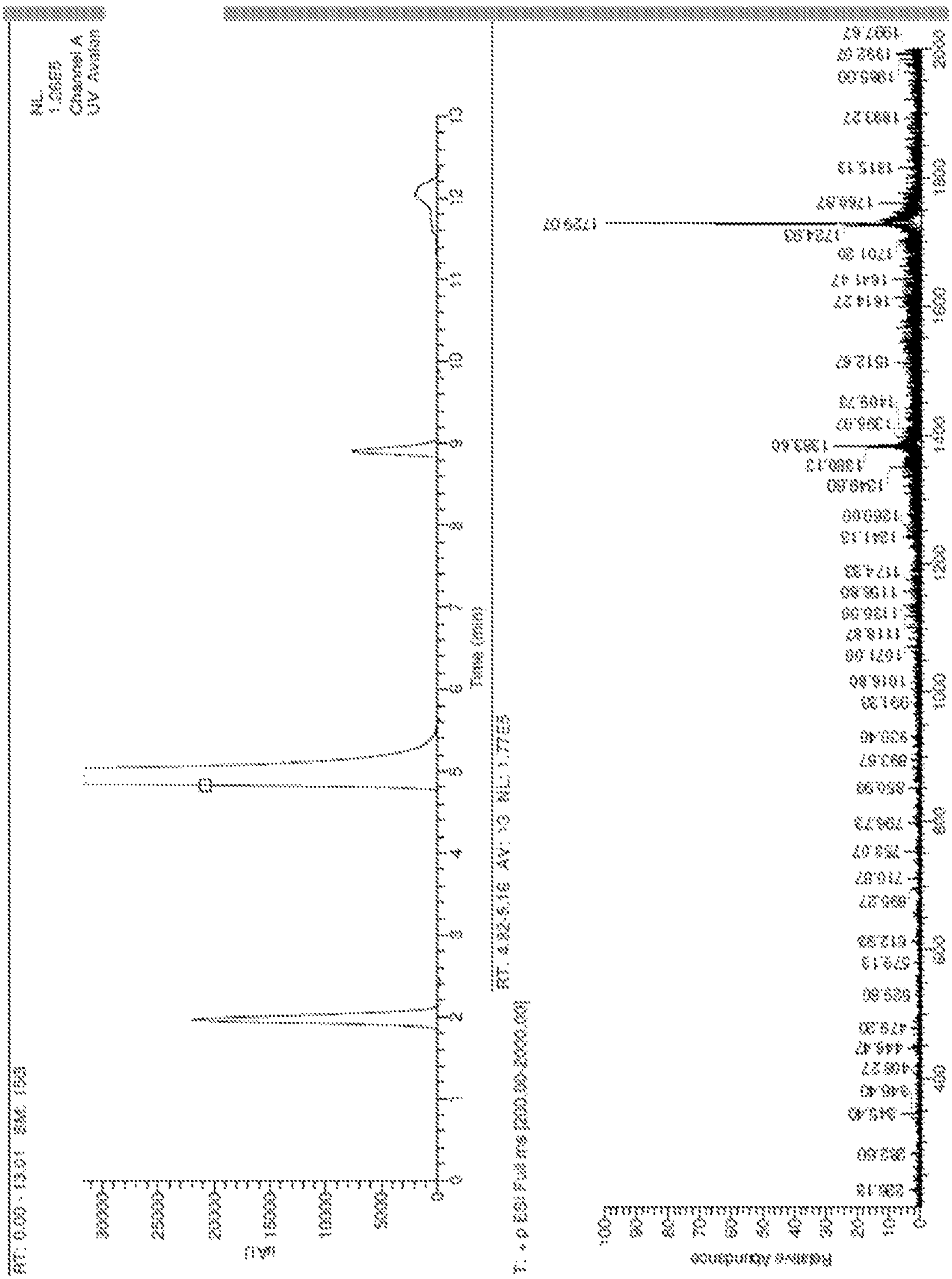
FIG. 25 is a mass spectrum plot confirming the synthesis of modified insulin 1.

FIG. 25 is a mass spectrum plot confirming the synthesis of Example 25.

Modified Insulin 2

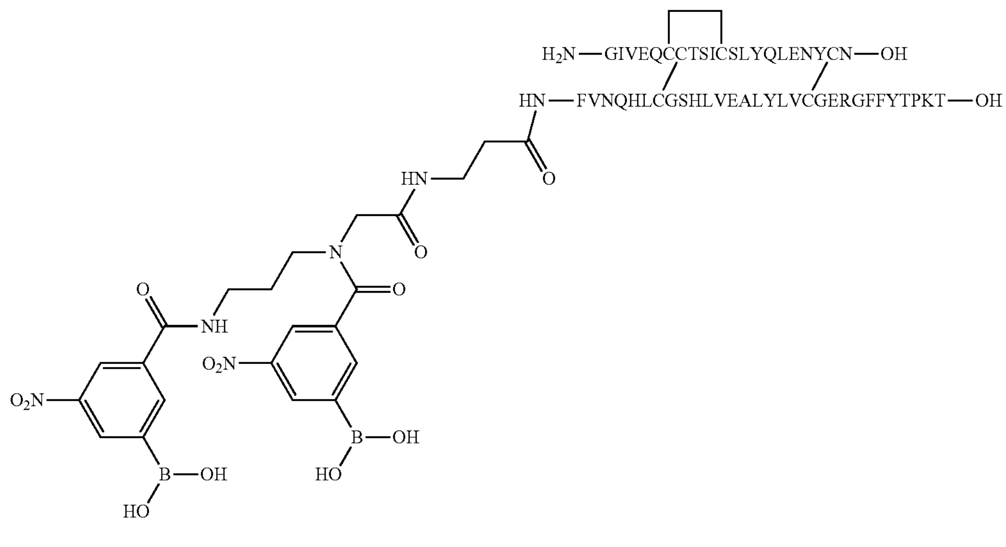

Synthesis of modified insulin 2

In the example synthesis of modified insulin 2, a modifying agent (e.g., a sensor precursor) is coupled to a complete insulin (in which the A-chain and B-chain are already combined) to thereby generate the modified insulin. For example, the following example method describes the synthesis of a modifying agent, and the coupling of the modifying agent to wild-type insulin.

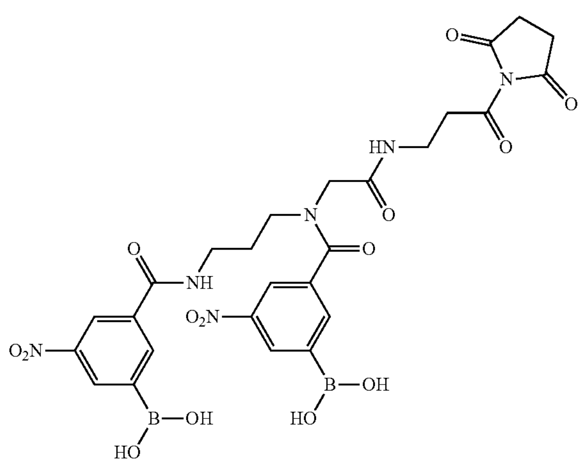 [SMILES: O=C(CN(CCCNC(=O)c1cc(B(O)O)cc([N+](=O)[O-])c1)C(=O)c1cc(B(O)O)cc([N+](=O)[O-])c1)NCCC(=O)N1C(=O)CCC1=O]

Synthesis of the modifying agent

Chlorotrityl resin (1.5 mmol/eq, 300 mg) was swelled in dry DCM (5 mL) for 30 mins. The solvent was removed under a stream of nitrogen, and a solution of Fmoc-beta-Ala-OH (0.5M) in DCM with DIPEA (1M) was added immediately and gently mixed for 1 hr. The mixture was washed with DCM, and unreacted sites were capped with a solution of 20% MeOH in a solution of DCM and DIEA (1M) and mixed for 1 hr. The resin was washed with DCM (2×5 mL) and then DMF (2×5 mL). A. solution of 20% piperidine in DMF (3×5 mL) was added to the resin and washed with DMF (3×5 mL). A solution of bromoacetic acid (1M) with 1 M N,N'-diisopropylcarbodiimide (DIC, 1M, 1 mL) in DMF and heated at 50° C. for 30 min. A solution of 1,3-diaminopropane (1M) in DMF (5 mL) was added to the resin and heated at 50° C. for 10 minutes. The resin was washed with DMF (3×5 mL) and a solution of 3-borono-5-nitrobenzoic acid (0.2 M, 5 mL) in DMF with 1 M N,N'-diisopropylcarbodiimide (DIC, 1M, 1 mL), Oxyma (0.5 M, 2 mL) in DMF and heated at 50° C. for 30 min. The resin was washed with DMF (3×5 mL) and then DCM (3×5 mL). A cleavage solution of 20% 1,1,1,3,3,3-Hexafluoro-propan-2-ol (HFIP) in DCM (5 mL) was added to the resin and agitated for 90 minutes. The solution was collected and the resin was washed with an additional solution of HFIP in DCM (5 mL). Solutions were combined and dried under vacuum to yield a crude product. The crude product was dissolved in dry DMF, and 3-(Ethyliminomethyl-eneamino)— N,N-dimethylpropan-1-amine (EDC, 60 mg, 2 equiv. assuming 100% yield from previous steps) and N-hydroxysuccinimide (NHS, 30 mg, 2 equiv assuming 100% yield from previous steps) were added to the crude product and agitated for 90 minutes. Dilute acid (100 mM HCl in water, 20 mL) was added to the mixture, and the product was extracted with ethyl acetate (2×50 mL). The ethyl acetate layers were combined, dried over magnesium sulfate, filtered, then dried under vacuum to give (3-((3-((3-borono-5-nitrophenyl)(2-((2,5-dioxopyrrolidin-1-yl)oxy)-2-oxo-ethyl)amino)propyl)amino)-5-nitrophenyl)boronic acid as a crude crystalline. The crude product was dissolved in DMSO (100 μL) and fractionated by flash chromatography on a C18 column. Pure fractions were combined, frozen, and lyophilized to give pure NHS-activated modifying agent. Expected mass $[M+H]^{+1}$: 671.18, observed $[M+H]^{+1}$: 671.33.

Figure 26A:
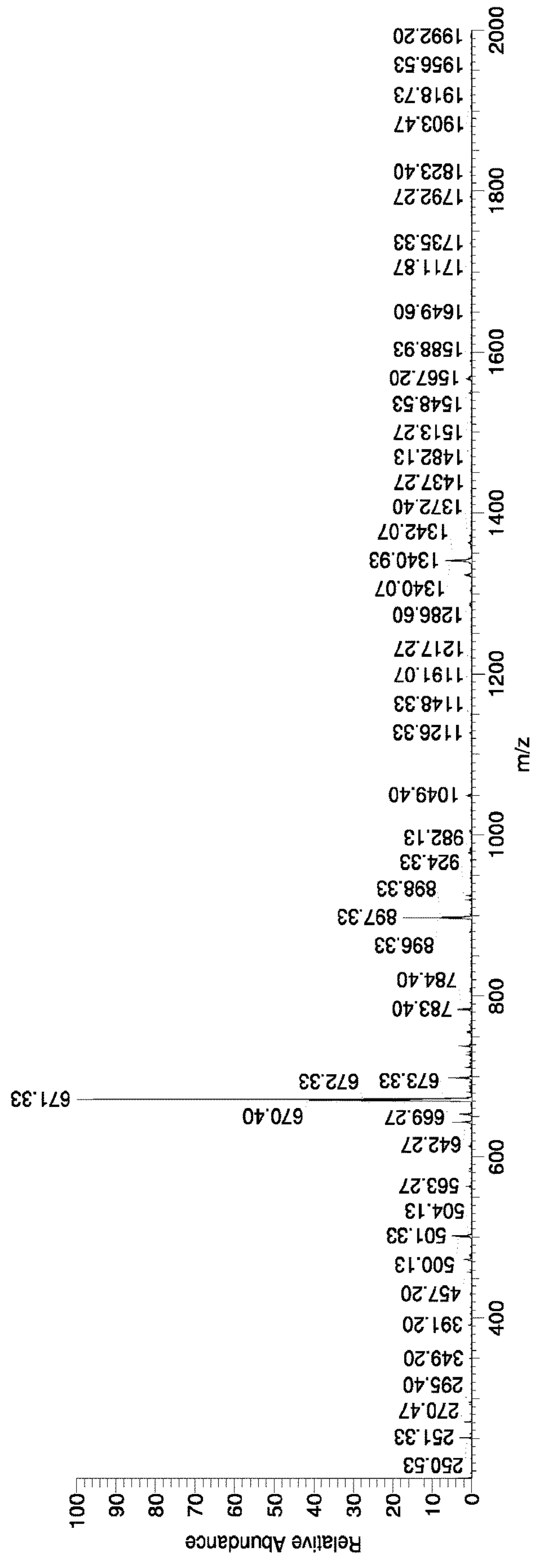
FIG. 26A is a mass spectrum plot confirming the synthesis of a modifying agent conjugated to modified insulin 2.

FIG. 26A is a mass spectrum plot confirming the synthesis of the modifying agent.

Addition of Modifying Agent to WT Insulin

Wild type (WT) insulin (10 mg) was dissolved in 100 mM potassium phosphate at pH 11.5 (1 mL). The NHS-activated modifying agent was dissolved in DMSO (10 mg/mL) and 50 μL was added to the WT insulin solution. The mixture was gently agitated for 1 hour, diluted with 20% ACN in water (3 mL) and fractionated by RP-HPLC on a C18 column. Pure fractions were combined, frozen, and lyophilized to yield pure modified insulin. Expected mass $[M+4H]^{+4}$ 1595.75, observed $[M+4H-4H_2O]^{+4}$: 1577.8.

Figure 26B:
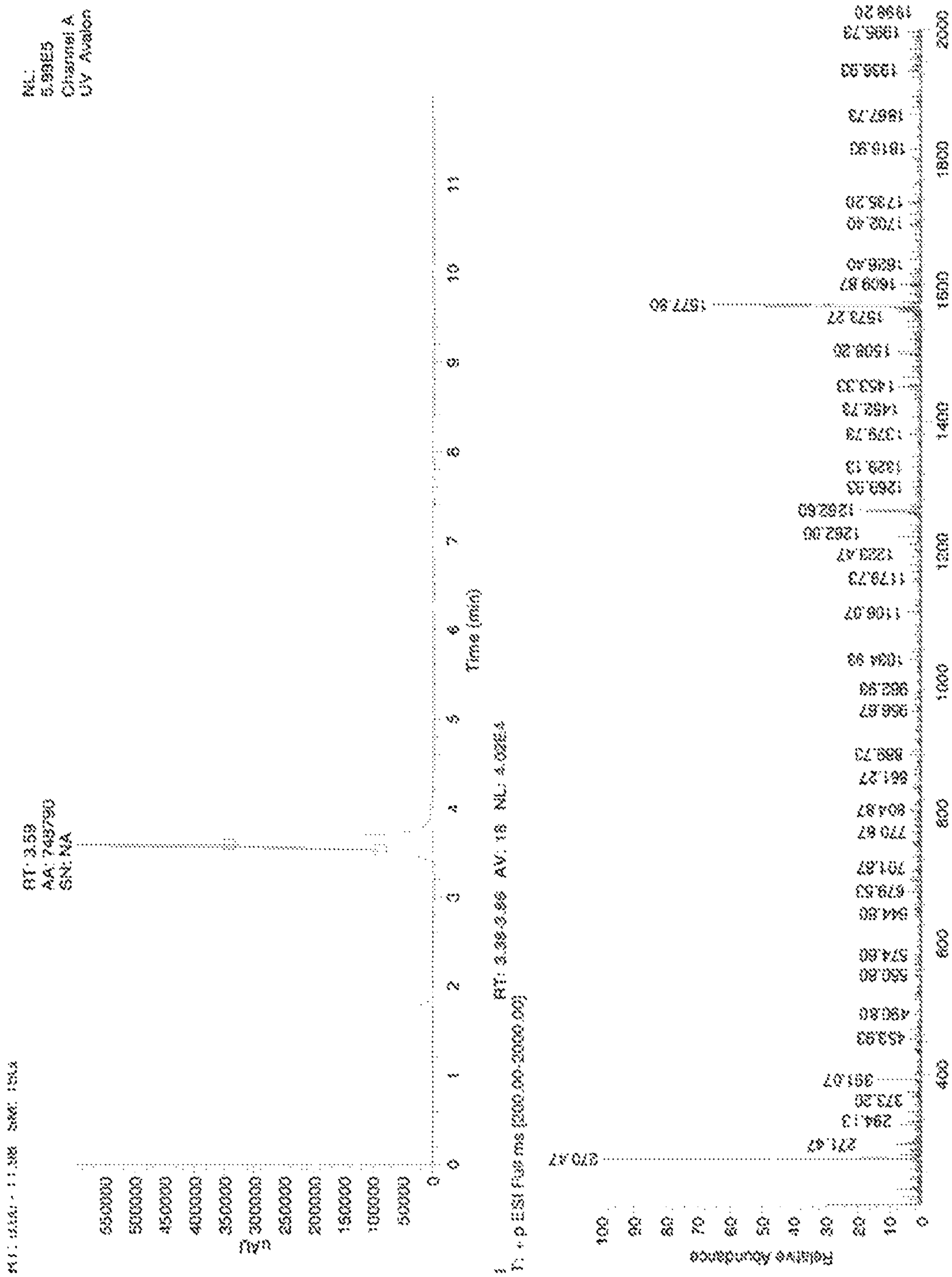
FIG. 26B is a mass spectrum plot confirming the synthesis of modified insulin 2.

FIG. 26B is a mass spectrum plot confirming the synthesis of the modified insulin.

Modified Insulin 3

Addition of 1-hydroxy-4-(trifluoromethyl)-1,3-dihydrobenzo[c][1,2]oxaborole-6-carboxylic acid to 4-Pro of the modified B-chain.

The free amines of the 4-amino proline (4-Pro) were coupled to 1-hydroxy-4-(trifluoromethyl)-1,3-dihydrobenzo[c][1,2]oxaborole-6-carboxylic acid (0.2 M, 5 mL) in DMF with 1 M N,N'-diisopropylcarbodiimide (DIC, 1M, 1 mL), Oxyma (0.5 M, 2 mL) in DMF and heated at 50° C. for 30 min. The resin was washed with DMF (3×5 mL) resulting in the functionalized sequence.

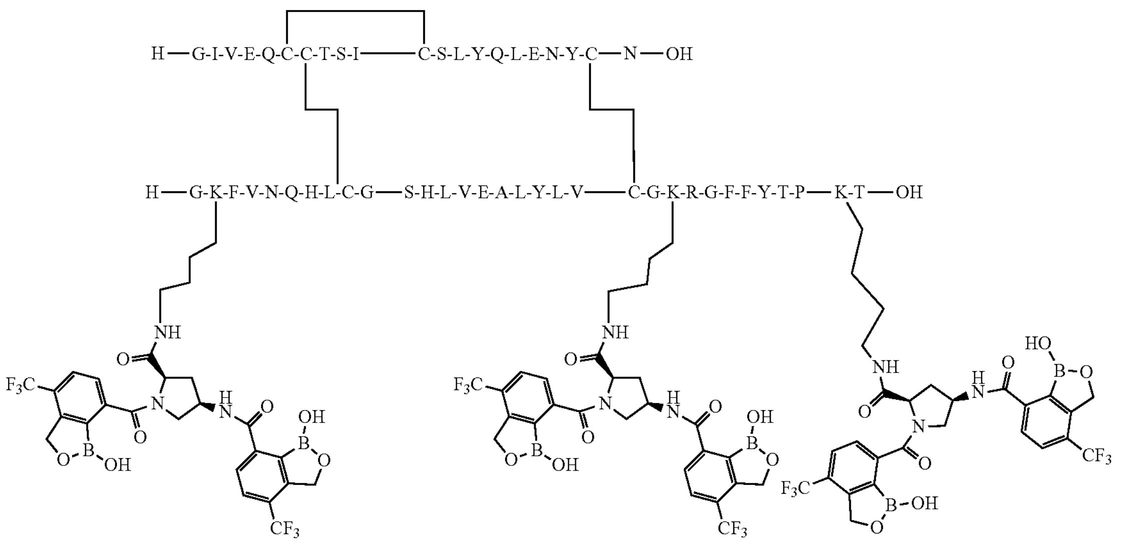

Synthesis of modified insulin 3

The A-chain of modified insulin 3 was synthesized using the method described n connection with modified insulin 1. Further, the crude peptide with the sequence Boc-GK(Dde)FVNQHLC(Acm)GSHLVEALYLVCGK(Dde)RGFFYTPK(Dde)T attached to resin was synthesized using the method described for the B-chain of modified insulin 1.

B-chain synthesis continued: Deprotection of Lys-N- ϵ-1-(4,4-dimethyl-2,6-dioxocyclohex-1-ylidene)ethyl (Dde) on Lys residues within the B-chain and addition of 4-amino-pyrrolidine-2-carboxylic acid (4-Pro).

The Dde protecting group on the lysine residue was removed with 4% hydrazine in 20 DMF (3×5 mL, 3 min mixing), and then washed with DMF (5×5 mL). The side-chain of thelysine residue was coupled to 1-(((9H-fluoren-9-yl)methoxy)carbonyl)-4-((((9H-fluoren-9-yl)methoxy)carbonyl)amino)pyrrolidine-2-carboxylic acid (Fmoc-4-amino-Fmoc-Pro-OH) in DMF (0.2 M, 5 mL) with 1 M N,N'-diisopropylcarbodiimide (DIC, 1M, 1 mL), Oxyma (0.5 M, 2 mL) in DMF and heated at 50° C. for 30 min. Fmoc protecting groups on the 4-amino-Pro 25 were removed with 20% piperidine in DMF (2×3 mL) at 50° C. and washed with DMF (3× 5 mL) to provide the sequence: Boc-GK(4-Pro)FVNQHLC(Acm)GSHLVEALYLVCGK(4-Pro)RGFFYTPK(4-Pro)T Global Deprotection, Resin Cleavage, and Addition of DTDP to Crude B-Chain.

The crude functionalized B-chain sequence from the previous step was deprotected and combined with the A-chain utilizing a similar method to that described in connection with modified insulin 1. The resulting complete insulin was further deprotected as described in connection with modified insulin 1 to provide modified insulin 3. Expected mass [M+4]+4: 1924.5 observed $[M+4-6H_2O]^{+4}$ 1897.7.

Figure 27:
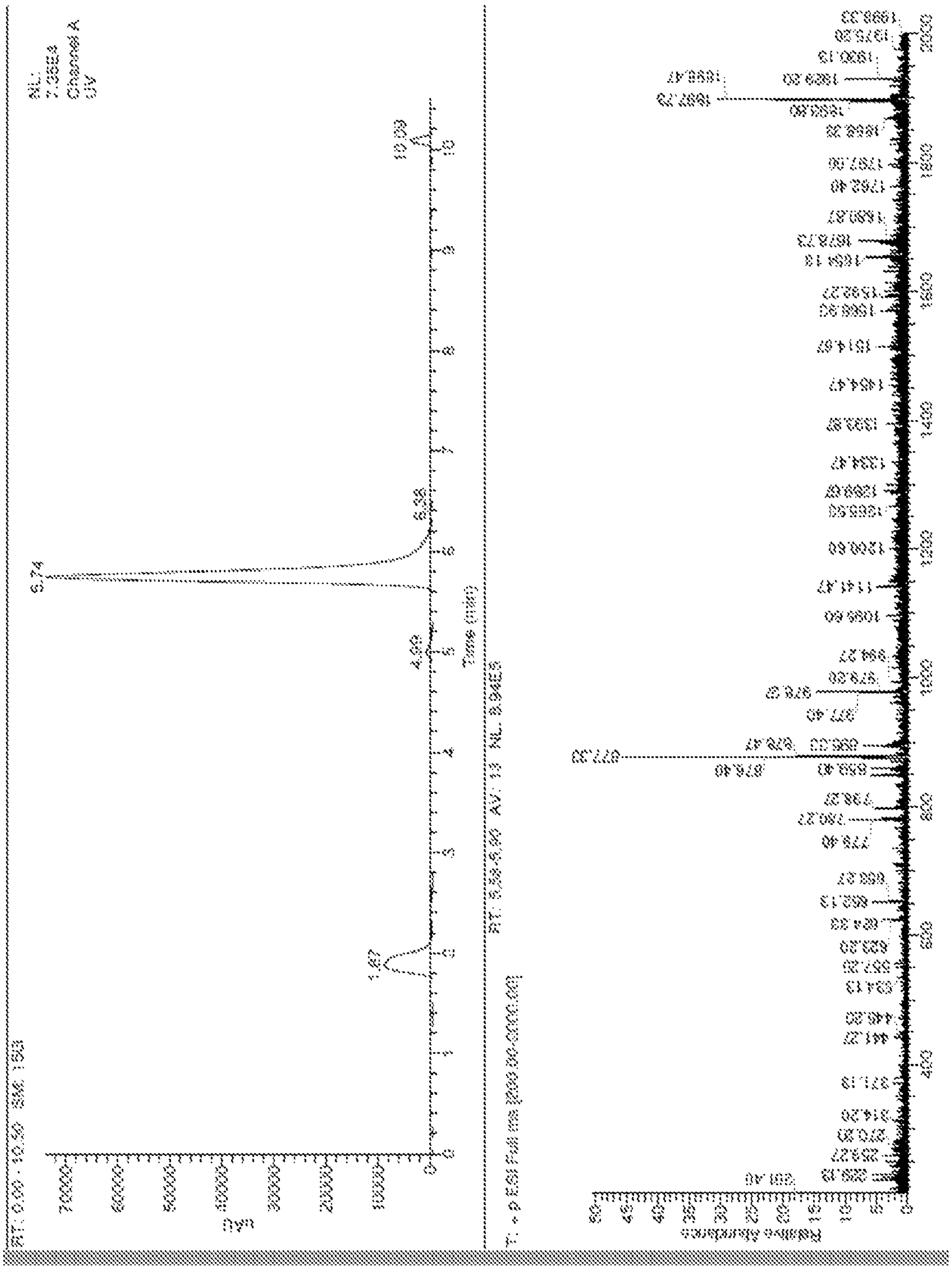
FIGS. 27-28 are mass spectrum plots confirming the synthesis of modified insulins 3 and 4, respectively.

FIG. 27 is a mass spectrum plot confirming the synthesis of the insulin.

Figure 28:
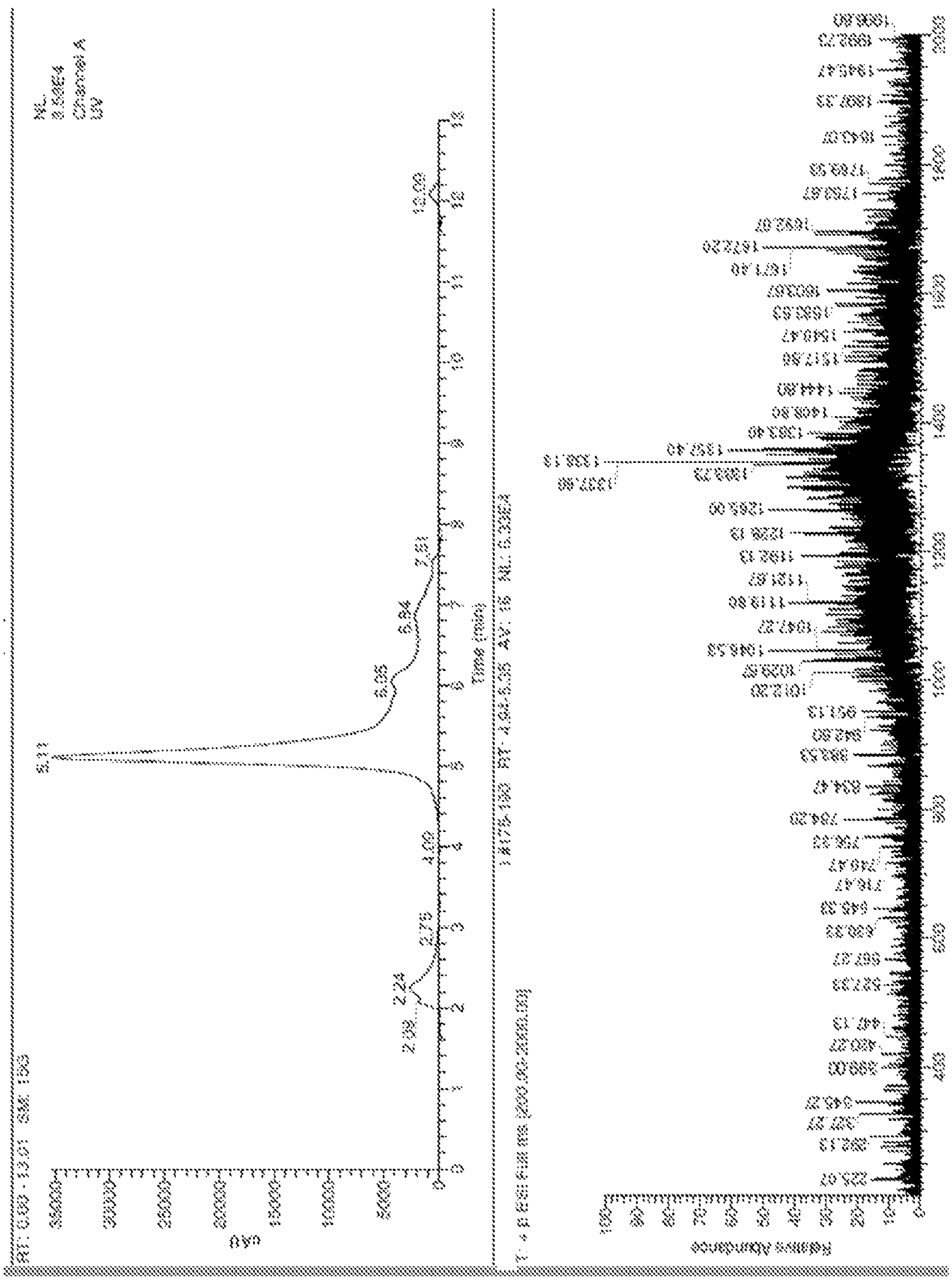

Example 28: Modified insulin 4
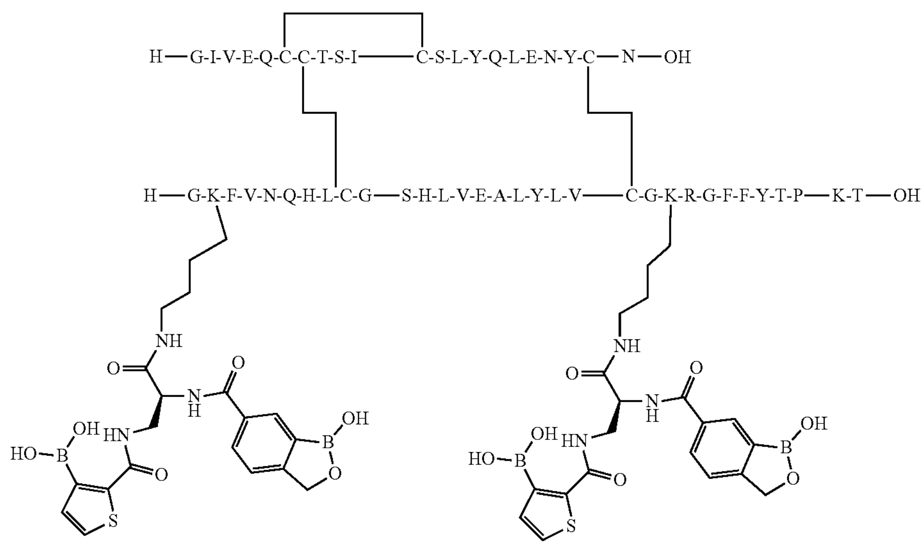
Modified insulin 4 was synthesized similar to modified insulin 3. Expected mass $[M+5]+^5$: 1359.5 observed $[M+5-6H2O]+^5$ 1338.1.
FIG. 28 is a mass spectrum plot confirming the synthesis of the insulin.
Modified Insulin 5
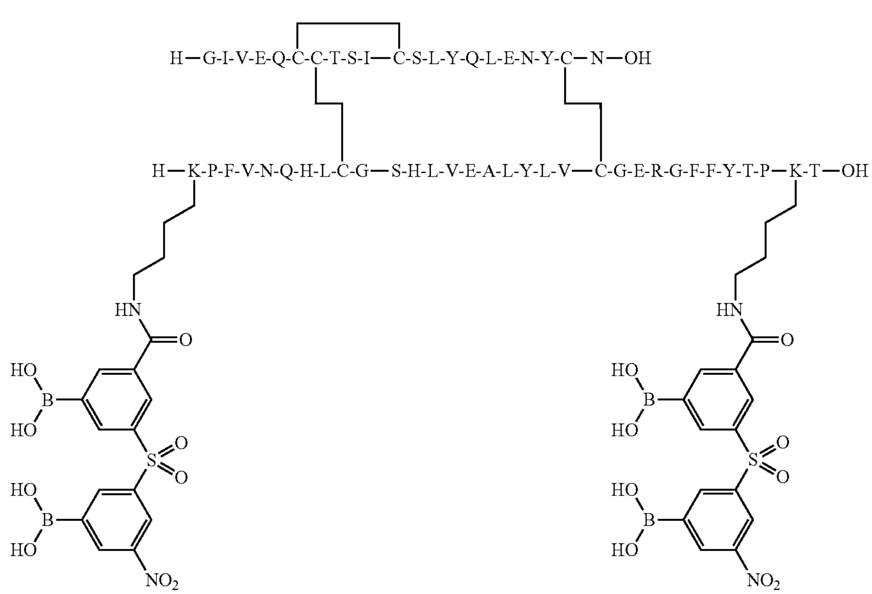

Modified insulin 5 can be made similar to modified insulin 2.
Modified Insulin 6
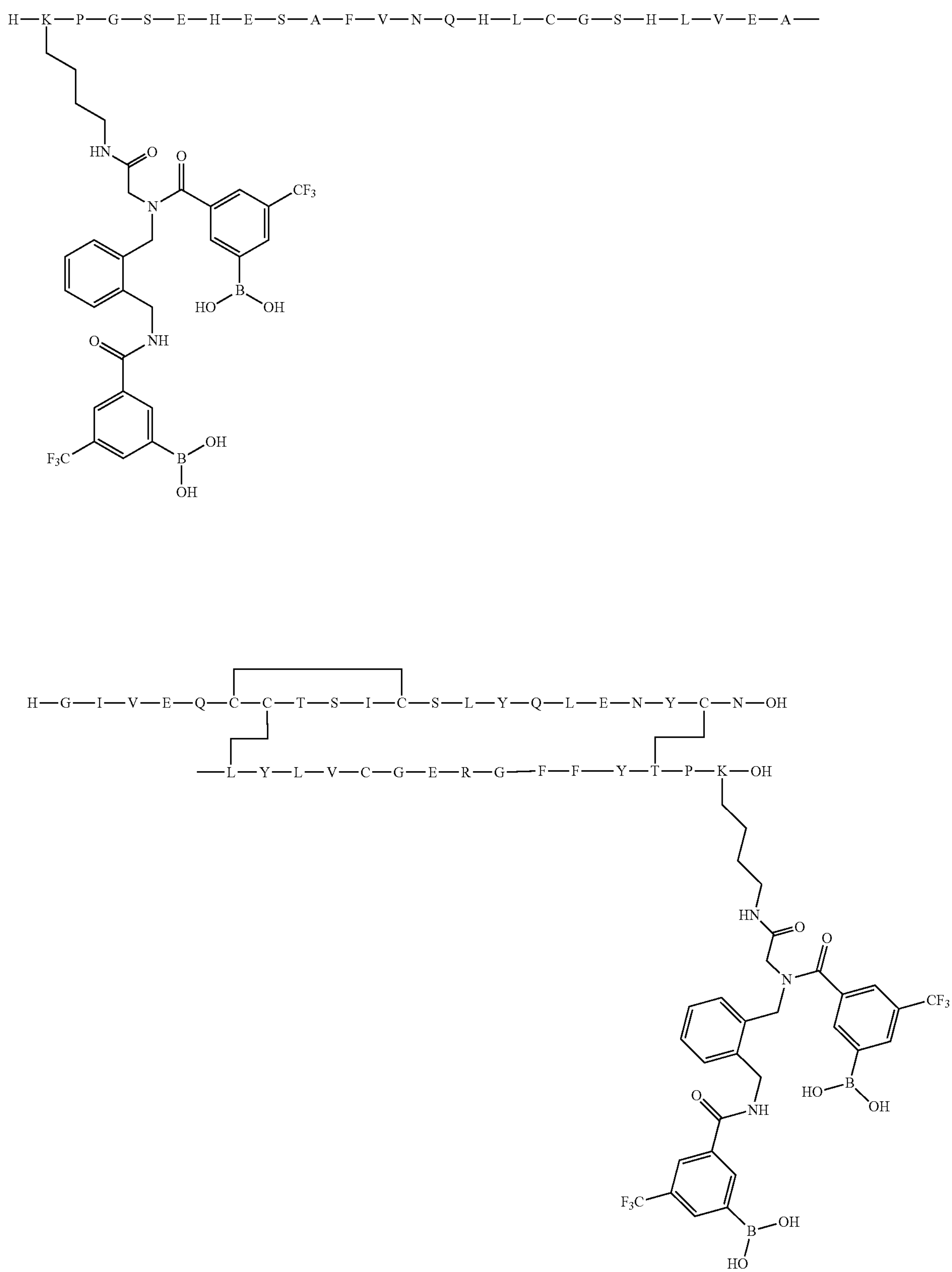

Modified insulin 6 can be made similar to modified insulin 1.
Modified Insulin 7
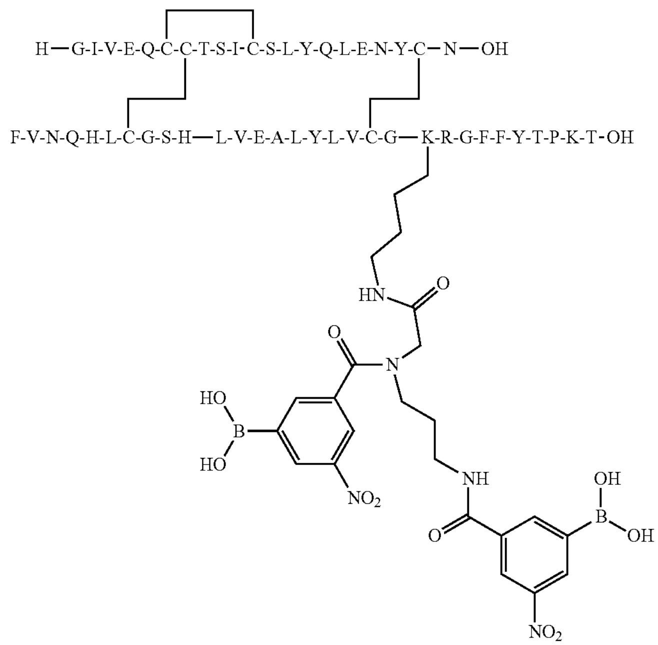
Modified insulin 7 can be made similar to modified insulin 1.
Modified Insulin 8
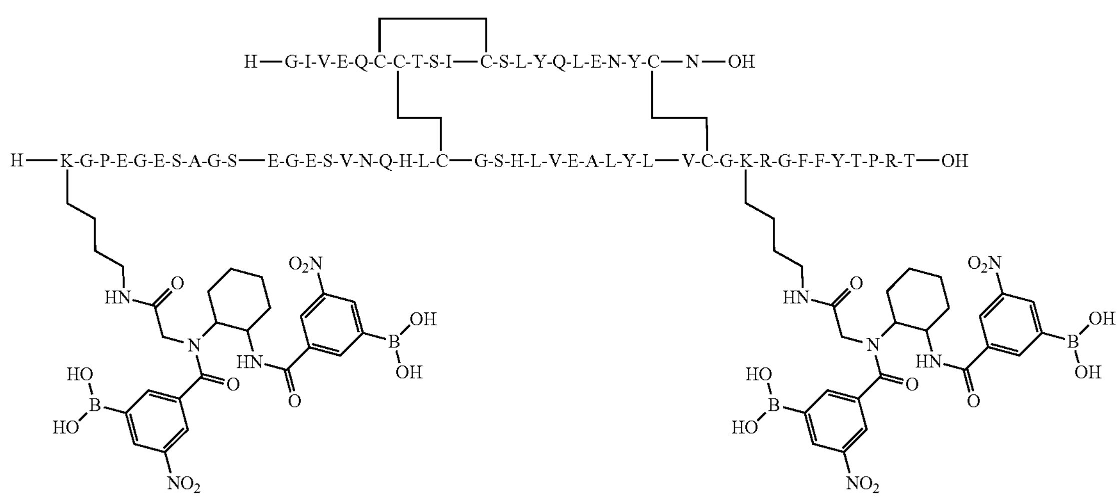

Modified insulin 8 can be made similar to modified insulin 1.
Modified Insulin 9
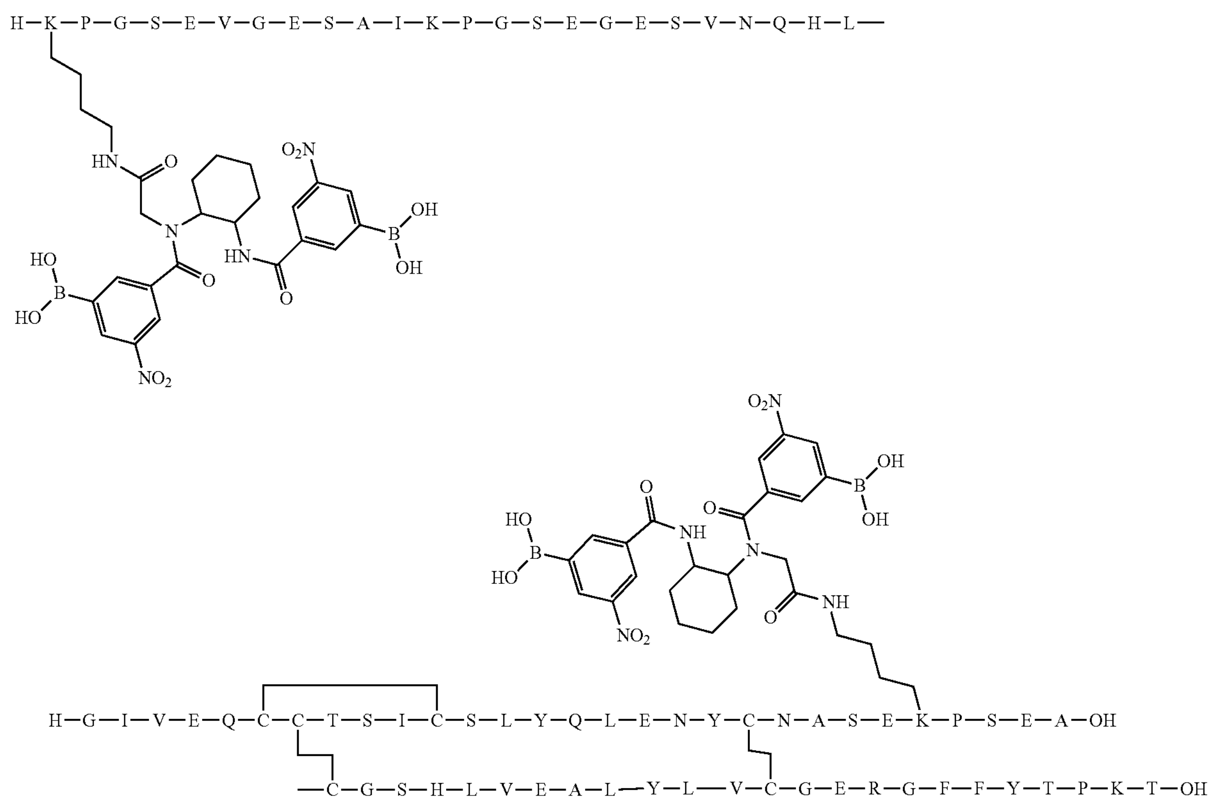
Modified insulin 9 can be made similar to modified insulin 1.
Modified Insulin 10
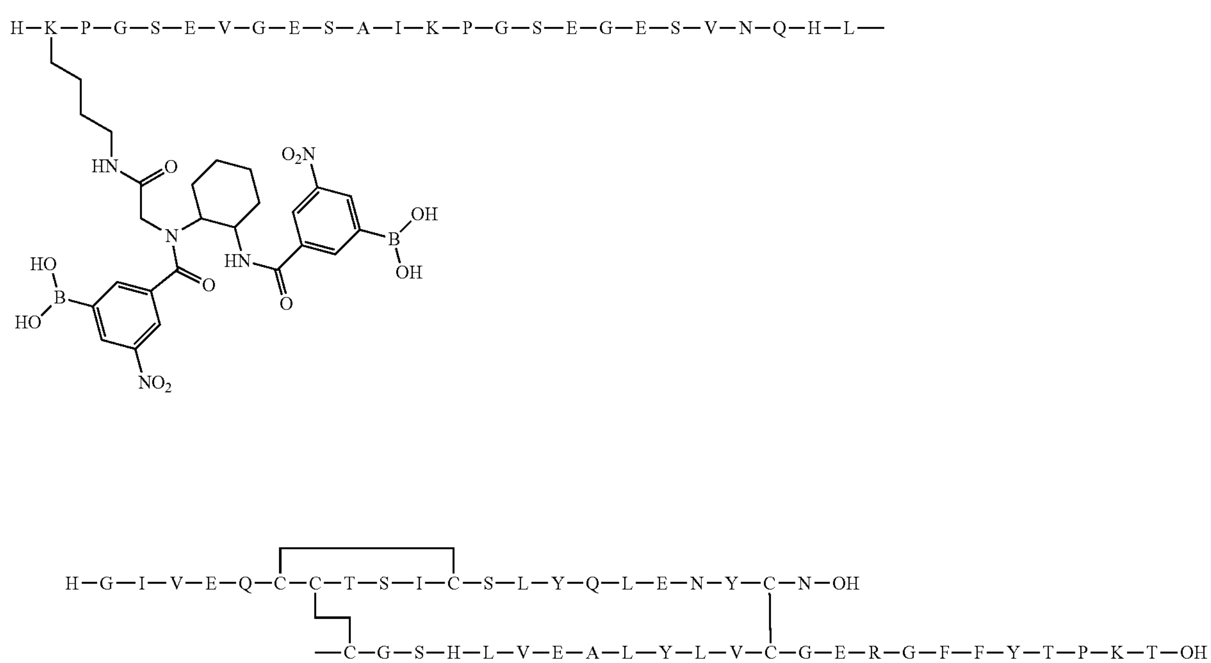

Modified insulin 10 can be made similar to modified insulin 1.
Modified Insulin 11
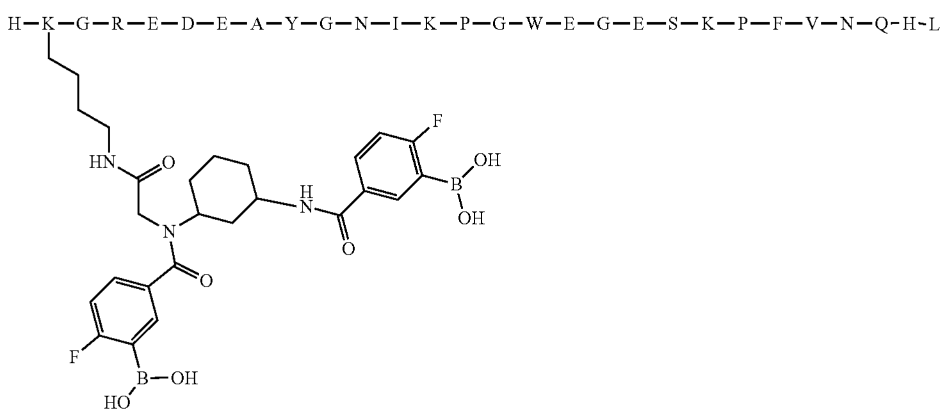
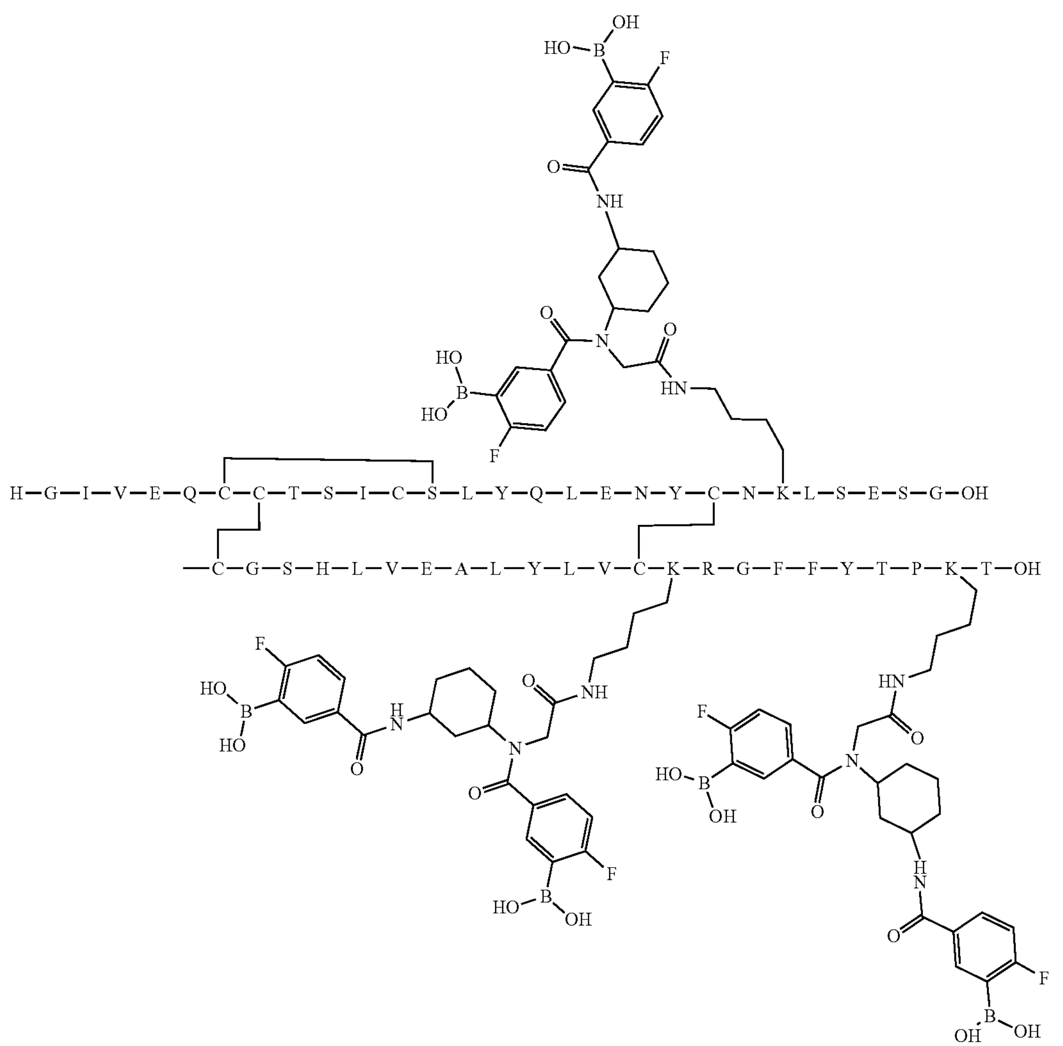

Modified insulin 11 can be made similar to modified insulin 1.
Modified Insulin 12
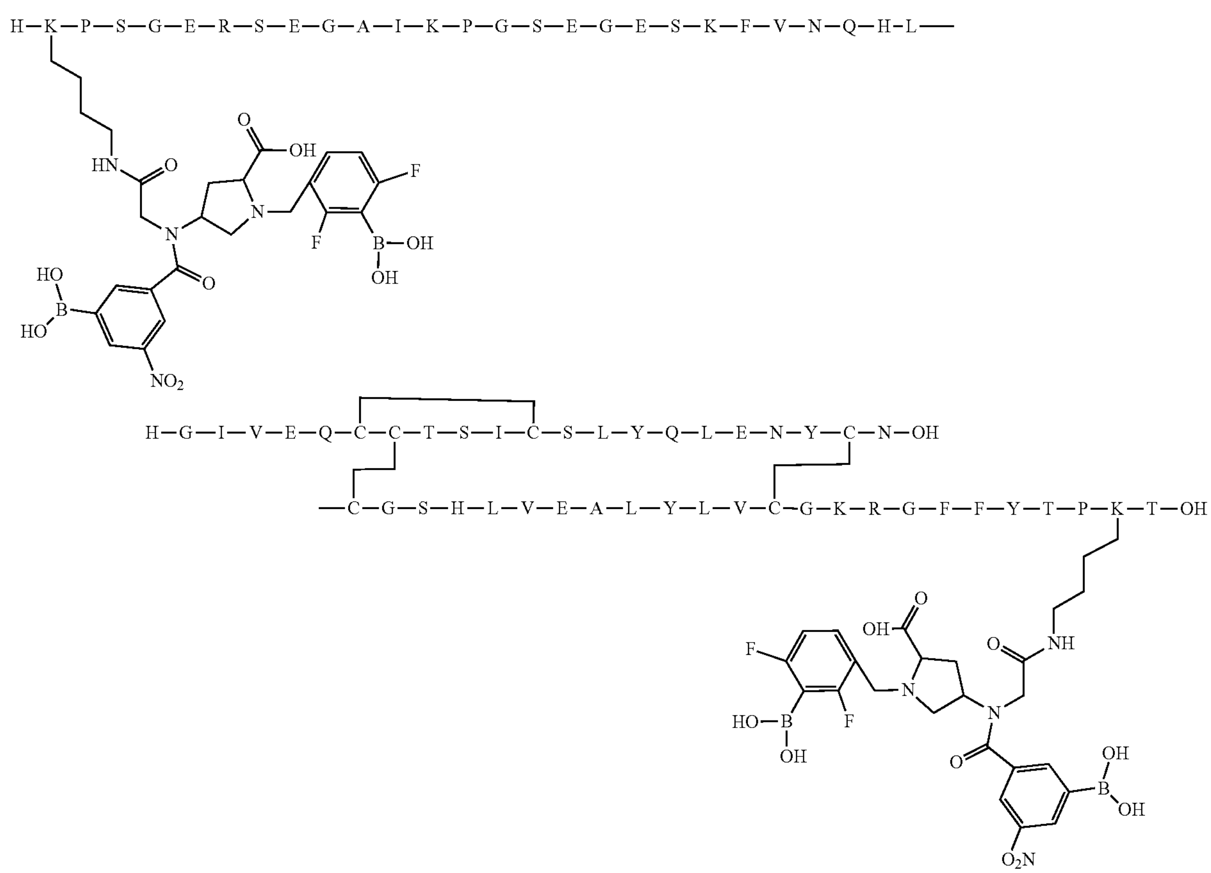
Modified insulin 12 can be made similar to modified insulin 3.
Modified Insulin 13

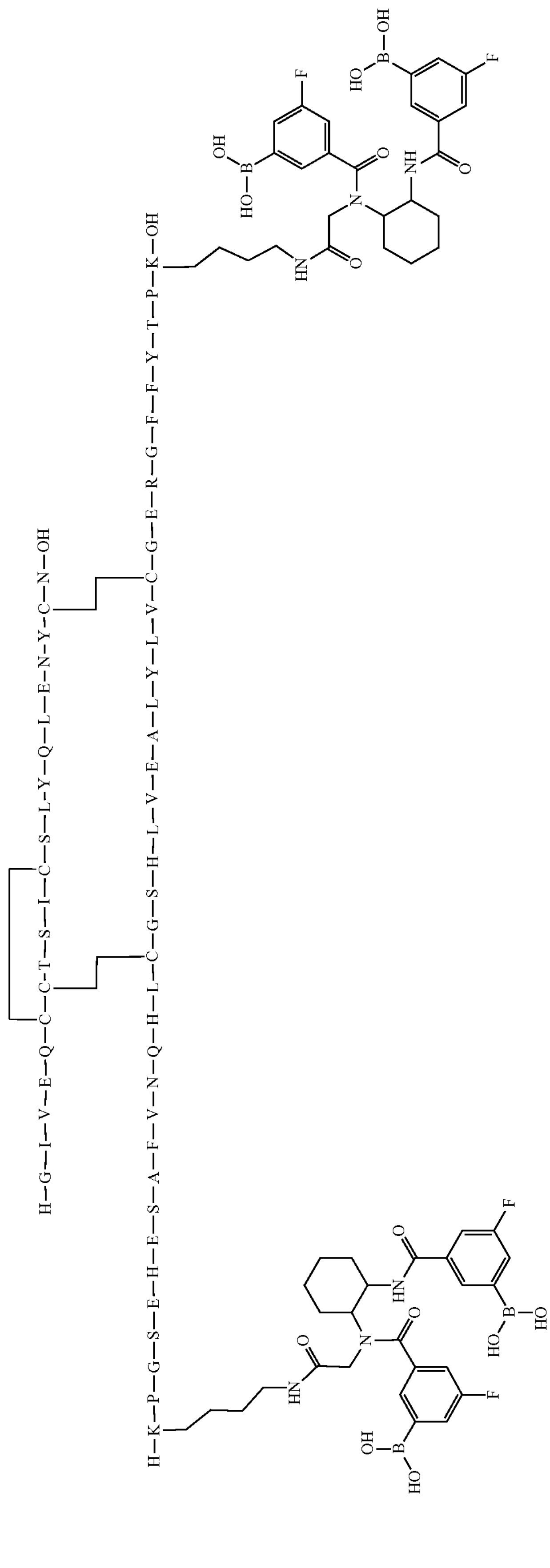

Modified insulin 13 can be made similar to modified insulin 1.

Modified Insulin 14

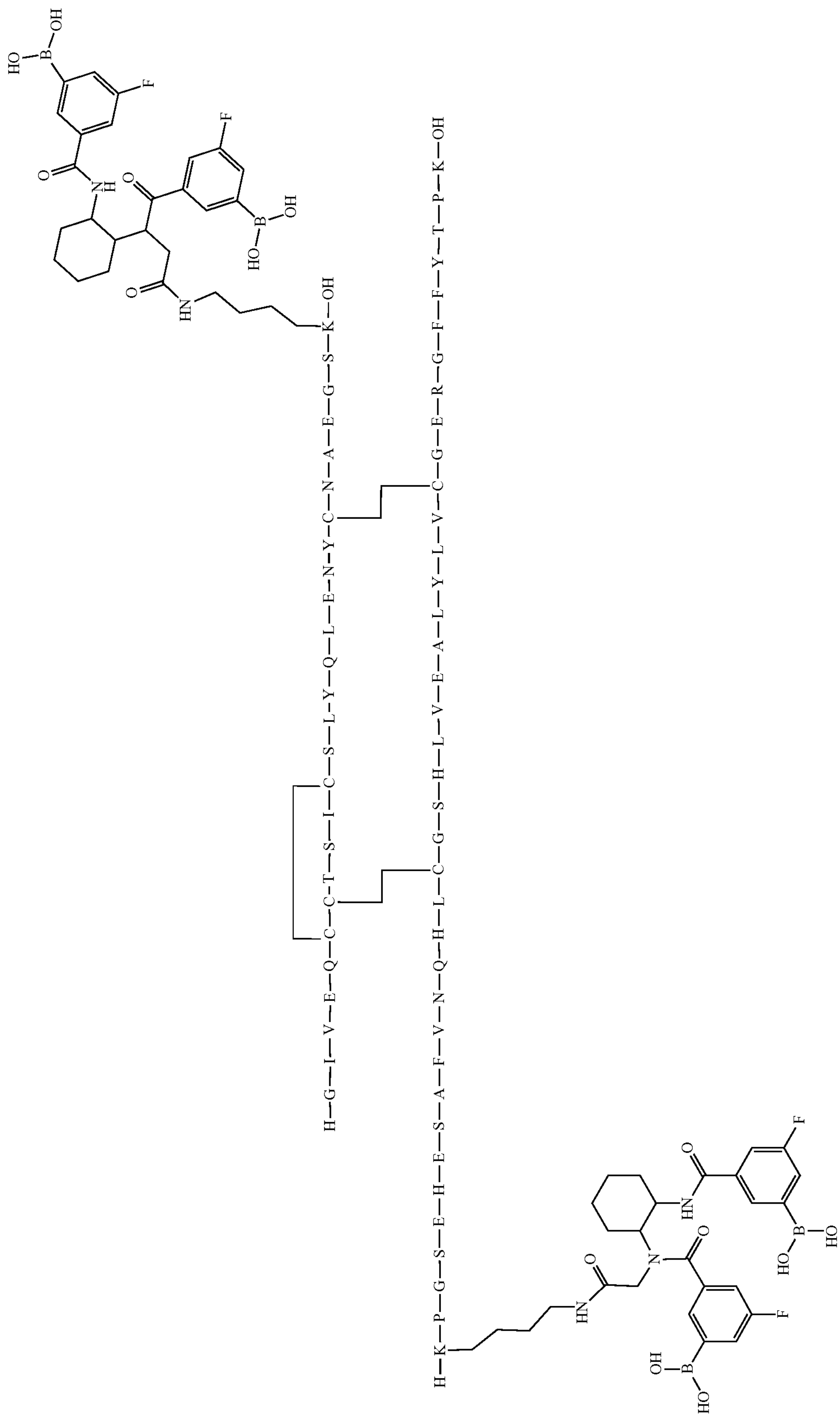

Modified insulin 14 can be made similar to modified insulin 1.

Modified Insulin 15

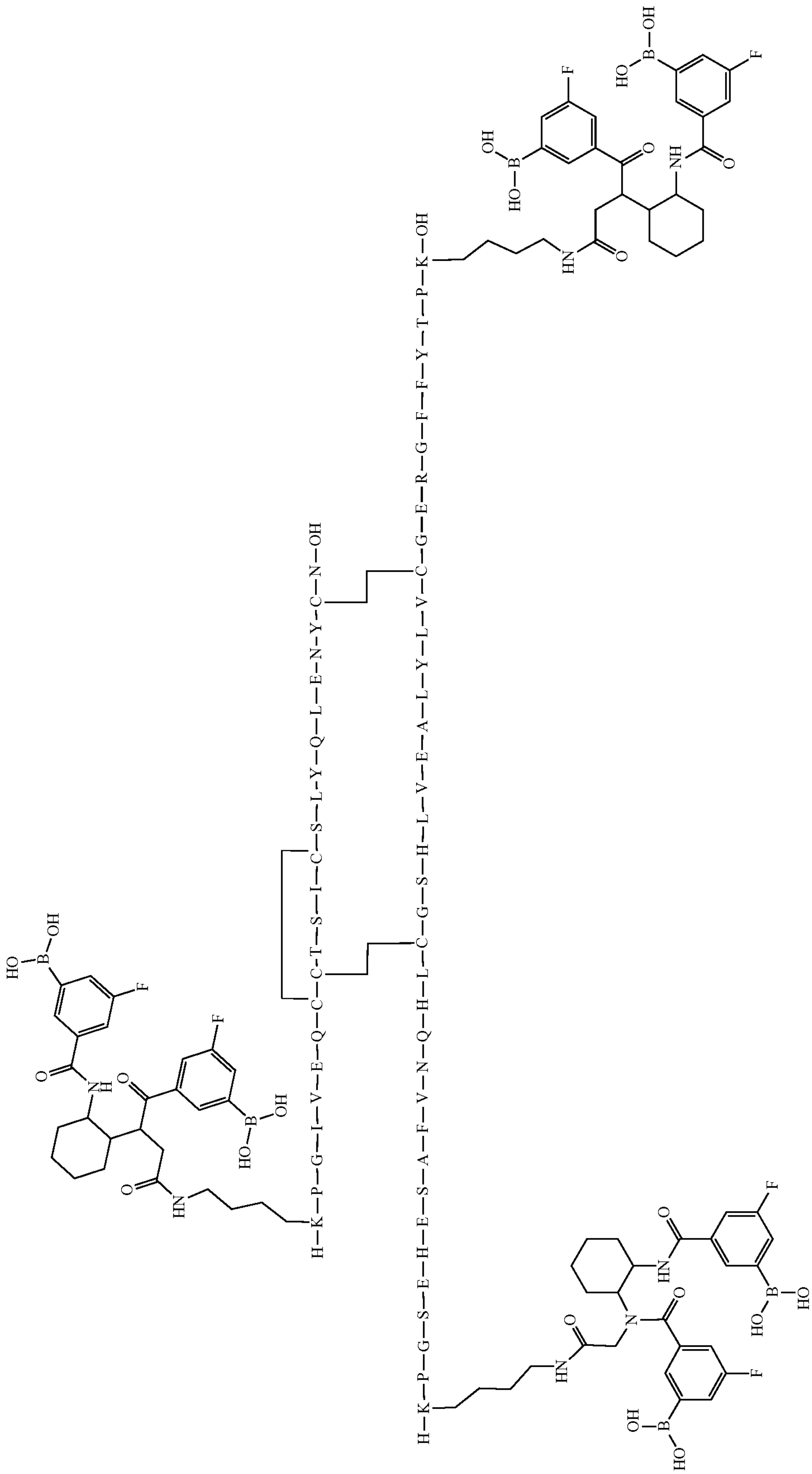

Modified insulin 15 can be made similar to modified insulin 1.

Modified Insulin 16

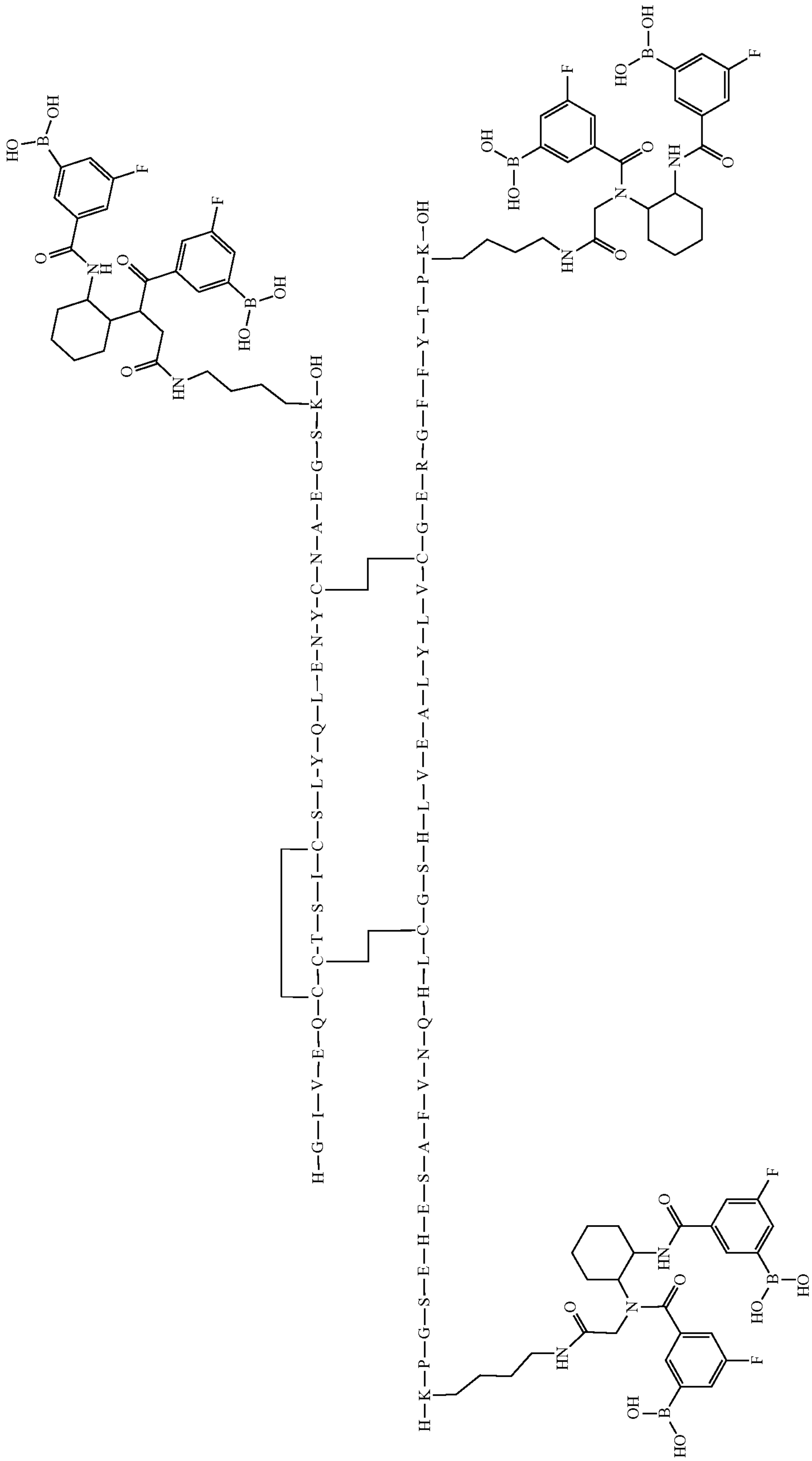

Modified insulin 16 can be made similar to modified insulin 1.

Modified Insulin 17

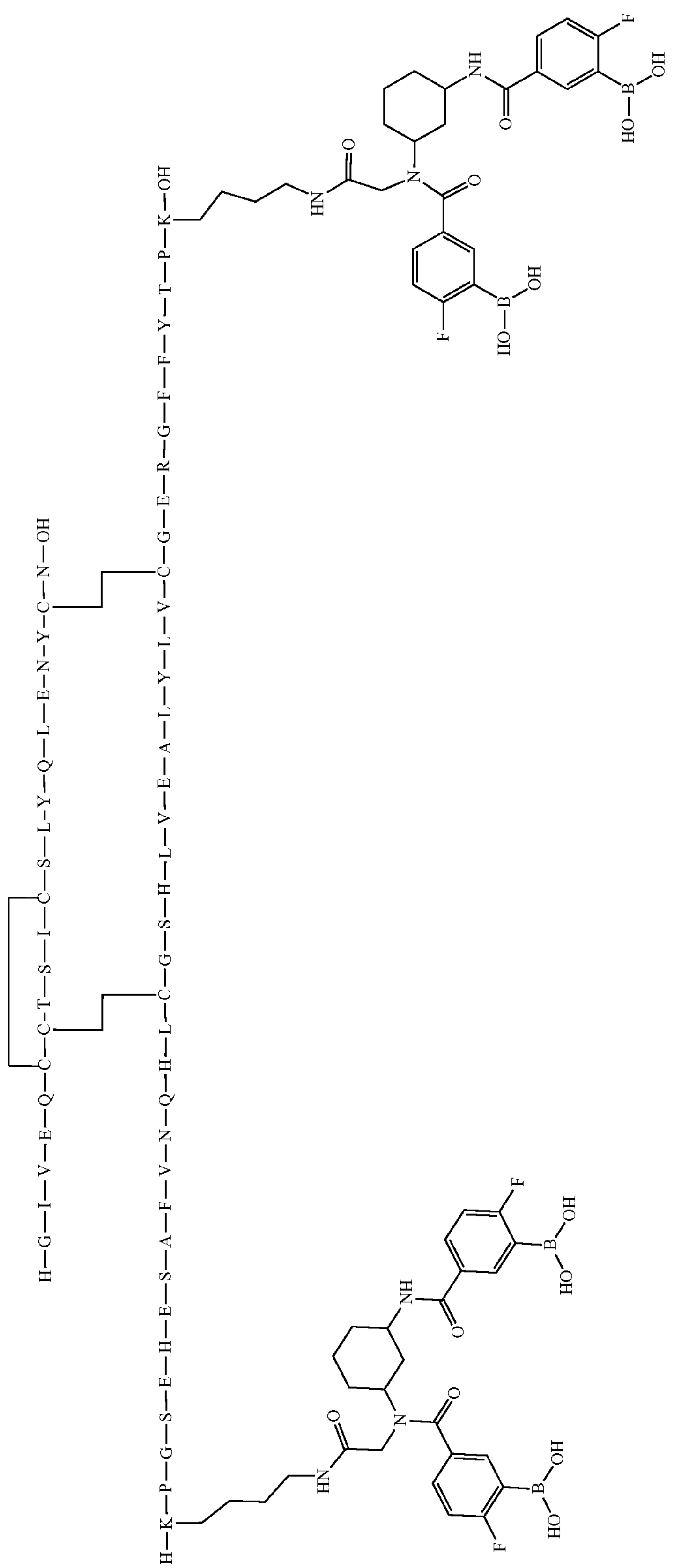

Modified insulin 17 can be made similar to modified insulin 1.

Modified Insulin 18

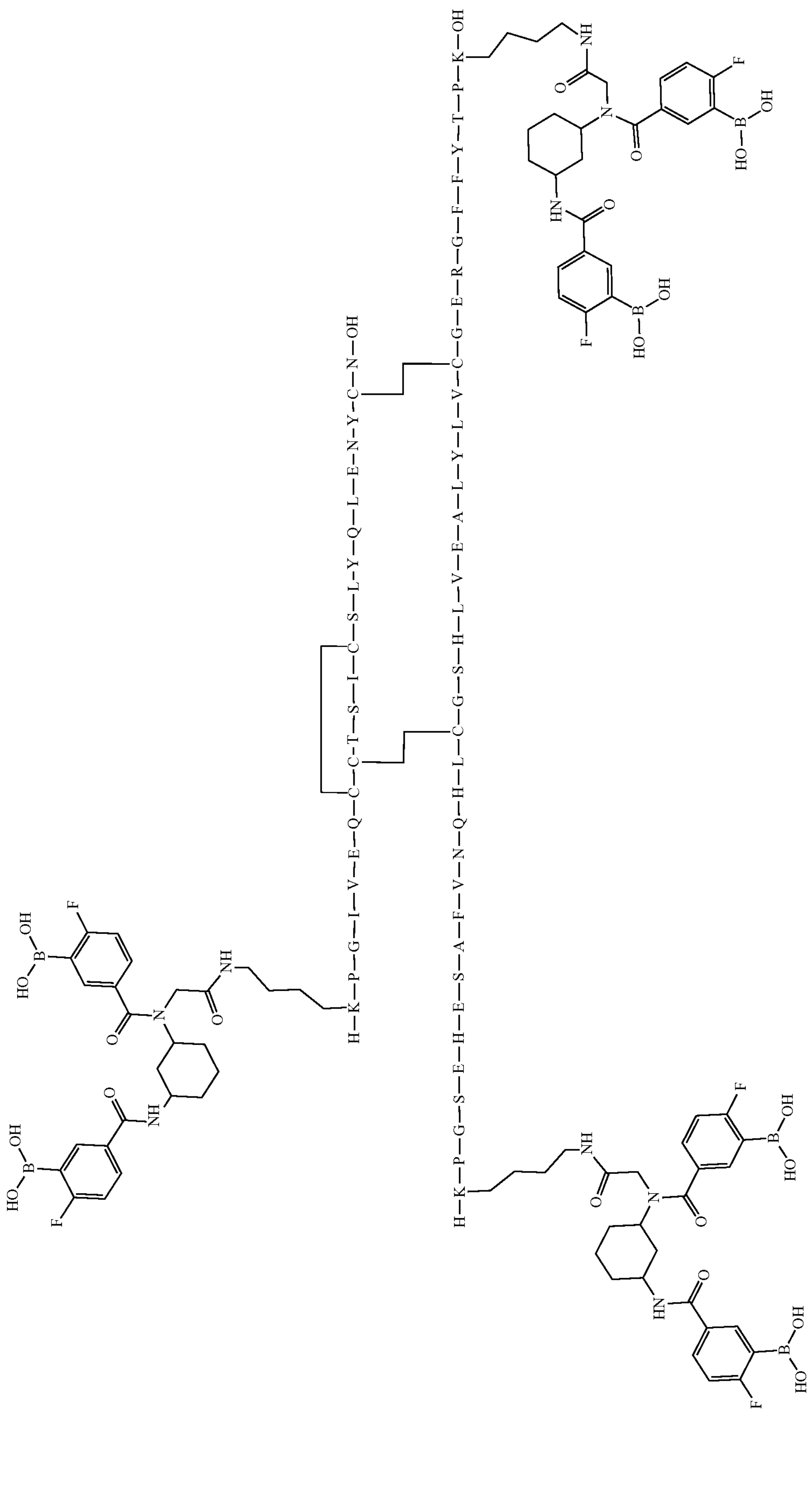

Modified insulin 18 can be made similar to modified insulin 1.

Modified Insulin 19

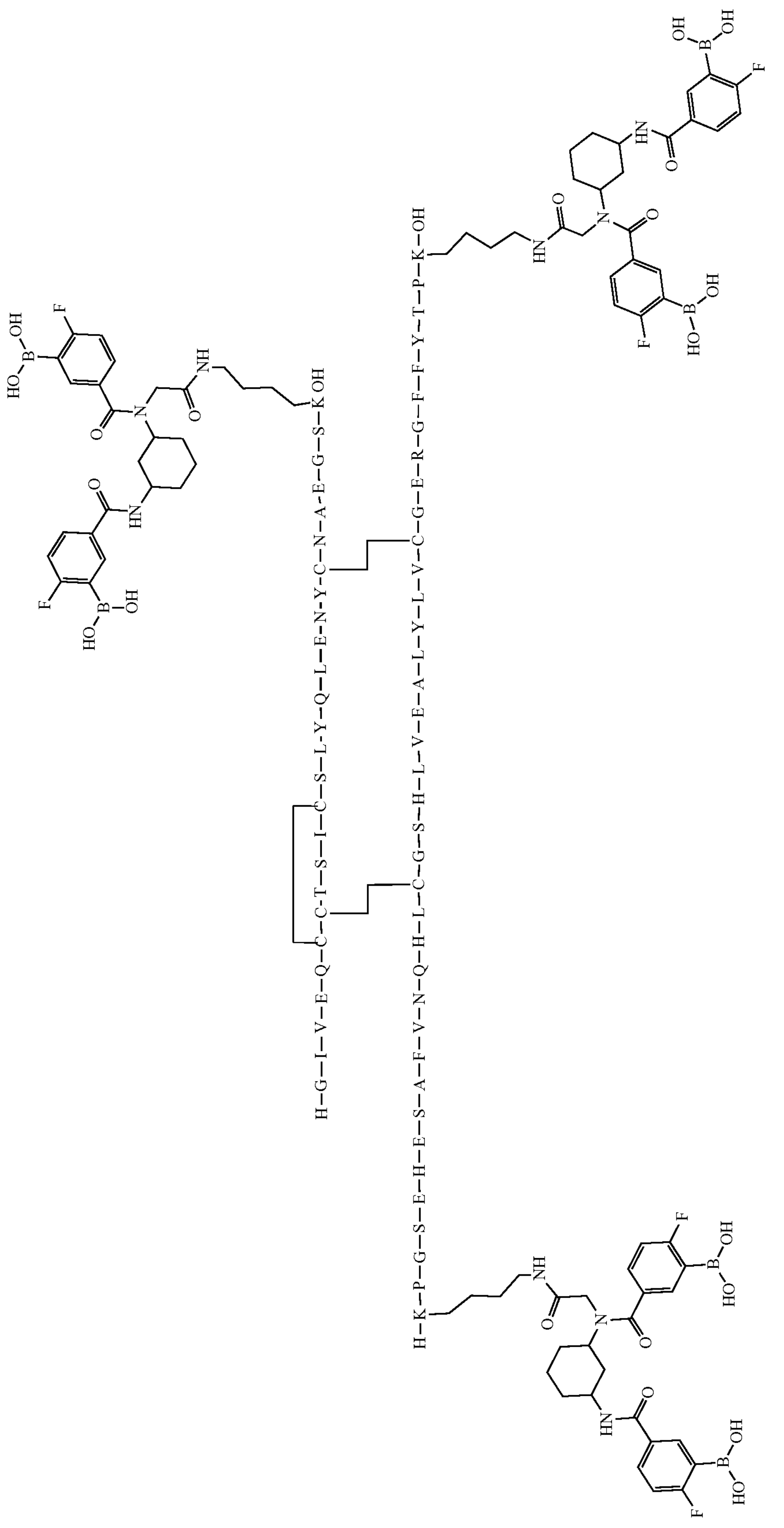

Modified insulin 19 can be made similar to modified insulin 1.

Modified Insulin 20

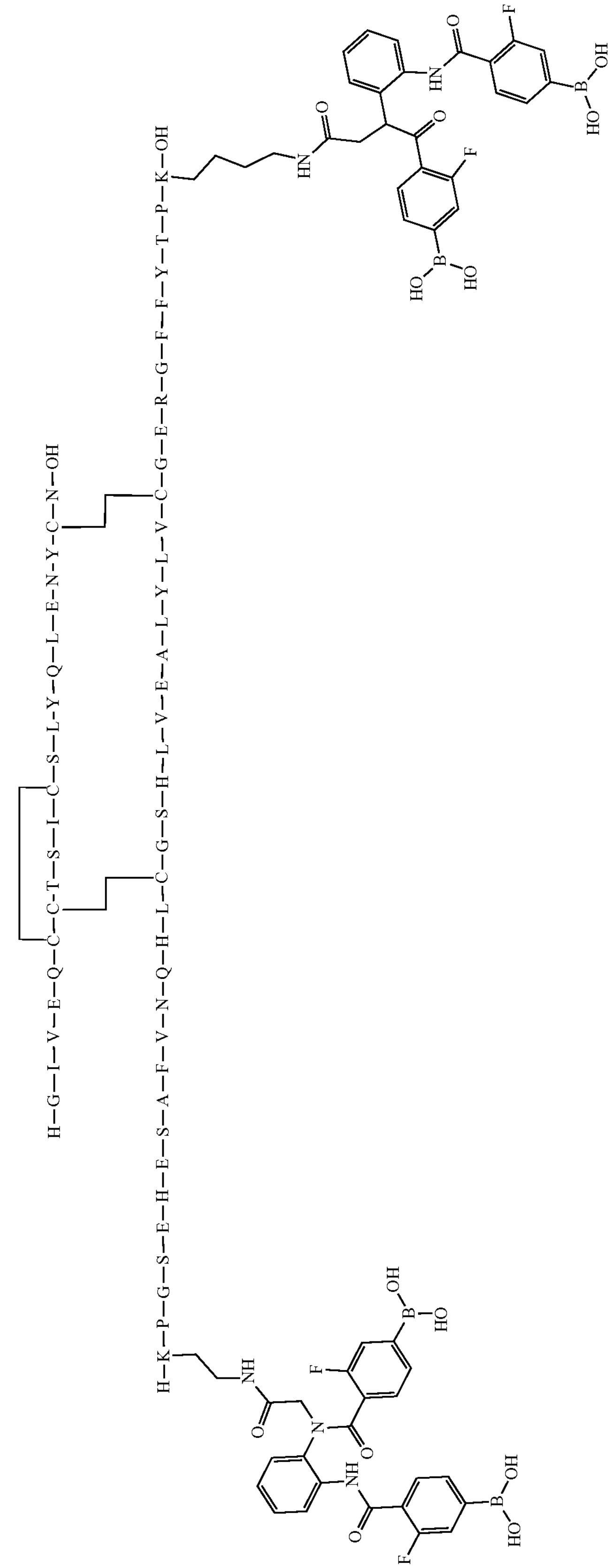

Modified insulin 20 can be made similar to modified insulin 1.

Modified Insulin 21

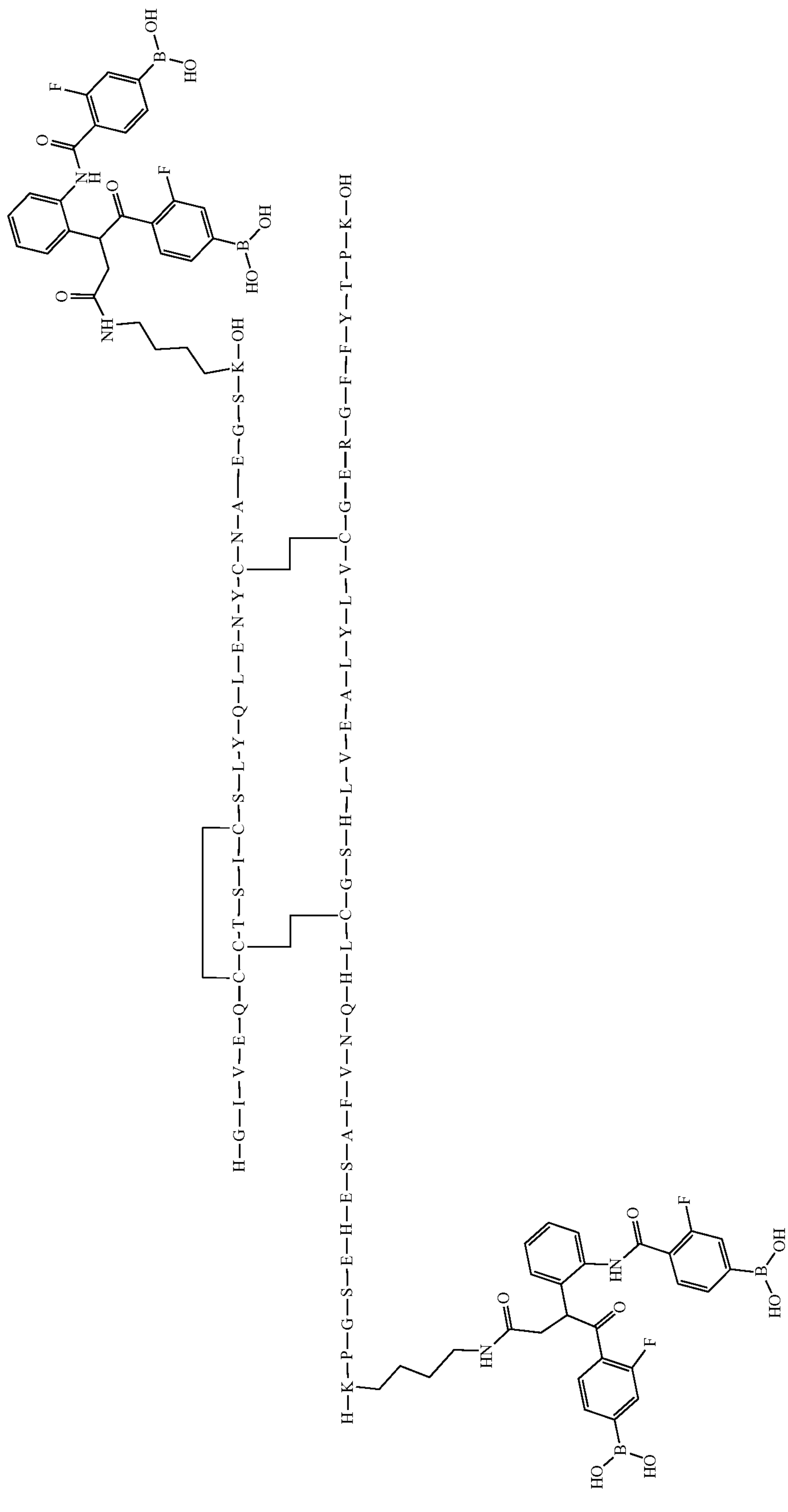

Modified insulin 21 can be made similar to modified insulin 1.
Modified Insulin 22
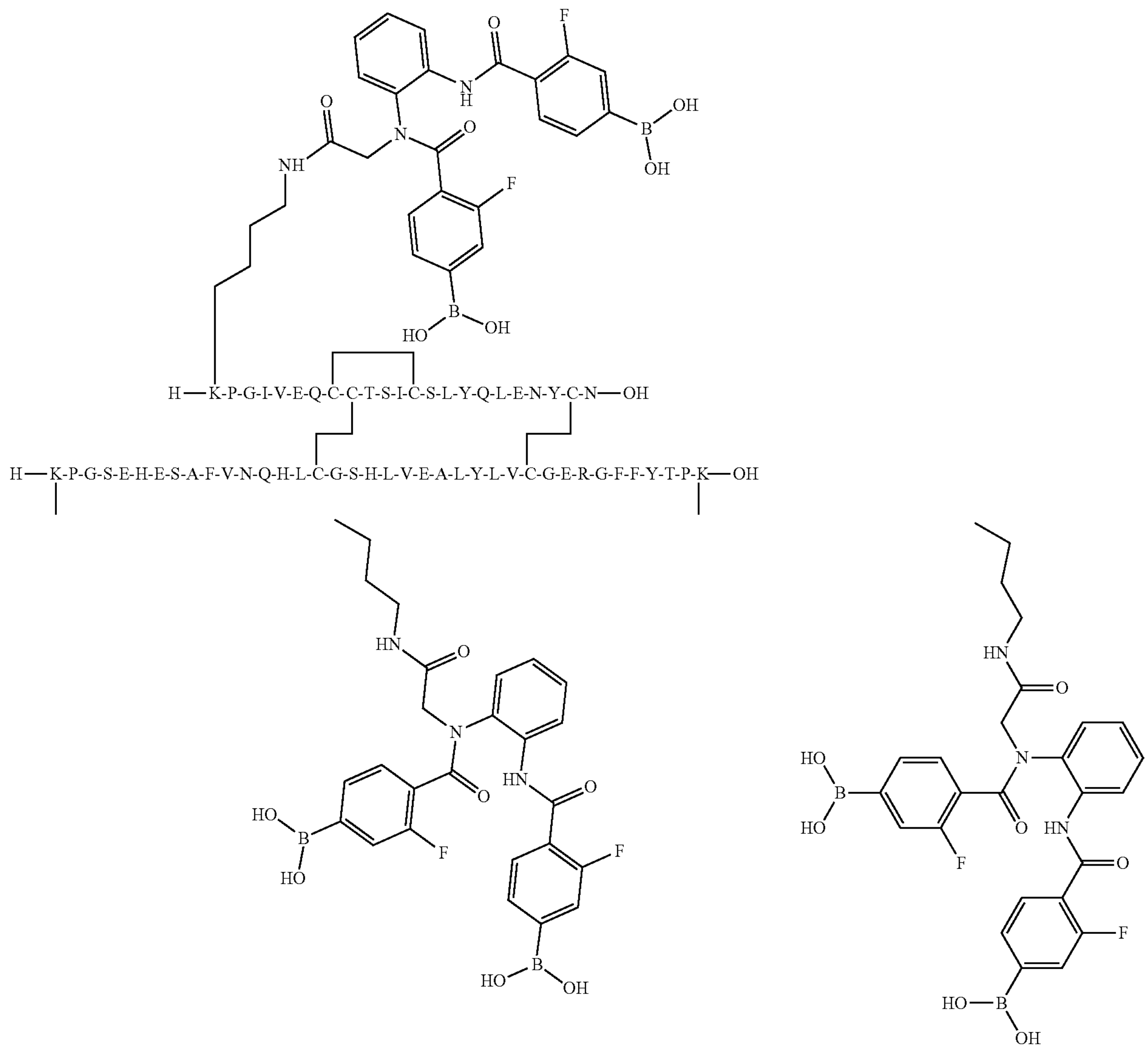
Modified insulin 22 can be made similar to modified insulin 1.
Modified Insulin 23

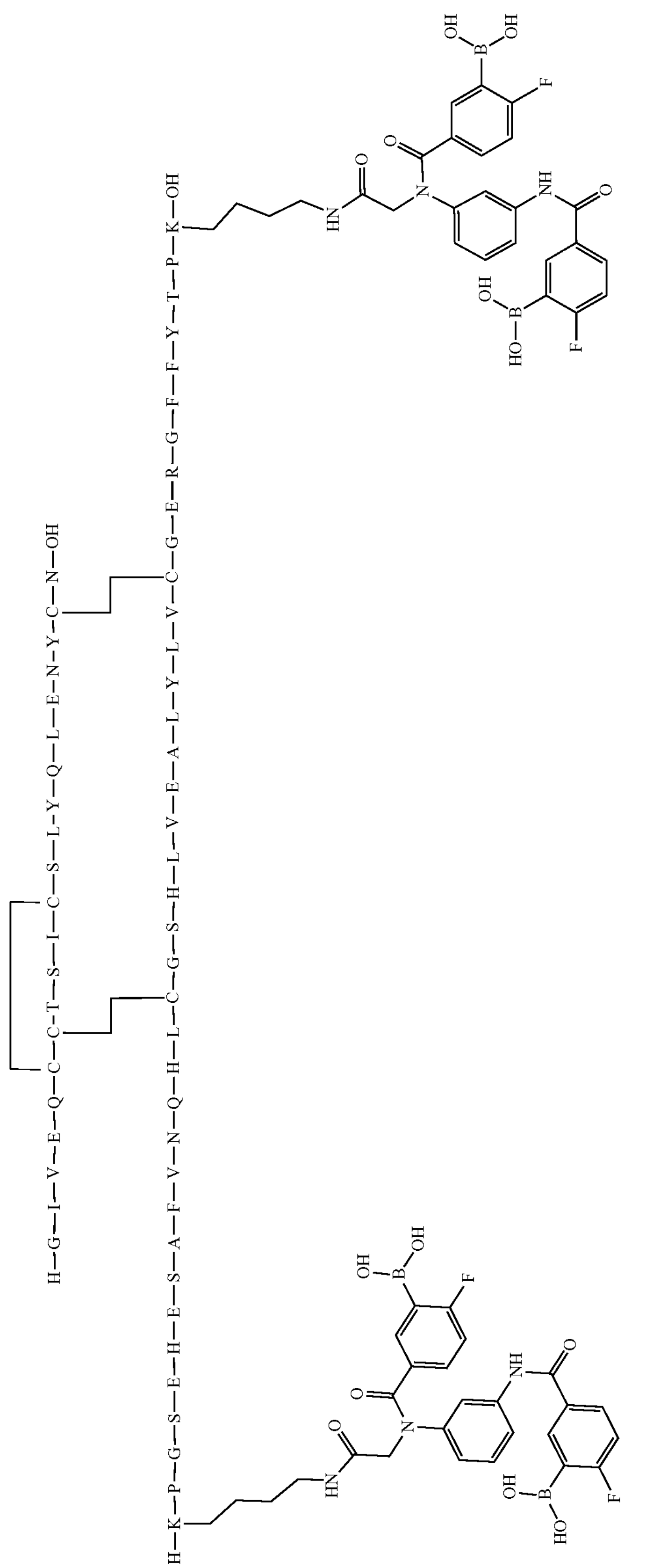

Modified insulin 23 can be made similar to modified insulin 1.
Modified Insulin 24
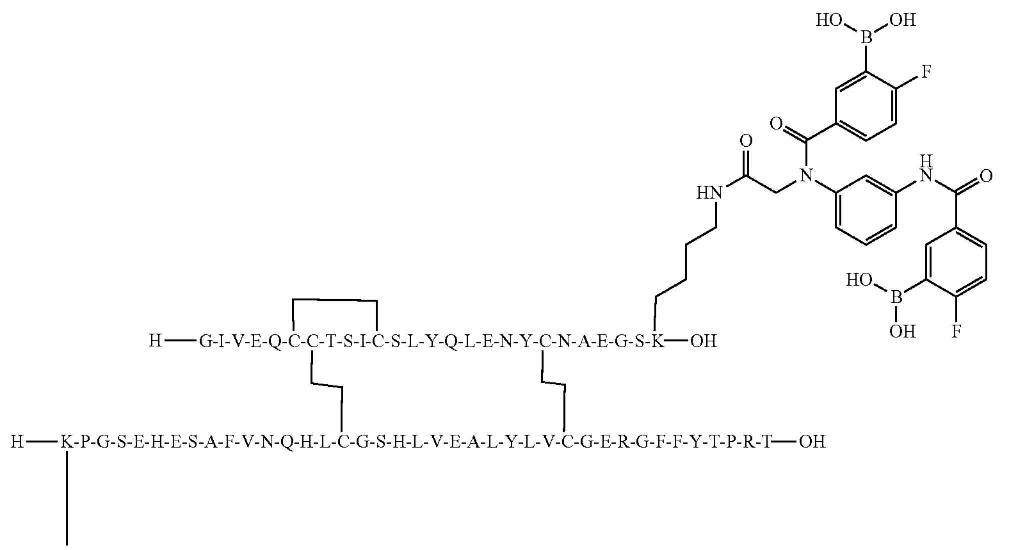
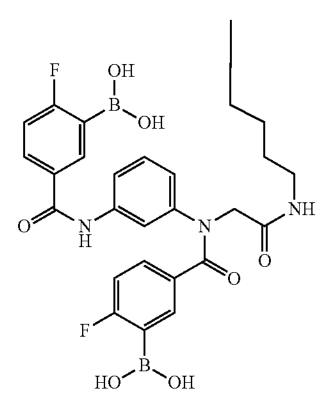

Modified insulin 24 can be made similar to modified insulin 1.
Modified Insulin 25
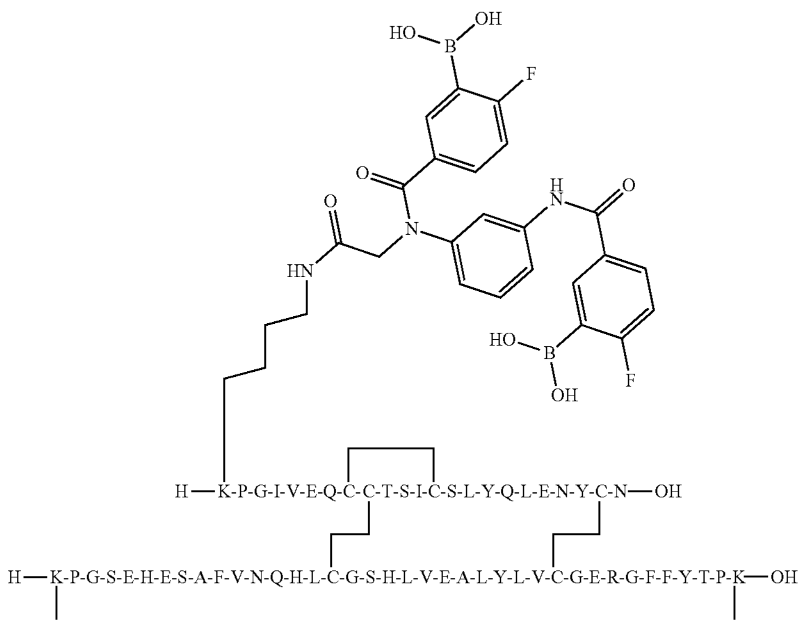
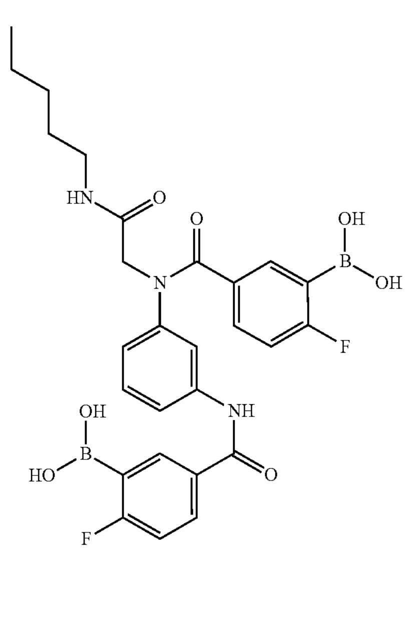
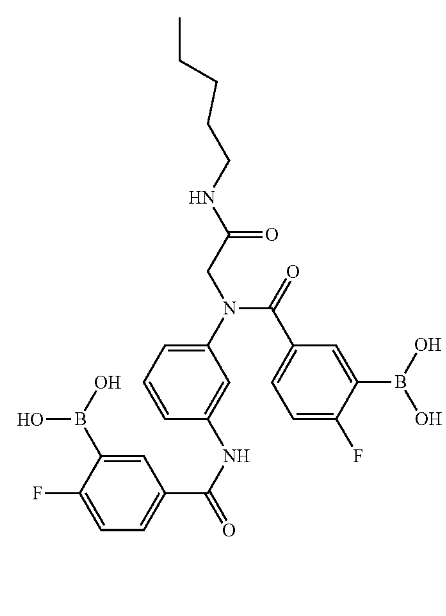

Modified insulin 25 can be made similar to modified insulin 1.
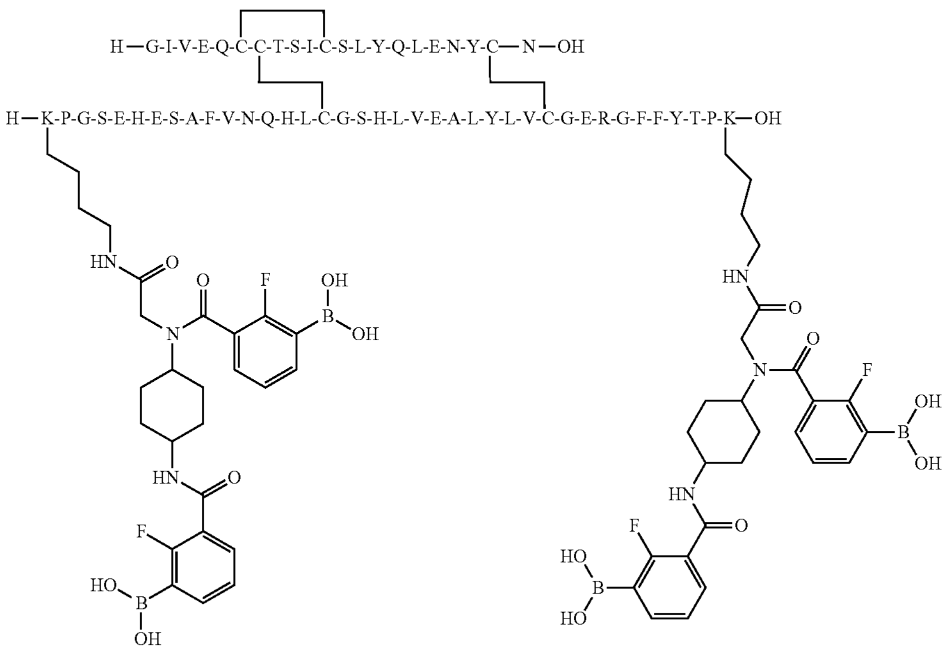
Modified insulin 26 can be made similar to insulin 1.
Modified Insulin 27
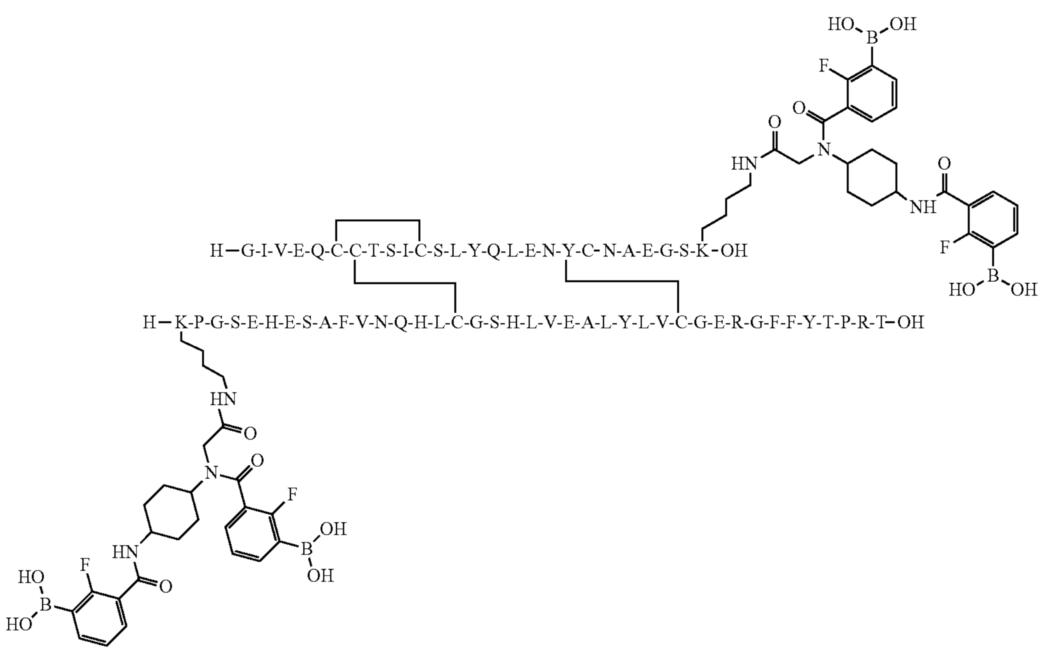

Modified insulin 27 can be made similar to insulin 1.
Modified Insulin 28
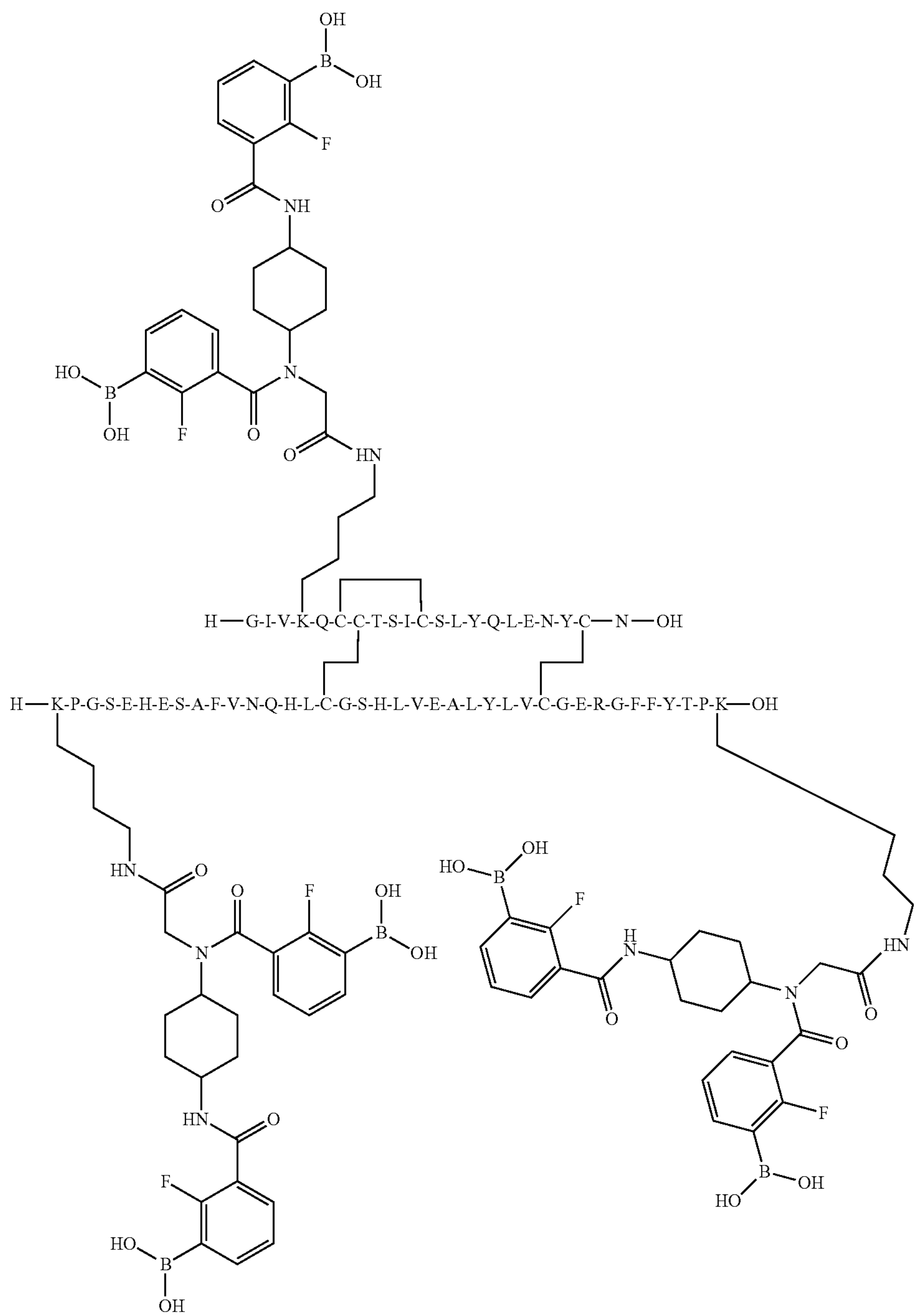

Modified insulin 28 can be made similar to insulin 1.
Modified Insulin 29
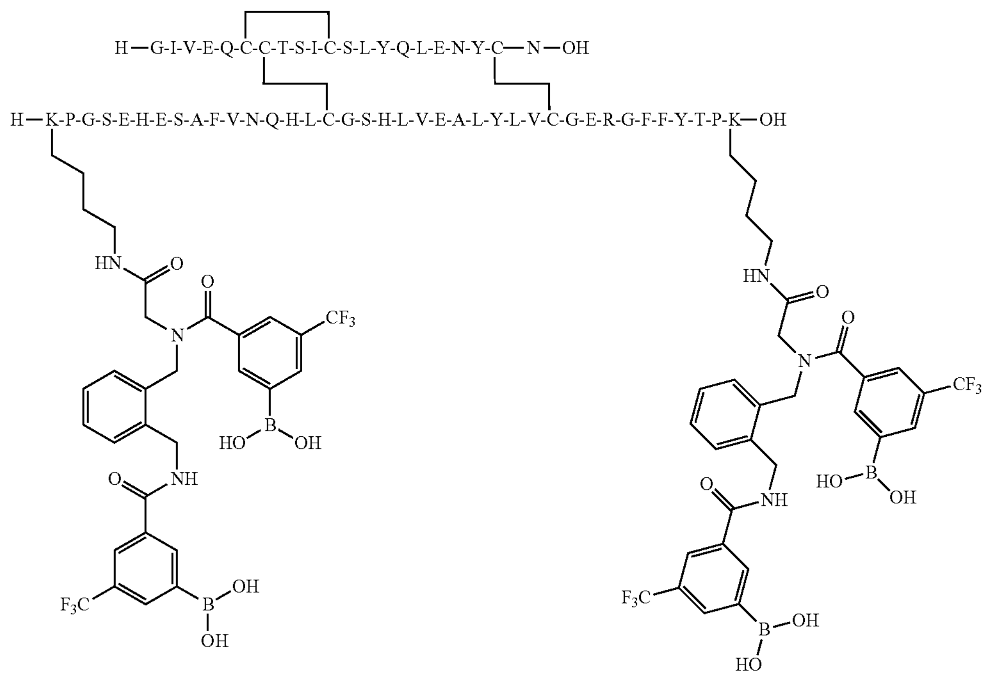
Modified insulin 29 can be made similar to insulin 1.
Modified Insulin 30
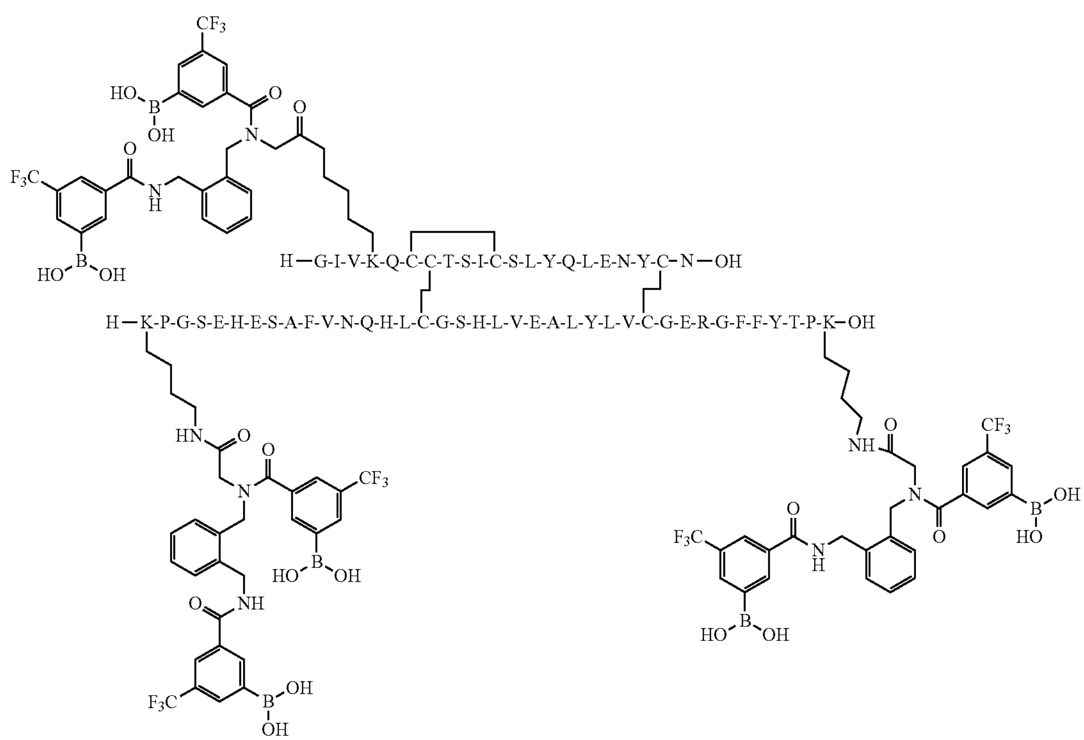

Modified insulin 30 can be made similar to insulin 1.
Modified Insulin 31
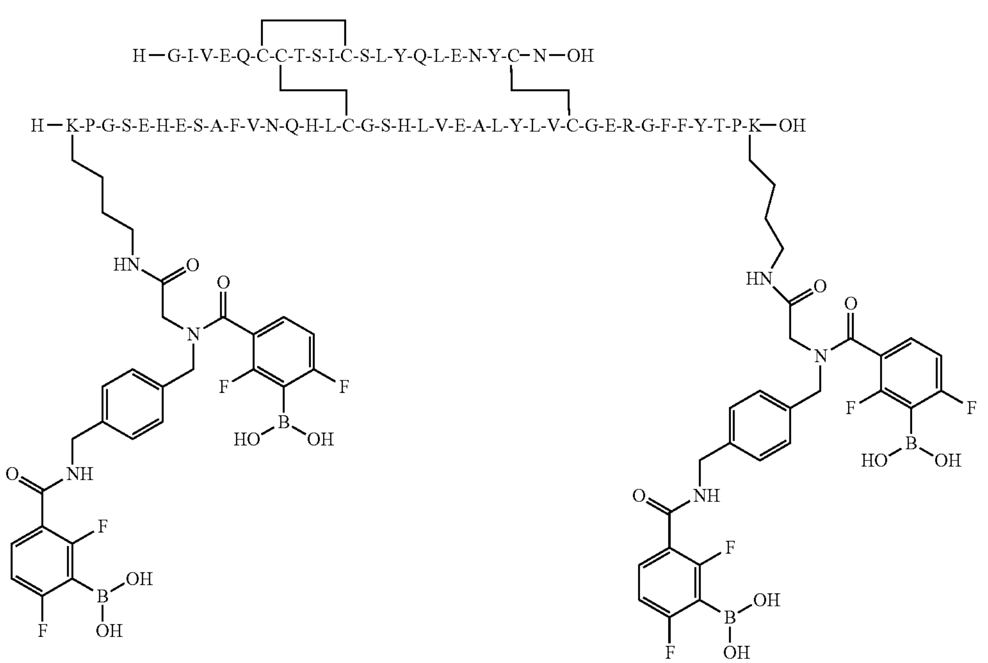

Modified insulin 31 can be made similar to insulin 1.
Modified Insulin 32
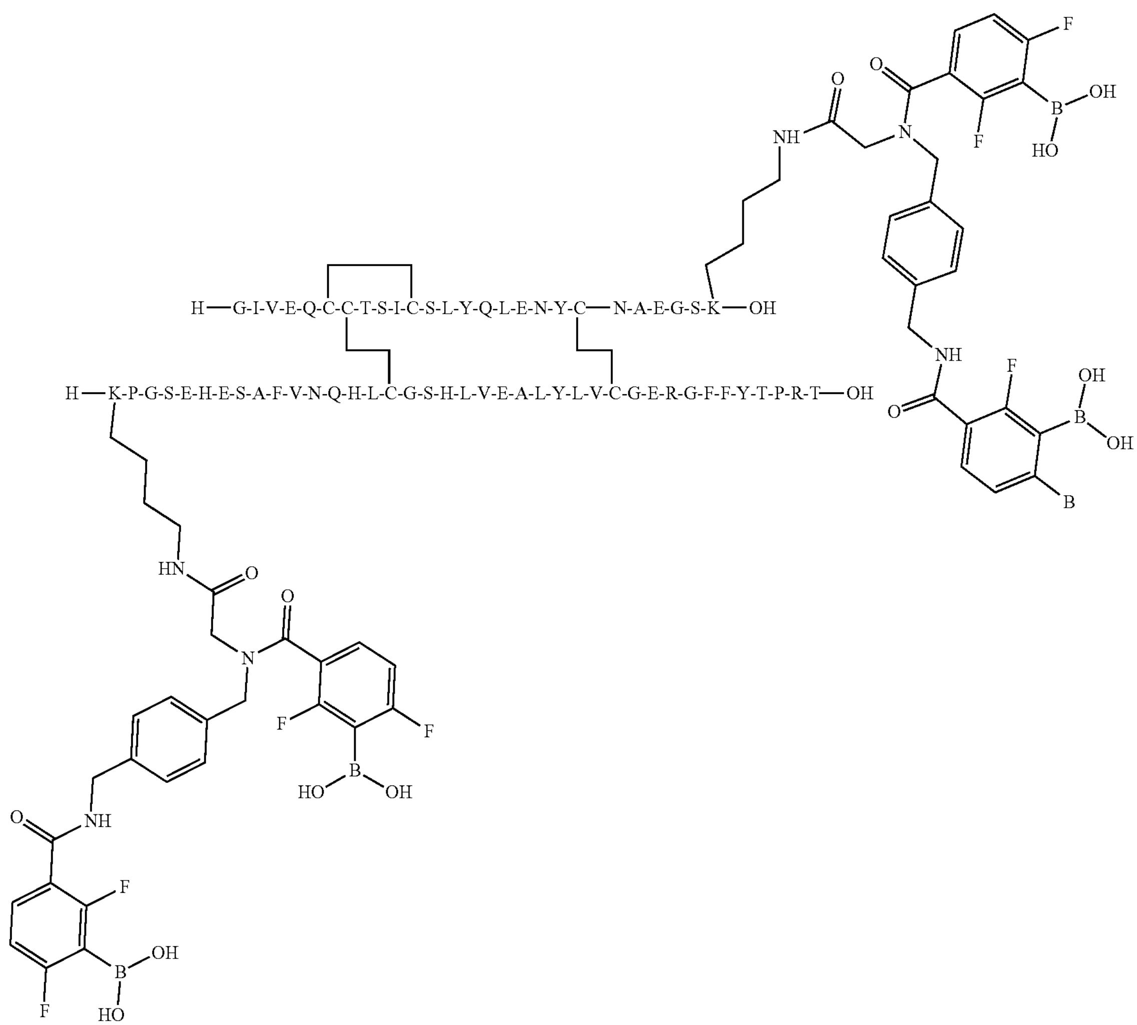

Modified insulin 32 can be made similar to insulin 1.
Modified insulin 33 1
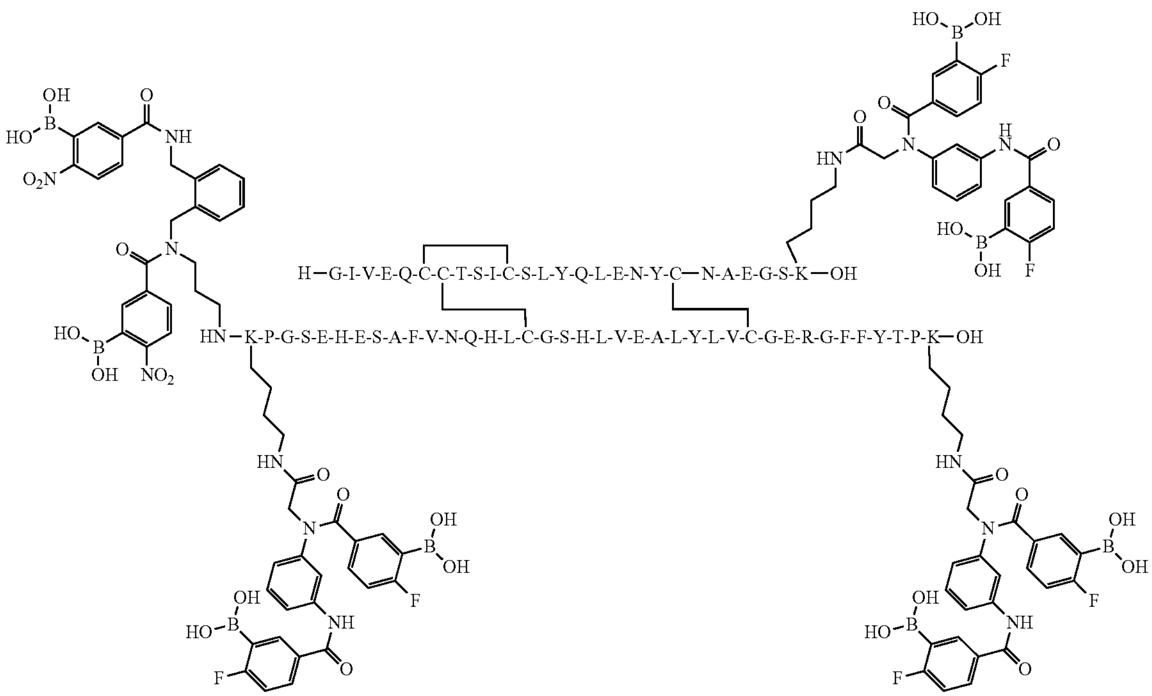
Modified insulin 33 can be made similar to modified insulin 1.
Modified Insulin 34
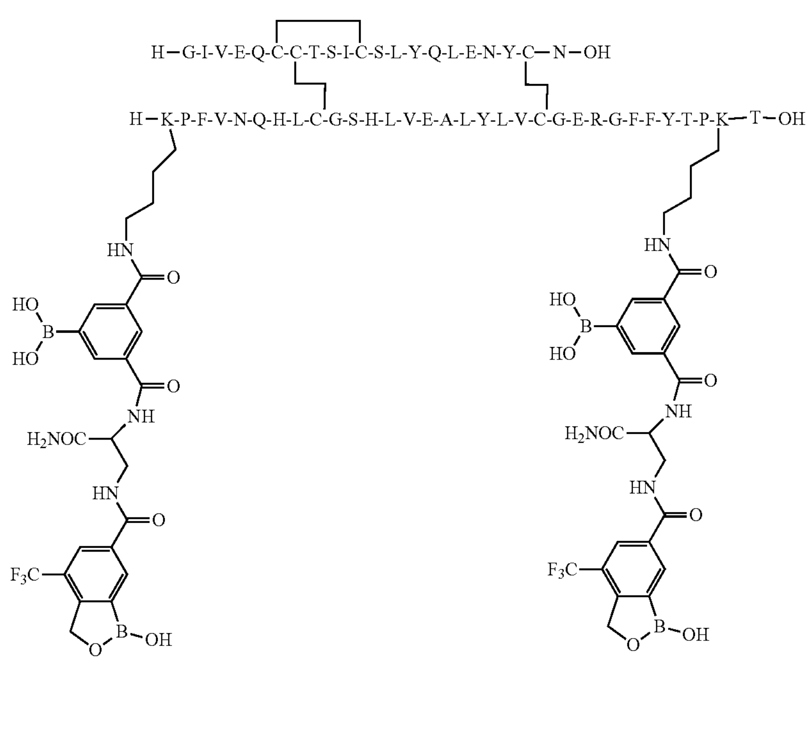

Modified insulin 34 can be made similar to modified insulin 2.

Determination of the Glucose Binding (Kd) Using Alizarin Red S (ARS) Displacement Assay.

The association constant for the binding event between Alizarin Red S (ARS) and the compounds of each of examples 1-24 was determined using standard methods in the art. Triplicate titrations of 10-5 M ARS in 0.1M phosphate buffer, pH 7.4, were performed in a 96-well plate against serial dilutions of example compounds, ranging in concentration from 0-0.1M at 25° C. The example compound-ARS solution was incubated for 5-45 minutes at 25° C., and absorbance intensity was measured using excitation wavelength 468 nm and emission wavelength 585 nm. Changes in intensity were plotted against the concentration of the example compound, and the intensity data was fitted to yield an association constant for ARS binding.

The association constant for the binding between a target sugar compound (e.g., glucose) and a boronate compound was determined via the displacement of ARS bound to the example compounds. Triplicate wells of 10-5 M ARS and 0.1M example compounds in 0.1M phosphate buffer, pH 7.4, were titrated in a 96-well plate against serial dilutions of the target sugar compound, ranging in concentration from 0-2.0 M at 25° C. The boronate-ARS-carbohydrate solution was incubated for 30-60 minutes at 25° C. and the intensity of each well was measured in a plate reader at excitation wavelength 468 nm and emission wavelength 585 nm. Changes in intensity were plotted against concentration of the target sugar compound, and the data was fitted to a one-site competition equation:

$$y=\min(y)+(\max(y)-\min(y))/\left(1+10^{x-logEC50}\right)$$

to yield an association constant for the boronate compound-target sugar compound binding event.

Table 1 shows the binding constants of Examples 1-24 to glucose, fructose, and lactate.

TABLE 1

| Example | Kd (mM) glucose | Kd (mM) fructose | Kd (mM) lactate |
|---|---|---|---|
| Example 1 | 25.2 | 1.7 | 38.3 |
| Example 2 | 3.7 | 2.0 | 58 |
| Example 3 | 14 | 1.9 | 48 |
| Example 4 | 13 | 5.6 | 132.6 |
| Example 5 | 29.4 | 11 | 224.8 |
| Example 6 | 3.4 | 4.6 | 74.1 |
| Example 7 | 4.4 | 1.2 | 39.5 |
| Example 8 | 32 | 2.2 | 184 |
| Example 9 | 6.5 | 10.63 | 261 |
| Example 10 | 99.85 | 11.48 | 183.47 |
| Example 11 | 210.83 | 24.7 | 241.65 |
| Example 12 | 197.6 | 12.09 | 201.1 |
| Example 13 | 371.45 | 17.8 | 196.7 |
| Example 14 | 1.642 | 5.882 | 59.8 |
| Example 15 | 59.02 | 4.8 | 51.6 |
| Example 17 | 88.6 | 6.5 | 53.52 |
| Example 18 | 95.4 | 6.04 | 67.5 |
| Example 19 | 43.02 | 2.87 | 31.02 |
| Example 20 | 30.36 | 5.86 | 70.27 |
| Example 21 | 127.38 | 13.54 | 116.85 |
| Example 22 | 16.127 | 9.522 | 97.3 |
| Example 23 | 28.09 | 4 | 53.36 |
| Example 24 | 93.7 | 9.36 | 134.69 |

One or more embodiments of the present disclosure include the following embodiments 1 to 43:

1. A compound represented by Formula I:

Z—R (Formula 1)

wherein, in Formula I,

R is selected from Formulae FF1-FF24; and

Z is selected from one of:

a) $NH_2$ or OH, b) a covalent linkage, either directly or via an optional linker, to a drug substance, c) a covalent linkage, either directly or via the optional linker, to an N-terminal amine or an epsilon amino group of one or more amino acids in a polypeptide drug substance, and d) a group represented by J-$SCH_2$-ø, J-$S(CH_2)_2$-ø, J-NH—ø, J-NH—(the optional linker)-ø, J-$S(CH_2)_k$NH—-ø, or J-triazole$(CH_2)_k$NH—ø;

wherein —ø is the covalent bond towards R;

index k is an integer in the range of 3 to 14, for example, 4 to 12, 5 to 10, or 6 to 8; and J is an amino acid or one or more amino acids in a polypeptide drug substance, wherein each of the one or more amino acids in the polypeptide drug substance is represented by Formula I':

(Formula I')

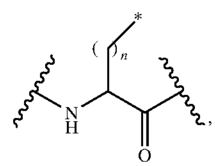

, wherein, in Formula I',

and

indicate points of attachment to remaining portions of the polypeptide drug substance;

indicates the point of attachment to the remaining portion of Z; and index n is an integer in the range of 1 to 8, for example, 1,2, 3,4,5,6,7 or 8, wherein for Formulae FF1-FF24:

(FF1)

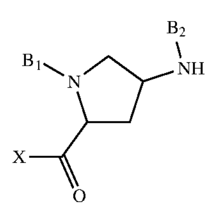

(FF2)

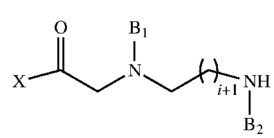

-continued
(FF3)
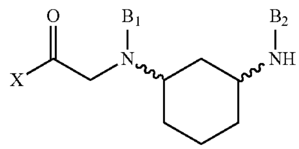
(FF4)
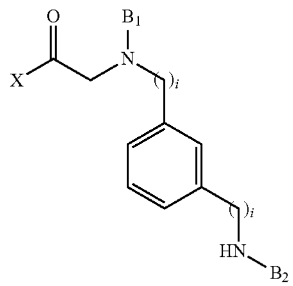
(FF5)
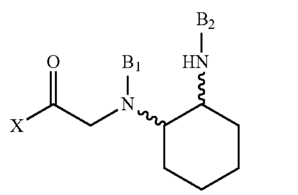
(FF6)
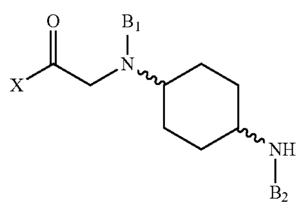
(FF7)
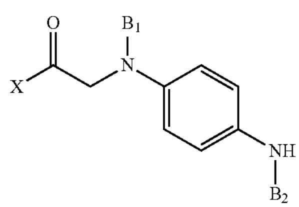
(FF8)
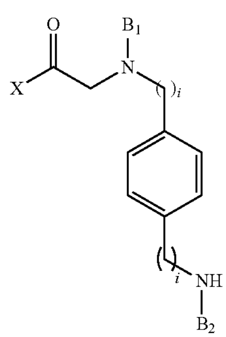
(FF9)
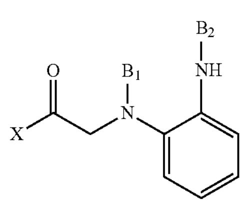
-continued
(FF10)
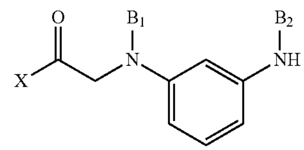
(FF11)
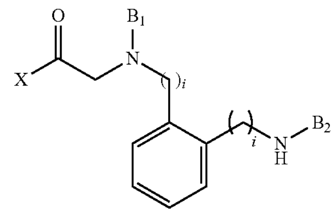
(FF12)
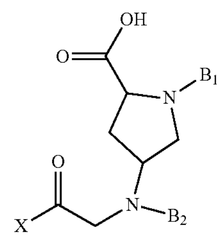
(FF13)
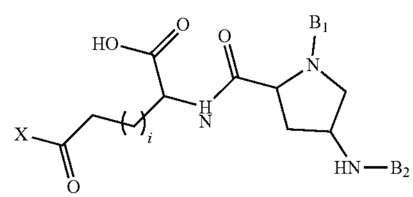
(FF14)
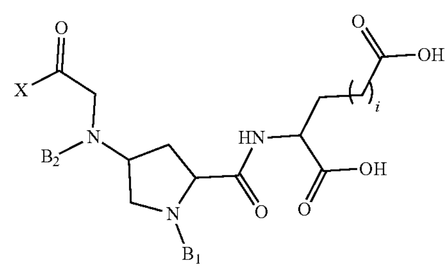
(FF15)
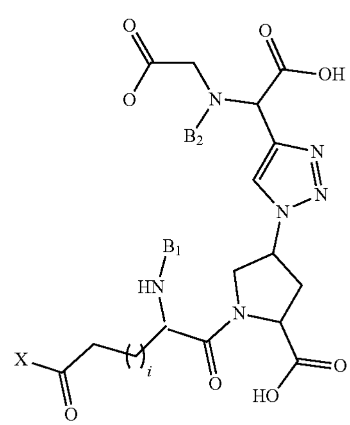

-continued (FF16)

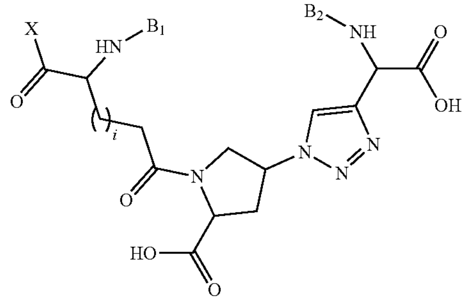

(FF17)

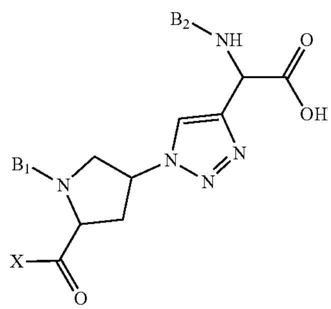

(FF18)

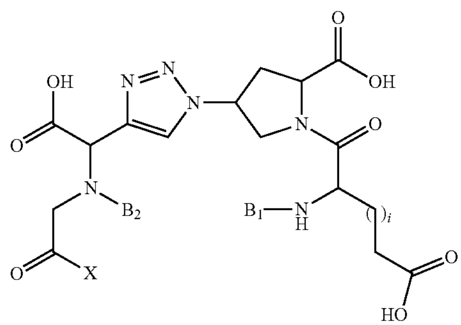

(FF19)

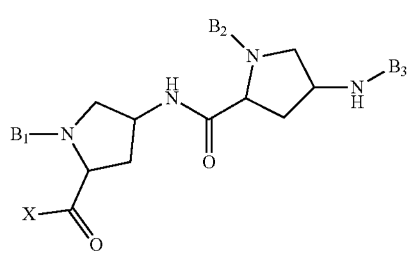

(FF20)

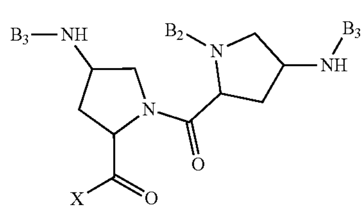

-continued (FF21)

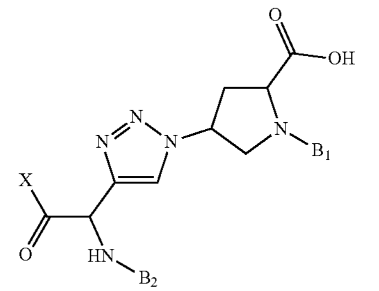

(FF22)

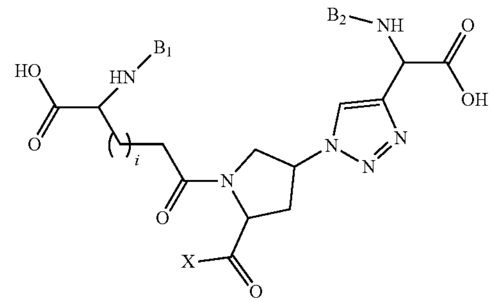

(FF23)

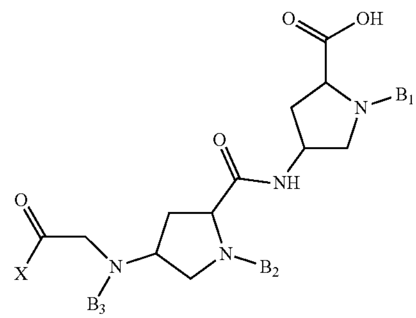

(FF24)

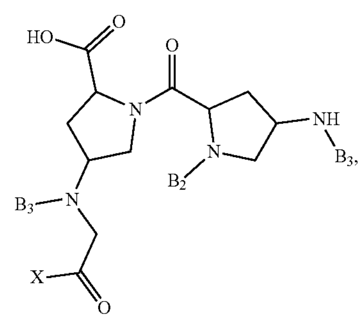

X represents a covalent linkage, either directly or via the optional linker, towards Z in Formula I;

index i is an integer in the range of 1 to 20, for example, 2 to 18, 3 to 16, 4 to 14, 6 to 12, or 8 to 10;

$B_1$ and $B_2$ are identical or different, and are each independently a group represented by one selected from Formulae F1-F9; and $B_3$ is a group represented by one selected from Formulae F1-F1 1, (F1)

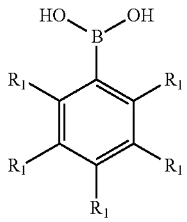

(F2)

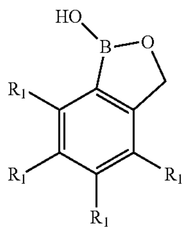

(F3)

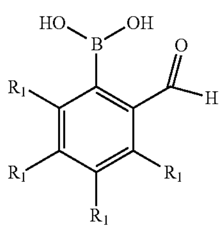

(F4)

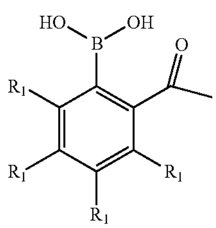

(F5)

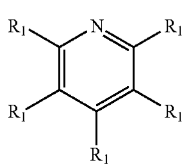

(F6)

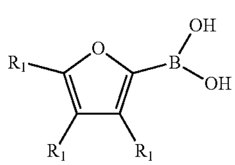

(F7)

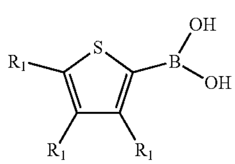

(F8)

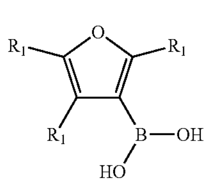

-continued (F9)

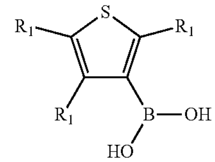

F10

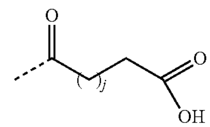

F11 wherein, for each of Formulae F1-F9:

one $R_1$ represents (C═O)—, S(═O)(═O)—, $(CH_2)_m$(C═O)—, or $(CH_2)_m$—, wherein —represents a covalent bond to the remainder of R in Formula I;

none, one, or two $R_1$ each independently represent F, Cl, Br, OH, $CH_2$—$NH_2$, $NH_2$, (C═O)—$NH_2$, $SO_2CH_3$, $CF_3$, $NO_2$, $CH_3$, $OCH_3$, $O(CH_2)_mCH_3$, —$(SO_2)NHCH_3$, —$(SO_2)NH(CH_2)_mCH_3$, or $OCF_3$, index m is an integer in the range of 1 to 14, for example, 2 to 12, 3 to 10, 4 to 8, or 5 to 7;

one $R_1$ in F5 represents $B(OH)_2$, and all remaining $R_1$ represent H, and in Formula F10, index j is an integer in the range of I to 13, for example, 2 to 12, 3 to 10, 4 to 8, or 5 to 7.

2. A compound represented by Formula II:

Z—R (Formula II)

wherein, in Formula II, either:

(i) R is selected from Formulae FF25-FF31;

$B_1$ and $B_2$ in FF25-FF31 are identical or different, and are each independently selected from Formulae F12-F19; and Z is $NH_2$ and is not conjugated to any drug substance;

or (ii) R is selected from Formulae FF25-FF31;

$B_1$ and $B_2$ are each independently selected from Formulae F20-F27; and

Z is selected from one of:

a) OH b) a covalent linkage, either directly or via an optional linker, to a drug substance, c) a covalent linkage, either directly or via the optional linker, to an N-terminal amine or an epsilon amino group of one or more amino acids in a polypeptide drug substance, and d) a group represented by J-$SCH_2$-ø, J-$S(CH_2)_2$—ø, J—NH-ø, J—NH—(the optional linker)—ø, J-S$(CH_2)_k$NH—ø, or J-triazole$(CH_2)_k$NH—ø, wherein —ø is the covalent bond towards R, index k is an integer in the range of 3 to 14, for example, 4 to 12, 5 to 10, or 6 to 8; and J is an amino acid or one or more amino acids in a polypeptide drug substance, wherein each of the one or more amino acids in the polypeptide drug substance is represented by Formula II';

or (iii) R is selected from Formulae FF32-FF33, $B_1$ and $B_2$ in FF32 are each independently selected from Formulae F28-F35;

$B_1$ and $B_2$ in FF33 are each independently selected from Formulae F36-F43; and Z is selected from one of:

a) a drug substance, b) a covalent linkage, either directly or via an optional linker, to the N-terminal amine or the epsilon amino group of an amino acid in a polypeptide drug substance, and c) a group represented by J-$SCH_2$-ø, J-$S(CH_2)_{2-ø}$, J—NH—-ø, J—NH—(the optional linker)-ø, J—S$(CH_2)_k$NH—ø, or J-triazole$(CH_2)_k$NH—ø, wherein —ø is the covalent bond towards R, index k is an integer in the range of 3 to 14, for example, 4 to 12, 5 to 10, or 6 to 8; and J is an amino acid or one or more amino acids in a polypeptide drug substance, wherein each of the one or more amino acids in the polypeptide drug substance is represented by Formula II';

wherein, for Formula II':

(Formula II')

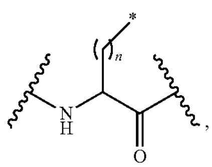

and

indicate points of attachment to remaining portions of the polypeptide drug substance;

indicates the point of attachment to the remaining portion of Z; and index n is an integer in the range of 1 to 8, for example, 2 to 7, 3 to 6, or 4 to 5;

wherein for Formulae FF25-FF33:

(FF25)

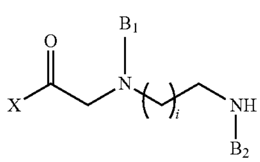

(FF26)

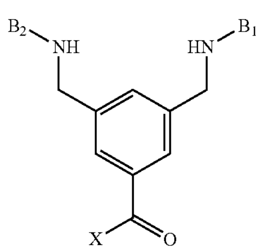

(FF27)

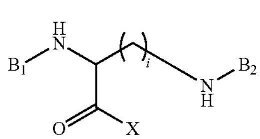

-continued (FF28)

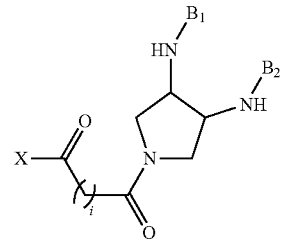

(FF29)

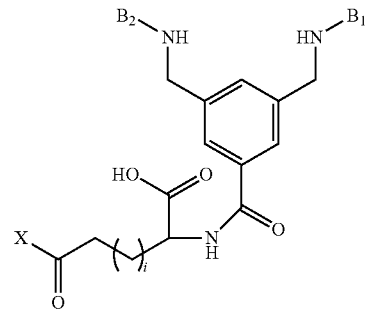

(FF30)

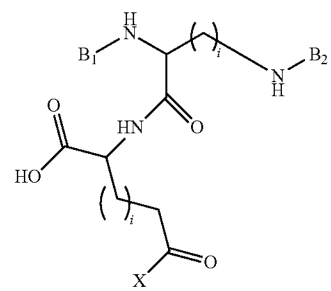

(FF31)

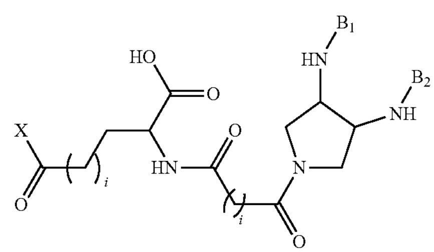

(FF32)

X—$B_1$•$B_2$ (FF33)

$B_1$—$B_2$,

X represents a covalent linkage, either directly or via the optional linker, towards Z in Formula II; and index i is an integer in the range of 1 to 20, for example, 1, 2, 3, 4, 2 to 18, 3 to 16, 4 to 14, 6 to 12, or 8 to 10;

wherein, for each of Formulae F12-F19:

(F12)

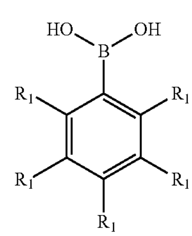

-continued (F13)

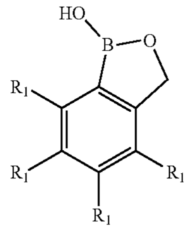

(F14)

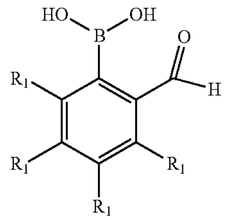

(F15)

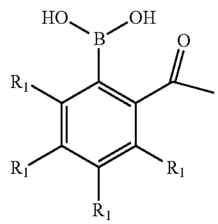

(F16)

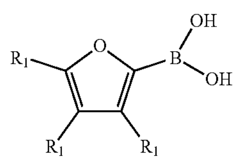

(F17)

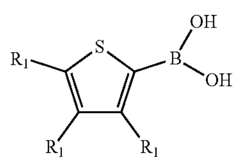

(F18)

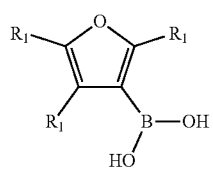

(F19)

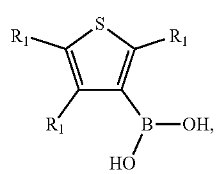

one $R_1$ from either $B_1$ or $B_2$ represents a covalent linkage, either directly or via an optional linker, to a drug substance;

one $R_1$ in each of $B_1$ and $B_2$ is (C═O)—, S(═O)(═O)—, $(CH_2)_m$(C═O)—, or $(CH_2)_m$—, wherein — represents a covalent bond to the remainder of R in Formula II;

none, one, or two $R_1$ in each of $B_1$ and $B_2$ independently represent COOH, F, Cl, Br, OH, $CH_2$—$NH_2$, $NH_2$, (C═O)—$NH_2$, $SO_2CH_3$, $CF_3$, $NO_2$, $CH_3$, $OCH_3$, $O(CH_2)_mCH_3$, —($SO_2$)NH $CH_3$, —($SO_2$) $NH(CH_2)_mCH_3$ or $OCF_3$;

index m is an integer in the range of 1 to 14, for example, 2 to 12, 3 to 10, 4 to 8, or 5 to 7; and all remaining $R_1$ represent H;

wherein, for each of Formulae F20-F25:

(F20)

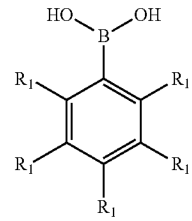

(F21)

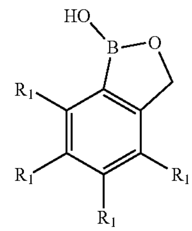

(F22)

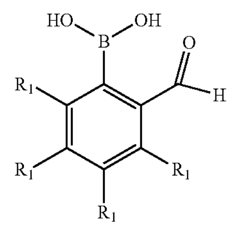

(F23)

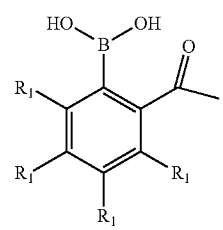

(F24)

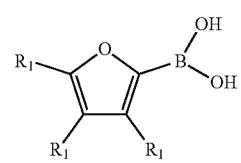

(F25)

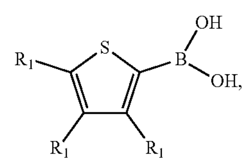

one $R_1$ is (C═O)—, S(═O)(═O)—, $(CH_2)_m$(C═O)—, or $(CH_2)_m$—, wherein — represents a covalent bond to the remainder of R in Formula II;

either:

(a) one or two $R_1$ on the same $B_1$ and/or $B_2$represent COOH, wherein at least one COOH is not conjugated to a drug substance, and/or (b) one or two $R_1$ each independently represent $NO_2$, $CH_3$, $OCH_3$, $O(CH_2)_mCH_3$, —$(SO_2)NH$ $CH_3$, —$(SO_2)NH(CH_2)_mCH_3$, wherein index m is an integer in the range of 1 to 14, for example, 2 to 12, 3 to 10, 4 to 8, or 5 to 7, and none, one, or two $R_1$ each independently represent $NO_2$, F, Cl, Br, OH, $CH_2$—$NH_2$, $NH_2$, (C═O)—$NH_2$, $SO_2CH_3$, $CH_3$, $CF_3$ or $OCF_3$, and all remaining $R_1$ represent H;

wherein, for each of Formulae F26-F27:

(F26)

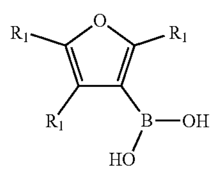

(F27)

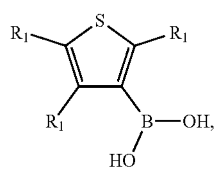

one $R_1$ is (C═O)—, S(═O)(═O)—, $(CH_2)_m$(C═O)—, or $(CH_2)_m$—, wherein — represents a covalent bond to the remainder of R in Formula II;

none, one, or two $R_1$ each independently represent COOH, F, Cl, Br, OH, $CH_2$—$NH_2$, $NH_2$, (C═O)—$NH_2$, $SO_2CH_3$, $CF_3$, $NO_2$, $CH_3$, $OCH_3$, $O(CH_2)_mCH_3$, —$(SO_2)NH$ $CH_3$, —$(SO_2)NH(CH_2)_mCH_3$ or $OCF_3$;

index m is an integer in the range of 1 to 14, for example, 2 to 12, 3 to 10, 4 to 8, or 5 to 7; and all remaining $R_1$ represent H;

wherein, for each of Formulae F28-F35:

(F28)

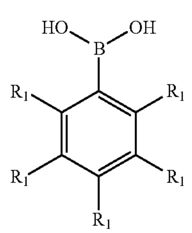

(F29)

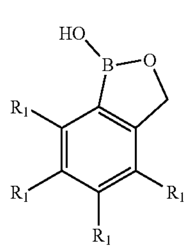

-continued (F30)

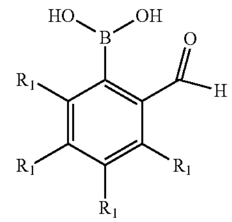

(F31)

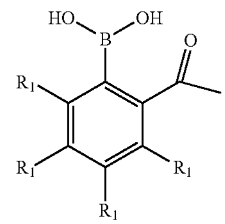

(F32)

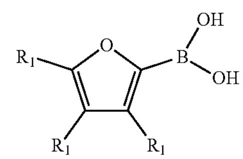

(F33)

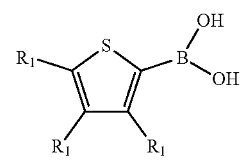

(F34)

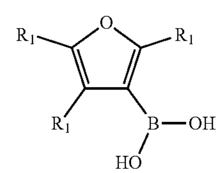

(F35)

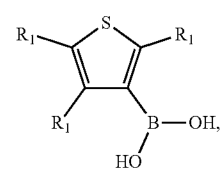

one $R_1$ in $B_1$ represents (C═O)—, S(═O)(═O)—, $(CH_2)_m$(C═O)—, or $(CH_2)_m$—, wherein — represents a covalent linkage, either directly or via an optional linker, to Z in Formula II;

one $R_1$ for each of $B_1$ and $B_2$ is a covalent linkage between $B_1$ and $B_2$, wherein the covalent linkage is selected from —(S═O)—, —(S(═O)(═O)—, —$(CF_2)$—, —(C═O)—, —$(CH_2)_m$ $SCH_2CO(CH_2)_k$—, —$(CH_2)_m$ $S(CH_2)_2CO(CH_2)_k$—, and —$(CH_2)_m$ (CO) $NH(CH_2)_k$—;

either (i) two $R_1$ groups in $B_2$ are COOH and these two $R_1$ groups are not conjugated to a drug substance, or (ii) one or two $R_1$ in either $B_1$ and/or $B_2$ each independently represent $NO_2$, CH═O, $CH_3$, $OCH_3$, $O(CH_2)_mCH_3$, —$(SO_2)NH$ $CH_3$, or —$(SO_2)NH(CH_2)_mCH_3$;

none, one, or two $R_1$ in either $B_1$ and/or $B_2$ each independently represent CH═O, F, Cl, Br, OH, $CH_2$—$NH_2$, $NH_2$, (C═O)—$NH_2$, $SO_2CH_3$, $CH_3$, $CF_3$, $CHF_2$, or $OCF_3$;

the remaining $R_1$ represent H;

index k is an integer in the range of 1 to 7, for example, 2 to 6 or 3 to 5; and index m is an integer in the range of 1 to 7, for example, 2 to 6 or 3 to 5;

wherein, for each of Formulae F36-F43:

(F36)

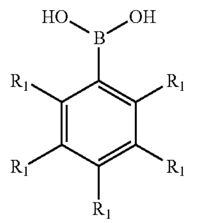

(F37)

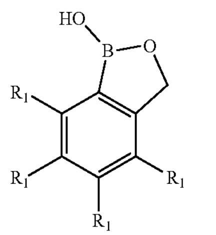

(F38)

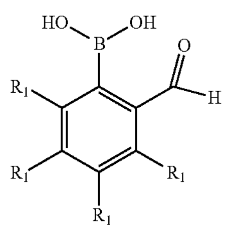

(F39)

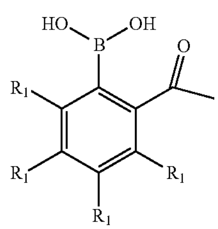

(F40)

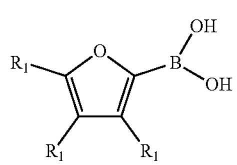

(F41)

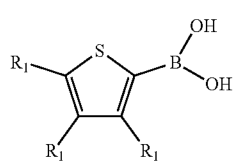

(F42)

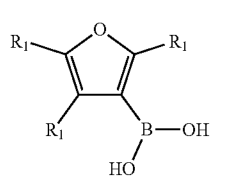

-continued (F43)

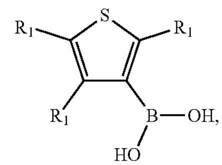

one $R_1$ for each of $B_1$ and $B_2$ is a covalent linkage to a sulfoximine group such that $B_1$ and $B_2$ are connected together by the sulfoximine group, and wherein the amino group of the sulfoximine is covalently linked, either directly through an acid containing linker or via an optional linker, to Z in Formula II;

either (i) two $R_1$ groups in $B_1$ and/or $B_2$ are COOH and these two $R_1$ groups are not conjugated to a drug substance, or (ii) one or two $R_1$ in either $B_1$ and/or $B_2$ each independently represent $NO_2$, CH═O, $CH_3$, $OCH_3$, $O(CH_2)_mCH_3$, —$(SO_2)$NH $CH_3$, or —$(SO_2)$NH $(CH_2)_mCH_3$; none, one, or two $R_1$ in either $B_1$ and/or $B_2$ each independently represent CH═O, F, Cl, Br, OH, $CH_2$—$NH_2$, $NH_2$, (C═O)—$NH_2$, $SO_2CH_3$, $CH_3$, $CF_3$, $CHF_2$, or $OCF_3$;

the remaining $R_1$ represent H;

index k is an integer in the range of 1 to 7, for example, 2 to 6 or 3 to 5; and index m is an integer in the range of 1 to 7, for example, 2 to 6 or 3 to 5.

3. A compound including a drug substance, wherein the drug substance includes an insulin and the insulin contains one or more modified amino acids represented by Formula III:

Z—R (Formula III)

wherein, in Formula III,

R is selected from Formulae FF1-FF24; and

Z is selected from an optional linker, J—$SCH_2$-ø, J—S$(CH_2)_2$—ø, J—NH—ø, J-NH(CO) linker-ø, J—S$(CH_2)_k$NH—ø, and J-triazole$(CH_2)_k$NH—ø, wherein —ø is the covalent bond towards R, index k is an integer in the range of 3 to 14, for example, 4 to 12, 5 to 10, or 6 to 8; and J is described by Formula III':

(Formula III')

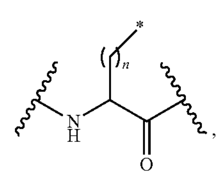

wherein, in Formula III':

 and 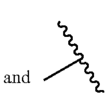

* indicates the point of attachment to the remaining portion of Z; and index n is an integer in the range of 1 to 8, for example, 2 to 7, 3 to 6, or 4 to 5;

wherein for Formulae FF1-FF24:
(FF1)
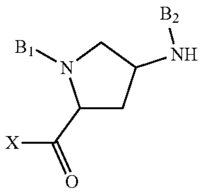
(FF2)
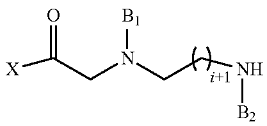
(FF3)
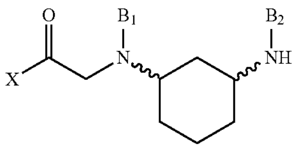
(FF4)
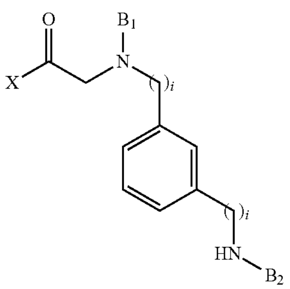
(FF5)
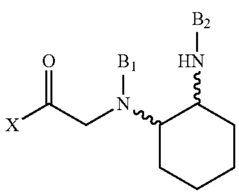
(FF6)
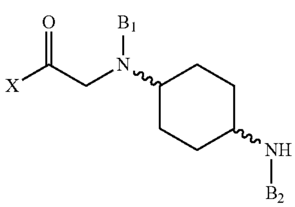
(FF7)
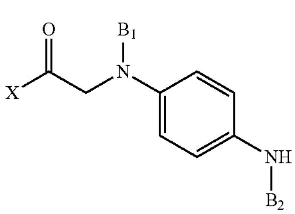
-continued
(FF8)
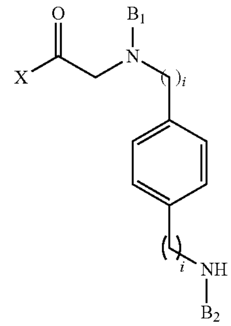
(FF9)
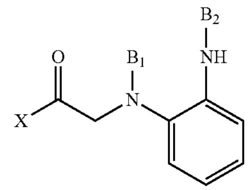
(FF10)
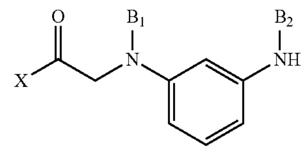
(FF11)
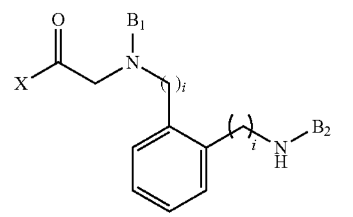
(FF12)
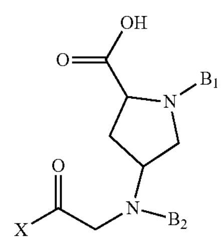
(FF13)
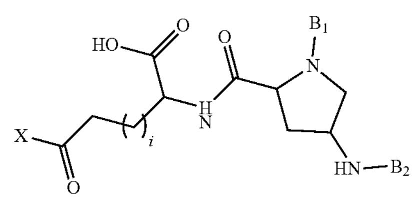
(FF14)
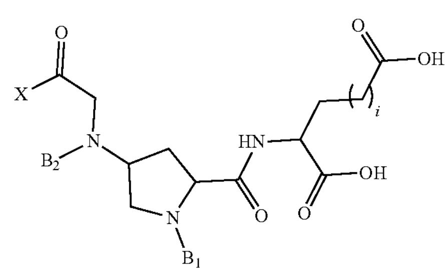

(FF15)
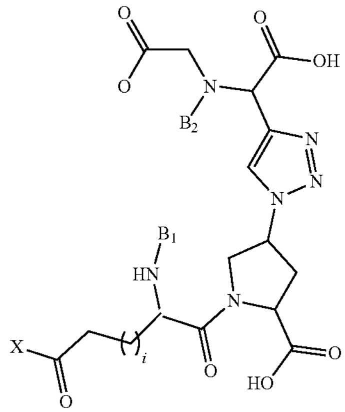
(FF16)
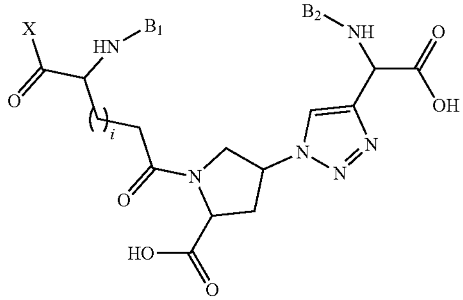
(FF17)
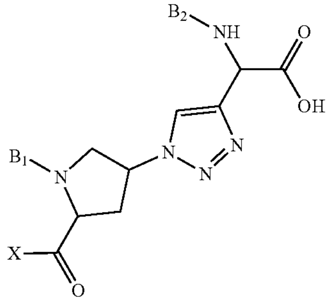
(FF18)
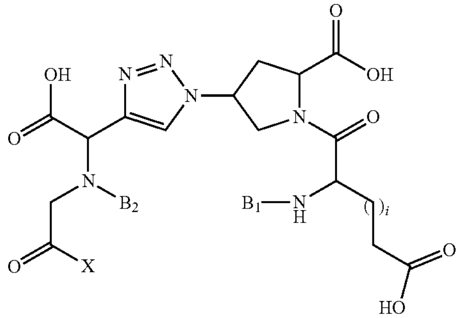
(FF19)
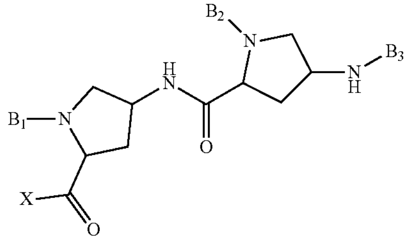
(FF20)
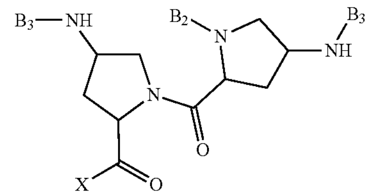
(FF21)
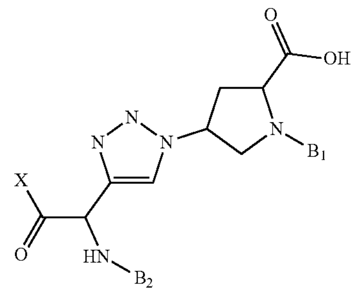
(FF22)
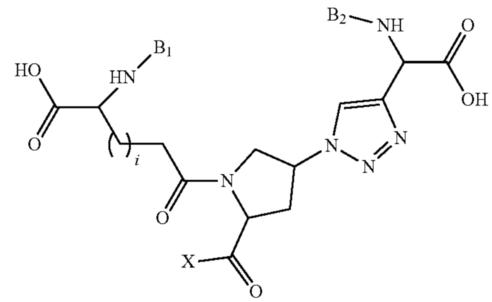
(FF23)
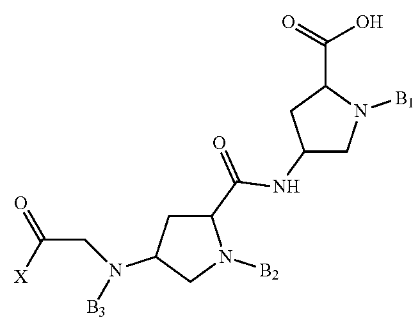
(FF24)
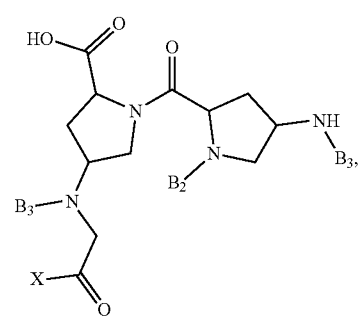
X represents a covalent linkage, either directly or via the optional linker, towards Z in Formula III;
index i is an integer in the range of 1 to 20, for example, 2 to 18, 3 to 16, 4 to 14, 6 to 12, or 8 to 10;
$B_1$ and $B_2$ are identical or different, and are each independently a group represented by one selected from Formulae F1-F9; and $B_3$ is a group represented by one selected from Formulae F1-F1 1;

(F1)

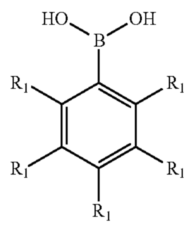

(F2)

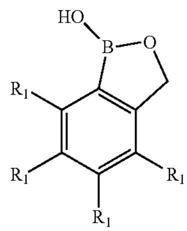

(F3)

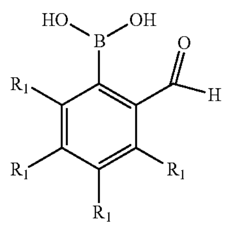

(F4)

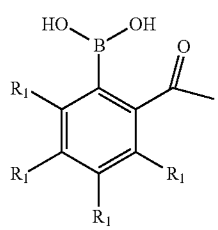

(F5)

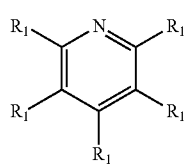

(F6)

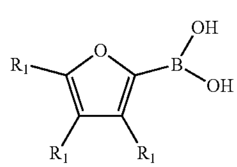

-continued (F7)

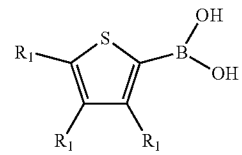

(F8)

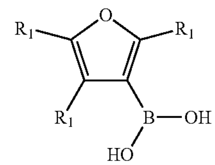

(F9)

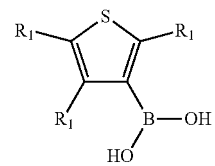

F10

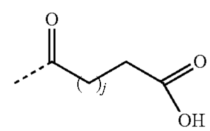

F11

----H, wherein, for each of Formulae F1-F9:

one $R_1$ represents (C═O)—, S(═O)(═O)—, $(CH_2)_m$(C═O)—, or $(CH_2)_m$—, wherein — represents a covalent bond to the remainder of R;

none, one, or two $R_1$ each independently represent F, Cl, Br, OH, $CH_2$—$NH_2$, $NH_2$, (C═O)—$NH_2$, $SO_2CH_3$, $CF_3$, $NO_2$, $CH_3$, $OCH_3$, $O(CH_2)_mCH_3$, —($SO_2$)NH$CH_3$, —($SO_2$)NH$(CH_2)_mCH_3$ or $OCF_3$;

index m is an integer in the range of 1 to 14, for example, 2 to 12, 3 to 10, 4 to 8, or 5 to 7;

one $R_1$ in F5 represents $B(OH)_2$; and all remaining $R_1$ represent H, and in Formula F10, index j is an integer in the range of 1 to 13, for example, 2 to 12, 3 to 10, 4 to 8, or 5 to 7.

4. The compound of any one of embodiments 1-3, wherein the optional linker is an L- or D-amino acid having at least one functional group directly conjugated to R, or the optional linker is selected from Formulae FL1-FL9:

(FL1)

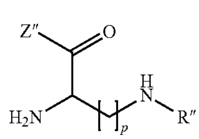

-continued (FL2)

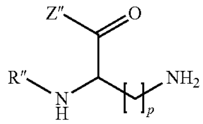

(FL3)

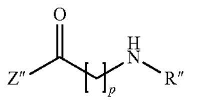

(FL4)

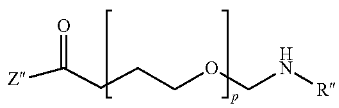

(FL5)

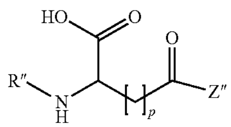

(FL6)

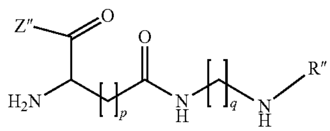

(FL7)

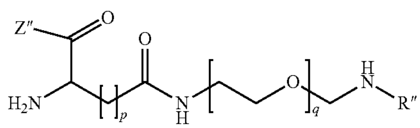

(FL8)

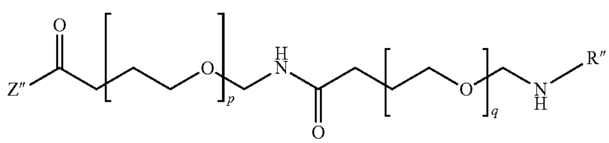

(FL9)

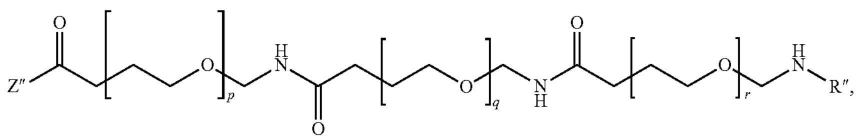

wherein, in Formulae FL1-FL9:

Z" represents a covalent bond towards Z;

R" represents a covalent bond towards R;

p is an integer in the range of 1 to 5;

q is an integer in the range of 1 to 5; and r is an integer in the range of 1 to 5.

5. The compound of any one of embodiments 1-3, wherein the compound is a drug substance that is additionally modified as described by embodiments 1-3 and/or wherein one or more amine are each independently acetylated or alkylated.

6. The compound of any one of embodiments 1-3, wherein the drug substance is an insulin including human insulin or an analog thereof, and the insulin includes an A-chain and a B-chain.

7. The compound of any of embodiments 1-2, wherein the drug substance includes a polypeptide drug substance or a human peptide hormone.

8. The compound of embodiment 6, wherein the insulin includes one or two peptide sequences each independently added to the A-chain and/or the B-chain of insulin, and each peptide sequence independently includes 1 to 20 continuous residues, for example, 2 to 18, 3 to 16, 4 to 14, 6 to 12, or 8 to 10 continuous residues.

9. The compound of embodiment 6, wherein the insulin includes 2 to 10 amino acids that are each independently modified as described by Formula I, II or III.

10. The compound of embodiment 6, wherein the insulin includes one or more modifications each independently described by Formula I, II or III, wherein each of the one or more modifications is positioned:

(i) on the side chain of an amino acid and/or to the N-terminus of a polypeptide of up to 20 residues appended to the N- and/or C- terminus of the A-chain and/or the B-chain of insulin; and/or (ii) within 4 residues of the B1, B21, B22, B29, A1, A22 or A3 residues in the insulin A- or B-chain; and/or (iii) on the side chain of an amino acid and/or to the N-terminus of a polypeptide appended or integrated into the A-chain and or the B-chain of insulin, wherein the polypeptide includes the sequence $(X_2)_nX_1(X_2)_m$ (SEQ ID NO:3) wherein: $X_1$ is a lysine residue in which the side chain of the lysine residue is modified as described by Formulae I, II, or III; each $X_2$ is independently selected from the group of amino acids K, P, E, G, N, M, A, R, L, W, S, F, V, C, H, D, I, Y, Q, T or $X_1$; index m is an integer in the range of 0 to 20 (for example, 1 to 18, 2 to 16, 3 to 14, 4 to 12, 5 to 10, or 6 to 8); and index n is an integer in the range of 0 to 18 (for example, 1 to 16, 2 to 14, 3 to 12, 4 to 10, 5 to 9, or 6 to 8). SEQ ID NO:3 represents the longest variant of the polypeptide sequence, and encompasses shorter subsequences thereof.

11. A conjugate including the compound according to any one of embodiments 1-2, wherein the compound according to any one of embodiments 1-2 is conjugated, either directly or via an covalent linker, to a drug substance, provided that the conjugation is not through Z when Z is $NH_2$ in Formula II.

12. The compound of any one of embodiments 1-3, wherein the compound of any one of embodiments 1-3 is used as an intermediate compound for the manufacture of any compounds in embodiments 1-11.

13. The compound of any one of embodiments 5-6, wherein the compound contains one or more modifications as described by Formulae IV, V or VI, wherein for Formula IV:

(Formula IV)

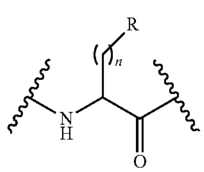

,

and

and indicate points of attachment to remaining portions of the drug substance; index n is an integer in the range of 1 to 8, for example, 2 to 7, 3 to 6, or 4 to 5; and R is selected from the group consisting of Formulae F111, F222, F333, F444, and F555:

(F111)

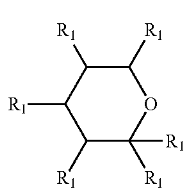

(F222)

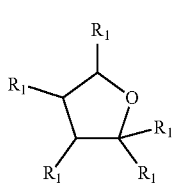

-continued (F333)

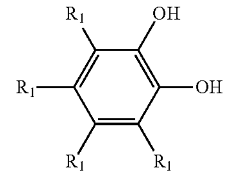

(F444)

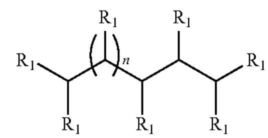

(F555)

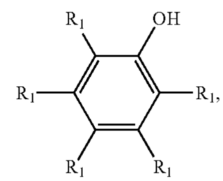

, wherein in Formulae F111, F222, F333, F444, and F555:

index n is an integer in the range of 1 to 8, for example, 2 to 7, 3 to 6, or 4 to 5;

each carbon atom attached to an $R^1$ independently has (R) or (S) stereochemistry;

each $R_1$ is independently selected from —H, —$OR^3$, —$N(R^3)_2$, —$SR^3$, —OH, —$OCH_3$, —$OR^5$, NHC(O)$CH_3$, —$CH_2R^3$, —C(O)NHOH, —NHC(O)$CH_3$, —$CH_2OH$, —$CH_2OR^5$, —$NH_2$, —$CH_2R^4$, —OR', —$R^6$, —$R^8$, and —$R^7$, each $R^3$ is independently selected from —H, acetyl, phosphate, —$R^2$, —$SO_2R^2$, —S(O)$R^2$, —P(O)$(OR^2)_2$, —C(O)$R^2$, —$CO_2R^2$, and —C(O)$N(R^2)_2$, each $R^2$ is independently selected from —H, an optionally substituted $C_1$0.6 aliphatic ring, an optionally substituted phenyl ring, an optionally substituted 5-6 membered monocyclic heteroaryl ring having 1-4 heteroatoms selected from nitrogen, oxygen, and sulfur, a 4-7 membered heterocyclic ring having 1-2 heteroatoms selected from nitrogen, oxygen, and sulfur, and an alkyl or amide covalent linkage to R in Formula IV, each $R^4$ is independently selected from —H, —OH, —$OR^3$, —$N(R^3)_2$, —$OR^5$ and —$SR^3$;

each $R^5$ is independently selected from a mono-saccharide, a di-saccharide, a tri-saccharide, a pentose, and a hexose, each $R^6$ is independently selected from —$NCOCH_2$—, —$(OCH_2CH_2)$—, a —O—$C_{1-9}$ alkylene group, and a substituted $C_1$>alkylene group in which one or more methylene groups are optionally replaced by —O—, —$(CH_2)$,—, —$OCH_2$—, —$N(R^2)C(O)$—, —$N(R^2)C(O)N(R^2)$—, —$SO_2$—, —$SO_2N(R^2)$—, —$N(R^2)SO_2$—, —S—, —$N(R^2)$—, —C(O)—, —OC(O)—, —C(O)O—, —C(O)$N(R^2)$—, or —$N(R^2)SO_2N(R^2)$—, wherein index n is an integer in a range 1 to 8, for example, 2 to 7, 3 to 6, or 4 to 5, each $R^7$ is independently selected from —$N(R^2)_2$, —F, —Cl, —Br, —I, —SH, —$OR^2$, —$SR^2$, —$NH_2$, —$N_3$, —C≡$CR^2$, —$CH_2$CECH, —C═CH, —$CO_2R^2$, —C(O)$R^2$, —$OSO_2R^2$—$N(R^2)_2$, —$OR^2$, —$SR^2$, —$CH_3$, —$CH_2NH_2$, and a direct linkage to R in Formula IV, $R^8$ is (i) the sidechain of one of L-serine, D-serine, L-threonine, D-threonine, L-allothreonine, or D-allothreonine and corresponds to R in Formula IV, wherein index n=1 in Formula IV, (ii) an amide linkage to the C-terminus of lysine, cysteine, 2,3-diaminopropionic acid, or (iii) $—CH_2C(CH_2OH)_2CH_2NH_2$, and structures F111, F222, F333, F444, and/or F555 optionally include one or more acetyl, acetylene, acetonide, and/or pinacol protecting groups;

wherein for Formula V:

(Formula V)

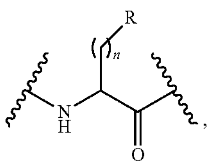

 and 

indicate points of attachment to remaining portions of the drug substance; index n is an integer in the range of 1 to 8, for example, 2 to 7, 3 to 6, or 4 to 5;

R represents X-Y, wherein X is a covalent linkage selected from the group consisting of a triazole, an amide bond, an imine bond or a thioether bond;

Y is selected from the group consisting of structures represented by Formulae F200-F203:

($F_{200}$)

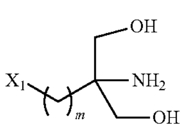

($F_{201}$)

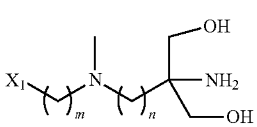

($F_{202}$)

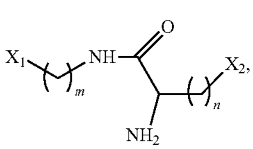

$X_1$ represents the covalent bond towards X;

$X_2$ represents SH, OH or $NH_2$;

index m is an integer in the range of 1 to 8, for example, 2 to 7, 3 to 6, or 4 to 5; and index n is an integer in the range of 1 to 8, for example, 2 to 7, 3 to 6, or 4 to 5;

wherein for Formula VI:

(Formula VI)

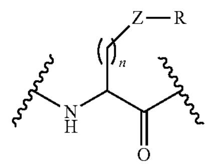

 and 

indicate points of attachment to remaining portions of the drug substance; index n is an integer in the range of 1 to 8, for example, 2 to 7, 3 to 6, or 4 to 5; Z is selected from the group consisting of: an amino acid, $—(CH_2)_p—$, $—CH_2(OCH_2CH_2)_p—$, $—SCH_2—$, $—S(CH_2)_2—$, —NH—, —NH(CO)—, —(CO)NH—, $—S(CH_2)_kNH—$, -triazole-$(CH_2)_k$—NH—, a triazole, an amide bond, an imine bond, and a thioether bond;

index k is an integer in the range of 3 to 5;

index p is an integer in the range of 1 to 8, for example, 2 to 7, 3 to 6, or 4 to 5; and R is selected from the group consisting of structures represented by Formulae F203-F205:

(F203)

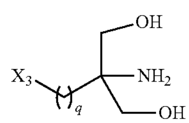

(F204)

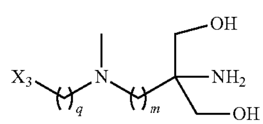

(F205)

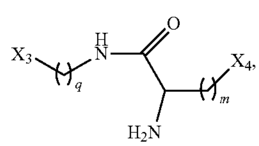

wherein $X_3$ represents the covalent bond towards Z;

$X_4$ represents SH, OH or $NH_2$ index q is an integer in the range of 1 to 8, for example, 2 to 7, 3 to 6, or 4 to 5; and index m is an integer in the range of 1 to 8, for example, 2 to 7, 3 to 6, or 4 to 5.

14. A method of manufacturing the compound of any one of embodiments 1-13, wherein optionally, $B_1$ and $B_2$ are first conjugated to one of structures represented by FF1-FF33 and the resultant conjugate is then covalently linked to a drug substance, or optionally, structures represented by FF1-FF33 are first conjugated to a drug substance and thereafter $B_1$ and $B_2$ are covalently linked to the corresponding structures in FF1-FF33.

15. A method of administering the compound of any one of embodiments 1-13 to a human subject as a therapeutic or prophylactic agent.

16. The compound of any of embodiments 1-13, wherein one or more amine groups are independently acetylated or alkylated.
17. The compound of embodiment 6, wherein the insulin includes two, three, or four modifications each independently described by Formulae I, II, or III.
18. The compound of embodiments 1-3, wherein the drug substance is a human polypeptide hormone or a peptide includes at least 10% homology to one, two, three, or four different human peptide hormones and which includes dual or triple agonists, hybrid synthetic peptides based on one or more human polypeptide hormones or analogs thereof.
19. The compound of embodiments 1-3, in which the drug substance is insulin, and the amino acid at residue 21 of the B-chain is a modified amino acid represented by Formulae I, II, or III.
20. The compound of embodiments 1-3, in which the drug substance is insulin, and in which one or more residues that are within 4 residues of residue 22 of the B-chain of insulin are represented each independently by Formulae I, II, or III, and one or more additional residues in a polypeptide appended to the C- and/or N-terminus of B- and/or A-chain, is independently represented by Formulae I, II, or III.
21. The compound of embodiments 1-3, in which the drug substance is insulin, wherein the modified amino acids either replace an amino acid at a given residue in the peptide sequence of A- and/or the B-chain or the modified amino acids are appended to the peptide sequence of the A- and/or the B-chain either at the ends and/or inside the peptide sequences of the A- and/or the B-chain.
22. The compound of embodiments 1-3 and 13, in which the drug substance is insulin, and wherein the amino acid at residue 21 of the B-chain is a modified amino acid represented by Formulae IV, V or VI, and the residue at the C-terminus of the A-chain is represented by Formulae I, II, or III.
23. The compound of embodiments 1-3 and 13, in which the drug substance is insulin, in which one or more residues that are within 4 residues of C-terminus of the A-chain, or which are appended to the C-terminus of A-chain, are represented each independently by Formulae I, II, or III, and one or more residues that are within 4 residues of residue 22 of the B-chain are represented each independently by Formulae IV, V, or VI.
24. The compound of embodiments 1-3 and 13, in which the drug substance is insulin, in which one or more residues that are within 4 residues of C-terminus of the A-chain, or which are appended to the C-terminus of A-chain, are represented each independently by Formulae IV, V, or VI, and one or more residues that are within 4 residues of residue 22 of the B-chain are represented each independently by Formulae I, II, or III.
25. The compound of any one of embodiments 1-3 and 13, in which the drug substance is insulin, wherein two modified amino acids are introduced to the B-chain of insulin at any position between the C-terminal cysteine of the B-chain and the C-terminus of B-chain, and two additional modified amino acids are introduced anywhere in the A-chain of insulin including being appended to one or both ends of the A-chain.
26. The compound of any one of embodiments 1-3 and 13, in which the drug substance is insulin, wherein one or more residues that are (i) within 4 residues of residue 21 of the B-chain and/or (ii) within 6 residues of the N- or C-terminus of the A- and/or B-chain and/or (iii) within 4 residues of residue 13 of the A-chain and/or (iv) are represented each independently by Formulae I, 11, 111, IV, V, or VI, and one or more residues that are within 4 residues of the C-terminus of the A-chain are represented each independently by Formulae I, II, III, IV, V, or VI.
27. A modified insulin of any one of embodiments 1, 2, or 3, in which two or more amino acids of B-chain in range of $B_1$ to B29 are replaced with natural or non-canonical or artificial amino acids.
28. The compound of any one of embodiments 1-3 and 13, in which the drug substance is insulin, in which one or more amino acids of A- or B-chain are replaced with natural or non-canonical amino acids.
29. The compound of any one of embodiments 1-3 and 13, in which the drug substance is insulin, wherein the insulin is further conjugated either directly or through an optional linker to a polypeptide including up to 31 amino acids.
30. The compound of any one of embodiments 1-3 and 13, in which the drug substance is insulin, wherein the insulin conjugated at the N- or C-terminus of the A- or B-chain to a polypeptide including up to 31 amino acids.
31. The compound of any one of embodiments 1-3 and 13, in which the drug substance is insulin, wherein the insulin is conjugated at the N- or C-terminus of the A- or B-chain to a polypeptide including up to 31 amino acids and the polypeptide is connected to the insulin through a peptide bond.
32. The compound of any one of embodiments 1-3 and 13, in which the drug substance is insulin, wherein the insulin is further conjugated either directly or through an optional linker to a polypeptide including up to 31 amino acids and wherein one or more pairs of the side chains of the polypeptide are covalently linked, and in certain embodiments thereof the covalent bond between the side chains is a bond selected from the group consisting of a triazole bond, a bond resulting from an azide-alkyne cycloaddition, a disulfide bond, a thioester bond, an oxime bond, an amide bond, a lactam bond, an ester bond, an olefin bond, an imine bond, an ester bond, and a thioether bond.
33. The compound of any one of embodiments 1-3 and 13, in which the drug substance is insulin, wherein at least one primary or one secondary amine group in R in Formula I is covalently conjugated through an amide bond to a side chain of an L- and D-gamma-glutamic acid, and the N-terminus of the glutamic acid is covalently conjugated through an amide bond to an unsubstituted or monosubstituted diacid alkyl chain containing 3 to 16 carbons, for example, 4 to 14, 5 to 12, 6 to 11, or 7 to 9 carbons.
34. A modified insulin of embodiment 2, wherein for Formula FF25 the index i is 0.
35. The compound of any one of embodiments 1-3 and 13, in which the drug substance is insulin, wherein between 1-10 amino acids are appended to the polypeptide sequence of insulin and these are appended N-terminal to residues 1 of the B-chain of insulin and wherein the residue that is inserted at N-terminal to residues 1 is a modified amino acid described by Formulae, II or III.
36. The compound of any one of embodiments 1-3 and 13, in which the drug substance is insulin, wherein between 1-10 amino acids are appended to the C-terminus of the B-chain of insulin and wherein the residue at position B29 of the insulin is a modified amino acid described by Formula I.

37. The compound of any one of embodiments 1-3 and 13, in which the drug substance is insulin, wherein up to 6 residues are appended to the polypeptide sequence of insulin and wherein at least two of those are modified amino acids described by Formulae I-VI.

38. The compound of any one of embodiments 1-3 and 13, in which the drug substance is insulin, and the insulin is modified to have 4 or 5 intramolecular disulfide bonds.

39. The compound of any one of embodiments 1-3 and 13, in which the drug substance is insulin, and the insulin is linked to a polypeptide using an enzyme.

40. The compound of any one of embodiments 1-3 and 13, in which the drug substance is insulin, and the insulin is linked to a non-boronated polypeptide including up to 31 amino acids using an enzyme.

41. The compound of any one of embodiments 1-3 and 13, in which the drug substance is insulin, the insulin is linked to a polypeptide including up to 31 amino acids and the side chains of at least two amino acids in the polypeptide sequence are covalently linked together or through an optional linker.

42. The compound of any one of embodiments 1-3 and 13, wherein the drug substance is insulin and the insulin is covalently conjugated using an amide bond to structures described by Formulae F411-F416 or structures including a structure in which F411 is further covalently conjugated using amide bonds to structures described by Formulae F412-F416, (F411)

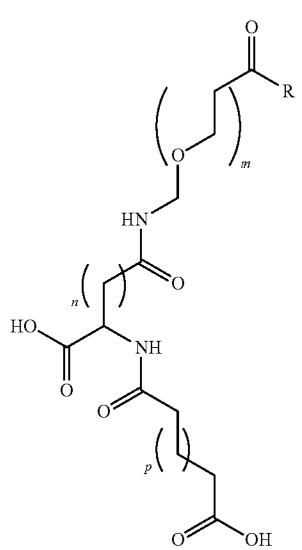

-continued (F412)

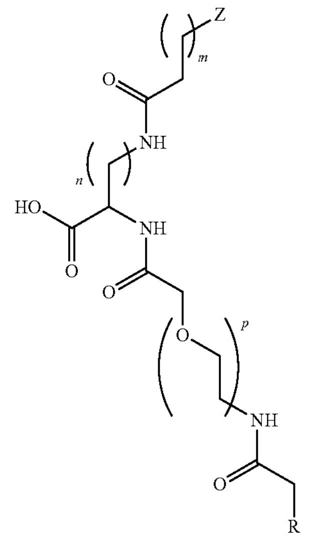

(F413)

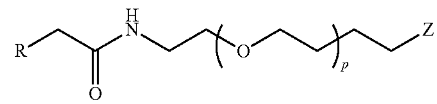

(F414)

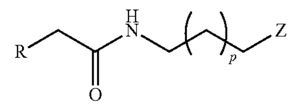

(F415)

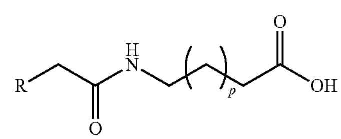

(F416)

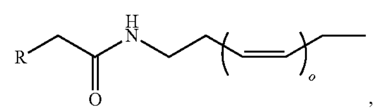

, wherein R represents a primary or secondary amine either in the N-terminus of the modified insulin, or, a primary or secondary amine in the side chains of a subset of amino acids in the modified insulin, and wherein the attachment to R is the point of attachment towards the modified insulin; index n represents an integer in the range of 1 to 14 (for example, 2 to 12, 3 to 10, 4 to 8, or 5 to 7), index m represents an integer in the range of 1 to 12 (for example, 3 to 10, 4 to 8, or 5 to 7), index o represent an integer in the range of 1 to 6 (for example, 2 to 5 or 3 to 4), index p represents an integer in the range of 1 to 12 (for example, 3 to 10, 4 to 8, or 5 to 7), Z represents one of —(C═O)—OH, —$NH_2$, a cholesterol, 7-OH cholesterol, 7,25-dihydroxycholesterol, cholic acid, chenodeoxycholic acid, lithocholic acid, deoxycholic acid, glycocholic acid, glycodeoxycholic acid, glycolithocholic acid, glycochenodeoxycholic acid, a-tocopherol, β-tocopherol, γ-tocopherol, δ-tocopherol, αtocotrienol, β-tocotrienol, γ-tocotrienol or δ-tocotrienol.

43. The compound of any one of embodiments 1-3 and 13, wherein the drug substance includes one or more of structures represented by Formulae FX15-FX28:

FX15

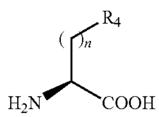

FX16

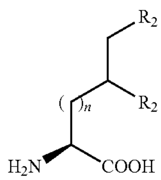

FX17

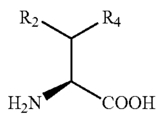

FX18

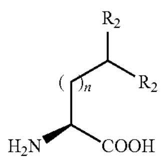

FX19

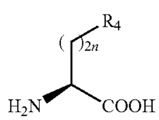

FX20

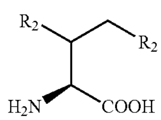

FX21

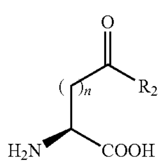

FX22

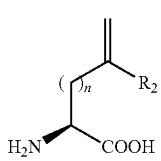

FX23

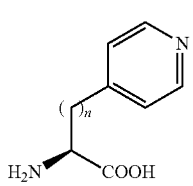

FX24

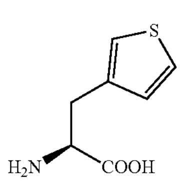

-continued

FX25

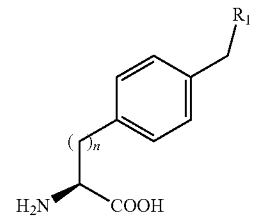

FX26

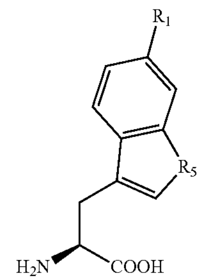

FX27

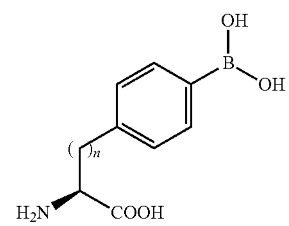

FX28

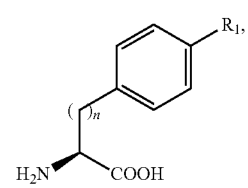

wherein, each $R_1$ is independently selected from H, $NH_2$, $NO_2$, Cl, $CF_3$, I, $COCH_3$, CN, C≡CH, $N_3$, or Br;

each $R_2$ is independently selected from $CF_3$, H, or $CH_3$;

each $R_3$ is independently selected from C≡CH, H, $N_3$, or a vinyl group;

each $R_4$ is independently selected from $NH_2$, $R_2$ or $R_3$;

each $R_5$ is independently selected from S or NH; and the index n is an integer in the range of 1 to 4, for example, 2 to 3.

While the present disclosure has been described in connection with certain example embodiments, it is to be understood that the disclosure is not limited to the disclosed embodiments, but, on the contrary, is intended to cover various modifications and equivalent arrangements included within the spirit and scope of the following claims and equivalents thereof.

What is claimed is:

1. A compound represented by Formula I:

Z—R (Formula I)

wherein, in Formula I,

R is selected from Formulae FF1-FF24; and

Z is selected from one of:

a) $NH_2$ or OH, b) a covalent linkage, either directly or via an optional linker, to a drug substance, wherein the drug substance is insulin, a polypeptide, Drug substance, or a human peptide hormone, and wherein the insulin comprising human insulin or an analog thereof comprising 2 to 10 amino acids that are each independently modified as described by Formula I c) a covalent linkage, either directly or via the optional linker, to an N-terminal amine or an epsilon amino group of one or more amino acids in a polypeptide drug substance, and d) a group represented by $J—SCH_{2\text{-}ø}$, $J—S(CH_2)_2—ø$, J—NH—ø, J—NH—(the optional linker)-ø, $J—S(CH_2)_kNH—ø$, or $J\text{-triazole}(CH_2)_kNH—ø$;

wherein —ø is the covalent bond towards R;

index k is an integer in the range of 3 to 14; and

J is an amino acid or one or more amino acids in a polypeptide drug substance, wherein each of the one or more amino acids in the polypeptide drug substance is represented by Formula I':

(Formula I')

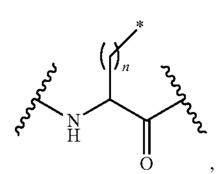

, wherein, in Formula I',

and

indicate points of attachment to remaining portions of the polypeptide drug substance;

* indicates the point of attachment to the remaining portion of Z; and
index n is an integer in the range of 1 to 8,
wherein for Formulae FF1-FF24:
(FF1)
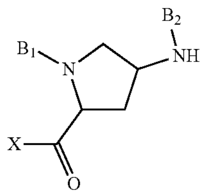
(FF2)
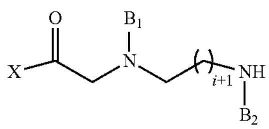
(FF3)
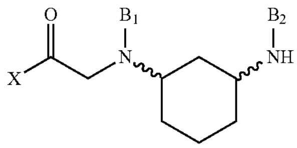
(FF4)
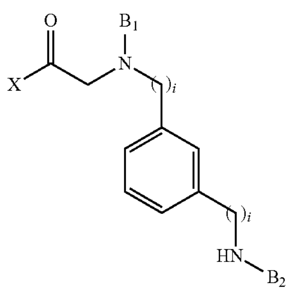
(FF5)
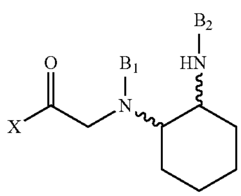
(FF6)
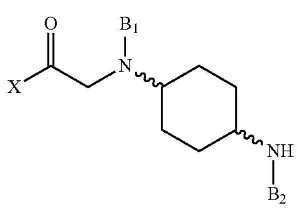
(FF7)
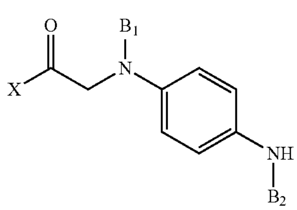
-continued
(FF8)
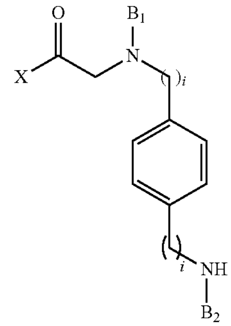
(FF9)
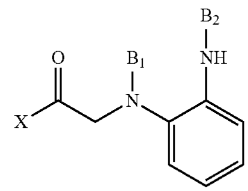
(FF10)
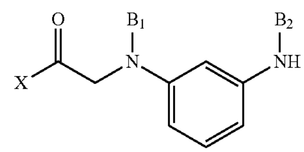
(FF11)
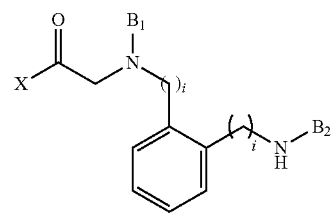
(FF12)
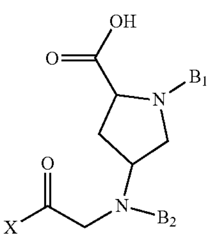
(FF13)
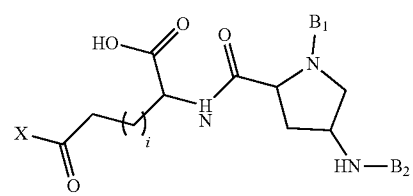
(FF14)
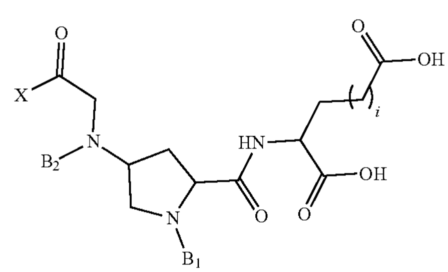

-continued
(FF15)
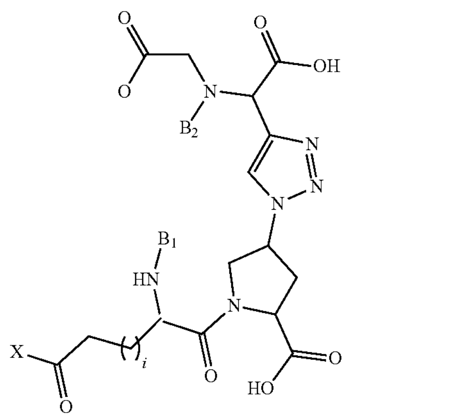
(FF16)
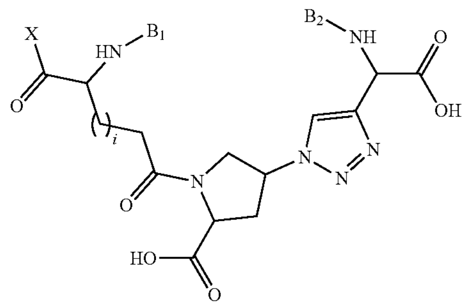
(FF17)
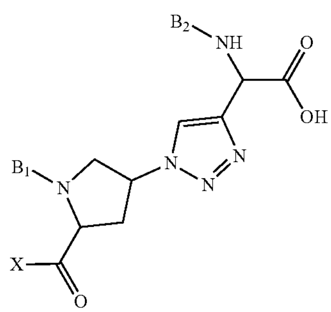
(FF18)
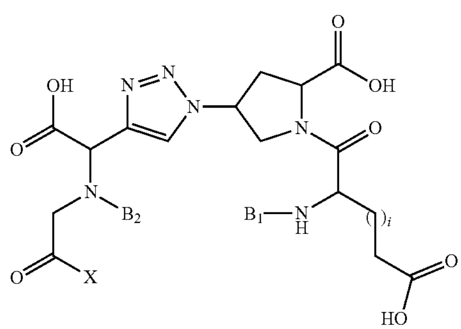
(FF19)
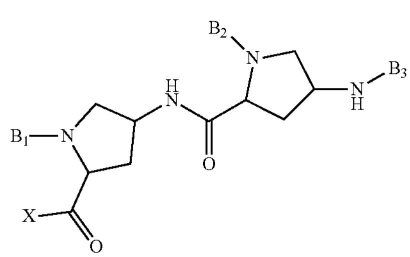
-continued
(FF20)
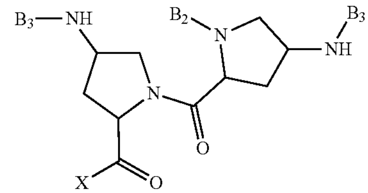
(FF21)
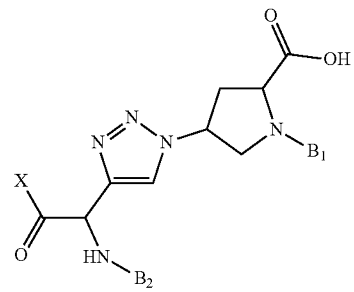
(FF22)
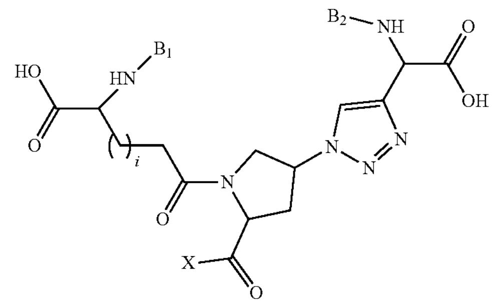
(FF23)
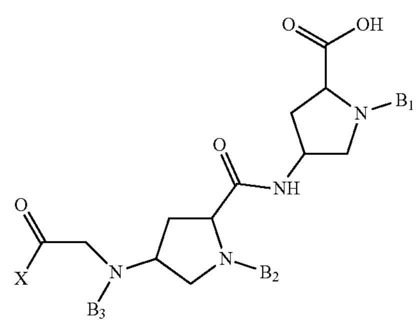
(FF24)
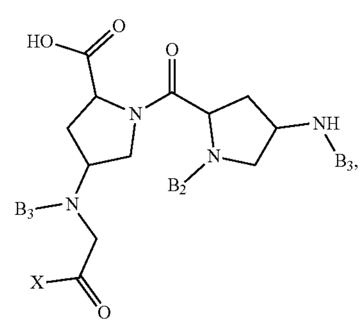
X represents a covalent linkage, either directly or via the optional linker, towards Z in Formula I;
index i is an integer in the range of 1 to 20;
$B_1$ and $B_2$ are identical or different, and each independently represent a group selected from Formulae F1-F9; and $B_3$ represents a group selected from Formulae F1-F11, (F1)

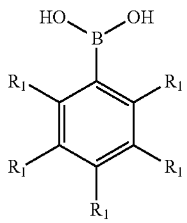

(F2)

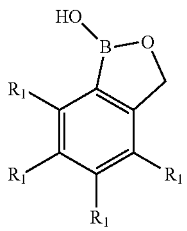

(F3)

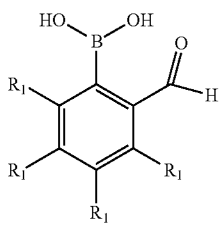

(F4)

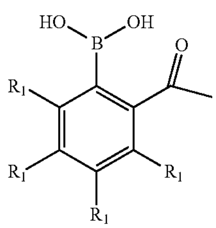

(F5)

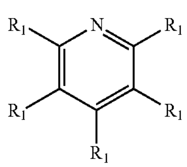

(F6)

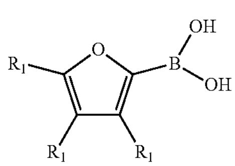

-continued (F7)

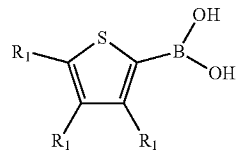

(F8)

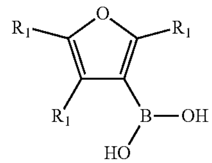

(F9)

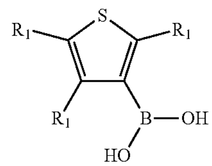

F10

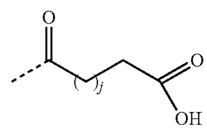

F11

----H, wherein, for each of Formulae F1-F9:

one $R_1$ represents (C═O)—, S(═O)(═O)—, $(CH_2)_m$(C═O)—, or $(CH_2)_m$—, wherein —represents a covalent bond to the remainder of R in Formula I;

none, one, or two $R_1$ each independently represent F, Cl, Br, OH, $CH_2$—$NH_2$, $NH_2$, (C═O)—$NH_2$, $SO_2CH_3$, $CF_3$, $NO_2$, $CH_3$, $OCH_3$, $O(CH_2)_mCH_3$, —$(SO_2)NH CH_3$, —$(SO_2)NH(CH_2)_mCH_3$, or $OCF_3$, index m is an integer in the range of 1 to 14;

one $R_1$ in F5 represents $B(OH)_2$, and all remaining $R_1$ represent H, and in Formula F10, index j is an integer in the range of 1 to 13.

2. The compound of claim 1, wherein the optional linker is an L- or D-amino acid having at least one functional group directly conjugated to R, or the optional linker is selected from Formulae FL1-FL9:

(FL1)

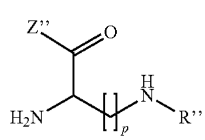

(FL2)

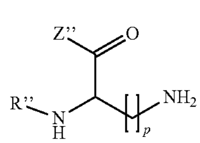

-continued (FL3)

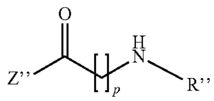

(FL4)

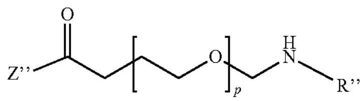

(FL5)

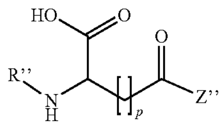

(FL6)

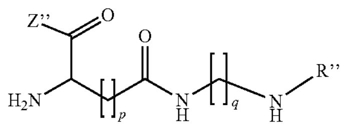

(FL7)

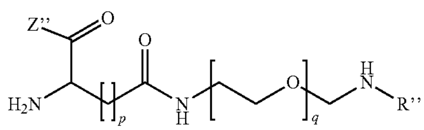

(FL8)

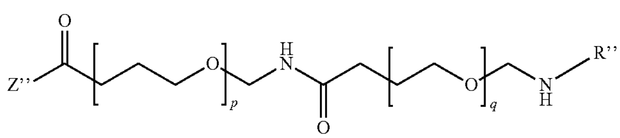

(FL9)

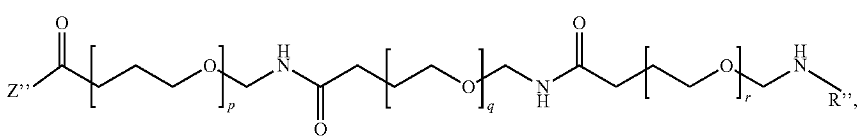

wherein, in Formulae FL1-FL9:

Z" represents a covalent bond towards Z;

R" represents a covalent bond towards R;

p is an integer in the range of 1 to 5;

q is an integer in the range of 1 to 5; and r is an integer in the range of 1 to 5.

3. The compound claim 1, wherein the compound is a drug substance that is additionally modified as described by claim 1 and/or wherein one or more amines are each independently acetylated or alkylated.

4. The compound of claim 1, wherein the insulin comprises an A-chain and/or the B-chain comprising one or two peptide sequences added to the A-chain and/or the B-chain of the insulin, and each peptide sequence independently comprises 1 to 20 continuous residues.

5. The compound of any one of claim 1, wherein the insulin is further conjugated either directly or through the optional linker to a polypeptide including up to 31 amino acids.

6. The compound of any one of claim 1, wherein the insulin conjugated at the N- or C-terminus of the A- or B-chain to a polypeptide including up to 31 amino acids.

7. The compound of any one of claim 4, wherein the insulin is conjugated at the N- or C-terminus of the A- or B-chain to a polypeptide including up to 31 amino acids and the polypeptide is connected to the insulin through a peptide bond.

8. The compound of any one of claim 1, wherein between 1-10 amino acids are appended to the polypeptide sequence of insulin and these are appended N-terminal to residue 1 of the B-chain of insulin and wherein the residue that is inserted at N-terminal to residue 1 is a modified amino acid described by Formulae I.

9. The compound of any one of claim 1 wherein the insulin has 4 or 5 intramolecular disulfide bonds.

10. The compound of any one of claim 1, wherein the insulin is linked to a polypeptide including up to 31 amino acids and the side chains of at least two amino acids in the polypeptide sequence are covalently linked together or through the optional linker.

11. The compound of any one of claim 1, wherein the insulin is covalently conjugated using an amide bond to structures described by Formulae F411-F416 or structures comprising a structure in which F411 is further covalently conjugated using amide bonds to structures described by Formulae F412-F416, (F411)

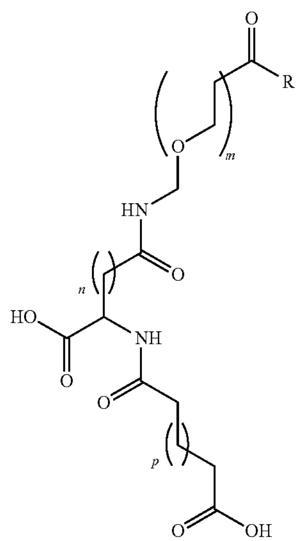

(F412)

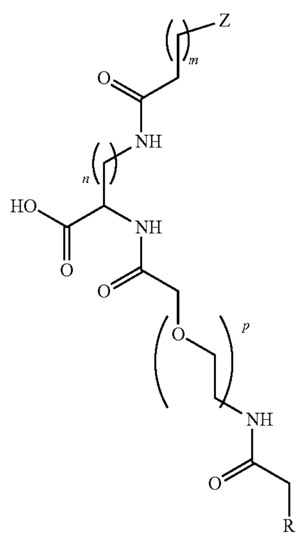

(F413)

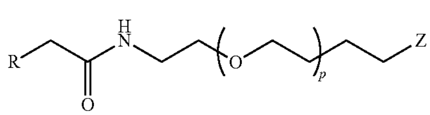

(F414)

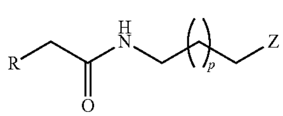

(F415)

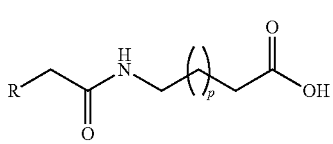

-continued (F416)

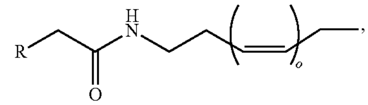

wherein R represents a primary or secondary amine either in the N-terminus of the insulin, or, a primary or secondary amine in the side chains of a subset of amino acids in the insulin, and wherein the attachment to R is the point of attachment towards the insulin; index n represents an integer in the range of 1 to 14, index m represents an integer in the range of 1 to 12, index o represent an integer in the range of 1 to 6, index p represents an integer in the range of 1 to 12, Z represents one of —(C═O)—OH, —$NH_2$, a cholesterol, 7-OH cholesterol, 7,25-dihydroxycholesterol, cholic acid, chenodeoxycholic acid, lithocholic acid, deoxycholic acid, glycocholic acid, glycodeoxycholic acid, glycolithocholic acid, glycochenodeoxycholic acid, α-tocopherol, β-tocopherol, γ-tocopherol, δ-tocopherol, αtocotrienol, β-tocotrienol, γ-tocotrienol or δ-tocotrienol.

12. The compound of any one of claim 1, wherein the drug substance includes one or more of structures represented by Formulae FX15-FX28:

FX15

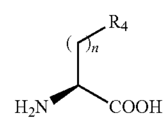

FX16

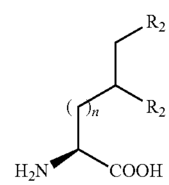

FX17

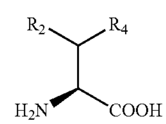

FX18

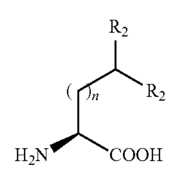

FX19

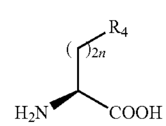

FX20

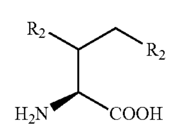

-continued

FX21

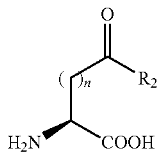

FX22

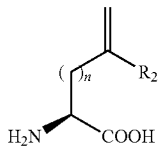

FX23

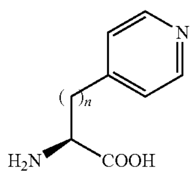

FX24

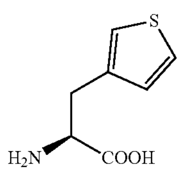

FX25

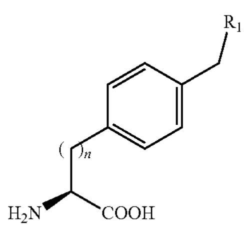

-continued

FX26

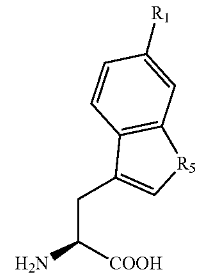

FX27

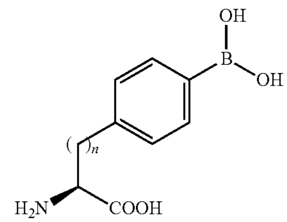

FX28

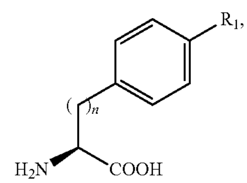

wherein, each $R_1$ is independently selected from H, $NH_2$, $NO_2$, Cl, $CF_3$, I, $COCH_3$, CN, C≡CH, $N_3$, or Br;

each $R_2$ is independently selected from $CF_3$, H, or $CH_3$;

each $R_3$ is independently selected from C≡CH, H, $N_3$, or a vinyl group;

each $R_4$ is independently selected from $NH_2$, $R_2$ or $R_3$;

each $R_5$ is independently selected from S or NH; and the index n is an integer in the range of 1 to 4.

* * * * *